(12) United States Patent
Maori et al.

(10) Patent No.: US 11,555,199 B2
(45) Date of Patent: Jan. 17, 2023

(54) MODIFYING THE SPECIFICITY OF PLANT NON-CODING RNA MOLECULES FOR SILENCING GENE EXPRESSION

(71) Applicant: Tropic Biosciences UK Limited, Norwich (GB)

(72) Inventors: Eyal Maori, Cambridge (GB); Yaron Galanty, Cambridge (GB); Cristina Pignocchi, Norwich (GB); Angela Chaparro Garcia, Norwich (GB); Ofir Meir, Norwich (GB)

(73) Assignee: Tropic Biosciences UK Limited, Norwich (GB)

( * ) Notice: Subject to any disclaimer, the term of this patent is extended or adjusted under 35 U.S.C. 154(b) by 13 days.

(21) Appl. No.: 16/648,748

(22) PCT Filed: Sep. 18, 2018

(86) PCT No.: PCT/IB2018/057160
§ 371 (c)(1),
(2) Date: Mar. 19, 2020

(87) PCT Pub. No.: WO2019/058255
PCT Pub. Date: Mar. 28, 2019

(65) Prior Publication Data
US 2020/0248196 A1    Aug. 6, 2020

(30) Foreign Application Priority Data

Sep. 19, 2017  (GB) ..................... 1715113
Sep. 19, 2017  (GB) ..................... 1715116
Nov. 23, 2017  (GB) ..................... 1719516

(51) Int. Cl.
| | | |
|---|---|---|
| C12N 15/82 | (2006.01) | |
| C12N 9/22 | (2006.01) | |
| C12N 15/113 | (2010.01) | |
| C12N 15/85 | (2006.01) | |
| C12N 15/90 | (2006.01) | |

(52) U.S. Cl.
CPC ........... *C12N 15/8218* (2013.01); *C12N 9/22* (2013.01); *C12N 15/113* (2013.01); *C12N 15/8213* (2013.01); *C12N 15/8279* (2013.01); *C12N 15/85* (2013.01); *C12N 15/902* (2013.01); *C12N 2310/11* (2013.01); *C12N 2310/141* (2013.01); *C12N 2310/20* (2017.05)

(58) Field of Classification Search
CPC ....................................................... C12N 9/22
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | Mcconnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella et al. |
| 4,683,202 A | 7/1987 | Mullis |
| 4,801,531 A | 1/1989 | Frossard |
| 4,855,237 A | 8/1989 | Morinaga et al. |
| 4,879,219 A | 11/1989 | Wands et al. |
| 4,945,050 A | 7/1990 | Sanford et al. |
| 5,011,771 A | 4/1991 | Bellet et al. |
| 5,015,580 A | 5/1991 | Christou et al. |
| 5,192,659 A | 3/1993 | Simons et al. |
| 5,272,057 A | 12/1993 | Smulson et al. |
| 5,281,521 A | 1/1994 | Trojanowski et al. |
| 5,302,523 A | 4/1994 | Coffee et al. |
| 5,316,931 A | 5/1994 | Donson et al. |
| 5,384,253 A | 1/1995 | Krzyzek et al. |
| 5,464,765 A | 11/1995 | Coffee et al. |

(Continued)

FOREIGN PATENT DOCUMENTS

| | | |
|---|---|---|
| CN | 105647962 | 6/2016 |
| CN | 105647962 | 8/2016 |
| CN | 106367435 | 2/2017 |
| WO | WO-1987006261 A1 | 10/1987 |
| WO | WO 96/00232 | 1/1996 |

(Continued)

OTHER PUBLICATIONS

Jianping et al 2017 Frontiers in Plant Science 8:1-12 (provided by Applicant) (Year: 2017).*
Jacobs et al (2015 BMC Technology 15:1-10 (provided by Applicant) (Year: 015).*
Kawahara et al (2007 Science 315:1137-1140 (Year: 2007).*

(Continued)

*Primary Examiner* — Brent T Page
(74) *Attorney, Agent, or Firm* — Morrison & Foerster LLP

(57) ABSTRACT

A method of modifying a gene encoding or processed into a non-coding RNA molecule having no RNA silencing activity in a plant cell is disclosed. The method comprising introducing into the plant cell a DNA editing agent conferring a silencing specificity of the non-coding RNA molecule towards a target RNA of interest. A method of modifying a gene encoding or processed into a RNA silencing molecule in a plant cell is also disclosed. The method comprising introducing into the plant cell a DNA editing agent which redirects the silencing specificity of the non-coding RNA molecule towards a target RNA of interest. Plant cells, plant seeds, plants, and methods of generating plants are also disclosed.

12 Claims, 20 Drawing Sheets
(18 of 20 Drawing Sheet(s) Filed in Color)
Specification includes a Sequence Listing.

(56) References Cited

U.S. PATENT DOCUMENTS

| | | | |
|---|---|---|---|
| 5,508,184 | A | 4/1996 | Negrutiu et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,591,616 | A | 1/1997 | Hiei et al. |
| 5,693,507 | A | 12/1997 | Daniell et al. |
| 5,693,512 | A | 12/1997 | Finer et al. |
| 5,824,877 | A | 10/1998 | Hinchee et al. |
| 5,981,840 | A | 11/1999 | Zhao et al. |
| 6,160,208 | A | 12/2000 | Lundquist et al. |
| 6,384,301 | B1 | 5/2002 | Martinell et al. |
| 6,399,861 | B1 | 6/2002 | Anderson et al. |
| 6,403,865 | B1 | 6/2002 | Koziel et al. |
| 8,021,867 | B2 | 9/2011 | Smith et al. |
| 8,119,381 | B2 | 2/2012 | Smith et al. |
| 8,124,369 | B2 | 2/2012 | Smith et al. |
| 8,129,134 | B2 | 3/2012 | Smith et al. |
| 8,133,697 | B2 | 3/2012 | Smith et al. |
| 8,143,015 | B2 | 3/2012 | Smith et al. |
| 8,143,016 | B2 | 3/2012 | Smith et al. |
| 8,148,098 | B2 | 4/2012 | Smith et al. |
| 8,163,514 | B2 | 4/2012 | Smith et al. |
| 8,304,222 | B1 | 11/2012 | Smith et al. |
| 2005/0203047 | A1 | 9/2005 | Thomann et al. |
| 2008/0293143 | A1 | 11/2008 | Lin et al. |
| 2015/0047062 | A1 | 2/2015 | Lai et al. |
| 2015/0082478 | A1 | 3/2015 | Cigan et al. |
| 2016/0076093 | A1 | 3/2016 | Shendure et al. |
| 2016/0289675 | A1 | 10/2016 | Ryan et al. |

FOREIGN PATENT DOCUMENTS

| | | |
|---|---|---|
| WO | WO 2005/111211 | 11/2005 |
| WO | WO 2007/048628 | 5/2007 |
| WO | WO-2008148223 A1 | 12/2008 |
| WO | WO-2009046384 A1 | 4/2009 |
| WO | WO-2011026644 A2 | 3/2011 |
| WO | WO 2015/123339 | 8/2015 |
| WO | WO 2016/100333 | 6/2016 |
| WO | WO 2016/196887 | 12/2016 |
| WO | WO 2017/036351 | 3/2017 |
| WO | WO 2017/123910 | 7/2017 |
| WO | WO 2018/183878 | 10/2018 |
| WO | WO 2019/058253 | 3/2019 |
| WO | WO 2019/058255 | 3/2019 |
| WO | WO-2020178099 A1 | 9/2020 |

OTHER PUBLICATIONS

Bhattacharya and Cui (2017 Journal of Integrative Bioinformatics 2017:1-7 (Year: 2017).*
International Preliminary Report on Patentability dated Apr. 2, 2020 From the International Bureau of WIPO Re. Application No. PCT/IB2018/057143. (12 Pages).
International Preliminary Report on Patentability dated Apr. 2, 2020 From the International Bureau of WIPO Re. Application No. PCT/IB2018/057160. (11 Pages).
International Search Report and the Written Opinion dated Feb. 20, 2019 From the International Searching Authority Re. Application No. PCT/IB2018/057143. (25 Pages).
International Search Report and the Written Opinion dated Feb. 25, 2019 From the International Searching Authority Re. Application No. PCT/IB2018/057160.(23 Pages).
Invitation to Pay Additional Fees, Communication Relating to the Results of the Partial International Search and the Provisional Opinion dated Dec. 21, 2018 From the International Searching Authority Re. Application No. PCT/IB2018/057143. (19 Pages).
Invitation to Pay Additional Fees, Communication Relating to the Results of the Partial International Search and the Provisional Opinion dated Dec. 21, 2018 From the International Searching Authority Re. Application No. PCT/IB2018/057160. (18 Pages).
Patents Act 1977: Patents Rules 2007: Preliminary Examination Report Under Section 15A dated Oct. 9, 2017 From the Intellectual Property Office fo the United Kingdom of Great Britain Re. Application No. 1715113.5. (2 Pages).
Patents Act 1977: Patents Rules 2007: Preliminary Examination Report Under Section 15A dated Sep. 26, 2017 From the Intellectual Property Office fo the United Kingdom of Great Britain Re. Application No. 1715116.8. (2 Pages).
Patents Act 1977: Search Report Under Section 17(5) dated Jun. 13, 2018 From the Intellectual Property Office of the United Kingdom of Great Britain Re. Application No. 1715113.5. (4 Pages).
Patents Act 1977: Search Report Under Section 17(5) dated Jun. 13, 2018 From the Intellectual Property Office of the United Kingdom of Great Britain Re. Application No. 1715116.8. (5 Pages).
Basak et al. "Targeting Non-Coding RNAs in Plant With the CRISPR-Cas Technology Is a Challenge Yet Worth Accepting", Frontiers in Plant Science, XP055528168, 6: 1001-1-1001-8, Published Online Nov. 19, 2015.
Bortesi et al. "The CRISPR/Cas9 System for Plant Genome Editing and Beyond", Biotechnology Advances, 33(1): 41-52, Available Online Dec. 20, 2014.
Carbonell et al. "New Generation of Artificial MicroRNA and Synthetic Trans-Acting Small Interfering RNA Vectors for Efficient Gene Silencing in *Arabidopsis*", Plant Physiology, 165(1): May 15-29, 2014.
Cheng et al. "Positional Cloning of Quantitative Trait Nucelotides for Blood Pressure and Cardiac QT-Interval by Targeted CRISPR/Cas9 Editing of a Novel Long Non-Coding RNA", PLOS Genetics, XP055528205, 13(8): e1006961-1-e1006961-20, Published Online Aug. 21, 2017. Fig. 1.
Cho et al. "Heritable Gene Knockout in Caenorhabditis Elegans by Direct Injection of Cas-SgRNA Ribonucleoproteins", Genetics, 195(3): 1177-1180, Nov. 2013.
Dai et al. "Exploiting *Drosophila* Genetics to Understand MicroRNA Function and Regulation", Current Topics in Developmental Biology, XP055550050, 99(Chap.8): 201-235, Jan. 2012.
Dowdy "Overcoming Cellular Barriers for RNA Therapeutics", Nature Biotechnology, 35(3): 1-8, Published Online Feb. 27, 2017.
Fei "Functional Analysis of MicroRNA Triggers of Phased SiRNA Biogenesis in Plants", A Dissertation Submitted to the Faculty of the University of Delaware in Partial Filfillment of the Requirements for the Degree of Doctor of Philosophy in Plant and Soil Sciences, XP055529765, p. 1-133, Summer 2016. p. 79-82.
Gaspar et al. "Long-Term Persistence of a Polyclonal T Cell Repertoire After Gene Therapy for X-Linked Severe Combined Immunodeficiency", Science Transalational Medicine, 3(97): 97ra79-1- 97ra79-7, Aug. 24, 2011.
Gutschner et al. "Noncoding RNA Gene Silencing Through Genomic Integration of RNA Destabilizing Elements Using Zinc Finger Nucleases", Genome Research, XP055197552, 21(11): 1944-1954, Published Online Aug. 15, 2011. p. 1953, Figs.2-4.
Howe et al. "Insertional Mutagenesis Combined With Acquired Somatic Mutations Cuases Leukomogenesis Following Gene Therapy of SCID-X1 Patients", The Journal of Clinical Investigation, 118(9): 3143-3150, Published Online Aug. 7, 2008.
Huo et al. "Lentiviral CRISPR/Cas9 Vector Mediated MiR-21 Gene Editing Inhibits the Epithelial to Mesenchymal Transition in Ovarian Cancer Cells", Journal of Cancer, XP055550172, 8(1): 57-64, Published Online Jan. 1, 2017.
Jacobs et al. "Targeted Genome Modifications in Soybean With CRISPR/Cas9", CRISPR/Cas9, BMC Biotechnology, XP021219338,15,16: 1-10, Mar. 12, 2015.
Jiang et al. "Small Indels Induced by CRISPR/Cas9 in the 5' Region of MicroRNA Lead to Its Depletion and Drosha Processing Retardance", RNA Biology, 11(10): 1243-1249, Oct. 2014.
Jing et al. "CRISPR/CAS9-Mediated Genome Editing of MiRNA-155 Inhibits Proinflammatory Cytokine Production by RAW264.7 Cells", Biomed Research International, XP055549680, 2015(Art.ID 326042): 1-7, Published Online Nov. 30, 2015.
Kim et al. "Highlv Efficient RNA-Guided Genome Editing in Human Cells Via Delivery of Purified Cas9 Ribonucleoproteins", Genome Research, 24(6): 1012-1019, Jun. 2014.

(56) References Cited

OTHER PUBLICATIONS

Lataniotis et al. "CRISPR/Cas9 Editing Reveals Novel Mechanisms of Clustered MicroRNA Regulation and Function", Scientific Reports, XP055528159, 7(8585): 1-14, Published Online Aug. 17, 2017.
Miura et al. "CRISPR/Cas9-Based Generation of Knockdown Mice by Intronic Insertion of Artificial MicroRNA Using Longer Single-Stranded DNA", Scientific Reports, XP055333089, 5: 12799-1-12799-11, Published Online Aug. 5, 2015. Figs.2-4.
Narayanan et al. In Vivo Mutagenesis of MiRNA Gene Families Using a Scalable Multiplexed CRISPR/Cas9 Nuclease System:, Scientific Reports, 6(32386): 1-9, Pubhshed Online Aug. 30, 2016.
Porteus "Genome Editing: A New Approach to Human Therapeutics", Annual Review of Pharmacology and Toxicology, Review in Advance, 56: 29.1-29.28, Oct. 28, 2015.
Qi et al. "High-Efficiency CRISPR/Cas9 Multiplex Gene Editing Using the Glycine tRNA-Processing System-Based Strategy in Maize", BMC Biotechnology, XP055515108, 16(1): 58-1-58-8, Published Online Aug. 11, 2016. Fig.3.
Rybak-Wolf et al. "A Variety of Dicer Substrates in Human and C. Elegans", Cell, 159(5): 1153-1167, Nov. 20, 2014.
Schwab et al. "Highly Specific Gene Silencing by Artificial MicroRNAs in *Arabidopsis*", The Plant Cell, XP002520528, 18(5): 1121-1133, Published Online Mar. 10, 2006. Fig.1, Table 1.
Senis et al. "A Therapeutic Anti-Hepatitis C Virus ShmiRNA Integrated Into the MiR-122 Genomic Locus Mediates a Potent Anti-Viral Response", Human Gene Therapy, XP055529717, 25(11): A51-A52, # OR081, Nov. 15, 2014.
Senis et al. "TALEN/CRISPR-Mediated Engineering of a Promoter-less Anti-Viral RNAi Hairpin Into an Endogenous MiRNA Locus", Nucleic Acids Research, XP055527360, 45(1): e3-1-e3-17, Published Online Sep. 9, 2016. Figs.1, 3.
Tiwari et al. "Artificial MicroRNA Mediated Gene Silencing in Plants: Progress and Perspectives", Plant Molecular Biology. 86(1-2): 1-18, Published Online Jul. 15, 2014.
Truscott et al. "Novel Regulation and Functional Interaction of Polycistronic MiRNAs", RNA, XP055530916, 22(1): 129-138, Nov. 9, 2015.
Wang et al. "Construction and Characterization of a Synthetic MicroRNA Cluster for Multiplex RNA Interference in Mammalian Cells", ACS Synthetic Biology, XP055368273, 5(11): 1193-1200, Published Online Dec. 7, 2015. Fig.5.
Zhao et al. "Sequence-Specific Inhibition of MicroRNA Via CRISPR/CRISPRi System", Scientific Reports, 4: 3943-1- 3943-5, Published Online Feb. 3, 2014.
Zhou et al. "CRISPR-Cas9 Based Genome Editing Reveals New Insights Into MicroRNA Function and Regulation in Rice", Frontiers in Plant Science, XP055528166, 8: 1598-1-1598-12, Published Online Sep. 13, 2017. Fig.4.
Zuris et al. "Cationic Lipid-Mediated Delivery of Proetins Enables Efficient Protein-Based Genome Editing In Vitro and In Vivo", Nature Biotechnology, 33(1): 73-80, Published Online Oct. 30, 2014.
Camargo Ramirez. "Function of Micro RNAs in Plant Innate Immunity", Universitat Autonoma de Barcelona, PhHD Thesis, XP55550787, 209 Pages, Mar. 2017.
Albani et al., (1997). "The wheat transcriptional activator SPA: a seed-specific bZIP protein that recognizes the GCN4-like motif in the bifactorial endosperm box of prolamin genes," Plant Cell, 9:171-184.
An et al, (1996). "Strong, constitutive expression of the *Arabidopsis* ACT2/ACT8 actin subclass in vegetative tissues," Plant J., 10(1):107-121.
Bartel, (2004). "MicroRNAs: genomics, biogenesis, mechanism, and function," Cell, 116(2):281-297.
Borges et al., (2015). "The expanding world of small RNAs in plants," Nature Reviews Molecular Cell Biology, 16:727-741, 35 pages.
Cermak et al., (2011). "Efficient design and assembly of custom TALEN and other TAL effector-based constructs for DNA targeting," Nucleic Acids Research, 39(12):e82, 11 pages.

Certo et al., (2012). "Coupling endonucleases with DNA end-processing enzymes to drive gene disruption," Nature Methods, 9:973-975, 10 pages.
Chiang et al., (2016). "CRISPR-Cas9$^{D10A}$ Nickase-Based Genotypic and Phenotypic Screening to Enhance Genome Editing", Scientific Reports, 6:24356, 17 pages.
De Pater et al., (1992). "The promoter of the rice gene GOS2 is active in various different monocot tissues and binds rice nuclear factor ASF-1," Plant J, 2(6):837-844.
Faisal et al., (2017). "Downregulation of the DST Transcription Factor Using Artificial microRNA to Increase Yield, Salt and Drought Tolerance in Rice," American Journal of Plant Sciences, 8(9):2219-2237.
Fan et al., (2015). "Efficient CRISPR/Cas9-mediated Targeted Mutagenesis in Populus in the First Generation," Sci Rep., 5(12217), 7 pages.
Fujiki et al., (2008). "Development of a new cucumber mosaic virus-based plant expression vector with truncated 3a movement protein," Virology, 381(1):136-142.
Gallego-Giraldo et al., (2011). "Selective lignin downregulation leads to constitutive defense response expression in alfalfa (*Medicago sativa* L.)," New Phytologist, 190(3):627-639.
Garcia-Ruiz et al., (2010). "*Arabidopsis* RNA-Dependent RNA Polymerases and Dicer-Like Proteins in Antiviral Defense and Small Interfering RNA Biogenesis during Turnip Mosaic Virus Infection," The Plant Cell, 22:481-496.
Holen, (2006). "Efficient prediction of siRNAs with siRNArules 1.0: An open-source JAVA approach to siRNA algorithms," RNA, 12:1620-1625.
Holoch et al., (2015). "RNA-mediated epigenetic regulation of gene expression," Nat Rev Genet., 16(2):71-84, 34 pages.
Hu et al., (2015). "Down-regulation of Fusarium oxysporum endogenous genes by Host-Delivered RNA interference enhances disease resistance," Front Chem., 3:1-10.
Jinek et al., (2012). "A Programmable Dual-RNA-Guided DNA Endonuclease in Adaptive Bacterial Immunity," Science, 337:816-821.
Kozomara et al., (2014). "miRBase: annotating high confidence microRNAs using deep sequencing data," Nucleic Acids Res, 42:D68-D73.
Kukowska-Latallo et al., (1996). "Efficient transfer of genetic material into mammalian cells using Starburst polyamidoamine dendrimers," Proc. Natl. Acad. Sci. USA, 93:4897-4902.
Kumar et al., (2015). "The CRISPR-Cas system for plant genome editing: advances and opportunities," J Exp Bot, 66(1):47-57.
Lawrenson et al., (2015). "Induction of targeted, heritable mutations in barley and Brassica oleracea using RNA-guided Cas9 nuclease," Gen Biol, 16:258, 13 pages.
Lewis et al., (2005). "Conserved Seed Pairing, Often Flanked by Adenosines, Indicates that Thousands of Human Genes are MicroRNA Targets," Cell, 120:15-20.
Lorenz et al., (2011). "ViennaRNA Package 2.0.," Algorithms for Molecular Biology, 6(26), 14 pages.
Mae et al., (2005). "Internalisation of cell-penetrating peptides into tobacco protoplasts," Biochimica et Biophysica Acta., 1669(2):101-107.
Mathur et al., (1995). "A simple method for isolation, liquid culture, transformation and regeneration of *Arabidopsis thaliana* protoplasts," Plant Cell Rep., 14:221-226.
McElroy et al., (1990). "Isolation of an efficient actin promoter for use in rice transformation," Plant Cell, 2:163-171.
Miller et al., (2011). "A TALE nuclease architecture for efficient genome editing," Nat Biotechnol., 29(2):143-148.
Molnar et al., (2009). "Highly specific gene silencing by artificial microRNAs in the unicellular alga *Chlamydomonas reinhardtii*," Plant J., 58(1):165-174.
Müller et al., (1993). "The nitrogen response of a barley C-hordein promoter is controlled by positive and negative regulation of the GCN4 and endosperm box," Plant J., 4:343-355.
Ohta, (1986). "High-efficiency genetic transformation of maize by a mixture of pollen and exogenous DNA," Proc. Natl. Acad. Sci. USA, 83:715-719.

(56) References Cited

OTHER PUBLICATIONS

Opsahl-Ferstad et al., (1997). "ZmEsr, a novel endosperm-specific gene expressed in a restricted region around the maize embryo," Plant J., 12:235-246.
Paddison et al., (2002). "Stable suppression of gene expression by RNAi in mammalian cells," Proc. Natl. Acad. Sci. USA., 99:1443-1448.
Pan et al., (2017). "SlbZIP38, a Tomato bZIP Family Gene Downregulated by Abscisic Acid, Is a Negative Regulator of Drought and Salt Stress Tolerance," Genes, 8(12):402, 17 pages.
Park et al., (2015). "Cas-Designer: a web-based tool for choice of CRISPR-Cas9 target sites," Bioinformatics, 31(24):4014-4016.
Potrykus, (1991). "Gene Transfer to Plants: Assessment of Published Approaches and Results," Annu. Rev. Plant. Physiol., Plant. Mol. Biol., 42:205-225.
Rafalski et al., (1984). "Developmentally regulated plant genes: the nucleotide sequence of a wheat gliadin genomic clone," EMBO J., 3:1409-1415.
Ramirez et al., (2011). "Enhanced disease resistance to Botrytis cinerea in myb46 *Arabidopsis* plants is associated to an early down-regulation of CesA genes," Plant Signal Behav., 6(6):911-913.
Reyon et al., (2012). "FLASH Assembly of TALENs Enables High-Throughput Genome Editing," Nature Biotechnology, 30(5):460-465, 23 pages.
Sato et al., (1996). "A rice homeobox gene, OSH1, is expressed before organ differentiation in a specific region during early embryogenesis," Proc. Nati. Acad. Sci. USA, 93:8117-8122.
Scofield et al., (1987). "Nucleotide Sequence of a Member of the Napin Storage Protein Family from Brassica Napus," J. Biol. Chem., 262(25):12202-12208.
Sheen, (1993). "Protein phosphatase activity is required for light-inducible gene expression in maize," EMBO J., 12(9):3497-3505.
Shmakov et al., (2015). "Discovery and Functional Characterization of Diverse Class 2 CRISPR-Cas Systems," Mol Cell., 60(3):385-397.
Strat et al., (2006). "Specific and nontoxic silencing in mammalian cells with expressed long dsRNAs," Nucleic Acids Research, 34(13):3803-3810.
Svitashev et al., (2015). "Targeted Mutagenesis, Precise Gene Editing, and Site-Specific Gene Insertion in Maize Using Cas9 and Guide RNA," Plant Physiology, 169(2):931-945.
Takaiwa et al., (1987). "A rice glutelin gene family—a major type of glutelin mRNAs can be divided into two classes," Mol. Gen. Genet., 208:15-22.
Takamatsu et al. (1987). "Expression of bacterial chloramphenicol acetltransferase gene in tobacco plants mediated by TMV-RNA," EMBO J., 6:307-311.
Takamatsu et al., (1990). "Production of enkephalin in tobacco protoplasts using tobacco mosaic virus RNA vector," FEBS Letters, 269:73-76.
Toriyama et al., (1988). "Transgenic Rice Plants After Direct Gene Transfer into Protoplasts," Bio/Technology, 6:1072-1074.
Tran et al., (2004). "Control of specific gene expression in mammalian cells by co-expression of long complementary RNAs," FEBS Lett., 573:127-134.
Twell et al., (1989). "Isolation and expression of an anther-specific gene from tomato," Mol. Gen Genet., 217:240-245.
Uknes et al., (1992). "Acquired resistance in *Arabidopsis*," Plant Cell, 4:645-656.
Valvekens et al., (1988). "Agrobacterium tumefaciens-mediated transformation of *Arabidopsis thaliana* root explants by using kanamycin selection," Proc Natl Acad Sci USA, 85(15):5536-5540.
Van der Meer et al., (1990). "Promoter analysis of the chalcone synthase (chsA) gene of Petunia hybrida: a 67 bp promoter region directs flower-specific expression," Plant Mol. Biol., 15:95-109.
Verma et al., (2014). "Lignin genetic engineering for improvement of wood quality: Applications in paper and textile industries, fodder and bioenergy production," South African Journal of Botany, 91, pp. 107-125.
Vicente-Carbajosa et al., (1998). "Barley BLZ1: a bZIP transcriptional activator that interacts with endosperm-specific gene promoters," Plant J., 13:629-640.
Wang et al., (2009). "Shoot-Specific Down-Regulation of Protein Farnesyltransferase (Alpha-Subunit) for Yield Protection against Drought in Canola," Mol Plant., 2(1): 191-200.
Wu et al., (1998). "Genomic Cloning of 18 kDa Oleosin and Detection of Triacylglycerols and Oleosin Isoforms in Maturing Rice and Postgerminative Seedlings," J. Biochem., 123:386-391.
Wu et al., (1998). "Promoters of Rice Seed Storage Protein Genes Direct Endosperm-Specific Gene Expression in Transgenic Rice," Plant Cell Physiology, 39(8):885-889.
Xiao et al., (2014). "CasOT: a genome-wide Cas9/gRNA off-target searching tool," Bioinformatics, 30:1180-1182.
Yoon et al., (2018). "Downregulation of stress-associated protein 1 (PagSAP1) increases salt stress tolerance in poplar (*Populus alba×P. glandulosa*)," Trees 32:823-833.
Zetsche et al., (2015). "Cpf1 is a single RNA-guided endonuclease of a class 2 CRISPR-Cas system," Cell, 163(3):759-771.
Zhang et al., (2010). "Short biodegradable polyamines for gene delivery and transfection of brain capillary endothelial cells," J Control Release, 143(3):359-366, 22 pages.
Zhang et al., (2014). "tasiRNAdb: a database of ta-siRNA regulatory pathways," Bioinformatics, 30(7):1045-1046.
Zielezinski et al., (2015). "mirEX 2.0—an Integrated Environment for Expression Profiling of Plant microRNAs." BMC Plant Biology 15:144, 9 pages.
International Search Report and the Written Opinion dated May 20, 2020 From the International Searching Authority Re. Application No. PCT/IB2020/052245. (15 Pages).
International Search Report and the Written Opinion dated May 25, 2020 From the International Searching Authority Re. Application No. PCT/IB2020/052248. (17 Pages).
Invitation to Pay Additional Fees. Communication Relating to the Result of the Partial International Search and the Provisional Opinion dated Jun. 15, 2020 From the International Searching Authority Re. Application No. PCT/IB2020/052241. (20 Pages).
Ha et al. "Regulation of MicroRNA Biogenesis", Nature Reviews Molecular Cell Biology, XP055440474, 15(8): 509-524, Published Online Jul. 16, 2014.
Mao et al. "Manipulating Plant RNA-Silencing Pathways to Improve the Gene Editing Efficiency of CRISPR/Cas9 Systems", Genome Biology, XP055694770, 19(1): 149-1-149-15, Sep. 28, 2018.
Meister et al. "Mechanisms of Gene Silencing by Double-Stranded RNA", Nature, XP055153799, 431(7006): 343-349, Sep. 16, 2004.
Senis et al. "TALEN/CRISPR-Mediated Engineering of a Promoter-less Anti-Viral RNAi Hairpin Into an Endogenous MiRNA Locus—Supplementary Information", Retrieved From the Internet, XP055696419, p. 1-32, Sep. 9, 2016.
Zhang et al. "Next Generation Insect-Resistant Plants: RNAi-Mediated Crop Protection", Trends in Biotechnology, XP085171385, 35(9): 871-882, Sep. 2017.

* cited by examiner

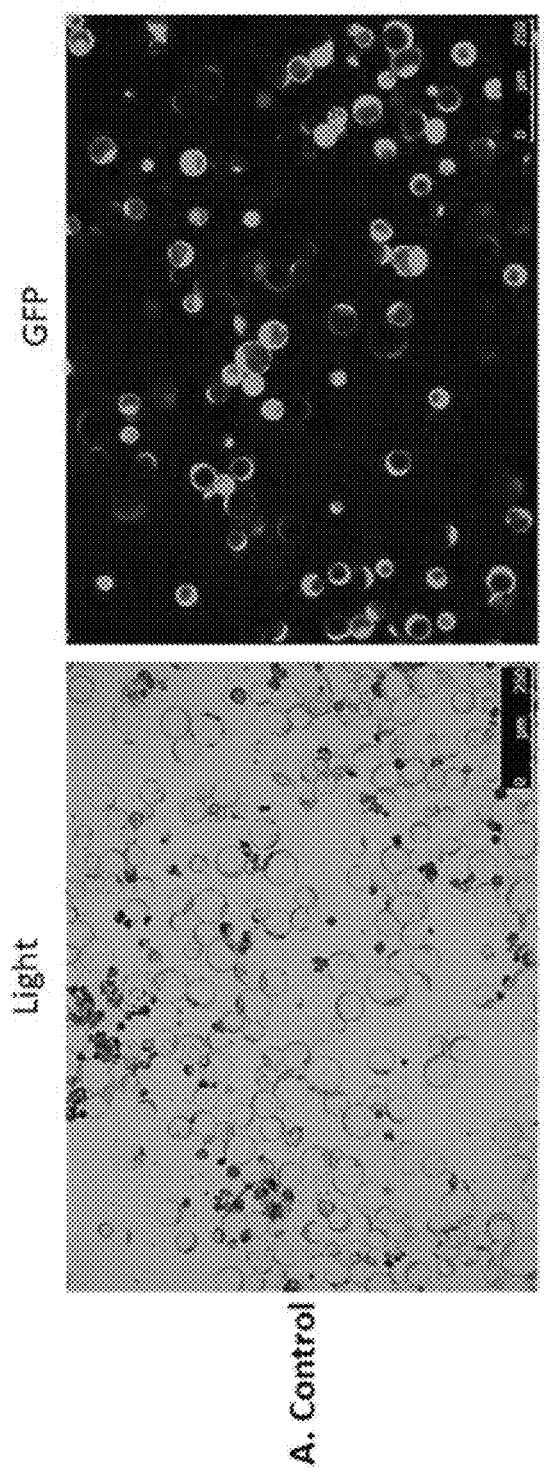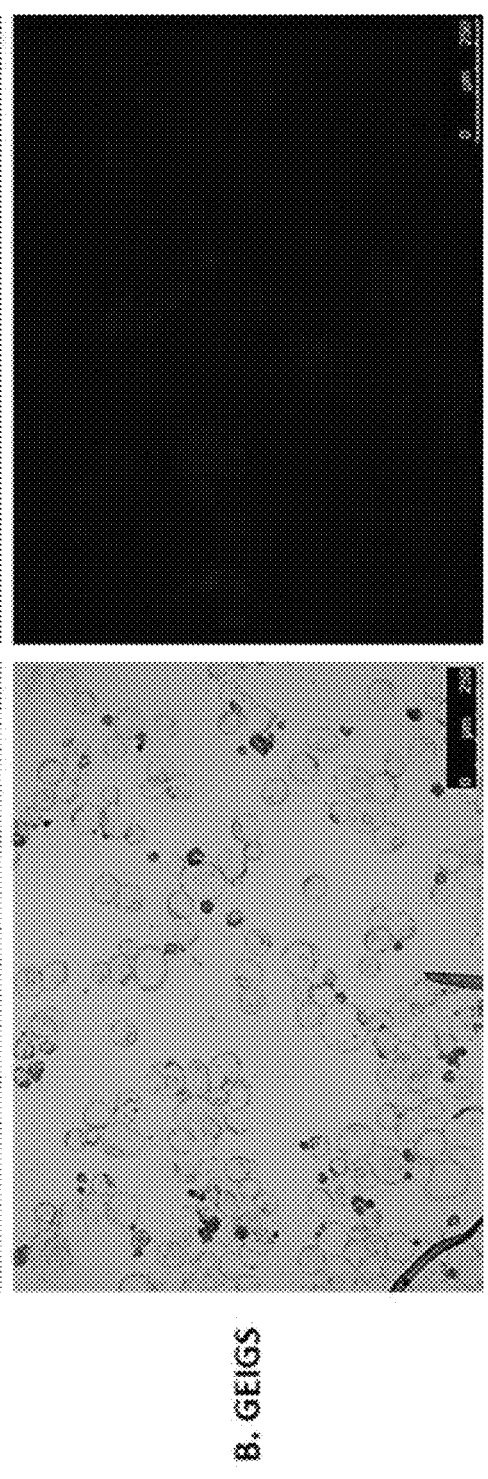

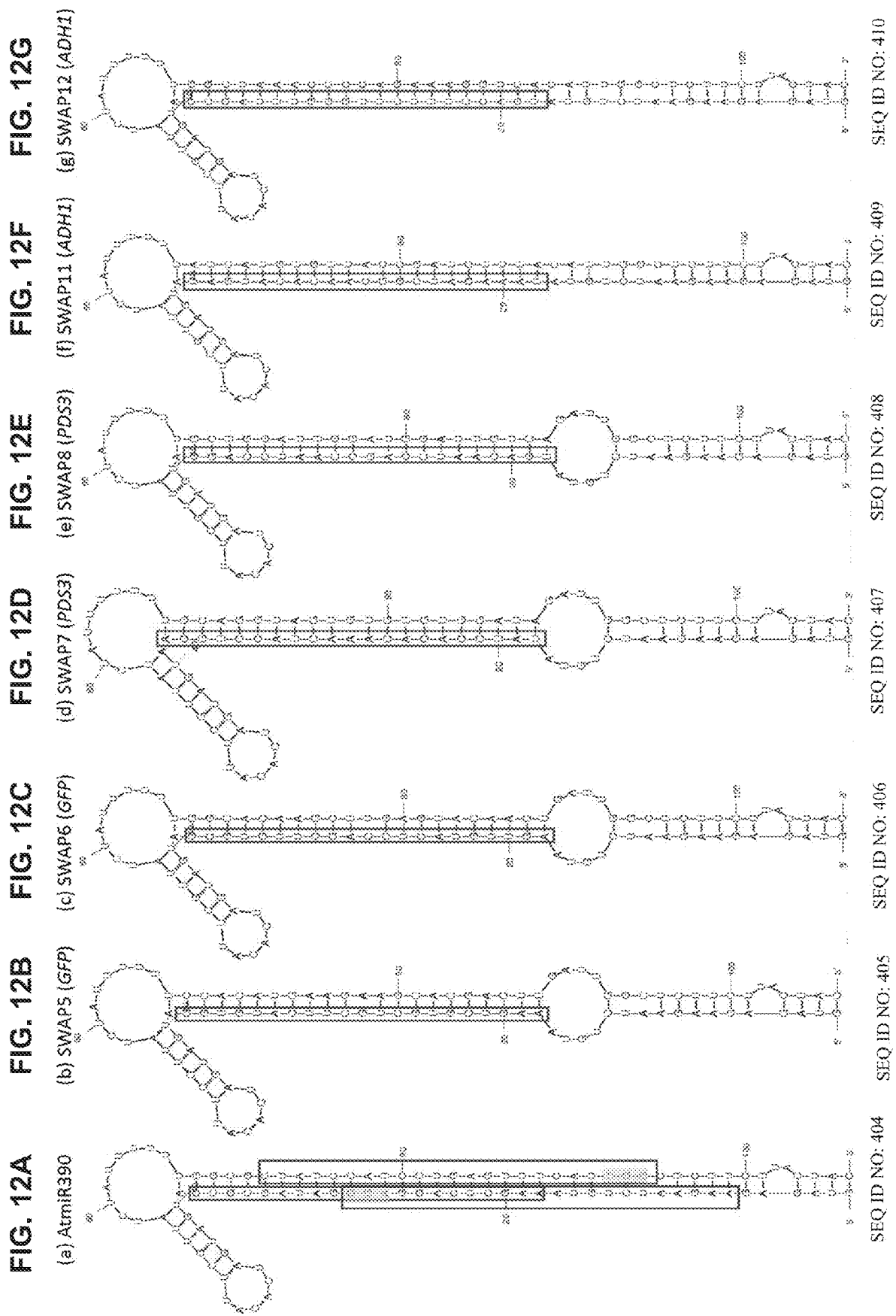

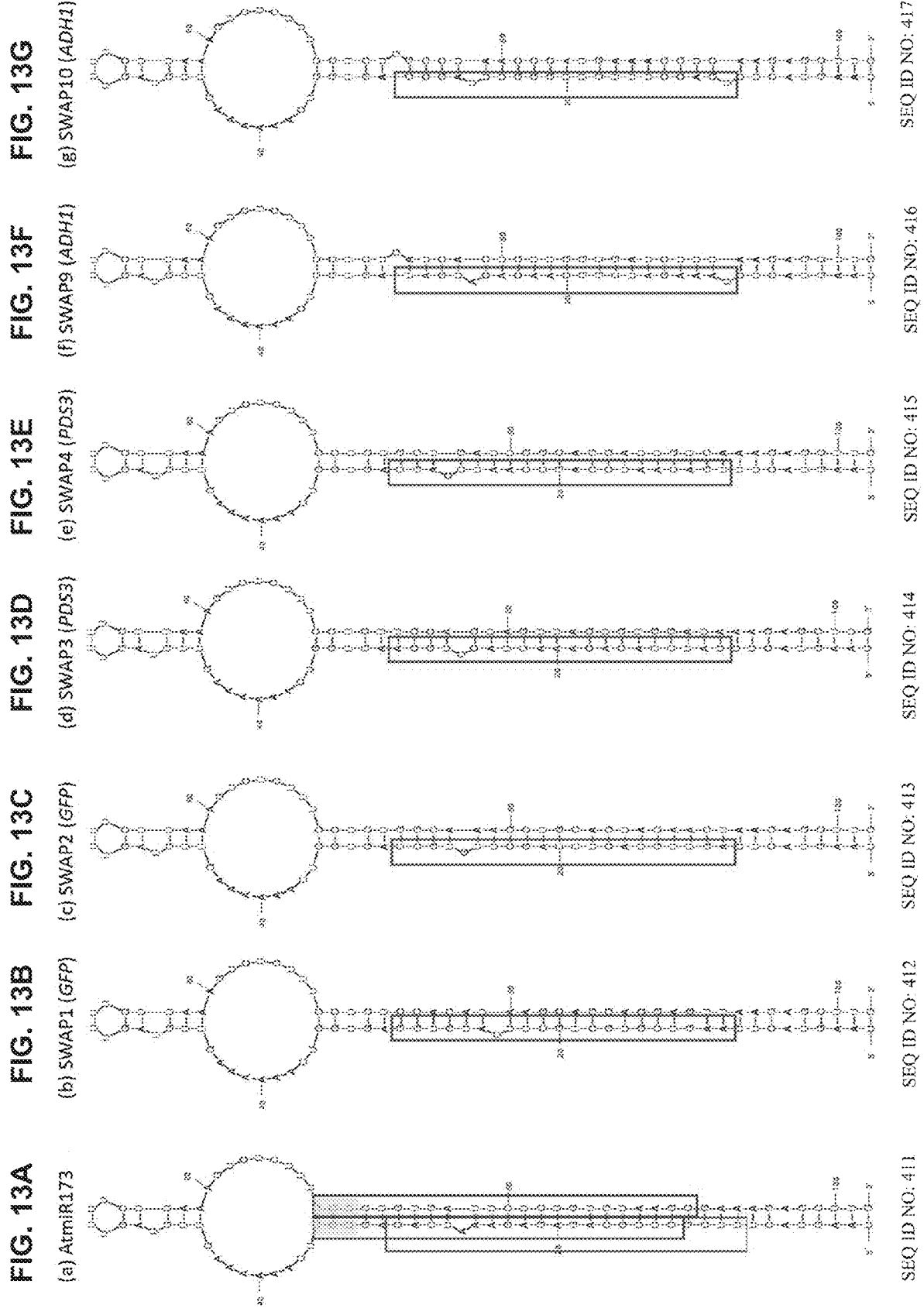

FIG. 13H
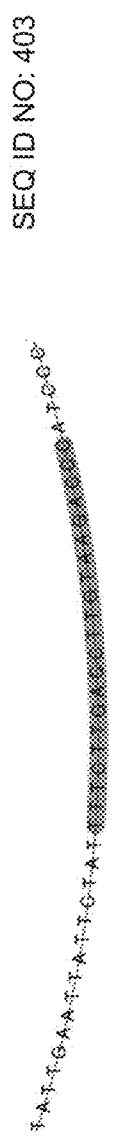
Wild-type
tasiRNA precursor
SEQ ID NO: 403
GEiGS-based
on tasiRNA precursor
(small nt change)
SEQ ID NO: 401
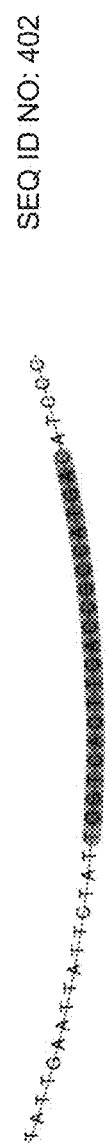
GEiGS-based
on tasiRNA precursor
(large nt change)
SEQ ID NO: 402

FIG. 14A (a) AtTAS1c  3'---ACCAGAAGCGAACATCTCTTTTAGTGTGTGTTTGTTTACGACAAAGTAGAGCTTTTGTAGGCATTGGGTTGCTTTAGTTCTTCTCCAGCCCTTC---5'  SEQ ID NO: 373
             |||||  |||||||||||
miR173 5'- TGGCTTGCAAGAGAGAAATCAC -3'  SEQ ID NO: 374

FIG. 14B (b) GFP  3'-------AACTTCTTCAGCGACGAAGTACACCAGCCCATGCCGACTTCGTGACGTGCGGCATCCAGTGCTCCCACCGGTCCGTGCCC-------5'  SEQ ID NO: 375
         |||||  |||||||||||
SWAP1 5'- aaGtcgtcgtgcttcAtgtgg -3'  SEQ ID NO: 376

GFP  3'-ACAACATCAACATGAGGTCGAACACGGGTCCGAACGAGGAACTTCAGTTACGAGGAAGTACGCCAAGTGGTCCACAGCGGG-------5'  SEQ ID NO: 377
     |||||  |||||||||||
SWAP2 5'- agttgTactccagtctgtgCC -3'  SEQ ID NO: 378

FIG. 14C (c) AtPDS3  3'----AACCTTATAGGTTCGTGTTTGATGGACGTTCCTGGTCGTCATGAGGAGGAACAAGAACAGAATTCGGAACTCTTCACCCTTGGGATTTCGAT-----5'  SEQ ID NO: 379
            |||||  |||||||||||
SWAP3 5'- TatCcacacaaaactaGCCgca -3'  SEQ ID NO: 380

AtPDS3  3'-----ACGTCAACTGGTTAGGTCGTTCGGTCGTCGGTTAATGTTGAAAGTTTCGAAACGTCCTGCTCCTACGTCTATTTGATC-----5'  SEQ ID NO: 381
        |||||  |||||||||||
SWAP4 5'- TgacaatccAGccBAtccbBgC -3'  SEQ ID NO: 382

FIG. 14D (d) AtADH1  3'-----GAGGCCATTTCTAGCCGTTGTGTACTAGAGAGACCGACTTCTAGTCAGTGAGGAAGAGTTGTGAGAGTTGTTAGGGAGGTCGAAGTACCGGCTT-----5'  SEQ ID NO: 383
            |||||  |||||||||||
SWAP9 5'- TaaagatcGGcaAACACAtGat -3'  SEQ ID NO: 384

AtADH1  3'-----TGTGAAACTGGAAGAACCAAATCGGTAAGTTCAAGAGGATGGGTCATCTGTTTGGGTTGACTGTTAAGTCGGAACAGTTCTCCTC-----5'  SEQ ID NO: 385
        |||||  |||||||||||
SWAP10 5'- TgaCCTTCCttGgatttagcC -3'  SEQ ID NO: 386

FIG. 15A
(a) AtTAS3

```
AtTAS3   3'------CTGATTTCCAGTCTABCCTATTGTGGCGAAATAGTAACTTTGACCTTACGGCTTCTTTGAGTTACAGAGTCGTGCCTAGGT------5'   SEQ ID NO: 387
                 |||||||||||||||||||||||||||||||
miR390           5'-- ARGCTCAGGSAGGATAGTGCCC -3'   SEQ ID NO: 388
```

FIG. 15B
(b) GFP

```
GFP     3'------AACTTCTTCAGCACGACGAAGTACACCAGCCCCATCGCCGACTTCGTGACGTGCGCATGCCAGTGTCTCCACCGGTC------5'   SEQ ID NO: 389
                |||||||||||||||||||||||||||
SWAP5           5'-- AAGtcgtgctGcttcAtgtgg -3'   SEQ ID NO: 390

GFP     3'------ACAACATCAACATGAGGTCGACACGGGGTCCTACGGAGGAACTCAGCTACGGAGTACGCCAAGTGGTCCC------5'   SEQ ID NO: 391
                |||||||||||||||||||||||||
SWAP6           5'-- AgttgtactccaGcCAtcCagC -3'   SEQ ID NO: 392
```

FIG. 15C
(c) AtPDS3

```
AtPDS3  3'------AACCCTTATAGAGGTGTGTTTGAATGGACGTTTCCTGGTCGTCATGAGGAGGAGGAACAAGACAGAATCGCGAACTCTTCACCCTTGGG------5'   SEQ ID NO: 393
                |||||||||||||||||||||||
SWAP7           5'-- tATCgacaCAaactaccctGCa -3'   SEQ ID NO: 394

AtPDS3  3'------ACGTCAACTGTTAGGTCGGTTAGGTCGTGGTCGTTAAAGTTGAAAGTTTCCGAATCGTCTCGTGATGCCTTCCTACGTCT------5'   SEQ ID NO: 395
                |||||||||||||||||||||
SWAP8           5'-- tgaCaatccAGccAatcCagC -3'   SEQ ID NO: 396
```

FIG. 15D
(d) AtADH1

```
AtADH1  3'------GAGGCCATTTCTAGCCGTTCGTGTACTAGAGGACCGACTTCTAGTCAGTGAGGAAGAGGTTGTTAGGGAGGTCGAAGTA------5'   SEQ ID NO: 397
                |||||||||||||||||||||
SWAP11          5'-- tAaagatcCgcaccacatGat -3'   SEQ ID NO: 398

AtADH1  3'------TGTGAAACTGAAAGAACCCAAATGGTGTAAGTTCAACGAGGATTGGGTCATCGTGTTGGTGTTGACTGTATGTCTGAACAGTTC------5'   SEQ ID NO: 399
                ||||||||||||||||||||
SWAP12          5'-- tgaCcttcttGggttcagCC -3'   SEQ ID NO: 400
```

MODIFYING THE SPECIFICITY OF PLANT NON-CODING RNA MOLECULES FOR SILENCING GENE EXPRESSION

RELATED APPLICATIONS

This application is a National Phase of PCT Patent Application No. PCT/IB2018/057160 having International filing date of Sep. 18, 2018, which claims the benefit of priority of Great Britain Patent Application No. 1719516.5 filed on Nov. 23, 2017, and Great Britain Patent Application Nos. 1715116.8 and 1715113.5 both filed on Sep. 19, 2017. The contents of the above applications are all incorporated by reference as if fully set forth herein in their entirety.

SEQUENCE LISTING STATEMENT

The ASCII file, entitled 81430SequenceListing.txt, created Mar. 19, 2020, comprising 267,440 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to modifying genes that encode or are processed into non-coding RNA molecules, including RNA silencing molecules and, more particularly, but not exclusively, to the use of same for silencing endogenous or exogenous target gene-expression of interest in plants.

RNA silencing or RNA interference RNAi), the endogenous co- or post-transcriptional genetic regulatory mechanism in which RNA molecules inhibit gene expression or translation, is generally mediated by non-coding RNA molecules including microRNAs (miRNAs), small interfering RNAs (siRNAs), trans-acting siRNA (ta-siRNA), piwi-interacting RNAs (piRNA), antisense RNA, etc. Recently, additional non-coding RNAs have been implicated to harbour a RNA silencing activity including transfer RNA (tRNA), small nuclear RNA (snoRNA), small nucleolar RNA (snoRNA) and repeats-derived RNA. These canonical and non-canonical RNA silencing molecules differ in their substrates, biogenesis, effector proteins and modes of target down regulation.

Moreover, Argonaute proteins, in complex with small RNAs, form the core of the RNA-induced silencing complex (RISC), the RNA-interference (RNAi) effector complex. The Argonaute superfamily segregates into two clades, termed Ago and Piwi. Ago proteins (e.g. Ago1 and Ago2) typically complex with miRNAs and siRNAs, while Piwi proteins (e.g. Piwi, Ago3 and Aubergine (Aub)) typically complex with piRNA.

Small interfering RNAs (siRNAs) are double-stranded RNA molecules of 20-25 nucleotides (nt) in length, which interfere with the expression of specific genes with complementary nucleotide sequences by degrading their transcript during or after transcription resulting in no translation.

MicroRNAs (miRNAs) are small endogenous non-coding RNAs (ncRNAs) of 20 to 24 nt in length, originating from long self-complementary precursors. Mature miRNAs regulate gene expression in two ways; (i) by inhibiting translation or (ii) by degrading coding mRNAs by perfect or near-perfect complement with the target transcript. The majority of plant target mRNAs contain a single miRNA-complementary site, which results in the target mRNAs being cleaved and degraded by the RNA silencing molecule and RNA decay machinery.

Piwi-interacting RNAs (piRNAs) are small non-coding RNAs which are the product of long single stranded precursor molecules, and which are generated without a dicing step. piRNAs are typically 26 to 31 nt in length and are mostly antisense. piRNAs form RNA-protein complexes through interactions with Piwi proteins. Antisense piRNAs are typically loaded into Piwi or Aub.

Transacting siRNA (tasiRNA) are a class of small interfering RNA (siRNA) that repress gene expression through post-transcriptional gene silencing. Their biogenesis is primed by association of miRNAs to tasiRNA precursors, which recruits RNA-dependent RNA-polymerases (RdRp) that synthesize dsRNA from the tasiRNA precursor template. Next, such dsRNA is processed by DICER-LIKE 4 (DCLA) into about 21-nucleotide "phased" intervals mature tasiRNAs.

Recent advances in genome editing techniques have made it possible to alter DNA sequences in living cells. By editing only a few of the billions of nucleotides in the cells of plants, these new techniques might be the most effective way to get crops to grow better in harsh climates (crop performance and abiotic stress) and enhance resistance to biotic stress (insects, viruses, bacteria, beetles, nematodes etc.). There are limited approaches to achieve resistance to pests using genome editing technologies such as CRISPR/Cas9: plant susceptible genes knock-out (such as the well-known MLO genes), by introduction of stop codons, frame shifts, insertions, deletions etc.; or up regulation of resistance genes, like R genes, by modification of regulatory elements like promoters, microRNA binding sites etc. Nevertheless, approaches that target specifically the pathogen are limited to transgenic CRISPR applications.

Previous work on genome editing of RNA molecules in various organisms (e.g. murine, human, shrimp, plants), focused on knocking-out miRNA activity or changing their binding site in target RNAs, for example:

Zhao et al., [Zhao et al., *Scientific Reports* (2014) 4:3943] provided a miRNA inhibition strategy employing the CRISPR system in murine cells. Zhao used a specifically designed gRNAs to cut a miRNA gene at a single site by Cas9, resulting in knockdown of the miRNA in murine cells.

Jiang et al. [Jiang et al., *RNA Biology* (2014) 11 (10): 1243-9] used CRISPR/Cas9 to deplete human miR-93 from a cluster by targeting its 5' region in HeLa cells. Various small indels were induced in the targeted region containing the Drosha processing site (i.e. the position at which Drosha, a double-stranded RNA-specific RNase III enzyme, binds, cleaves and thereby processes primary miRNAs (pri-miRNAs) into pre-miRNA in the nucleus of a host cell) and seed sequences (i.e. the conserved heptametrical sequences which are essential for the binding of the miRNA to mRNA, typically situated at positions 2-7 from the miRNA 5'-end). According to Jiang et al. even a single nucleotide deletion led to complete knockout of the target miRNA with high specificity.

With regard to plant genome editing, Bortesi and Fischer [Bortesi and Fischer, *Biotechnology Advances* (2015) 33: 41-52] discussed the use of CRISPR-Cas9 technology in plants compared to ZFNs and TALENs, and Basak and Nithin [Basak and Nithin, *Front Plant Sci*, (2015) 6: 1001] demonstrated the use of CRISPR-Cas9 technology for knockdown of protein-coding genes in model plants such as *Arabidopsis* and tobacco and crops like wheat, maize, and rice.

In addition to disruption of miRNA activity or target binding sites, gene silencing using artificial microRNAs (amiRNAs)-mediated gene silencing of endogenous and exogenous target genes were used [Tiwari et al. *Plant Mol Biol* (2014) 86: 1]. Similar to microRNAs, amiRNAs are single-stranded, approximately 21 nt long, and designed by replacing the mature miRNA sequences of duplex within pre-miRNAs [Tiwari et al. (2014) supra]. These amiRNAs are introduced as a transgene within an artificial expression cassette (including a promoter, ten etc.) [Carbonell et al., *Plant Physiology* (2014) pp. 113.234989], are processed via small RNA biogenesis and silencing machinery and downregulate target expression. According to Schwab et al. [Schwab et al. *The Plant cell* (2006) Vol. 18, 1121-1133], amiRNAs are active when expressed under tissue-specific or inducible promoters and can be used for specific gene silencing in plants, especially when several related, but not identical, target genes need to be downregulated.

Senis et al. [Senis et al., *Nucleic Acids Research* (2017) Vol. 45(1): e3] disclose engineering of a promoterless antiviral amiRNA into an endogenous miRNA locus. Specifically, Senis et al. insert a amiRNA precursor transgene (hairpin pri-amiRNA) adjacent to a naturally occurring miRNA gene (e.g. miR122) by homology-directed. DNA recombination that is induced by sequence-specific nuclease such as Cas9 or TALEN. This approach uses promoter- and terminator-free amiRNAs by utilizing transcriptionally active DNA that expresses natural miRNA (miR122), that is, the endogenous promoter and terminator drove and regulated the transcription of the inserted amiRNA transgene.

Various DNA-free methods of introducing RNA and/or proteins into cells have been previously described. For example, RNA transfection using electroporation and lipofection has been described in U.S. Patent Application No. 20160289675. Direct delivery of Cas9/gRNA ribonucleoprotein (RNP) complexes to cells by microinjection of Cas9 protein and gRNA complexes was described by Cho [Cho et al., "Heritable gene knockout in *Caenorhabditis elegans* by direct injection of Cas9-sgRNA ribonucleoproteins," *Genetics* (2013) 195:1177-1180]. Delivery of Cas9 protein/gRNA complexes via electroporation was described by Kim [Kim et al., "Highly efficient RNA-guided genome editing in human cells via delivery of purified Cas9 ribonucleoproteins" *Genome Res.* (2014) 24:1012-1019]. Delivery of Cas9 protein-associated gRNA complexes via liposomes was reported by Zuris [Zuris et al., "Cationic lipid-mediated delivery of proteins enables efficient protein-based genome editing in vitro and in vivo" *Nat Biotechnol.* (2014) doi: 10.1038/nbt.3081].

SUMMARY OF THE INVENTION

According to an aspect of some embodiments of the present invention, there is provided a method of modifying a gene encoding or processed into a non-coding RNA molecule having no RNA silencing activity in a plant cell, the method comprising introducing into the plant cell a DNA editing agent conferring a silencing specificity of the non-coding RNA molecule towards a target RNA of interest, thereby modifying the gene encoding or processed into the non-coding RNA molecule.

According to an aspect of some embodiments of the present invention, there is provided a method of modifying a gene encoding or processed into a non-coding RNA molecule having no RNA silencing activity in a plant cell, the method comprising introducing into the plant cell a DNA editing agent conferring a silencing specificity of the non-coding RNA molecule towards a target RNA of interest.

According to an aspect of some embodiments of the present invention, there is provided a method of modifying a gene encoding or processed into a RNA silencing molecule to a target RNA in a plant cell, the method comprising introducing into the plant cell a DNA editing agent which redirects a silencing specificity of the RNA silencing molecule towards a second target RNA, the target RNA and the second target RNA being distinct, thereby modifying the gene encoding the RNA silencing molecule.

According to an aspect of some embodiments of the present invention, there is provided a method of modifying a gene encoding or processed into a RNA silencing molecule to a target RNA in a plant cell, the method comprising introducing into the plant cell a DNA editing agent which redirects a silencing specificity of the RNA silencing molecule towards a second target RNA, the target RNA and the second target RNA being distinct.

According to an aspect of some embodiments of the present invention, there is provided a plant cell generated according to the method of some embodiments of the invention.

According to an aspect of some embodiments of the present invention, there is provided a plant comprising the plant cell of some embodiments of the invention.

According to an aspect of some embodiments of the present invention, there is provided a method of producing a plant with reduced expression of a target gene, the method comprising: (a) breeding the plant of some embodiments of the invention; and (b) selecting for progeny plants that have reduced expression of the target RNA of interest or the second target RNA, or progeny that comprises a silencing specificity in the non-coding RNA molecule towards a target RNA of interest, and which do not comprise the DNA editing agent, thereby producing the plant with reduced expression of a target gene.

According to an aspect of some embodiments of the present invention, there is provided a method of generating a plant with increased stress tolerance, increased yield, increased growth rate or increased yield quality, the method comprising modifying a gene encoding or processed into a non-coding RNA molecule or into a RNA silencing molecule in a plant cell according to some embodiments of the invention, wherein the target RNA of interest is of a gene of the plant conferring sensitivity to stress, decreased yield, decreased growth rate or decreased yield quality thereby generating the plant.

According to an aspect of some embodiments of the present invention, there is provided a method of generating a pathogen tolerant or resistant plant, the method comprising modifying a gene encoding or processed into a non-coding RNA molecule or into a RNA silencing molecule in a plant cell according to some embodiments of the invention, wherein the target RNA of interest is of a gene of the plant conferring sensitivity to the pathogen, thereby generating the pathogen tolerant or resistant plant.

According to an aspect of some embodiments of the present invention, there is provided a method of generating a pathogen tolerant or resistant plant, the method comprising modifying a gene encoding or processed into a non-coding RNA molecule or into a RNA silencing molecule in a plant cell according to some embodiments of the invention, wherein the target RNA of interest is of a gene of the pathogen, thereby generating the pathogen tolerant or resistant plant.

According to an aspect of some embodiments of the present invention, there is provided a method of generating a pest tolerant or resistant plant, the method comprising modifying a gene encoding or processed into a non-coding RNA molecule or into a RNA silencing molecule in a plant cell according to some embodiments of the invention, wherein the target RNA of interest is of a gene of the pest, thereby generating the pest tolerant or resistant plant.

According to an aspect of some embodiments of the present invention, there is provided a method of generating a pest tolerant or resistant plant, the method comprising modifying a gene encoding or processed into a non-coding RNA molecule or into a RNA silencing molecule in a plant cell according to some embodiments of the invention, wherein the target RNA of interest is of a gene of the plant conferring sensitivity to the pest, thereby generating the pest tolerant or resistant plant.

According to an aspect of some embodiments of the present invention, there is provided a method of generating a herbicide resistant plant, the method comprising modifying a gene encoding or processed into a non-coding RNA molecule or into a RNA silencing molecule in a plant cell according to some embodiments of the invention, wherein the target RNA of interest is of a gene of the plant conferring sensitivity to the herbicide, thereby generating the herbicide resistant plant.

According to an aspect of some embodiments of the present invention, there is provided a plant generated according to the method of some embodiments of the invention.

According to an aspect of some embodiments of the present invention, there is provided a seed of the plant of some embodiments of the invention.

According to some embodiments of the invention, the gene encoding or processed into the non-coding RNA molecule is endogenous to the plant cell.

According to some embodiments of the invention, the gene encoding the RNA silencing molecule is endogenous to the plant cell.

According to some embodiments of the invention, modifying the gene encoding or processed into the non-coding RNA molecule comprises imparting the non-coding RNA molecule with at least 45% complementarity towards the target RNA of interest.

According to some embodiments of the invention, modifying the gene encoding the RNA silencing molecule comprises imparting the RNA silencing molecule with at least 45% complementarity towards the second target RNA.

According to some embodiments of the invention, the silencing specificity of the non-coding RNA molecule is determined by measuring a RNA or protein level of the target RNA of interest.

According to some embodiments of the invention, the silencing specificity of the RNA silencing molecule is determined by measuring a RNA level of the second target RNA.

According to some embodiments of the invention, the silencing specificity of the non-coding RNA molecule or the RNA silencing molecule is determined phenotypically.

According to some embodiments of the invention, determined phenotypically is effected by determination of at least one plant phenotype selected from the group consisting of plant a leaf coloring, a flower coloring, a growth rate, a plant size, a crop yield, a fruit trait, a biotic stress resistance, and an abiotic stress resistance.

According to some embodiments of the invention, the silencing specificity of the non-coding RNA molecule is determined genotypically.

According to some embodiments of the invention, the plant phenotype is determined prior to a plant genotype.

According to some embodiments of the invention, the plant genotype is determined prior to a plant phenotype.

According to some embodiments of the invention, the non-coding RNA molecule or the RNA silencing molecule is processed from a precursor.

According to some embodiments of the invention, the non-coding RNA molecule or the RNA silencing molecule is a RNA interference (RNAi) molecule.

According to some embodiments of the invention, the RNAi molecule is selected from the group consisting of a small interfering RNA (siRNA), a short hairpin RNA (shRNA), a microRNA (miRNA), a Piwi-interacting RNA (piRNA) and trans-acting siRNA (tasiRNA).

According to some embodiments of the invention, the non-coding RNA molecule is selected from the group consisting of a small nuclear RNA (snRNA), a small nucleolar RNA (snoRNA), a long non-coding RNA (lncRNA), a ribosomal RNA (rRNA), transfer RNA (tRNA), a repeat-derived RNA, and a transposable element RNA.

According to some embodiments of the invention, the RNA molecule or RNAi molecule is designed such that a sequence of the RNAi molecule is modified to preserve originality of structure and to be recognized by cellular RNAi factors.

According to some embodiments of the invention, modifying the gene is effected by a modification selected from the group consisting of a deletion, an insertion, a point mutation and a combination thereof.

According to some embodiments of the invention, the modification is in a stem region of the non-coding RNA molecule or the RNA silencing molecule.

According to some embodiments of the invention, the modification is in a loop region of the non-coding RNA molecule or the RNA silencing molecule.

According to some embodiments of the invention, the modification is in a non-structured region of the non-coding RNA molecule or the RNA silencing molecule.

According to some embodiments of the invention, the modification is in a stem region and a loop region of the non-coding RNA molecule or the RNA silencing molecule.

According to some embodiments of the invention, the modification is in a stem region and a loop region and in non-structured region of the non-coding RNA molecule or the RNA silencing molecule.

According to some embodiments of the invention, the modification is an insertion.

According to some embodiments of the invention, the modification is a deletion.

According to some embodiments of the invention, the modification is a point mutation.

According to some embodiments of the invention, the modification comprises a modification of at most 200 nucleotides.

According to some embodiments of the invention, the method further comprises introducing into the plant cell donor oligonucleotides.

According to some embodiments of the invention, the DNA editing agent comprises at least one gRNA operatively linked to a plant expressible promoter.

According to some embodiments of the invention, the DNA editing agent does not comprise an endonuclease.

According to some embodiments of the invention, the DNA editing agent comprises an endonuclease.

According to some embodiments of the invention, the DNA editing agent is of a DNA editing system selected from the group consisting of a meganuclease, a zinc finger nucleases (ZFN), a transcription-activator like effector nuclease (TALEN) and CRISPR.

According to some embodiments of the invention, the endonuclease comprises Cas9.

According to some embodiments of the invention, DNA editing agent is applied to the cell as DNA, RNA or RNP.

According to some embodiments of the invention, the DNA editing agent is linked to a reporter for monitoring expression in a plant cell.

According to some embodiments of the invention, the reporter is a fluorescent protein.

According to some embodiments of the invention, the target RNA of interest or the second target RNA is endogenous to the plant cell.

According to some embodiments of the invention, the target RNA of interest or the second target RNA is exogenous to the plant cell.

According to some embodiments of the invention, the plant cell is a protoplast.

According to some embodiments of the invention, the breeding comprises crossing or selfing.

According to some embodiments of the invention, the plant is non-genetically modified non-GMO).

According to some embodiments of the invention, the plant is selected from the group consisting of a crop, a flower and a tree.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
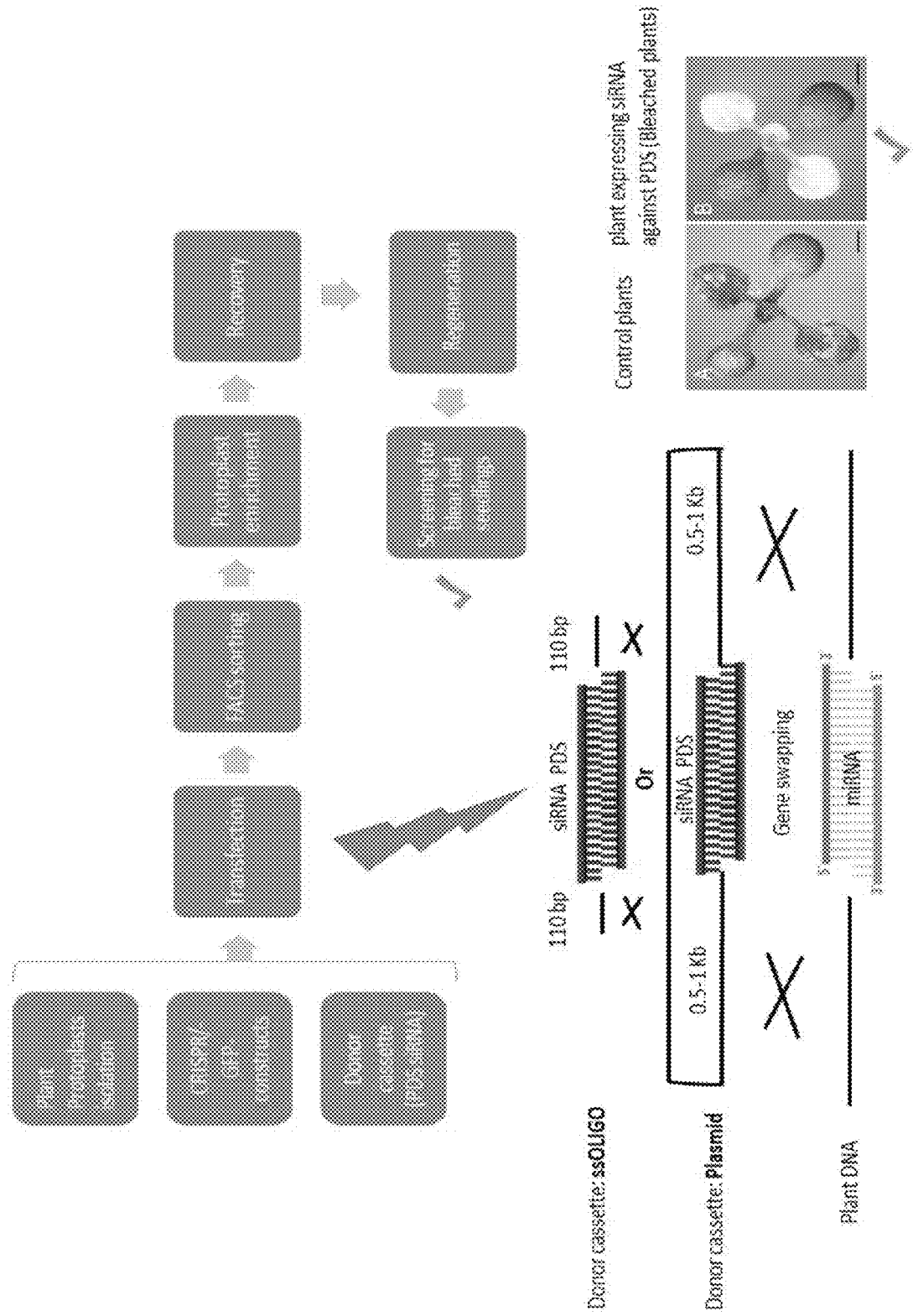

FIG. 1 is an embodiment flow chart of Genome Editing Induced Gene Silencing (GEiGS) replacement of endogenous miRNA with siRNA targeting the PDS gene, hence inducing gene silencing of the endogenous PDS gene. To introduce the modification, a 2-component system is being used. First, a CRISPR/CAS9 system, in a GFP containing vector, generates a cleavage in the chosen loci, through designed specific guide RNAs to promote homologous DNA repair (HDR) in the site. Second, A DONOR sequence, with the desired modification of the miRNA sequence, to target the newly assigned genes, is introduced as a template for the HDR. This system is being used in protoplast transformation, enriched by FACS due to the GFP signal in the CRISPR/CAS9 vector, recovered, and regenerated to plants.

Figure 2B:
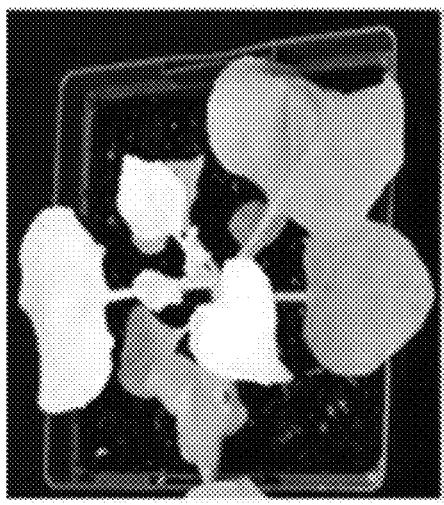
Figure 2A:
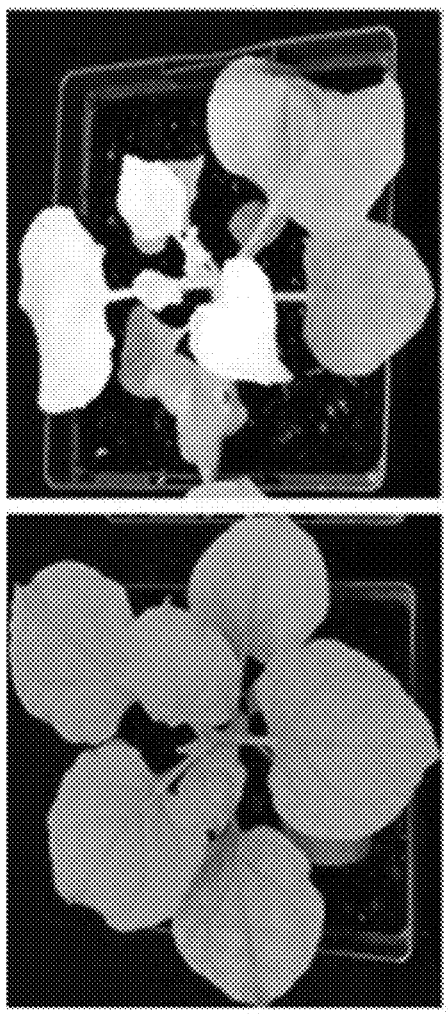
Figure 2C:
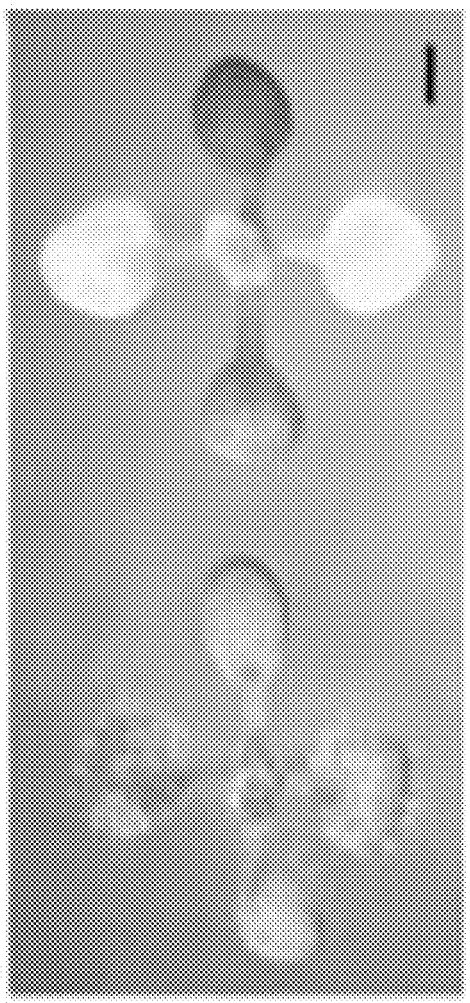

FIGS. 2A-C are photographs illustrating that silencing of the PDS gene causes photobleaching. Silencing of the PDS gene in *Nicotiana* (FIGS. 2A-B) and *Arabidopsis* (FIG. 2C) plants causes photobleaching in *N. benthamiana* (FIG. 2B) and *Arabidopsis* (FIG. 2C, right side). Photographs were taken 3½ weeks after PDS silencing.

FIG. 3A-l) are photographs of knock down of GFP expression levels in *Arabidopsis* using GEiGS. *Arabidopsis* protoplasts expressing GFP are illustrated as control (FIGS. 3A-B) compared to protoplasts edited using GEiGS to express GFP siRNA (FIGS. 3C-D). Of note, GEiGS protoplasts or plants are silenced for expression of GFP protein.

Figure 4:
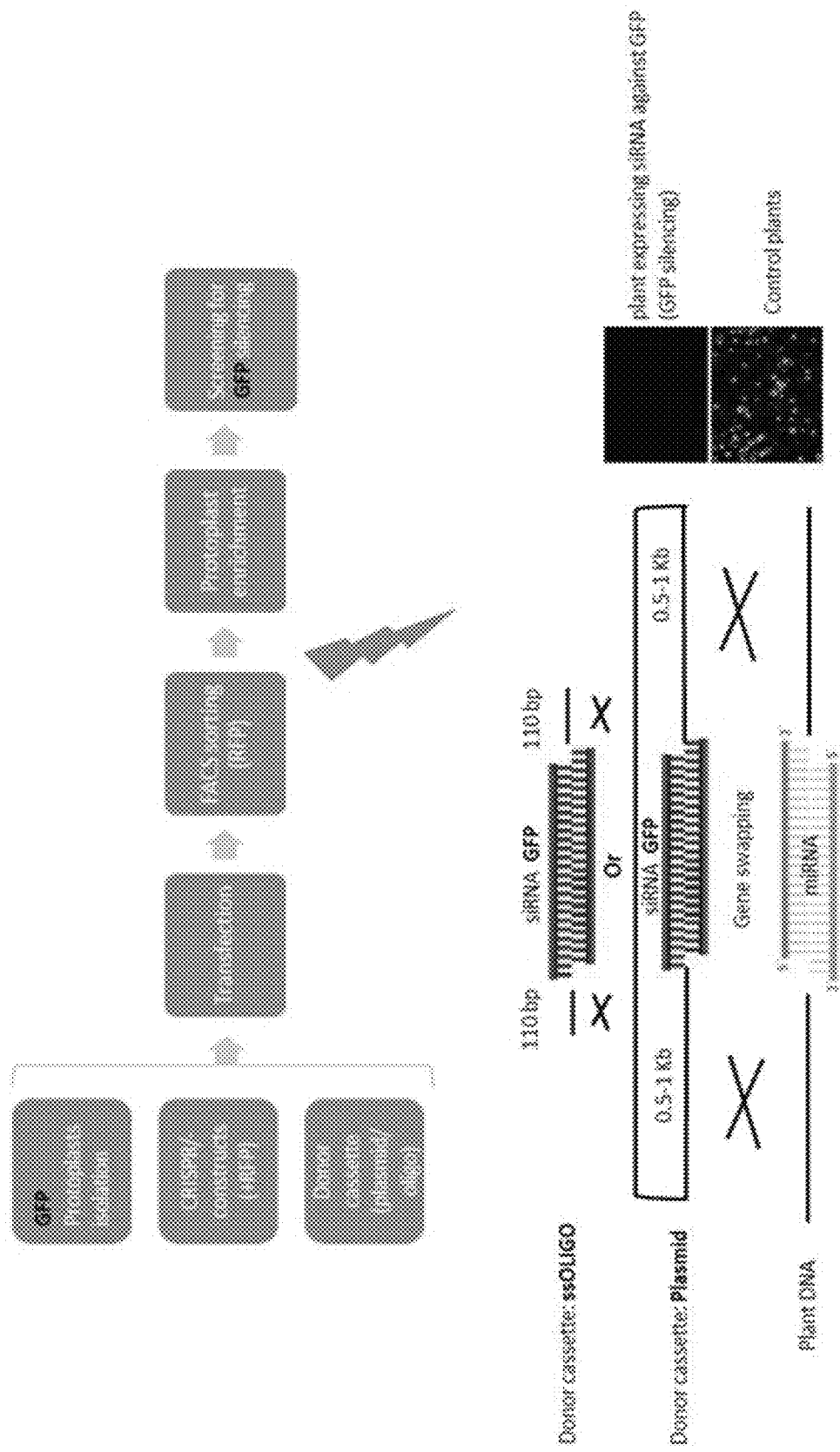

FIG. 4 is an embodiment flow chart of GEiGS replacement of endogenous miRNA with siRNA targeting GFP, generating *Arabidopsis* plants with active RNAi against GFP. To introduce the modification, a CRISPR/CAS9 system, in a RFP containing vector, generates a cleavage in the chosen loci, through designed specific guide RNAs to promote homologous DNA repair (HDR) in the site. Second, A DONOR sequence, with the desired modification of the miRNA sequence, to target the GFP gene, is introduced as a template for the HDR. This system is being used in GFP expressing protoplasts. Enrichment of putatively modified cells by FACS due to the RFP signal in the CRISPR/CAS9 vector, is being carried out and recovered. Regenerated plants are being analysed for intensity of GFP signal.

Figure 5:
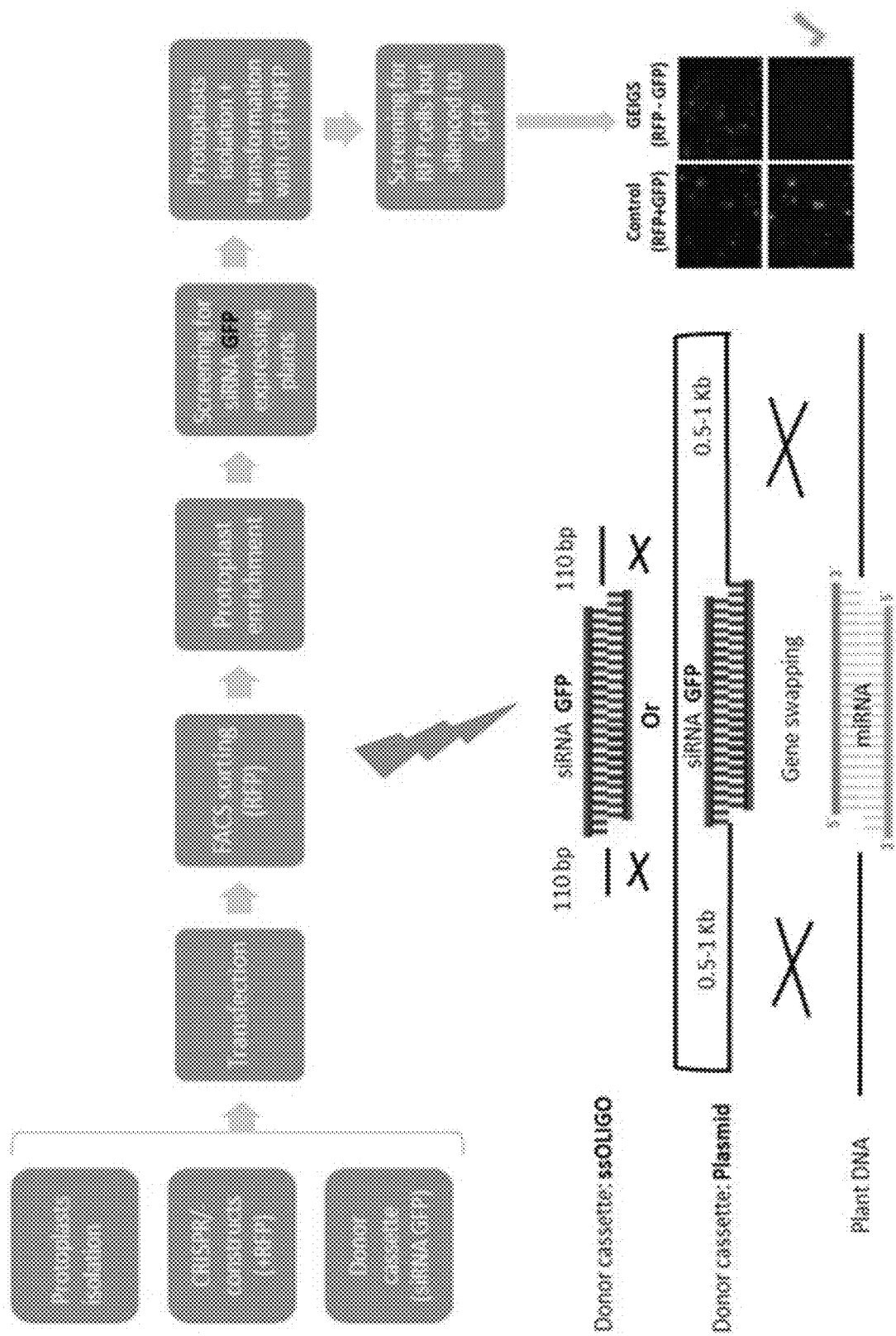

FIG. 5 is an embodiment flow chart of GEiGS replacement of endogenous miRNA with siRNA targeting GFP, generating *Arabidopsis* plants with GEiGS-directed RNAi against GFP. Of note, GEiGS plants are silenced for GFP expression after plant transformation. RFP is being used for the enrichment of cells with transient presence of CRISPR/CAS9 vector.

Figure 6:
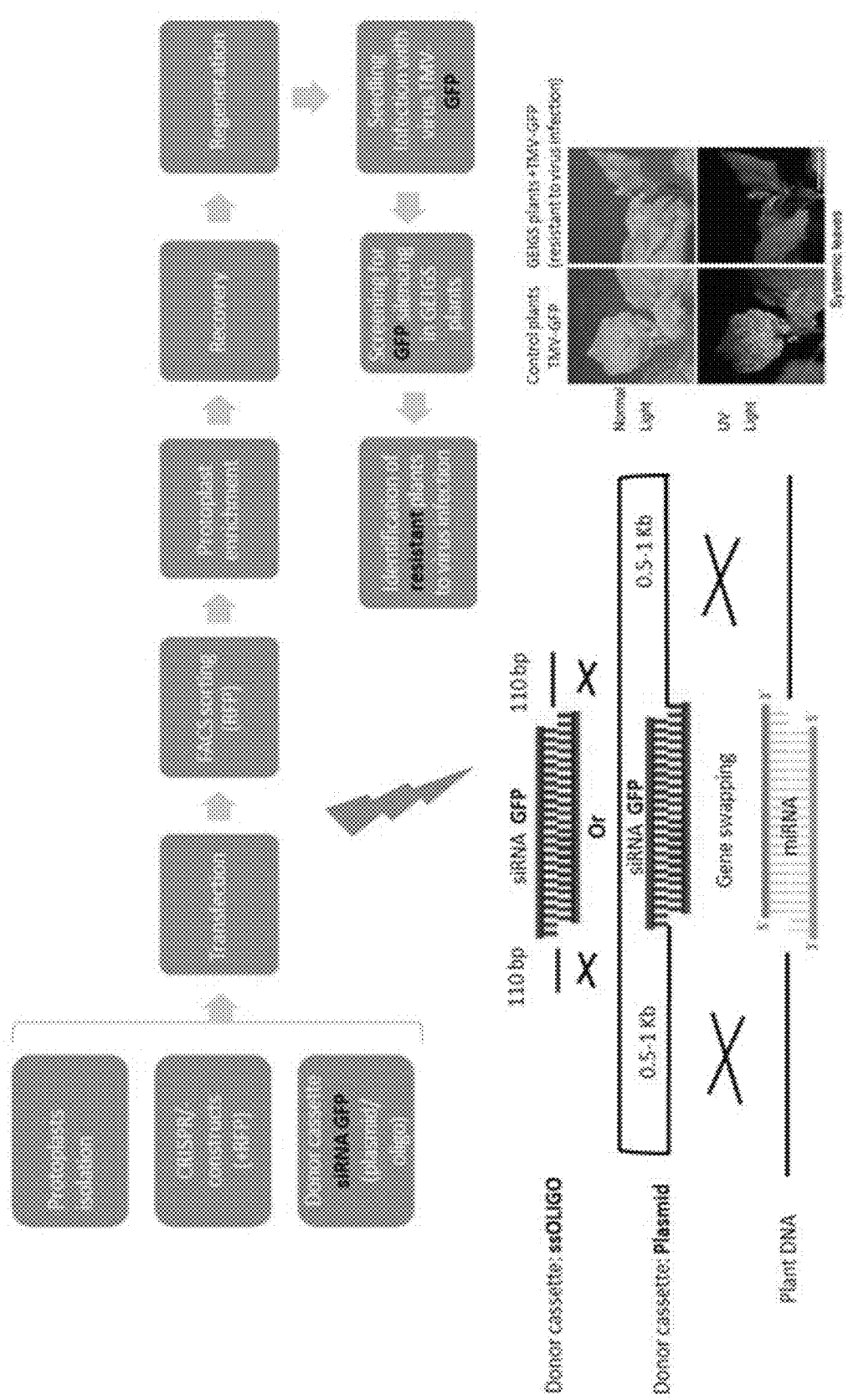

FIG. 6 is an embodiment flow chart of GEiGS replacement of endogenous miRNA with siRNA targeting GFP, generating plants resistant to viral infection e.g. TMV infection (i.e. exogenous gene). RFP is being used for the enrichment of cells with transient presence of CRISPR/CAS9 vector.

Figure 7:

FIG. 7 is a photograph of lodging banana plants suffering from Toppling Disease caused by the burrowing nematode, *Radopholus similis*.

Figure 8:
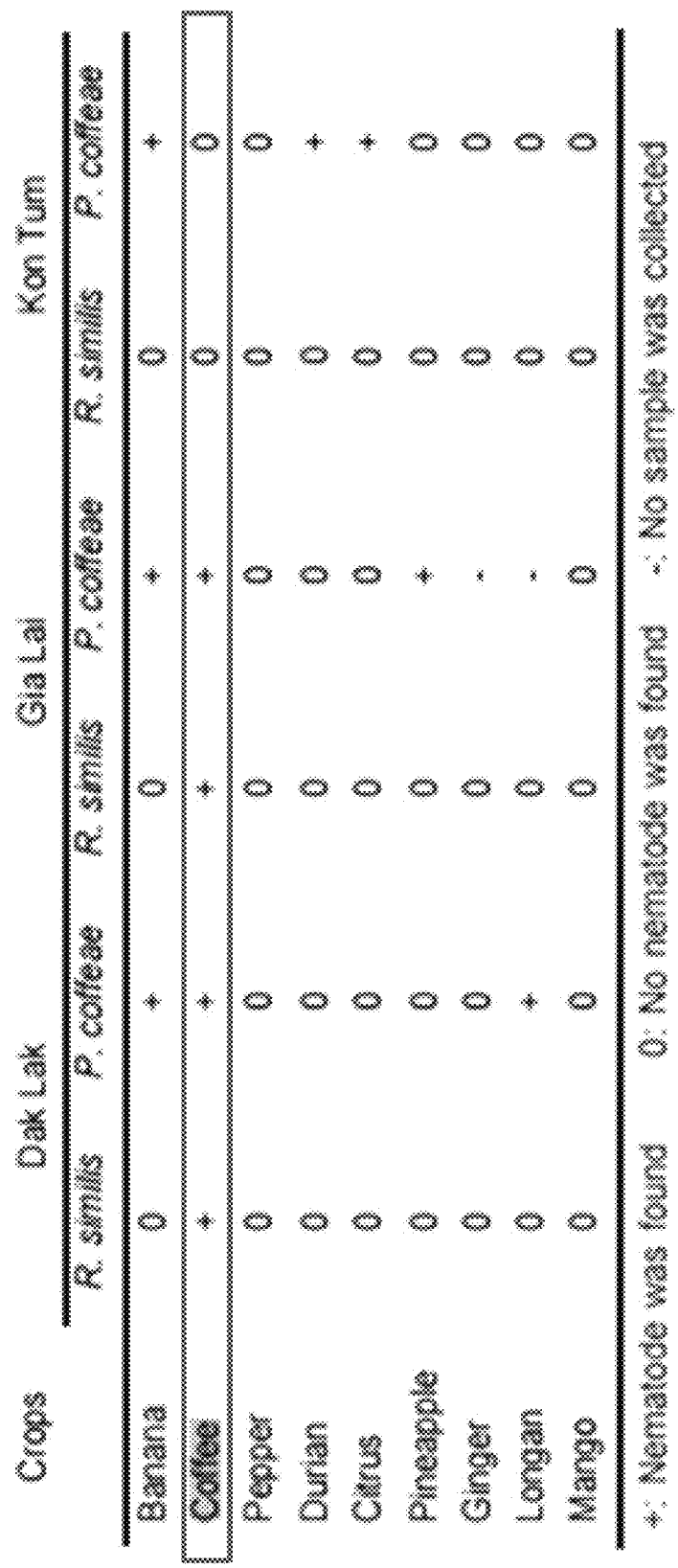

FIG. 8 is a table illustrating the occurrence of *Radopholus similis* and *Pratylenchus coffeae* on different crops in Tay Nguyen area.

Figure 9:
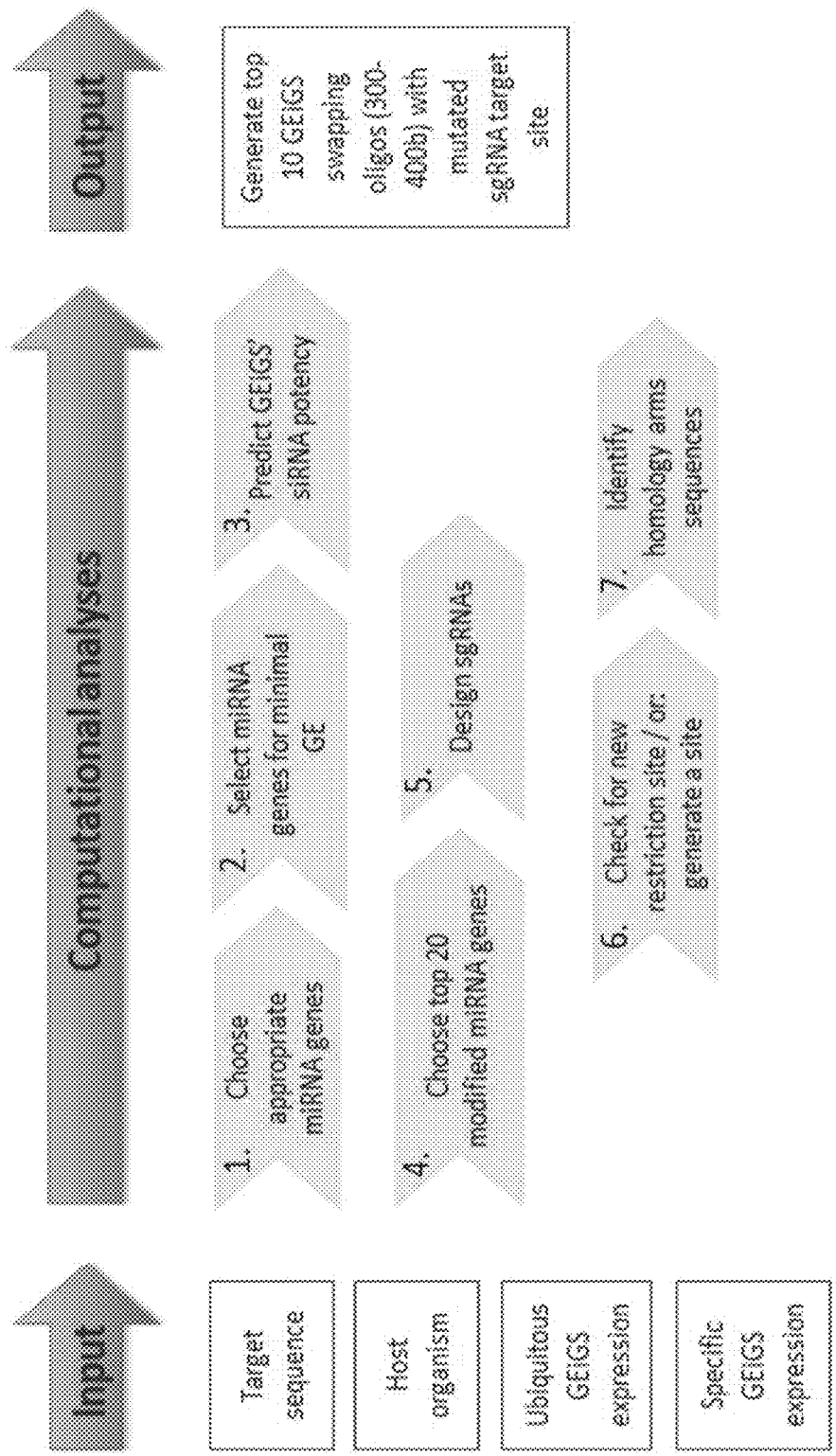

FIG. 9 is an embodiment flow chart of computational pipeline to generate GEiGS templates. The computational GEiGS pipeline applies biological metadata and enables an automatic generation of GEiGS DNA donor templates that are used to minimally edit endogenous non-coding RNA genes (e.g. miRNA genes), leading to a new gain of function, i.e. redirection of their silencing capacity to target gene expression of interest.

Figure 10:
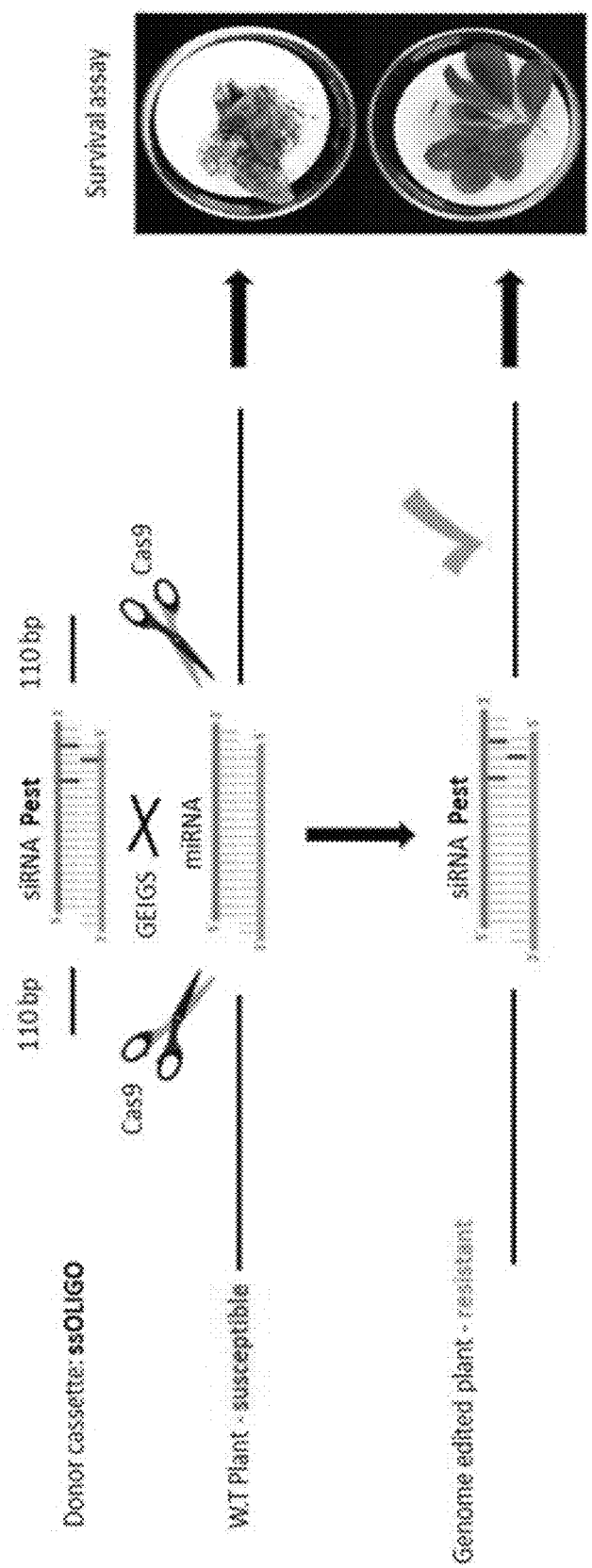

FIG. 10 is an embodiment flow chart illustrating design of resistant plant to pests targeting any desired exogenous pest gene. GEiGS replacement of endogenous miRNA with siRNA targeting pathogen/pest essential gene, generating plants resistant to pathogen/pest infection.

Figure 11:
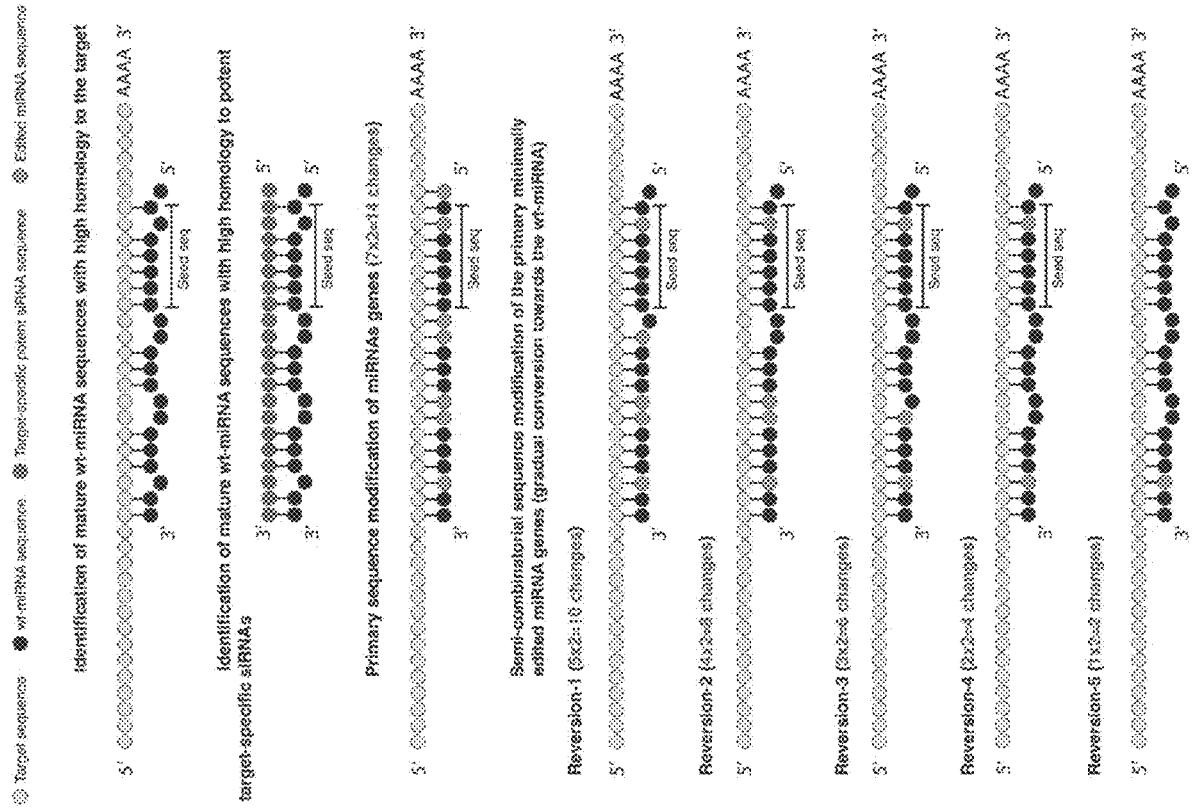

FIG. 11 is an embodiment drawing illustrating the main stages required to design RNA silencing molecule and with minimally edited miRNA gene bases.

FIGS. 12A-G illustrate primary transcripts of miR-390 and modified miR390-structure and targeted sequences. Secondary structure representation of primary transcripts of miR390, and its modified versions—(FIG. 12A) wild type; (FIGS. 12B-C) modified version to target GFP; (FIGS. 12D-E) modified version to target AtPDS3; (FIGS. 12F-G) modified version to target AtADH1. Mature miRNA/siRNAs are outlined in red, exhibiting structure conservation through design. The regions targeted for manipulation by CRISPR/CAS9 system are outlined in purple and the NGG sequence is highlighted in yellow (FIG. 12A).

FIGS. 13A-G illustrate primary transcripts of miR-173 and modified miR173-structure and targeted sequences. Secondary structure representation of primary transcripts of miR173, and its modified versions—(FIG. 13A) wild type; (FIGS. 13B-C) modified version to target GFP; (FIG. 13D-E) modified version to target AtPDS3; (FIG. 13F-G) modified version to target AtADH1. Mature miRNA/siRNAs are outlined in red, exhibiting structure conservation through design. The regions targeted for manipulation by CRISPR/CAS9 system are outlined in purple and the NGG sequence is highlighted in yellow (FIG. 13A).

FIG. 13H illustrates embodiment examples of GEiGS oligo designs in which the precursor structure does not play a role in the biogenesis, hence, it is not required to be maintained. Design based on the Brassica rapa bnTAS3B tasiRNA. From top to bottom: wild-type tasiRNA, GEiGS design with minimal sequence changes, and GEiGS design with maximal sequence changes. The selections of non-coding RNA precursors that give rise to mature small RNA molecules are highlighted in green. Sequence differences between the GEiGS oligos and the wild type sequence are highlighted in red. Of note, tasiRNA biogenesis, unlike miRNAs and tRNAs, does not rely on the precursor secondary structure.

FIGS. 14A-D illustrate gene targeting by miR-173 and its modified versions. (FIG. 14A) Wild type miR-173 target the TAS1c transcript by sequence complementarity of the mature miRNA to a sequence in the gene (in red). The newly modified miRNAs (SWAPs 1, 2, 3, 4, 9 and 10) were designed to target (FIG. 14B) GFP, (FIG. 14C) AtPDS3 and (FIG. 14D) AtADH1 by sequence complementarity to their sequence (in red). Modified nucleotide from wt sequence, are written in lowercase.

FIGS. 15A-D illustrate gene targeting by miR-390 and its modified versions. (FIG. 15A) Wild type miR-390 target the TAS3 transcript by sequence complementarity of the mature miRNA to a sequence in the gene (in red). The newly modified miRNAs (SWAPs 5, 6, 7, 8, 11 and 12) were designed to target (FIG. 15B) GFP, (FIG. 15C) AtPDS3 and (FIG. 15D) AtADH1 by sequence complementarity to their sequence (in red). Modified nucleotide from wt sequence, are written in lowercase.

Figure 16:
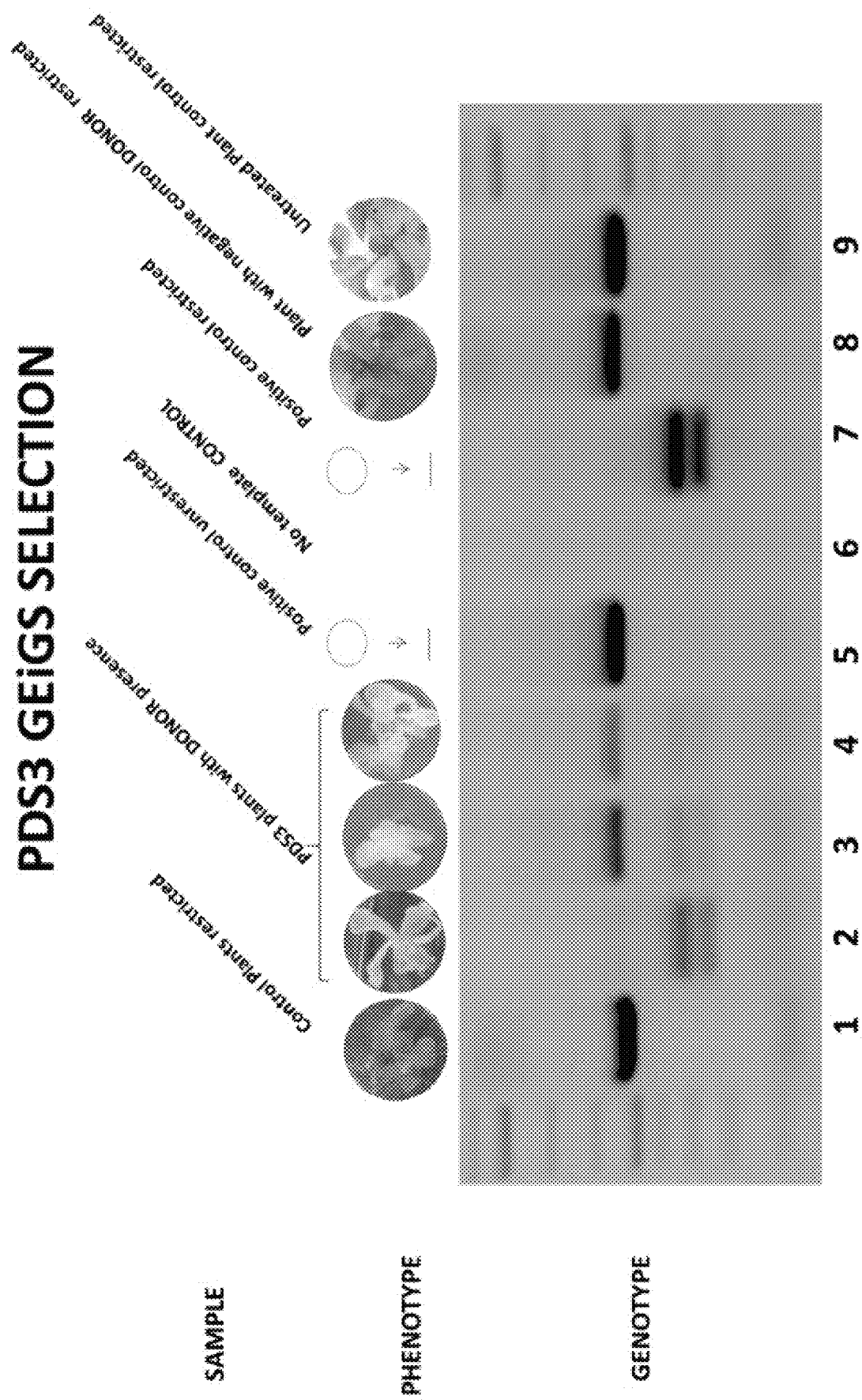

FIG. 16 illustrates PDS3 Phenotype/Genotype: bleached phenotype plants were selected and genotyped through internal amplicon PCR followed by restriction digest analysis with BtsαI (NEB) in order to verify donor presence vs. wild type sequence. Lane 1: Treated plants with NO DONOR, restricted, Lanes 2-4: PDS3 treated plants containing DONOR restricted, Lane 5: Positive plasmid DONOR control unrestricted, Lane 6: Water no template control, Lane 7: Positive Plasmid DONOR restricted, Lane 8: Plants bombarded with negative DONOR restricted, Lane 9: Untreated control plants restricted. Subsequent external PCR amplification of the amplicon was processed and sequenced in order to validate the insertion.

Figure 17:
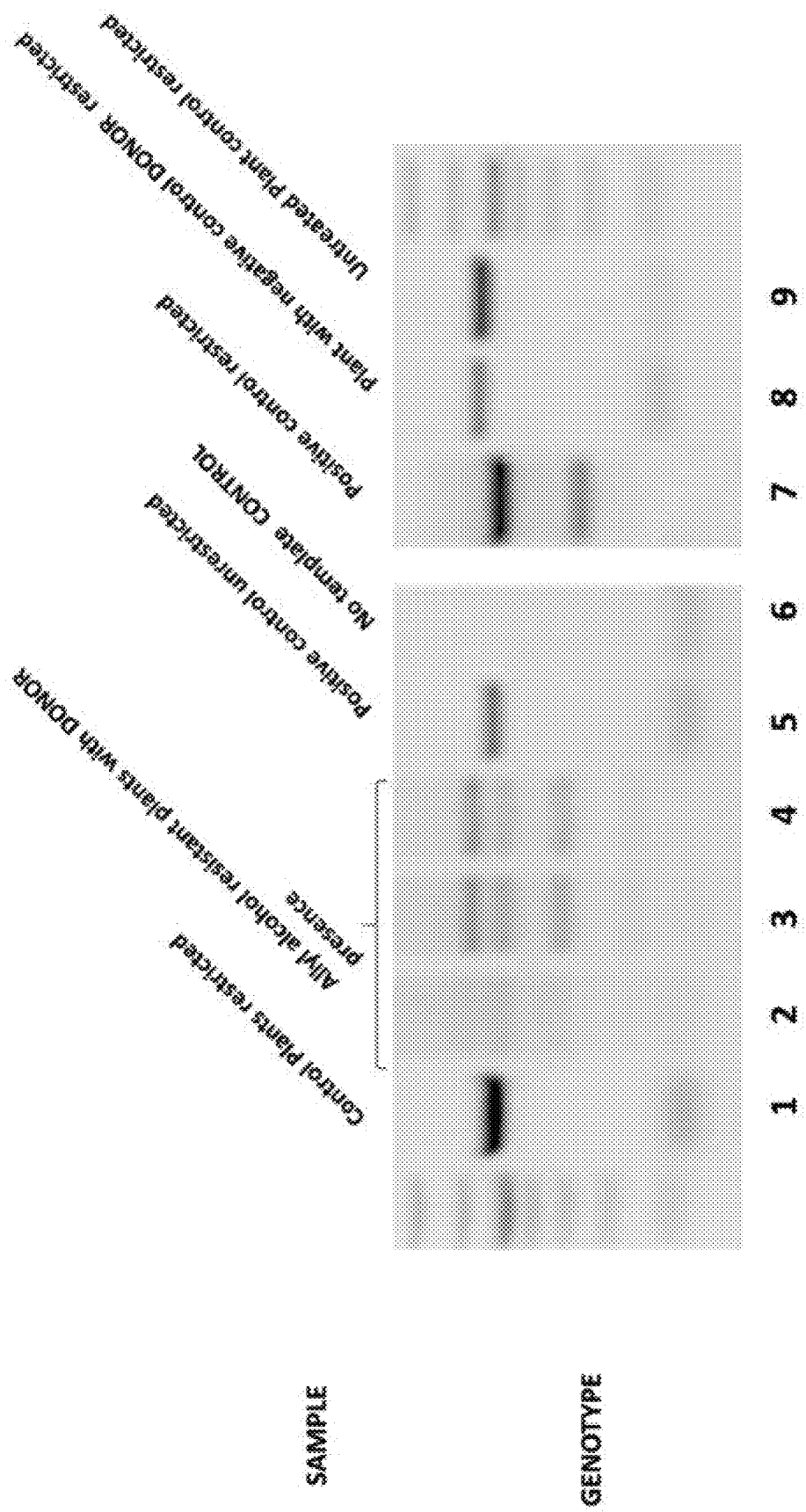

FIG. 17 illustrates ADH1 Phenotype/Genotype: Plants were selected through Allyl alcohol resistance and genotyped through internal amplicon PCR followed by Bcd (NEB) restriction digest in order to verify donor presence. Lane 1: Allyl alcohol sensitive control plant restricted, Lane2-4: Allyl alcohol resistant plants containing DONOR restricted, Lane5: Positive plasmid DONOR control unrestricted, Lane 6: no template control, Lane7: Positive Plasmid DONOR restricted, Lane 8: Plant bombarded with non-specific DONOR restricted, Lane 9: Non Allyl alcohol treated control restricted.

Figure 18:
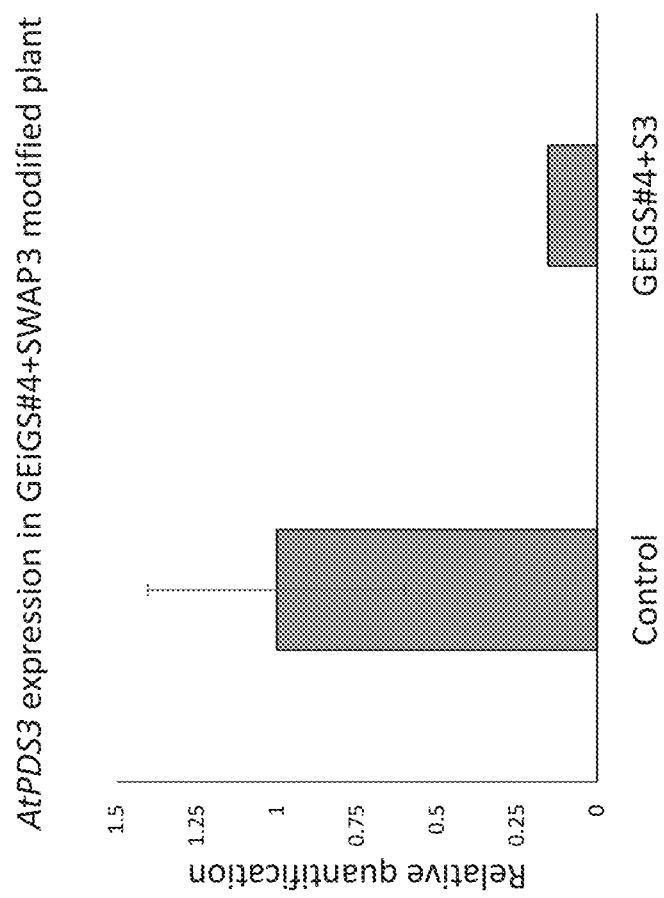

FIG. 18 is a graph illustrating gene expression analysis in miR-173 modified plant targeting AtPDS3 transcript. Analysis of AtPDS3 expression was carried out through qRT-PCR, in regenerating bombarded plants with GEiGS #4 and SWAP3 compared to plants bombarded with GEiGS #5 and SWAP1 and 2 (GFP). Of note, a reduction of 82% in gene expression level, on the average, was observed, when miR-173 was modified to target AtPDS3, compared to control plants (Error bars present SD; p-value <0.01 calculated on Ct values).

Figure 19:
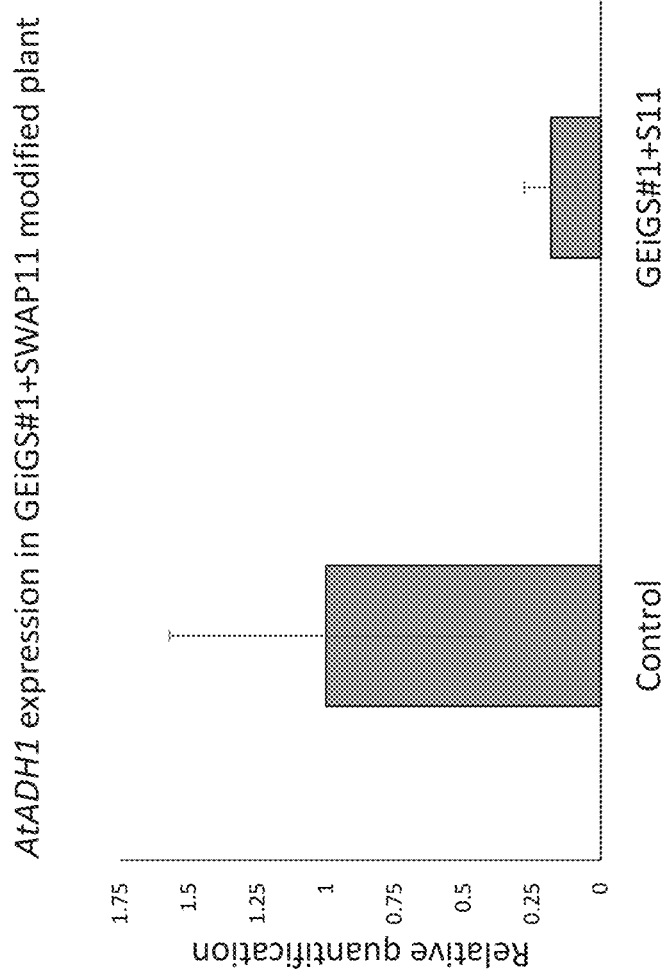

FIG. 19 is a graph illustrating gene expression analysis in miR-390 modified plant targeting AtPDS3 transcript. Analysis of AtADH1 expression was carried out through qRT-PCR, in regenerating bombarded plants with GEiGS #1 and SWAP11, compared to plants bombarded with GEiGS #5 and SWAP1 and 2 (GFP). Of note, a reduction of 82% in gene expression level, on the average, was observed, when miR-390 was modified to target AtADH1, compared to control plants (Error bars represent SD; p-value <0.01 calculated on Ct values).

DESCRIPTION OF SPECIFIC EMBODIMENTS OF THE INVENTION

The present invention, in some embodiments thereof, relates to modifying genes that encode or are processed into non-coding RNA molecules, including RNA silencing molecules and, more particularly, but not exclusively, to the use of same for silencing endogenous or exogenous target RNA of interest in plants.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

Previous work on genome editing of RNA molecules in various organisms (e.g. murine, human, plants), focused on disruption of miRNA activity or target binding sites using transgenesis. Genome editing in plants has further concentrated on the use of CRISPR-Cas9 technology, ZFNs and TALENs, for knockdown of genes or insertions in model plants. Furthermore, gene silencing in plants using artificial microRNAs transgenes to silence endogenous and exogenous target genes were described [Molnar A et al. Plant J. (2009) 58(1):165-74. doi: 10.1111/j.1365-313X.2008.03767.x. Epub 2009 Jan. 19; Borges and Martienssen, Nature Reviews Molecular cell Biology| AOP, published online 4 Nov. 2015; doi:10.1038/4085]. The artificial miRNAs transgenes are introduced into plant cells within an artificial expression cassette (including a promoter, terminator, selection marker, etc.) and downregulate target expression.

While reducing the present invention to practice, the present inventors have devised a gene editing technology directed to non-coding RNA molecules (e.g. endogenous) designed to target and interfere with a non-natural target gene of interest (endogenous or exogenous to the plant cell). The gene editing technology described herein does not implement the classical molecular genetic and transgenic tools comprising expression cassettes that have a promoter, terminator, selection marker.

As is shown herein below and in the examples section which follows, the present inventors have designed a Genome Editing Induced Gene Silencing (GEiGS) platform capable of utilizing a plant cell's endogenous non-coding RNA molecules including e.g. RNA silencing molecules (e.g. siRNA, miRNA, piRNA, tasiRNA, tRNA, rRNA, antisense RNA, snRNA, snoRNA etc.) and modifying them to target and down regulate any RNA target of interest (see Exemplary flowchart in FIG. 1). Using GEiGS, the present method enables screening of potential non-coding RNA molecules, editing nucleotides in these endogenous RNA molecules, and thereby redirecting their specificity to effectively and specifically target and down regulate any RNA of interest including, endogenous and/or exogenous RNA encoded by pathogens and pests (see Exemplary flowchart in FIG. 9). Taken together, GEiGS can be utilized as a novel non-GMO technology for increasing crop yield, crop growth rate, crop quality as well as for crop protection against stress, pathogens, pests and herbicides.

Thus, according to an aspect of the invention there is provided a method of modifying a gene encoding or processed into a non-coding RNA molecule having no RNA silencing activity in a plant cell, the method comprising introducing into the plant cell a DNA editing agent conferring a silencing specificity of the non-coding RNA molecule towards a target RNA of interest, thereby modifying the gene encoding or processed into the non-coding RNA molecule.

According to another aspect of the invention there is provided a method of modifying a gene encoding or processed into a RNA silencing molecule to a target RNA in a plant cell, the method comprising introducing into the plant cell a DNA editing agent which redirects the specificity of the RNA silencing molecule towards a second target RNA, the target RNA and the second target RNA being distinct, thereby modifying the gene encoding the RNA silencing molecule.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that may be useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffiis*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, banana, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifoliurn* spp., *Triticum* spp., *Tsuga heterophylla*, *Vaccinium* spp., *Vida* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

According to a specific embodiment, the plant is a crop, a flower or a tree.

According to a specific embodiment, the plant is a woody plant species e.g., *Actinidia chinensis* (Actinidiaceae), *Manihotesculenta* (Euphorbiaceae), *Firiodendron tulipifera* (Magnoliaceae), *Populus* (Salicaceae), *Santalum album* (Santalaceae), *Ulmus* (Ulmaceae) and different species of the Rosaceae (*Malus*, *Prunus*, *Pyrus*) and the Rutaceae (*Citrus*, *Microcitrus*), Gymnospermae e.g., *Picea glauca* and *Pinus taeda*, forest trees (e.g., Betulaceae, Fagaceae, Gymnospermae and tropical tree species), fruit trees, shrubs or herbs, e.g., (banana, cocoa, coconut, coffee, date, grape and tea) and oil palm.

According to a specific embodiment, the plant is of a tropical crop e.g., coffee, macadamia, banana, pineapple, taro, papaya, mango, barley, beans, cassava, chickpea, cocoa (chocolate), cowpea, maize (corn), millet, rice, sorghum, sugarcane, sweet potato, tobacco, taro, tea, yam.

"Grain," "seed," or "bean," refers to a flowering plant's unit of reproduction, capable of developing into another such plant. As used herein, the terms are used synonymously and interchangeably.

According to a specific embodiment, the plant is a plant cell e.g., plant cell in an embryonic cell suspension.

According to a specific embodiment, the plant cell is a protoplast.

The protoplasts are derived from any plant tissue e.g., fruit, flowers, roots, leaves, embryos, embryonic cell suspension, calli or seedling tissue.

As used herein, the term "non-coding RNA molecule" refers to a RNA sequence that is not translated into an amino acid sequence and does not encode a protein.

According to one embodiment, the non-coding RNA molecule is typically subject to the RNA silencing processing mechanism or activity. However, also contemplated herein are a few changes in nucleotides (e.g. for miRNA up to 24 nucleotides) which may elicit a processing mechanism that results in RNA interference or translation inhibition.

According to a specific embodiment, the non-coding RNA molecule is endogenous (naturally occurring, e.g. native) to the cell. It will be appreciated that the non-coding RNA molecule can also be exogenous to the cell (i.e. externally added and which is not naturally occurring in the cell).

According to some embodiments, the non-coding RNA molecule comprises an intrinsic translational inhibition activity.

According to some embodiments, the non-coding RNA molecule comprises an intrinsic RNAi activity.

According to some embodiments, the non-coding RNA molecule does not comprise an intrinsic translational inhibition activity or an intrinsic RNAi activity (i.e. the non-coding RNA molecule does not have an RNA silencing activity).

According to an embodiment of the invention, the non-coding RNA molecule is specific to a target RNA (e.g., a natural target RNA) and does not cross inhibit or silence a second target RNA or target RNA of interest unless designed to do so (as discussed below) exhibiting 100% or less global homology to the target gene, e.g., less than 99%, 98%, 97%, 96%, 95%, 94%, 93%, 92%, 91%, 90%, 89%, 88%, 87%, 86%, 85%, 84%, 83%, 82%, 81% global homology to the target gene; as determined at the RNA or protein level by RT-PCR, Western blot, Immunohistochemistry and/or flow cytometry, sequencing or any other detection methods.

According to one embodiment, the non-coding RNA molecule is a RNA silencing or RNA interference (RNAi) molecule.

The term "RNA silencing" or RNAi refers to a cellular regulatory mechanism in which non-coding RNA molecules (the "RNA silencing molecule" or "RNAi molecule") mediate, in a sequence specific manner, co- or post-transcriptional inhibition of gene expression or translation. According to one embodiment, the RNA silencing molecule is capable of mediating RNA repression during transcription (co-transcriptional gene silencing).

According to a specific embodiment, co-transcriptional gene silencing includes epigenetic silencing (e.g. chromatic state that prevents functional gene expression).

According to one embodiment, the RNA silencing molecule is capable of mediating RNA repression after transcription (post-transcriptional gene silencing).

Post-transcriptional gene silencing (PTGS) typically refers to the process (typically occurring in the cell cytoplasm) of degradation or cleavage of messenger RNA (mRNA) molecules which decrease their activity by preventing translation. For example, and as discussed in detail below, a guide strand of a RNA silencing molecule pairs with a complementary sequence in a mRNA molecule and induces cleavage by e.g. Argonaute 2 (Ago2).

Co-transcriptional gene silencing typically refers to inactivation of gene activity (i.e. transcription repression) and typically occurs in the cell nucleus. Such gene activity repression is mediated by epigenetic-related factors, such as e.g. methyl-transferases, that methylate target DNA and histones. Thus, in co-transcriptional gene silencing, the association of a small RNA with a target RNA (small RNA-transcript interaction) destabilizes the target nascent transcript and recruits DNA- and histone-modifying enzymes (i.e. epigenetic factors) that induce chromatin remodeling into a structure that repress gene activity and transcription. Also, in co-transcriptional gene silencing, chromatin-associated long non-coding RNA scaffolds may recruit chromatin-modifying complexes independently of small RNAs. These co-transcriptional silencing mechanisms form RNA surveillance systems that detect and silence inappropriate transcription events, and provide a memory of these events via self-reinforcing epigenetic loops [as described in D. Hoch and D. Moazed, RNA-mediated epigenetic regulation of gene expression, *Nat Rev Genet*. (2015) 16(2): 71-84].

According to an embodiment of the invention, the RNAi biogenesis/processing machinery generates the RNA silencing molecule.

According to an embodiment of the invention, the RNAi biogenesis/processing machinery generates the RNA silencing molecule, but no specific target has been identified.

According to one embodiment, the non-coding RNA molecule is a capable of inducing RNA interference (RNAi).

Following is a detailed description of non-coding RNA molecules which comprise an intrinsic RNAi activity (e.g. are RNA silencing molecules) that can be used according to specific embodiments of the present invention.

According to one embodiment, the non-coding RNA molecule or the RNA silencing molecule is processed from a precursor.

According to one embodiment, the non-coding RNA molecule or the RNA silencing molecule is processed from a single stranded RNA (ssRNA) precursor.

According to one embodiment, the non-coding RNA molecule or the RNA silencing molecule is processed from a duplex-structured single-stranded RNA precursor.

According to one embodiment, the non-coding RNA molecule or the RNA silencing molecule is processed from a dsRNA precursor (e.g. comprising perfect and imperfect base pairing).

According to one embodiment, the non-coding RNA molecule or the RNA silencing molecule is processed from a non-structured RNA precursor.

According to one embodiment, the non-coding RNA molecule or the RNA silencing molecule is processed from a protein-coding RNA precursor.

According to one embodiment, the non-coding RNA molecule or the RNA silencing molecule is processed from a non-coding RNA precursor.

According to one embodiment, the dsRNA can be derived from two different complementary RNAs, or from a single RNA that folds on itself to form dsRNA.

Perfect and imperfect based paired RNA (i.e. double stranded RNA; dsRNA), siRNA and shRNA—The presence of long dsRNAs in cells stimulates the activity of a ribonuclease III enzyme referred to as dicer. Dicer (also known as endoribonuclease Dicer or helicase with RNase motif) is an enzyme that in plants is typically referred to as Dicer-like (DCL) protein. Different plants have different numbers of DCL genes, thus for example, *Arabidopsis* genome typically has four DCL genes, rice has eight DCL genes, and maize genome has five DCL genes. Dicer is involved in the processing of the dsRNA into short pieces of dsRNA known as short interfering RNAs (siRNAs). siRNAs derived from dicer activity are typically about 21 to about 23 nucleotides in length and comprise about 19 base pair duplexes with two 3' nucleotides overhangs.

Accordingly, some embodiments of the invention contemplate modifying a gene encoding a dsRNA to redirect a silencing specificity (including silencing activity) towards a second target RNA (i.e. RNA of interest).

According to one embodiment dsRNA precursors longer than 21 bp are used. Various studies demonstrate that long dsRNAs can be used to silence gene expression without inducing the stress response or causing significant off-target effects—see for example [Strat et al., Nucleic Acids Research, 2006, Vol. 34, No, 13 3803-3810; Bhargava A et al. Brain Res. Protoc. 2004; 13:115-125; Diallo M., et al., Oligonucleotides. 2003; 13:381-392; Paddison P. J., et al., Proc. Natl. Acad. Sci. USA. 2002; 99:1443-1448; Tran N., et al., FEBS Lett. 2004; 573:127-134].

The term "siRNA" refers to small inhibitory RNA duplexes (generally between 18-30 base pairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is suggested to result from providing Dicer with a substrate (27 mer) instead of a product (21 mer) and that this improves the rate or efficiency of entry of the siRNA duplex into RISC.

It has been found that position, but not the composition, of the 3'-overhang influences potency of a siRNA and asymmetric duplexes having a Y-overhang on the antisense strand are generally more potent than those with the 3'-overhang on the sense strand (Rose et al., 2005).

The strands of a double-stranded interfering RNA (e.g., a siRNA) may be connected to form a hairpin or stem-loop structure (e.g., a shRNA). Thus, as mentioned, the RNA silencing molecule of some embodiments of the invention may also be a short hairpin RNA (shRNA).

The term short hairpin RNA, "shRNA", as used herein, refers to a RNA molecule having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

The RNA silencing molecule of some embodiments of the invention need not be limited to those molecules containing only RNA, but further encompasses chemically-modified nucleotides and non-nucleotides.

Various types of siRNAs are contemplated by the present invention, including trans-acting siRNAs (Ta-siRNAs), repeat-associated siRNAs (Ra-siRNAs) and natural-antisense transcript-derived siRNAs (Nat-siRNAs).

According to one embodiment, silencing RNA includes "piRNA" which is a class of interacting RNAs of about 26 and 31 nucleotides in length. piRNAs typically form RNA-protein complexes through interactions with Piwi proteins, i.e. antisense piRNAs are typically loaded into Piwi proteins (e.g. Piwi, Ago3 and Aubergine (Aub)).

miRNA—According to another embodiment the RNA silencing molecule may be a miRNA.

The term "microRNA", "miRNA", and "miR" are synonymous and refer to a collection of non-coding single-stranded RNA molecules of about 19-24 nucleotides in length, which regulate gene expression. miRNAs are found in a wide range of organisms (e.g. insects, mammals, plants, nematodes) and have been shown to play a role in development, homeostasis, and disease etiology.

Initially the pre-miRNA is present as a long non-perfect double-stranded stem loop RNA that is further processed by Dicer into a siRNA-like duplex, comprising the mature guide strand (miRNA) and a similar-sized fragment known as the passenger strand (miRNA*). The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the to miRNA:miRNA* have roughly equivalent 5' pairing, both miRNA and miRNA* may have gene silencing activity.

The DISC identifies target nucleic acids based on high levels of complementarity between the miRNA and the mRNA, especially by nucleotides 2-8 of the miRNA (referred as "seed sequence").

A number of studies have looked at the base-pairing requirement between miRNA and its mRNA target for achieving efficient inhibition of translation (reviewed by Bartel 2004, Cell 116-281). Computational studies, analyzing miRNA binding on whole genomes have suggested a specific role for bases 2-8 at the 5' of the miRNA (also referred to as "seed sequence") in target binding but the role of the first nucleotide, found usually to be "A" was also recognized (Lewis et al. 2005 Cell 120-15). Similarly, nucleotides 1-7 or 2-8 were used to identify and validate targets by Krek et al. (2005, Nat Genet 37-495). The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

It will be appreciated that the pre-miRNA sequence may comprise from 45-90, 60-80 or 60-70 nucleotides while the pri-miRNA sequence may comprise from 45-30,000, 50-25,000, 100-20,000, 1,000-1,500 or 80-100 nucleotides.

According to one embodiment, the miRNA comprises miR-390a (as set forth in SEQ ID NO: 28).

According to one embodiment, the miRNA comprises milt-173 (as set forth in SEQ ID NO: 29).

Antisense—Antisense is a single stranded RNA designed to prevent or inhibit expression of a gene by specifically hybridizing to its mRNA. Downreguiation of a target RNA can be effected using an antisense polynucleotide capable of specifically hybridizing with an mRNA transcript encoding the target RNA.

As mentioned, the non-coding RNA molecule may not comprise a canonical (intrinsic) RNAi activity (e.g. is not a canonical RNA silencing molecule, or its target has not been identified). Such non-coding RNA molecules include the following:

According to one embodiment, the non-coding RNA molecule is a transfer RNA (tRNA). The term "tRNA" refers to a RNA molecule that serves as the physical link between nucleotide sequence of nucleic acids and the amino acid sequence of proteins, formerly referred to as soluble RNA or sRNA. tRNA is typically about 76 to 90 nucleotides in length.

According to one embodiment, the non-coding RNA molecule is a ribosomal RNA (rRNA). The term "tRNA" refers to the RNA component of the ribosome i.e. of either the small ribosomal subunit or the large ribosomal subunit.

According to one embodiment, the non-coding RNA molecule is a small nuclear RNA (snRNA or U-RNA). The terms "sRNA" or "U-RNA" refer to the small RNA molecules found within the splicing speckles and Cajal bodies of the cell nucleus in eukaryotic cells. snRNA is typically about 150 nucleotides in length.

According to one embodiment, the non-coding RNA molecule is a small nucleolar RNA (snoRNA). The teen "snoRNA" refers to the class of small RNA molecules that primarily guide chemical modifications of other. RNAs, e.g. rRNAs, tRNAs and snRNAse snoRNA is typically classified into one of two classes: the C/D box snoRNAs are typically about 70-120 nucleotides in length and are associated with methylation, and the H/ACA box snoRNAs are typically about 101-200 nucleotides in length and are associated with pseudouridylation.

Similar to snoRNAs are the scaRNAs (i.e. Small Cajal body RNA genes) which perform a similar role in RNA maturation to snoRNAs, but their targets are spliceosomal snRNAs and they perform site-specific modifications of spliceosomal snRNA precursors (in the Cajal bodies of the nucleus).

According to one embodiment, the non-coding RNA molecule is an extracellular RNA (exRNA). The term "exRNA" refers to RNA species present outside of the cells from which they were transcribed (e.g. exosomal RNA).

According to one embodiment, the non-coding RNA molecule is a long non-coding RNA (lncRNA). The term "lncRNA" or "long ncRNA" refers to non-protein coding transcripts typically longer than 200 nucleotides.

According to one embodiment, non-limiting examples of non-coding RNA molecules include, but are not limited to, microRNA (miRNA), piwi-interacting RNA (piRNA), short interfering RNA (siRNA), short-hairpin RNA (shRNA), trans-acting siRNA (tasiRNA), small nuclear RNA (snRNA or URNA), small nucleolar RNA (snoRNA), Small Cajal body RNA (scaRNA), transfer RNA (tRNA), ribosomal RNA (rRNA), extracellular RNA (exRNA), repeat-derived RNA, transposable element RNA and long non-coding RNA (lncRNA).

According to one embodiment, non-limiting examples of RNAi molecules include, but are not limited to, small interfering RNA (siRNA), short hairpin RNA (shRNA), microRNA (miRNA), Piwi-interacting RNA (piRNA) and trans-acting siRNA (tasiRNA).

As mentioned above, the methods of some embodiments of the invention are utilized to redirect a silencing activity and/or specificity of the non-coding RNA molecule (or to generate a silencing activity and/or specificity if the non-coding RNA molecule does not have an intrinsic capability to silence a RNA molecule) towards a second target RNA or towards a target RNA of interest.

According to one embodiment, the target RNA and the second target RNA are distinct.

According to one embodiment, the method of modifying a gene encoding or processed into a RNA silencing molecule to a target RNA in a plant cell comprises introducing into the plant cell a DNA editing agent which redirects a silencing activity and/or specificity of the RNA silencing molecule towards a second target RNA, the target RNA and the second target RNA being distinct, thereby modifying the gene encoding the RNA silencing molecule.

As used herein, the term "redirects a silencing specificity" refers to reprogramming the original specificity of the non-coding RNA (e.g. RNA silencing molecule) towards a non-natural target of the non-coding RNA (e.g. RNA silencing molecule). Accordingly, the original specificity of the non-coding RNA is abolished (i.e. loss of function) and the new specificity is towards a RNA target distinct of the natural target (i.e. RNA of interest), i.e., gain of function. It will be appreciated that only gain of function occurs in cases that the non-coding RNA has no silencing activity.

As used herein, the term "target RNA" refers to a RNA sequence naturally bound by a non-coding RNA molecule. Thus, the target RNA is considered by the skilled artisan as a substrate for the non-coding RNA.

As used herein, the term "second target RNA" refers to a RNA sequence (coding or non-coding) not naturally bound by a non-coding RNA molecule. Thus, the second target RNA is not a natural substrate of the non-coding RNA.

As used herein, the term "target RNA of interest" refers to a RNA sequence (coding or non-coding) to be silenced by the designed non-coding RNA molecule.

As used herein, the phrase "silencing a target gene" refers to the absence or observable reduction in the level of mRNA and/or protein products from the target gene (e.g. due to co- and/or post-transcriptional gene silencing). Thus, silencing of a target gene can be by 5%, 10%, 20%, 30%, 40%, 50%, 60%, 70%, 80%, 90%, 95% or 100% as compared to a target gene not targeted by the designed non-coding RNA molecule of the invention.

The consequences of silencing can be confirmed by examination of the outward properties of a plant cell or whole plant or other organism that take up the designed non-coding RNA from the plant or by biochemical techniques (as discussed below).

It will be appreciated that the designed non-coding RNA molecule of some embodiments of the invention can have some off-target specificity effect's provided that it does not affect an agriculturally valuable trait (e.g., biomass, yield etc.).

According to one embodiment, the second target RNA or target RNA of interest is endogenous to the plant cell. Exemplary endogenous second target RNA or target RNA of interest include, but are not limited to, a product of a gene conferring sensitivity to stress, to infection, to herbicides, or a product of a gene related to plant growth rate, crop yield, as further discussed herein below.

According to one embodiment, the second target RNA or target RNA of interest is exogenous to the plant cell (also referred to herein as heterologous). In such a case, the second target RNA or target RNA of interest is a product of a gene that is not naturally part of the plant genome. Exemplary exogenous second target RNA include, but are not limited to, a product of a gene of a plant pathogen such as, but not limited to, an insect, a virus, a bacteria, a fungi, a nematode, as further discussed herein below. An exogenous target RNA (coding or non-coding) may comprise a nucleic acid sequence which shares sequence identity with an endogenous RNA sequence (e.g. may be partially homologous to an endogenous nucleic acid sequence) of the plant.

The specific binding of an endogenous non-coding RNA molecule with a target RNA can be determined by computational algorithms (such as BLAST) and verified by methods including e.g. Northern blot, In Situ hybridization, QuantiGene Plex Assay etc.

By use of the term "complementarity" or "complementary" is meant that the non-coding RNA molecule (or at least a portion of it that is present in the processed small RNA form, or at least one strand of a double-stranded polynucleotide or portion thereof, or a portion of a single strand polynucleotide) hybridizes under physiological conditions to the target RNA, or a fragment thereof, to effect regulation or function or suppression of the target gene. For example, in some embodiments, a non-coding RNA molecule has 100 percent sequence identity or at least about 30, 40, 45, 50, 55, 60, 65, 70, 75, 80, 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 150, 200, 300, 400, 500 or more contiguous nucleotides in the target RNA (or family members of a given target gene).

As used herein, a non-coding RNA molecules, or their processed small RNA forms, are said to exhibit "complete complementarity" when every nucleotide of one of the sequences read 5' to 3' is complementary to every nucleotide of the other sequence when read 3' to 5'. A nucleotide sequence that is completely complementary to a reference nucleotide sequence will exhibit a sequence identical to the reverse complement sequence of the reference nucleotide sequence.

Methods for determining sequence complementarity are well known in the art and include, but not limited to, bioinformatics tools which are well known in the art (e.g. BLAST, multiple sequence alignment).

According to one embodiment, if the non-coding RNA molecule is or processed into a siRNA, the complementarity is in the range of 90-100% (e.g. 100%) to its target sequence.

According to one embodiment, if the non-coding RNA molecule is or processed into a miRNA or piRNA the complementarity is in the range of 33-100% to its target sequence.

According to one embodiment, if the non-coding RNA molecule is a miRNA, the seed sequence complementarity (i.e. nucleotides 2-8 from the 5') is in the range of 85-100% (e.g. 100%) to its target sequence.

According to one embodiment, the non-coding RNA can be further processed into a small RNA form (e.g. pre-miRNA is processed into a mature miRNA). In such a case, homology is measured based on the processed small RNA form (e.g. the mature miRNA sequence).

As used herein, the term "small RNA form" refers to the mature small RNA being capable of hybridizing with a target RNA (or fragment thereof). According to one embodiment, the small RNA form has a silencing activity.

According to one embodiment, the complementarity to the target sequence is at least about 33% of the processed small RNA form (e.g. 33 of the 21-28 nt). Thus, for example, if the non-coding RNA molecule is a miRNA, 33% of the mature miRNA sequence (e.g. 21 nt) comprises seed complementation (e.g. 7 nt out of the 21 nt).

According to one embodiment, the complementarity to the target sequence is at least about 45% of the processed small RNA form (e.g. 45% of the 21-28 nt). Thus, for example, if the non-coding RNA molecule is a miRNA, 45% of the mature miRNA sequence (e.g. 21 nt) comprises seed complementation (e.g. 9-10 nt out of the 21 rit).

According to one embodiment, the non-coding RNA molecule (i.e. prior to modification) is typically selected as one having about 10%, 20%, 30%, 33%, 40%, 50%, 60%, 70%, 80%, 85%, 90%, 95%, 96%, 97%, 98% or up to 99% complementarity towards the sequence of the second target RNA or target RNA of interest.

According to a specific embodiment, the non-coding RNA molecule (i.e. prior to modification) is typically selected as one having no more than 99% complementarity towards the sequence of the second target RNA or target RNA of interest.

According to a specific embodiment, the non-coding RNA molecule (i.e. prior to modification) is typically selected as one having no more than 98% complementarity towards the sequence of the second target RNA or target RNA of interest.

According to a specific embodiment, the non-coding RNA molecule (i.e. prior to modification) is typically selected as one having no more than 97% complementarity towards the sequence of the second target RNA or target RNA of interest.

According to a specific embodiment, the non-coding RNA molecule (i.e. prior to modification) is typically selected as one having no more than 96% complementarity towards the sequence of the second target RNA or target RNA of interest.

According to a specific embodiment, the non-coding RNA molecule (i.e. prior to modification) is typically selected as one having no more than 95% complementarity towards the sequence of the second target RNA or target RNA of interest.

According to a specific embodiment, the non-coding RNA molecule (i.e. prior to modification) is typically selected as one having no more than 94% complementarity towards the sequence of the second target RNA or target RNA of interest.

According to a specific embodiment, the non-coding RNA molecule (i.e. prior to modification) is typically selected as one having no more than 93% complementarity towards the sequence of the second target RNA or target RNA of interest.

According to a specific embodiment, the non-coding RNA molecule (i.e. prior to modification) is typically selected as one having no more than 92% complementarity towards the sequence of the second target RNA or target RNA of interest.

According to a specific embodiment, the non-coding RNA molecule (i.e. prior to modification) is typically selected as one having no more than 91% complementarity towards the sequence of the second target RNA or target RNA of interest.

According to a specific embodiment, the non-coding RNA molecule (i.e. prior to modification) is typically selected as one having no more than 90% complementarity towards the sequence of the second target RNA or target RNA of interest.

According to a specific embodiment, the non-coding RNA molecule (i.e. prior to modification) is typically selected as one having no more than 85% complementarity towards the sequence of the second target RNA or target RNA of interest.

According to a specific embodiment, the non-coding RNA molecule (i.e. prior to modification) is typically selected as one having no more than 50% complementarity towards the sequence of the second target RNA or target RNA of interest.

According to a specific embodiment, the non-coding RNA molecule (i.e. prior to modification) is typically selected as one having no more than 33% complementarity towards the sequence of the second target RNA or target RNA of interest.

According to one embodiment, the non-coding RNA molecule (e.g. RNA silencing molecule) is designed so as to comprise at least about 33%, 40%, 45%, 50%, 55%, 60%, 70%, 80%, 85%, 90%, 91%, 92%, 93%, 94%, 95%, 96%, 97%, 98%, 99% or even 100% complementarity towards the sequence of the second target RNA or target RNA of interest.

According to a specific embodiment, the non-coding RNA molecule (e.g. RNA silencing molecule) is designed so as to comprise a minimum of 33% complementarity towards the second target RNA or target RNA of interest (e.g. 85-100% seed match).

According to a specific embodiment, the non-coding RNA molecule (e.g. RNA silencing molecule) is designed so as to comprise a minimum of 40% complementarity towards the second target RNA or target RNA of interest.

According to a specific embodiment, the non-coding RNA molecule (e.g. RNA silencing molecule) is designed so as to comprise a minimum of 45% complementarity towards the second target RNA or target RNA of interest.

According to a specific embodiment, the non-coding RNA molecule (e.g. RNA silencing molecule) is designed so as to comprise a minimum of 50% complementarity towards the second target RNA or target RNA of interest.

According to a specific embodiment, the non-coding RNA molecule (e.g. RNA silencing molecule) is designed so as to comprise a minimum of 45% complementarity towards the second target RNA or target RNA of interest.

According to a specific embodiment, the non-coding RNA molecule (e.g. RNA silencing molecule) is designed so as to comprise a minimum of 60% complementarity towards the second target RNA or target RNA of interest.

According to a specific embodiment, the non-coding RNA molecule (e.g. RNA silencing molecule) is designed so as to comprise a minimum of 70% complementarity towards the second target RNA or target RNA of interest.

According to a specific embodiment, the non-coding RNA molecule (e.g. RNA silencing molecule) is designed so as to comprise a minimum of 80% complementarity towards the second target RNA or target RNA of interest.

According to a specific embodiment, the non-coding RNA molecule (e.g. RNA silencing molecule) is designed so as to comprise a minimum of 85% complementarity towards the second target RNA or target RNA of interest.

According to a specific embodiment, the non-coding RNA molecule (e.g. RNA silencing molecule) is designed so as to comprise a minimum of 90% complementarity towards the second target RNA or target RNA of interest.

According to a specific embodiment, the non-coding RNA molecule (e.g. RNA silencing molecule) is designed so as to comprise a minimum of 91% complementarity towards the second target RNA or target RNA of interest.

According to a specific embodiment, the non-coding RNA molecule (e.g. RNA silencing molecule) is designed so as to comprise a minimum of 92% complementarity towards the second target RNA or target RNA of interest.

According to a specific embodiment, the non-coding RNA molecule (e.g. RNA silencing molecule) is designed so as to comprise a minimum of 93% complementarity towards the second target RNA or target RNA of interest.

According to a specific embodiment, the non-coding RNA molecule (e.g. RNA silencing molecule) is designed so as to comprise a minimum of 94% complementarity towards the second target RNA or target RNA of interest.

According to a specific embodiment, the non-coding RNA molecule (e.g. RNA silencing molecule) is designed so as to comprise a minimum of 95% complementarity towards the second target RNA or target RNA of interest.

According to a specific embodiment, the non-coding RNA molecule (e.g. RNA silencing molecule) is designed so as to comprise a minimum of 96% complementarity towards the second target RNA or target RNA of interest.

According to a specific embodiment, the non-coding RNA molecule (e.g. RNA silencing molecule) is designed so as to comprise a minimum of 97% complementarity towards the second target RNA or target RNA of interest.

According to a specific embodiment, the non-coding RNA molecule (e.g. RNA silencing molecule) is designed so as to comprise a minimum of 98% complementarity towards the second target RNA or target RNA of interest.

According to a specific embodiment, the non-coding RNA molecule (e.g. RNA silencing molecule) is designed so as to comprise a minimum of 99% complementarity towards the second target RNA or target RNA of interest.

According to a specific embodiment, the non-coding RNA molecule (e.g. RNA silencing molecule) is designed so as to comprise 100% complementarity towards the second target RNA or target RNA of interest.

In order to induce silencing activity and/or specificity of a non-coding RNA molecule or redirect a silencing activity and/or specificity of a non-coding RNA molecule (e.g. RNA silencing molecule) towards a second target RNA or target RNA of interest, the gene encoding a non-coding RNA molecule (e.g. RNA silencing molecule) is modified using a DNA editing agent.

Following is a description of various non-limiting examples of methods and DNA editing agents used to introduce nucleic acid alterations to a gene encoding a non-coding RNA molecule (e.g. RNA silencing molecule) and agents for implementing same that can be used according to specific embodiments of the present disclosure.

Genome Editing using engineered endonucleases—this approach refers to a reverse genetics method using artificially engineered nucleases to typically cut and create specific double-stranded breaks (DSBs) at a desired location(s) in the genome, which are then repaired by cellular endogenous processes such as, homologous recombination (HR) or non-homologous end-joining (NHEJ). NHEJ directly joins the DNA ends in a double-stranded break (DSB) with or without minimal ends trimming, while HR utilizes a homologous donor sequence as a template (i.e. the sister chromatid formed during S-phase) for regenerating/copying the missing DNA sequence at the break site. In order to introduce specific nucleotide modifications to the genomic DNA, a donor DNA repair template containing the desired sequence must be present during HR (exogenously provided single stranded or double stranded DNA).

Genome editing cannot be performed using traditional restriction endonucleases since most restriction enzymes recognize a few base pairs on the DNA as their target and these sequences often will be found in many locations across the genome resulting in multiple cuts which are not limited to a desired location. To overcome this challenge and create site-specific single- or double-stranded breaks (DSBs), several distinct classes of nucleases have been discovered and bioengineered to date. These include the meganucleases, Zinc finger nucleases (ZFNs), transcription-activator like effector nucleases (TALENs) and CRISPR/Cas9 system.

*Meganucleases*—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. *Meganucleases* are found commonly in microbial species and have the unique property of having very long recognition sequences (>14 bp) thus making them naturally very specific for cutting at a desired location.

This can be exploited to make site-specific double-stranded breaks (DSBs) in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence.

Alternatively, DNA interacting amino acids of the meganuclease can be altered to design sequence specific meganucleases (see e.g., U.S. Pat. No. 8,021,867). Meganucleases can be designed using the methods described in e.g., Certo, Mont. et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (DSBs) (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heroditner functioning nucleases avoid the possibility of unwanted homodimer activity and thus increase specificity of the double-stranded break (DSB).

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break (DSB). Repair of these double-stranded breaks (DSBs) through the non-homologous end-joining (NHEJ) pathway often results in small deletions or small sequence insertions (Indels). Since each repair made by NHEJ is unique, the use of a single nuclease pair can produce an allelic series with a range of different insertions or deletions at the target site.

In general NHEJ is relatively accurate (about 85% of DSBs in human cells are repaired by NHEJ within about 30 min from detection) in gene editing erroneous NHEJ is relied upon as when the repair is accurate the nuclease will keep cutting until the repair product is mutagenic and the recognition/cut site/PAM motif is gone/mutated or that the transiently introduced nuclease is no longer present.

The deletions typically range anywhere from a few base pairs to a few hundred base pairs in length, but larger deletions have been successfully generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break (DSB) can be repaired via homologous recombination (HR) to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers are typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, Calif.).

T-GEE system (TargetGene's Genome Editing Engine)—A programmable nucleoprotein molecular complex containing a polypeptide moiety and a specificity conferring nucleic acid. (SCNA) which assembles in-vivo, in a target cell, and is capable of interacting with the predetermined target nucleic acid sequence is provided. The programmable nucleoprotein molecular complex is capable of specifically modifying and/or editing a target site within the target nucleic acid sequence and/or modifying the function of the target nucleic acid sequence. Nucleoprotein composition comprises (a) polynucleotide molecule encoding a chimeric polypeptide and comprising (i) a functional domain capable of modifying the target site, and (ii) a linking domain that is capable of interacting with a specificity conferring nucleic acid, and (b) specificity conferring nucleic acid (SCNA) comprising (i) a nucleotide sequence complementary to a region of the target nucleic acid flanking the target site, and (ii) a recognition region capable of specifically attaching to the linking domain of the polypeptide. The composition enables modifying a predetermined nucleic acid sequence target precisely, reliably and cost-effectively with high specificity and binding capabilities of molecular complex to the target nucleic acid through base-pairing of specificity-conferring nucleic acid and a target nucleic acid. The composition is less genotoxic, modular in their assembly, utilize single platform without customization, practical for independent use outside of specialized core-facilities, and has shorter development time frame and reduced costs.

CRISPR-Cas system and all its variants (also referred to herein as "CRISPR")—Many bacteria and archea contain endogenous RNA-based adaptive immune systems that can degrade nucleic acids of invading phages and plasmids. These systems consist of clustered regularly interspaced short palindromic repeat (CRISPR) nucleotide sequences that produce RNA components and CRISPR associated (Cas) genes that encode protein components. The CRISPR. RNAs (crRNAs) contain short stretches of homology to the DNA of specific viruses and plasmids and act as guides to direct Cas nucleases to degrade the complementary nucleic acids of the corresponding pathogen. Studies of the type II CRISPR-Cas system of *Streptococcus pyogenes* have shown that three components form a RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821).

It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded breaks (DSBs) in a variety of different species (Cho et al., 2013; Cong et al., 2013; DiCarlo et al., 2013; Hwang et 2013a,b; Jinek et al., 2013; Mali et al., 2013).

The CRISPR/Cas system for genome editing contains two distinct components: a gRNA and an endonuclease e.g. Cas9.

The gRNA (also referred to herein as short guide RNA (sgRNA)) is typically a 20-nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break (DSB). Just as with ZFNs and TALENs, the double-stranded breaks (DSBs) produced by CRISPR/Cas can undergo homologous recombination or NHEJ and are susceptible to specific sequence modification during DNA repair.

The Cas9 nuclease has two functional domains: RuvC and HNH, each cutting a different DNA strand. When both of these domains are active, the Cas9 causes double strand breaks (DSBs) in the genomic DNA.

A significant advantage of CRISPR/Cas is that the high efficiency of this system is coupled with the ability to easily create synthetic gRNAs. This creates a system that can be readily modified to target modifications at different genomic sites and/or to target different modifications at the same site. Additionally, protocols have been established which enable simultaneous targeting of multiple genes. The majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is mostly repaired by single strand break repair mechanism involving proteins such as but not only, PARP (sensor) and XRCC1/LIG III complex (ligation). If a single strand break (SSB) is generated by topoisomerase I poisons or by drugs that trap PARP1 on naturally occurring SSBs then these could persist and when the cell enters into S-phase and the replication fork encounter such SSBs they will become single ended DSBs which can only be repaired by HR. However, two proximal, opposite strand nicks introduced by a Cas9 nickase are treated as a double-strand break, in what is often referred to as a 'double nick' CRISPR system. A double-nick, which is basically non-parallel DSB, can be repaired like other DSBs by HR or NHEJ depending on the desired effect on the gene target and the presence of a donor sequence and the cell cycle stage (HR is of much lower abundance and can only occur in S and G2 stages of the cell cycle). Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that are not likely to change the genomic DNA, even though these events are not impossible.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publicly available tools available to help choose and/or design target sequences as well as lists of bioinfomiatically determined unique gRNAs for different genes in different species such as, but not limited to, the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and a Cas endonuclease (e.g. Cas9) should be expressed or present (e.g., as a ribonucleoprotein complex) in a target cell. The insertion vector can contain both cassettes on a single plasmid or the cassettes are expressed from two separate plasmids. CRISPR plasmids are commercially available such as the px330 plasmid from Addgene (75 Sidney St, Suite 550A • Cambridge, Mass. 02139). Use of clustered regularly interspaced short palindromic repeats (CRISPR)-associated (Cas)-guide RNA technology and a Cas endonuclease for modifying plant genomes are also at least disclosed by Svitashev et al., 2015, Plant Physiology, 169 (2): 931-945; Kumar and Jain, 2015, J Exp Bot 66: 47-57; and in U.S. Patent Application Publication No. 20150082478, which is specifically incorporated herein by reference in its entirety. Cas endonucleases that can be used to effect DNA editing with gRNA include, but are not limited to, Cas9, Cpf1 (Zetsche et al., 2015, Cell. 163(3):759-71), C2c1, C2c2, and C2c3 (Shmakov et al., Mol Cell. 2015 Nov. 5; 60(3):385-97).

According to a specific embodiment, the CRISPR comprises a short guide RNA (sgRNA) comprising a nucleic acid sequence selected from the group consisting of SEQ ID NOs: 1-4 or SEQ ID NOs: 235-366.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, introduced into the cells, and positive selection is performed to isolate homologous recombination mediated events. The DNA carrying the homologous sequence can be provided as a plasmid, single or double stranded oligo. These homologous recombinants contain a local duplication that is separated by intervening vector sequence, including the selection cassette. In the second step, targeted clones are subjected to negative selection to identify cells that have lost the selection cassette via intra-chromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After the system components have been introduced to the cell and positive selection applied, HR mediated events could be identified. Next, a second targeting vector that contains a region of homology with the desired mutation is introduced into targeted clones, and negative selection is applied to remove the selection cassette and introduce the mutation. The final allele contains the desired mutation while eliminating unwanted exogenous sequences.

According to a specific embodiment, the DNA editing agent comprises a DNA targeting module (e.g., gRNA).

According to a specific embodiment, the DNA editing agent does not comprise an endonuclease.

According to a specific embodiment, the DNA editing agent comprises a nuclease (e.g. an endonuclease) and a DNA targeting module (e.g., gRNA).

According to a specific embodiment, the DNA editing agent is CRISPR/Cas, e.g. gRNA and Cas9.

According to a specific embodiment, the DNA editing agent is TALEN.

According to a specific embodiment, the DNA editing agent is ZFN.

According to a specific embodiment, the DNA editing agent is meganuclease.

According to one embodiment, the DNA editing agent is linked to a reporter for monitoring expression in a plant cell.

According to one embodiment, the reporter is a fluorescent reporter protein.

The term "a fluorescent protein" refers to a polypeptide that emits fluorescence and is typically detectable by flow cytometry, microscopy or any fluorescent imaging system, therefore can be used as a basis for selection of cells expressing such a protein.

Examples of fluorescent proteins that can be used as reporters are, without being limited to, the Green Fluorescent Protein (GFP), the Blue Fluorescent Protein (BFP) and the red fluorescent proteins (e.g. dsRed, mCherry, RFP). A non-limiting list of fluorescent or other reporters includes proteins detectable by luminescence (e.g. luciferase) or colorimetric assay (e.g. GUS). According to a specific embodiment, the fluorescent reporter is a red fluorescent protein (e.g. dsRed, mCherry, RFP) or GFP.

A review of new classes of fluorescent proteins and applications can be found in Trends in Biochemical Sciences [Rodriguez, Erik A.; Campbell, Robert E.; Lin, John Y.; Lin, Michael Z.; Miyawaki, Atsushi; Palmer, Amy E.; Shu, Xiaokun; Mang, Jin; Tsien, Roger Y. *"The Growing and Glowing hotbox of Fluorescent and Photoactive Proteins"*. *Trends in Biochemical Sciences*. doi:10.1016/j.tibs.2016.09.010].

According to another embodiment, the reporter is an endogenous gene of a plant. An exemplary reporter is the phytoene desaturase gene (PDS3) which encodes one of the important enzymes in the carotenoid biosynthesis pathway. Its silencing produces an albino/bleached phenotype. Accordingly, plants with reduced expression of PDS3 exhibit reduced chlorophyll levels, up to complete albino and dwarfism. Additional genes which can be used in accordance with the present teachings include, but are not limited to, genes which take part in crop protection. Exemplary genes are described in Table 1B, below.

According to another embodiment, the reporter is an antibiotic selection marker. Examples of antibiotic selection markers that can be used as reporters are, without being limited to, neomycin phosphotransferase II (nptII) and hygromycin phosphotransferase (hpt). Additional marker genes which can be used in accordance with the present teachings include, but are not limited to, gentamycin acetyltransferase (accC3) resistance and bleomycin and phleomycin resistance genes.

It will be appreciated that the enzyme NPTII inactivates by phosphorylation a number of aminoglycoside antibiotics such as kanamycin, neomycin, geneticin (or G418) and paromomycin. Of these, kanamycin, neomycin and paromomycin are used in a diverse range of plant species.

According to another embodiment, the reporter is a toxic selection marker. An exemplary toxic selection marker that can be used as a reporter is, without being limited to, allyl alcohol selection using the Alcohol dehydrogenase (ADH1) gene. ADH1, comprising a group of dehydrogenase enzymes which catalyse the interconversion between alcohols and aldehydes or ketones with the concomitant reduction of NAD+ or NADP+, breaks down alcoholic toxic substances within tissues. Plants harbouring reduced ADH1 expression exhibit increase tolerance to allyl alcohol. Accordingly, plants with reduced ADH1 are resistant to the toxic effect of allyl alcohol.

Regardless of the DNA editing agent used, the method of the invention is employed such that the gene encoding the non-coding RNA molecule (e.g. RNA silencing molecule) is modified by at least one of a deletion, an insertion or a point mutation.

According to one embodiment, the modification is in a structured region of the non-coding RNA molecule or the RNA silencing molecule.

According to one embodiment, the modification is in a stem region of the non-coding RNA molecule or the RNA silencing molecule.

According to one embodiment, the modification is in a loop region of the non-coding RNA molecule or the RNA silencing molecule.

According to one embodiment, the modification is in a stem region and a loop region of the non-coding RNA molecule or the RNA silencing molecule.

According to one embodiment, the modification is in a non-structured region of the non-coding RNA molecule or the RNA silencing molecule.

According to one embodiment, the modification is in a stem region and a loop region and in non-structured region of the non-coding RNA molecule or the RNA silencing molecule.

According to a specific embodiment, the modification comprises a modification of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the modification comprises a modification of at most 1, 2, 3, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to one embodiment, the modification can be in a consecutive nucleic acid sequence at least 5, 10, 20, 30, 40, 50, 100, 150, 200 bases).

According to one embodiment, the modification can be in a non-consecutive manner, e.g. throughout a 20, 50, 100, 150, 200, 500, 1000 nucleic acid sequence.

According to a specific embodiment, the modification comprises a modification of at most 200 nucleotides.

According to a specific embodiment, the modification comprises a modification of at most 150 nucleotides.

According to a specific embodiment, the modification comprises a modification of at most 100 nucleotides.

According to a specific embodiment, the modification comprises a modification of at most 50 nucleotides.

According to a specific embodiment, the modification comprises a modification of at most 25 nucleotides.

According to a specific embodiment, the modification comprises a modification of at most 20 nucleotides.

According to a specific embodiment, the modification comprises a modification of at most 15 nucleotides.

According to a specific embodiment, the modification comprises a modification of at most 10 nucleotides.

According to a specific embodiment, the modification comprises a modification of at most 5 nucleotides.

According to one embodiment, the modification depends on the structure of the RNA silencing molecule.

Accordingly, when the RNA silencing molecule contains a non-essential structure (i.e. a secondary structure of the RNA silencing molecule which does not play a role in its proper biogenesis and/or function) or is purely dsRNA (i.e. the RNA silencing molecule having a perfect or almost perfect dsRNA), a few modifications (e.g. 20-30 nucleotides, e.g. 1-10 nucleotides, e.g. 5 nucleotides) are introduced in order to redirect the silence specificity of the RNA silencing molecule.

According to another embodiment, when the RNA silencing molecule has an essential structure (i.e. the proper biogenesis and/or activity of the RNA silencing molecule is dependent on its secondary structure), larger modifications (e.g. 10-200 nucleotides, e.g. 50-150 nucleotides, e.g., more than 30 nucleotides and not exceeding 200 nucleotides, 30-200 nucleotides, 35-200 nucleotides, 35-150 nucleotides, 35-100 nucleotides) are introduced in order to redirect the silence specificity of the RNA silencing molecule.

According to one embodiment, the modification is such that the recognition/cut site/PAM motif of the RNA silencing molecule is modified to abolish the original PAM recognition site.

According to a specific embodiment, the modification is in at least 1, 2, 3, 4, 5, 6, 7, 8, 9, 10 or more nucleic acids in a PAM motif.

According to one embodiment, the modification comprises an insertion.

According to a specific embodiment, the insertion comprises an insertion of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the insertion comprises an insertion of at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the insertion comprises an insertion of at most 200 nucleotides.

According to a specific embodiment, the insertion comprises an insertion of at most 150 nucleotides.

According to a specific embodiment, the insertion comprises an insertion of at most 100 nucleotides.

According to a specific embodiment, the insertion comprises an insertion of at most 50 nucleotides.

According to a specific embodiment, the insertion comprises an insertion of at most 25 nucleotides.

According to a specific embodiment, the insertion comprises an insertion of at most 20 nucleotides.

According to a specific embodiment, the insertion comprises an insertion of at most 15 nucleotides.

According to a specific embodiment, the insertion comprises an insertion of at most 10 nucleotides.

According to a specific embodiment, the insertion comprises an insertion of at most 5 nucleotides.

According to one embodiment, the modification comprises a deletion.

According to a specific embodiment, the deletion comprises a deletion of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the deletion comprises a deletion of at most 1, 2, 3, 4, 5, 6, 7, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e g. RNA silencing molecule).

According to a specific embodiment, the deletion comprises a deletion of at most 200 nucleotides.

According to a specific embodiment, the deletion comprises a deletion of at most 150 nucleotides.

According to a specific embodiment, the deletion comprises a deletion of at most 100 nucleotides.

According to a specific embodiment, the deletion comprises a deletion of at most 50 nucleotides.

According to a specific embodiment, the deletion comprises a deletion of at most 25 nucleotides.

According to a specific embodiment, the deletion comprises a deletion of at most 20 nucleotides.

According to a specific embodiment, the deletion comprises a deletion of at most 15 nucleotides.

According to a specific embodiment, the deletion comprises a deletion of at most 10 nucleotides.

According to a specific embodiment, the deletion comprises a deletion of at most 5 nucleotides.

According to one embodiment, the modification comprises a point mutation.

According to a specific embodiment, the point mutation comprises a point mutation of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the point mutation comprises a point mutation in at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the point mutation comprises a point mutation in at most 200 nucleotides.

According to a specific embodiment, the point mutation comprises a point mutation in at most 150 nucleotides.

According to a specific embodiment, the point mutation comprises a point mutation in at most 100 nucleotides.

According to a specific embodiment, the point mutation comprises a point mutation in at most 50 nucleotides.

According to a specific embodiment, the point mutation comprises a point mutation in at most 25 nucleotides.

According to a specific embodiment, the point mutation comprises a point mutation in at most 20 nucleotides.

According to a specific embodiment, the point mutation comprises a point mutation in at most 15 nucleotides.

According to a specific embodiment, the point mutation comprises a point mutation in at most 10 nucleotides.

According to a specific embodiment, the point mutation comprises a point mutation in at most 5 nucleotides.

According to one embodiment, the modification comprises a combination of any of a deletion, an insertion and/or a point mutation.

According to one embodiment, the modification comprises nucleotide replacement (e.g nucleotide swapping).

According to a specific embodiment, the swapping comprises swapping of about 10-250 nucleotides, about 10-200 nucleotides, about 10-150 nucleotides, about 10-100 nucleotides, about 10-50 nucleotides, about 1-50 nucleotides, about 1-10 nucleotides, about 50-150 nucleotides, about 50-100 nucleotides or about 100-200 nucleotides (as compared to the native non-coding RNA molecule, e.g. RNA silencing molecule).

According to one embodiment, the nucleotide swap comprises a nucleotide replacement at most 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 60, 70, 80, 90, 100, 110, 120, 130, 140, 150, 160, 170, 180, 190, 200 or at most 250 nucleotides (as compared to the native non-coding RNA molecule, e.g. RNA silencing molecule).

According to a specific embodiment, the nucleotide swapping comprises a nucleotide replacement in at most 200 nucleotides.

According to a specific embodiment, the nucleotide swapping comprises a nucleotide replacement in at most 150 nucleotides.

According to a specific embodiment, the nucleotide swapping comprises a nucleotide replacement in at most 100 nucleotides.

According to a specific embodiment, the nucleotide swapping comprises a nucleotide replacement in at most 50 nucleotides.

According to a specific embodiment, the nucleotide swapping comprises a nucleotide replacement in at most 25 nucleotides.

According to a specific embodiment, the nucleotide swapping comprises a nucleotide replacement in at most 20 nucleotides.

According to a specific embodiment, the nucleotide swapping comprises a nucleotide replacement in at most 15 nucleotides.

According to a specific embodiment, the nucleotide swapping comprises a nucleotide replacement in at most 10 nucleotides.

According to a specific embodiment, the nucleotide swapping comprises a nucleotide replacement in at most 5 nucleotides.

According to one embodiment, the gene encoding the non-coding RNA molecule (e.g. RNA silencing molecule) is modified by swapping a sequence of an endogenous RNA silencing molecule (e.g. miRNA) with a RNA silencing sequence of choice (e.g. siRNA).

According to a specific embodiment, the sequence of a siRNA used for gene swapping of an endogenous RNA silencing molecule (e.g. miRNA) comprising a nucleic acid sequence selected from the group consisting of SEQ ID NOs: 5-12 or SEQ ID NOs: 103-234.

According to one embodiment, the guide strand of the non-coding RNA molecule (e.g. RNA silencing molecule such as miRNA precursors (pri/pre-miRNAs) or siRNA precursors (dsRNA)) is modified to preserve originality of structure and keep the same base pairing profile.

According to one embodiment, the passenger strand of the non-coding RNA molecule (e.g. RNA silencing molecule such as miRNA precursors (pri/pre-miRNAs) or siRNA precursors (dsRNA)) is modified to preserve originality of structure and keep the same base pairing profile.

As used herein, the term "originality of structure" refers to the secondary RNA structure (i.e. base pairing profile). Keeping the originality of structure is important for correct and efficient biogenesis/processing of the non-coding RNA (e.g. RNA silencing molecule such as siRNA or miRNA) that is structure—and not purely sequence-dependent.

According to one embodiment, the non-coding RNA (e.g. RNA silencing molecule) is modified in the guide strand (silencing strand) as to comprise about 50-100% complementarity to the target RNA (as discussed above) while the passenger strand is modified to preserve the original (unmodified) non-coding RNA structure.

According to one embodiment, the non-coding RNA (e.g. RNA silencing molecule) is modified such that the seed sequence (e.g. for miRNA nucleotides 2-8 from the 5' terminal) is complimentary to the target sequence.

According to a specific embodiment, the RNA silencing molecule (i.e. RNAi molecule) is designed such that a sequence of the RNAi molecule is modified to preserve originality of structure and to be recognized by cellular RNAi processing and executing factors.

According to a specific embodiment, the non-coding RNA molecule (i.e. rRNA, tRNA, lncRNA, snoRNA, etc.) is designed such that a sequence of the RNAi molecule is modified to be recognized by cellular. RNAi processing and executing factors.

The DNA editing agent of the invention may be introduced into plant cells using DNA delivery methods (e.g. by expression vectors) or using DNA-free methods.

According to one embodiment, the gRNA (or any other DNA recognition module used, dependent on the DNA editing system that is used) can be provided as RNA to the cell.

Thus, it will be appreciated that the present techniques relate to introducing the DNA editing agent using transient DNA or DNA-free methods such as RNA transfection (e.g. mRNA+gRNA transfection), or Ribonucleoprotein (RNP) transfection (e.g. protein-RNA complex transfection, e.g. Cas9/gRNA ribonucleoprotein (RNP) complex transfection).

For example, Cas9 can be introduced as a DNA expression plasmid, in vitro transcript (i.e. RNA), or as a recombinant protein bound to the RNA portion in a ribonucleoprotein particle (RNP). gRNA, for example, can be delivered either as a DNA plasmid or as an in vitro transcript (i.e. RNA).

Any method known in the art for RNA or RNP transfection can be used in accordance with the present teachings, such as, but not limited to microinjection [as described by Cho et al., "Heritable gene knockout in *Caenorhabditis elegans* by direct injection of Cas9-sgRNA ribonucleoproteins," *Genetics* (2013) 195:1177-1180, incorporated herein by reference], electroporation [as described by Kim et al., "Highly efficient RNA-guided genome editing in human cells via delivery of purified Cas9 ribonucleoproteins" *Genome Res.* (2014) 24:1012-1019, incorporated herein by reference], or lipid-mediated transfection e.g. using liposomes [as described by Zuris et al., "Cationic lipid-mediated delivery of proteins enables efficient protein-based genome editing in vitro and in vivo" *Nat Biotechnol.* (2014) doi: 1.0.1038/nbt.3081, incorporated herein by reference]. Additional methods of RNA transfection are described in U.S. Patent Application No. 20160289675, incorporated herein by reference in its entirety.

One advantage of RNA transfection methods of the invention is that RNA transfection is essentially transient and vector-free. A RNA transgene can be delivered to a cell and expressed therein, as a minimal expressing cassette without the need for any additional sequences (e.g. viral sequences).

According to one embodiment, the DNA editing agent of the invention is introduced into the plant cell using expression vectors.

The "expression vector" (also referred to herein as "a nucleic acid construct", "vector" or "construct") of some embodiments of the invention includes additional sequences which render this vector suitable for replication in prokaryotes, eukaryotes, or preferably both (e.g., shuttle vectors).

Constructs useful in the methods according to some embodiments of the invention may be constructed using recombinant DNA technology well known to persons skilled in the art. The nucleic acid sequences may be inserted into vectors, which may be commercially available, suitable for transforming into plants and suitable for transient expression of the gene of interest in the transformed cells. The genetic construct can be an expression vector wherein the nucleic acid sequence is operably linked to one or more regulatory sequences allowing expression in the plant cells.

According to one embodiment, in order to express a functional DNA editing agent, in cases where the cleaving module (nuclease) is not an integral part of the DNA recognition unit, the expression vector may encode the cleaving module as well as the DNA recognition unit (e.g. gRNA in the case of CRISPR/Cas).

Alternatively, the cleaving module (nuclease) and the DNA recognition unit (e.g. gRNA) may be cloned into separate expression vectors. In such a case, at least two different expression vectors must be transformed into the same plant cell.

Alternatively, when a nuclease is not utilized (i.e. not administered from an exogenous source to the cell), the DNA recognition unit (e.g. gRNA) may be cloned and expressed using a single expression vector.

Typical expression vectors may also contain a transcription and translation initiation sequence, transcription and translation terminator and optionally a polyadenylation signal.

According to one embodiment, the DNA editing agent comprises a nucleic acid agent encoding at least one DNA recognition unit (e.g. gRNA) operatively linked to a cis-acting regulatory element active in plant cells (e.g., promoter).

According to one embodiment, the nuclease (e.g. endonuclease) and the DNA recognition unit (e.g. gRNA) are encoded from the same expression vector. Such a vector may comprise a single cis-acting regulatory element active in plant cells (e.g., promoter) for expression of both the nuclease and the DNA recognition unit. Alternatively, the nuclease and the DNA recognition unit may each be operably linked to a cis-acting regulatory element active in plant cells (e.g., promoter).

According to one embodiment, the nuclease (e.g. endonuclease) and the DNA recognition unit (e.g. gRNA) are encoded from different expression vectors whereby each is operably linked to a cis-acting regulatory element active in plant cells (e.g., promoter).

As used herein the phrase "plant-expressible" or "active in plant cells" refers to a promoter sequence, including any additional regulatory elements added thereto or contained therein, that is at least capable of inducing, conferring, activating or enhancing expression in a plant cell, tissue or organ, preferably a monocotyledonous or dicotyledonous plant cell, tissue, or organ.

The plant promoter employed can be a constitutive promoter, a tissue specific promoter, an inducible promoter, a chimeric promoter or a developmentally regulated promoter.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
| --- | --- | --- |
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107121, 1996 |
| CVMV (Cassava Vein Mosaic Virus) | constitutive | Lawrenson et al, Gen Biol 16: 258, 2015 |
| U6 (AtU626; TaU6) | constitutive | Lawrenson et al, Gen Biol 16: 258, 2015 |

TABLE II

Exemplary seed-preferred promoters for use in the performance of some embodiments of the invention

| Gene Source | Expression Pattern | Reference |
| --- | --- | --- |
| Seed specific genes | seed | Simon, et al., Plant Mol. Biol. 5. 191, 1985; Scofield, et al., J. Biol. Chem. 262: 12202, 1987; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltrl promoter | endosperm | |

TABLE II-continued

Exemplary seed-preferred promoters for use in the performance of some embodiments of the invention

| Gene Source | Expression Pattern | Reference |
|---|---|---|
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice -globulin Glb-1 | endosperm | Wu et al, Plant Cell Physiology 398) 885-889, 1998 |
| rice OSH1 | emryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorgum gamma- kafirin | endosperm | PMB 32: 1029-35, 1996 |
| KNOX | emryo | Postma-Haarsma ef al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, et al., Plant Mol. Biol. 19: 873-876, 1992 |

TABLE III

Exemplary flower-specific promoters for use in the performance of the invention

| Gene Source | Expression Pattern | Reference |
|---|---|---|
| AtPRP4 | flowers | www(dot)salus(dot)medium(dot)edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala- 3 | flowers | |

TABLE IV

Alternative rice promoters for use in the performance of the invention

| PRO # | Gene | Expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl- CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 | strong root |
| PR00111 | uclacyanin 3-like protein | weak discrimination center/shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha- globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |

TABLE IV-continued

Alternative rice promoters for use in the performance of the invention

| PRO # | Gene | Expression |
| --- | --- | --- |
| PRO0200 | OSHI | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PR00228 | BLZ-2_long (barley) | |

The inducible promoter is a promoter induced in a specific plant tissue, by a developmental stage or by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters NT, NPS, prxEa, Ha hsp17.7G4 and RD21 active in high salinity and osmotic stress, and the promoters hsr203J and str246C active in pathogenic stress.

According to one embodiment the promoter is a pathogen-inducible promoter. These promoters direct the expression of genes in plants following infection with a pathogen such as bacteria, fungi, viruses, nematodes and insects. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. I. Plant Pathol* 89:245-254; Uknes et al. (1992) *Plant cell* 4:645-656; and Van Loon (1985) *Plant Mol. Virol.* 4:111-116.

According to one embodiment, when more than one promoter is used in the expression vector, the promoters are identical (e.g., all identical, at least two identical).

According to one embodiment, when more than one promoter is used in the expression vector, the promoters are different (e.g., at least two are different, all are different).

According to one embodiment, the promoter in the expression vector includes, but is not limited to, CaMV 35S, 2× CaMV 35S, CaMV 19S, ubiquitin, AtU626 or. TaU6.

According to a specific embodiment, the promoter in the expression vector comprises a 35S promoter.

According to a specific embodiment, the promoter in the expression vector comprises a U6 promoter.

Expression vectors may also comprise transcription and translation initiation sequences, transcription and translation terminator sequences and optionally a polyadenylation signal.

According to a specific embodiment, the expression vector comprises a termination sequence, such as but not limited to, a G7 termination sequence, an AtuNos termination sequence or a CaMV-35S terminator sequence.

Plant cells may be transformed stably or transiently with the nucleic acid constructs of some embodiments of the invention. In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

According to one embodiment, an *agrobacterium*-free expression method is used to introduce foreign genes into plant cells. According to one embodiment, the *agrobacterium*-free expression method is transient. According to a specific embodiment, a bombardment method is used to introduce foreign genes into plant cells. According to another specific embodiment, bombardment of a plant root is used to introduce foreign genes into plant cells. An exemplary bombardment method which can be used in accordance with some embodiments of the invention is discussed in the examples section which follows.

Furthermore, various cloning kits or gene synthesis can be used according to the teachings of some embodiments of the invention.

According to one embodiment the nucleic acid construct is a binary vector. Examples for binary vectors are pBIN19, pBI101, pBinAR, pGPTV, pCAMBIA, pBIB-HYG, pBecks, pGreen or pPZP (Hajukiewicz, P. et at, Plant Mol. Biol. 25, 989 (1994), and Helens et al, Trends in Plant Science 5, 446 (2000)).

Examples of other vectors to be used in other methods of DNA delivery (e.g. transfection, electroporation, bombardment, viral inoculation as discussed below) are: pGE-sgRNA (Zhang et al. Nat. Comms. 2016 7:12697), pJIT163-Ubi-Cas9 (Wang et al. Nat. Biotechnol 2004 32, 947-951), pICH47742::2x35S-5'UTR-hCas9(STOP)-NOST (Belhan et al. Plant Methods 2013 11; 9(1):39), pAHC25 (Christensen, A. H. & P. H. Quail, 1996. Ubiquitin promoter-based vectors for high-level expression of selectable and/or screenable marker genes in monocotyledonous plants. Transgenic Research 5: 213-218), pHBT-sGFP(S65T)-NOS (Sheen et al. Protein phosphatase activity is required for light-inducible gene expression in maize, EMBO J. 12 (9), 3497-3505 (1993).

According to one embodiment, the method of some embodiments of the invention further comprises introducing into the plant cell donor oligonucleotides.

According to one embodiment, when the modification is an insertion, the method further comprises introducing into the plant cell donor oligonucleotides.

According to one embodiment, when the modification is a deletion, the method further comprises introducing into the plant cell donor oligonucleotides.

According to one embodiment, when the modification is a deletion and insertion (e.g. swapping), the method further comprises introducing into the plant cell donor oligonucleotides.

According to one embodiment, when the modification is a point mutation, the method further comprises introducing into the plant cell donor oligonucleotides.

As used herein, the term "donor oligonucleotides" or "donor oligos" refers to exogenous nucleotides, i.e. externally introduced into the plant cell to generate a precise change in the genome.

According to one embodiment, the donor oligonucleotides are synthetic.

According to one embodiment, the donor oligos are RNA oligos.

According to one embodiment, the donor oligos are DNA oligos.

According to one embodiment, the donor oligos are synthetic oligos.

According to one embodiment, the donor oligonucleotides comprise single-stranded donor oligonucleotides (ssODN).

According to one embodiment, the donor oligonucleotides comprise double-stranded donor oligonucleotides (dsODN).

According to one embodiment, the donor oligonucleotides comprise double-stranded DNA (dsDNA).

According to one embodiment, the donor oligonucleotides comprise double-stranded DNA-RNA duplex (DNA-RNA duplex).

According to one embodiment, the donor oligonucleotides comprise double-stranded DNA-RNA hybrid.

According to one embodiment, the donor oligonucleotides comprise single-stranded DNA-RNA hybrid.

According to one embodiment, the donor oligonucleotides comprise single-stranded DNA (ssDNA).

According to one embodiment, the donor oligonucleotides comprise double-stranded RNA (dsRNA).

According to one embodiment, the donor oligonucleotides comprise single-stranded RNA (ssRNA).

According to one embodiment, the donor oligonucleotides comprise the DNA or RNA sequence for swapping (as discussed above).

According to one embodiment, the donor oligonucleotides are provided in a non-expressed vector format or oligo.

According to one embodiment, the donor oligonucleotides comprise a DNA donor plasmid (e.g. circular or linearized plasmid).

According to one embodiment, the donor oligonucleotides comprise about 50-5000, about 100-5000, about 250-5000, about 500-5000, about 750-5000, about 1000-5000, about 1500-5000, about 2000-5000, about 2500-5000, about 3000-5000, about 4000-5000, about 50-4000, about 100-4000, about 250-4000, about 500-4000, about 750-4000, about 1000-4000, about 1500-4000, about 2000-4000, about 2500-4000, about 3000-4000, about 50-3000, about 100-3000, about 250-3000, about 500-3000, about 750-3000, about 1000-3000, about 1500-3000, about 2000-3000, about 50-2000, about 100-2000, about 250-2000, about 500-2000, about 750-2000, about 1000-2000, about 1500-2000, about 50-1000, about 100-1000, about 250-1000, about 500-1000, about 750-1000, about 50-750, about 150-750, about 250-750, about 500-750, about 50-500, about 150-500, about 200-500, about 250-500, about 350-500, about 50-250, about 150-250, or about 200-250 nucleotides.

According to a specific embodiment, the donor oligonucleotides comprising the ssODN (e.g. ssDNA or ssRNA) comprise about 200-500 nucleotides.

According to a specific embodiment, the donor oligonucleotides comprising the dsODN (e.g. dsDNA or dsRNA) comprise about 250-5000 nucleotides.

According to one embodiment, for gene swapping of an endogenous RNA silencing molecule (e.g. miRNA) with a RNA silencing sequence of choice (e.g. siRNA), the expression vector, ssODN (e.g. ssDNA or ssRNA) or dsODN (e.g. dsDNA or dsRNA) does not have to be expressed in a plant cell and could serve as a non-expressing template. According to a specific embodiment, in such a case only the DNA editing agent (e.g. Cas9/sgRNA modules) need to be expressed if provided in a DNA form.

According to some embodiments, for gene editing of an endogenous non-coding RNA molecule (e.g. RNA silencing molecule) without the use of a nuclease, the DNA editing agent (e.g., gRNA) may be introduced into the eukaryotic cell with our without (e.g. oligonucleotide donor DNA or RNA, as discussed herein).

According to one embodiment, introducing into the plant cell donor oligonucleotides is effected using any of the methods described above (e.g. using the expression vectors or RNP transfection).

According to one embodiment, the gRNA and the DNA donor oligonucleotides are co-introduced into the plant cell (e.g. via bombardment). It will be appreciated that any additional factors (e.g. nuclease) may be co-introduced therewith.

According to one embodiment, the gRNA is introduced into the plant cell prior to the DNA donor oligonucleotides (e.g. within a few minutes or a few hours). It will be appreciated that any additional factors (e.g. nuclease) may be introduced prior to, concomitantly with, or following the gRNA or the DNA donor oligonucleotides.

According to one embodiment, the gRNA is introduced into the plant cell subsequent to the DNA donor oligonucleotides (e.g. within a few minutes or a few hours). It will be appreciated that any additional factors (e.g. nuclease) may be introduced prior to, concomitantly with, or following the gRNA or the DNA donor oligonucleotides.

According to one embodiment, there is provided a composition comprising at least one gRNA and DNA donor oligonucleotides for genome editing.

According to one embodiment, there is provided a composition comprising at least one gRNA, a nuclease (e.g. endonuclease) and DNA donor oligonucleotides for genome editing.

There are various methods of direct DNA transfer into plant cells and the skilled artisan will know which to select. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or gold or tungsten particles, and the microprojectiles are physically accelerated into protoplasts, cells or plant tissues.

Thus, the delivery of nucleic acids may be introduced into a plant cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by Agrobacterium-mediated transformation (See, e.g., U.S. Pat. Nos. 5,563,055, 5,591,616, 5,693,512, 5,824,877, 5,981,840, and 6,384,301); by acceleration of DNA-coated particles (See, e.g., U.S. Pat. Nos. 5,015,580, 5,550,318, 5,538,880, 6,160,208, 6,399,861, and 6,403,865) and by Nanoparticles, nanocarriers and cell penetrating peptides (WO201126644A2; WO2009046384A1; WO2008148223A1) in the methods to deliver DNA, RNA, Peptides and/or proteins or combinations of nucleic acids and peptides into plant cells.

Other methods of transfection include the use of transfection reagents (e.g. Lipofectin, ThermoFisher), dendrimers (Kukowska-Latallo, J. F. et al., 1996, Proc. Natl. Acad. Sci. USA93, 4897-902), cell penetrating peptides (Mäe et al., 2005, Internalisation of cell-penetrating peptides into tobacco protoplasts, Biochimica et Biophysica Acta 1669 (2):101-7) or polyamines (Zhang and Vinogradov, 2010, Short biodegradable polyamines for gene delivery and transfection of brain capillary endothelial cells, J Control Release, 143(3):359-366).

According to a specific embodiment, for introducing DNA into plant cells (e.g. protoplasts) the method comprises polyethylene glycol (PEG)-mediated DNA uptake. For further details see Karesch et al. (1991) Plant Cell Rep. 9:575-578; Mathur et al. (1995) Plant Cell Rep. 14:221-226; Negrutiu et al. (1987) Plant Cell Mol. Biol. 8:363-373. Plant cells (e.g. protoplasts) are then cultured under conditions that allowed them to grow cell walls, start dividing to form a callus, develop shoots and roots, and regenerate whole plants.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the genetically identical transformed plants.

Micropropagation is a process of growing new generation plants from a single piece of tissue that has been excised from a selected parent plant or cultivar. This process permits the mass reproduction of plants having the desired trait. The new generated plants are genetically identical to, and have all of the characteristics of, the original plant. Micropropagation (or cloning) allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a mufti-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV, TRV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is a RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Regardless of the transformation/infection method employed, the present teachings further select transformed cells comprising a genome editing event.

According to a specific embodiment, selection is carried out such that only cells comprising a successful accurate modification (e.g. swapping, insertion, deletion, point mutation) in the specific locus are selected. Accordingly, cells comprising any event that includes a modification (e.g. an insertion, deletion, point mutation) in an unintended locus are not selected.

According to one embodiment, selection of modified cells can be performed at the phenotypic level, by detection of a molecular event, by detection of a fluorescent reporter, or by growth in the presence of selection (e.g., antibiotic).

According to one embodiment, selection of modified cells is performed by analyzing the biogenesis and occurrence of the newly edited non-coding RNA molecule (e.g. the presence of new miRNA version, the presence of novel edited siRNAs, piRNAs, tasiRNAs etc).

According to one embodiment, selection of modified cells is performed by analyzing the silencing activity and/or specificity of the non-coding RNA molecule (e.g. RNA silencing molecule) towards a second target RNA or target RNA of interest by validating at least one phenotype in the plant or the organism that encode the target RNA, e.g. plant leaf coloring, e.g. partial or complete loss of chlorophyll in leaves and other organs (bleaching), presence/absence of nacrotic patterns, flower coloring, fruit traits (such as shelf life, filminess and flavor), growth rate, plant size (e.g. dwarfism), crop yield, biotic stress resistance (e.g. disease resistance, nematode mortality, beetle's egg laying rate, or other resistant phenotypes associated with any of bacteria, viruses, fungi, parasites, insects, weeds, and cultivated or native plants), abiotic stress resistance (e.g. heat/cold resistance, drought resistance, salt resistance, resistance to allyl alcohol, or resistant to lack of nutrients e.g. Phosphorus (P)).

According to one embodiment, the silencing specificity of the non-coding RNA molecule is determined genotypically, e.g. by expression of a gene or lack of expression.

According to one embodiment, the silencing specificity of the non-coding RNA molecule is determined phenotypically.

According to one embodiment, a phenotype of the plant is determined prior to a genotype.

According to one embodiment, a genotype of the plant is determined prior to a phenotype.

According to one embodiment, selection of modified cells is performed by analyzing the silencing activity and/or specificity of the non-coding RNA molecule (e.g. RNA silencing molecule) towards a second target RNA or target RNA of interest by measuring a RNA level of the second target RNA or target RNA of interest. This can be performed using any method known in the art, e.g. by Northern blotting, Nuclease Protection Assays, In Situ hybridization, or quantitative RT-PCR.

According to one embodiment, selection of modified cells is performed by analyzing plant cells or clones comprising the DNA editing event also referred to herein as "mutation" or "edit", dependent on the type of editing sought e.g., insertion, deletion, insertion-deletion (Indel), inversion, substitution and combinations thereof.

Methods for detecting sequence alteration are well known in the art and include, but not limited to, DNA and RNA sequencing (e.g., next generation sequencing), electrophoresis, an enzyme-based mismatch detection assay and a hybridization assay such as PCR, RT-PCR, RNase protection, in-situ hybridization, primer extension, Southern blot, Northern Blot and dot blot analysis. Various methods used for detection of single nucleotide polymorphisms (SNPs) can also be used, such as PCR based T7 endonuclease, Hetroduplex and Sanger sequencing, or PCR followed by restriction digest to detect appearance or disappearance of unique restriction site/s.

Another method of validating the presence of a DNA editing event e.g., Indels comprises a mismatch cleavage assay that makes use of a structure selective enzyme (e.g. endonuclease) that recognizes and cleaves mismatched DNA.

According to one embodiment, selection of transformed cells is effected by flow cytometry (FACS) selecting transformed cells exhibiting fluorescence emitted by the fluorescent reporter. Following FACS sorting, positively selected pools of transformed plant cells, displaying the fluorescent marker are collected and an aliquot can be used for testing the DNA editing event as discussed above.

In cases where antibiotic selection marker was used, following transformation plant cell clones are cultivated in the presence of selection (e.g., antibiotic) until they develop into colonies i.e., clones and micro-calli. A portion of the cells of the calli are then analyzed (validated) for the DNA editing event, as discussed above.

Thus, according to one embodiment of the invention, the method further comprises validating in the transformed cells complementarity of the endogenous non-coding RNA molecule (e.g. RNA silencing molecule) towards the second target RNA.

As mentioned above, following modification of the gene encoding the non-coding RNA molecule (e.g. RNA silencing molecule), the non-coding RNA molecule (e.g. RNA silencing molecule) comprises at least about 30%, 33%, 40%, 50%, 60%, 70%, 80%, 85%, 90%, 91%, 92%, 93%, 94%, 95%, 96%, 97%, 98%, 99% or even 100% complementarity towards the sequence of the second target RNA or target RNA of interest.

The specific binding of designed non-coding RNA molecule with a target RNA of interest can be determined by any method known in the art, such as by computational algorithms (e.g. BLAST) and verified by methods including e.g. Northern blot, In Situ hybridization, QuantiGene Plex Assay etc.

It will be appreciated that positive clones can be homozygous or heterozygous for the DNA editing event. In case of a heterozygous cell, the cell (e.g., When diploid) may comprise a copy of a modified gene and a copy of a non-modified gene of the non-coding RNA molecule (e.g. RNA silencing molecule). The skilled artisan will select the clone for further culturing/regeneration according to the intended use.

According to one embodiment, when a transient method is desired, clones exhibiting the presence of a DNA editing event as desired are further analyzed and selected for the absence of the DNA editing agent, namely, loss of DNA sequences encoding for the DNA editing agent. This can be done, for example, by analyzing the loss of expression of the DNA editing agent (e.g., at the snRNA, protein) e.g., by fluorescent detection of GFP or q-PCR, HPLC.

According to one embodiment, when a transient method is desired, the cells may be analyzed for the absence of the nucleic acid construct as described herein or portions thereof e.g., nucleic acid sequence encoding the DNA editing agent. This can be affirmed by fluorescent microscopy, q-PCR, FACS, and or any other method such as Southern blot, PCR, sequencing, HPLC).

According to one embodiment, the plant is crossed in order to obtain a plant devoid of the DNA editing agent (e.g. of the endonuclease), as discussed below.

Positive clones may be stored (e.g., cryopreserved).

Alternatively, plant cells (e.g., protoplasts) may be regenerated into whole plants first by growing into a group of plant cells that develops into a callus and then by regeneration of shoots (callogenesis) from the callus using plant tissue culture methods. Growth of protoplasts into callus and regeneration of shoots requires the proper balance of plant growth regulators in the tissue culture medium that must be customized for each species of plant.

Protoplasts may also be used for plant breeding, using a technique called protoplast fusion. Protoplasts from different species are induced to fuse by using an electric field or a solution of polyethylene glycol. This technique may be used to generate somatic hybrids in tissue culture.

Methods of protoplast regeneration are well known in the art. Several factors affect the isolation, culture, and regeneration of protoplasts, namely the genotype, the donor tissue and its pre-treatment, the enzyme treatment for protoplast isolation, the method of protoplast culture, the culture, the culture medium, and the physical environment. For a thorough review see Maheshwari et al. 1986 Differentiation of Protoplasts and of Transformed Plant Cells: 3-36. Springer-Verlag, Berlin.

The regenerated plants can be subjected to further breeding and selection as the skilled artisan sees fit.

Thus, embodiments of the invention further relate to plants, plant cells and processed product of plants comprising the non-coding RNA molecule (e.g. RNA silencing molecule) capable of silencing a second target RNA generated according to the present teachings.

According to one aspect of the invention, there is provided a method of producing a plant with reduced expression of a target gene, the method comprising: (a) breeding the plant according to some embodiments of the invention and (h) selecting for progeny plants that have reduced expression of the target RNA of interest or the second target RNA, or progeny that comprises a silencing specificity in the non-coding RNA molecule towards a target RNA of interest, and which do not comprise said DNA editing agent, thereby producing the plant with reduced expression of a target gene.

According to one embodiment, breeding comprises crossing or selfing.

The term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum). "crossing" therefore generally refers to the fertilization of ovules of one individual with pollen from another individual, whereas "selfing" refers to the fertilization of ovules of an individual with pollen from the same individual. Crossing is widely used in plant breeding and results in a mix of genomic information between the two plants crossed one chromosome from the mother and one chromosome from the father. This will result in a new combination of genetically inherited traits.

As mentioned above, the plant may be crossed in order to obtain a plant devoid of undesired factors e.g. DNA editing agent (e.g. endonuclease).

According to one embodiment, there is provided a method of generating a plant with increased stress tolerance, increased yield, increased growth rate or increased yield quality, the method comprising modifying a gene encoding or processed into a non-coding RNA molecule or into a RNA silencing in a plant cell according to the method of some embodiments of the invention, wherein the target RNA of interest is of a gene of the plant conferring sensitivity to stress, decreased yield, decreased growth rate or decreased yield quality thereby generating the plant.

The phrase "stress tolerance" as used herein refers to the ability of a plant to endure a biotic or abiotic stress without suffering a substantial alteration in metabolism, growth, productivity and/or viability.

The phrase "abiotic stress" as used herein refers to the exposure of a plant, plant cell, or the like, to a non-living ("abiotic") physical or chemical agent that has an adverse effect on metabolism, growth, development, propagation, or survival of the plant (collectively, "growth"). An abiotic stress can be imposed on a plant due, for example, to an environmental factor such as water (e.g., flooding, drought, or dehydration), anaerobic conditions (e.g., a lower level of oxygen or high level of $CO_2$), abnormal osmotic conditions (e.g. osmotic stress), salinity, or temperature (e.g., hot/heat, cold, freezing, or frost), an exposure to pollutants (e.g. heavy metal toxicity), anaerobiosis, nutrient deficiency (e.g., nitrogen deficiency or limited nitrogen), atmospheric pollution or UV irradiation.

The phrase "biotic stress" as used herein refers to the exposure of a plant, plant cell, or the like, to a living ("biotic") organism that has an adverse effect on metabolism, growth, development, propagation, or survival of the plant (collectively, "growth"). Biotic stress can be caused by, for example, bacteria, viruses, fungi, parasites, beneficial and harmful insects, weeds, and cultivated or native plants.

The phrase "yield" or "plant yield" as used herein refers to increased plant growth (growth rate), increased crop growth, increased biomass, and/or increased plant product production (including grain, fruit, seeds, etc.).

According to one embodiment, in order to generate a plant with increased stress tolerance, increased yield, increased growth rate or increased yield quality the non-coding RNA molecule is designed to target a RNA of interest being of a gene of the plant conferring sensitivity to stress, decreased yield, decreased growth rate or decreased yield quality.

According to one embodiment, exemplary susceptibility plant genes to be targeted (e.g. knocked out) include, but are not limited to, the susceptibility S-genes, such as those residing at genetic loci known as MLO (Mildew Locus O).

According to one embodiment, the plants generated by the present method comprise increased stress tolerance, increased yield, increased yield quality, increased growth rate, by at least about 10%, 20%, 30%, 40%, 50%, 60%, 70%, 80%, 90%, 95% or 100% as compared to plants not generated by the present methods.

Any method known in the art for assessing increased stress tolerance may be used in accordance with the present invention. Exemplary methods of assessing increased stress tolerance include, but are not limited to, downregulation of PagSAP1 in poplar for increased salt stress tolerance as described in Yoon, S K., Bae, E K., Lee, H. et al. Trees (2018) 32: 823. www(dot)doi(dot)org/10.10071s00468-018-1675-2), and increased drought tolerance in tomato by downregulation of SlbZIP38 (Pan Y et al. Genes 2017, 8, 402; doi:10.3390/genes8120402, incorporated herein by reference.

Any method known in the art for assessing increased yield may be used in accordance with the present invention. Exemplary methods of assessing increased yield include, but are not limited to, reduced DST expression in rice as described in Ar-Rafi Md. Faisal, et al, AJPS> Vol. 8 No. 9, August 2017 DOI: 10.4236/ajps.2017.89149; and downregulation of BnFTA in canola resulted in increased yield as described in Wang Y et al., Mol Plant. 2009 January; 2(1): 191-200.doi: 10.1093/mp/ssn.088), both incorporated herein by reference.

Any method known in the art for assessing increased growth rate may be used in accordance with the present invention. Exemplary methods of assessing increased growth rate include, but are not limited to, reduced expression of BIG BROTHER in *Arabidopsis* or GA2-OXIDASE results in enhance growth and biomass as described in Marcelo de Freitas Lima et al. Biotechnology Research and Innovation (2017)1, 14-25, incorporated herein by reference.

Any method known in the art for assessing increased yield quality may be used in accordance with the present invention. Exampleary methods of assessing increased yield quality include, but are not limited to, down regulation of OsCKX2 in rice results in production of more tillers, more grains, and the grains were heavier as described in Yeh S_Y et al. Rice (N Y). 2015; 8: 36; and reduce OMT levels in many plants, which result in altered lignin accumulation, increase the digestibility of the material for industry purposes as described in Verma S R and Dwivedi U N, South African Journal of Botany Volume 91, March 2014, Pages 107-125, both incorporated herein by reference.

According to one embodiment, the method further enables generation of a plant comprising increased sweetness, increased sugar content, increased flavor, improved ripening control, increased water stress tolerance, increased heat stress tolerance, and increased salt tolerance. One of skill in the art will know how to utilize the methods described herein to choose target RNA sequences for modification.

According to one embodiment, there is provided a method of generating a pathogen tolerant or resistant plant, the method comprising modifying a gene encoding or processed into a non-coding RNA molecule or into a RNA silencing molecule in a plant cell according to the method of some embodiments of the invention, wherein the target RNA of interest is of a gene of the plant conferring sensitivity to the pathogen, thereby generating the pathogen tolerant or resistant plant.

According to one embodiment, there is provided a method of generating a pathogen tolerant or resistant plant, the method comprising modifying a gene encoding or processed into a non-coding RNA molecule or into a RNA silencing molecule in a plant cell according to the method of some embodiments of the invention, wherein the target RNA of interest is of a gene of the pathogen, thereby generating the pathogen tolerant or resistant plant.

According to one embodiment, there is provided a method of generating a pest tolerant or resistant plant, the method comprising modifying a gene encoding or processed into a non-coding RNA molecule or into a RNA silencing molecule in a plant cell according to the method of some embodiments of the invention, wherein the target RNA of interest is of a gene of the pest, thereby generating the pest tolerant or resistant plant.

As used herein the term "pathogen" refers to an organism that negatively affect plants by colonizing, damaging, attacking, or infecting them. Thus, pathogen may affect the growth, development, reproduction, harvest or yield of a plant. This includes organisms that spread disease and/or damage the host and/or compete for host nutrients. Plant pathogens include, but are not limited to, fungi, oomycetes, bacteria, viruses, viroids, virus-like organisms, phytoplasmas, protozoa, nematodes, insects and parasitic plants.

Non-limiting examples of pathogens include, but are not limited to, Roundheaded Borer such as long horned borers; psyllids such as red gum lerp psyllids (*Glycaspis brimblecombei*), blue gum psyllid, spotted gum lerp psyllids, lemon gum lerp psyllids; tortoise beetles; snout beetles; leaf beetles; honey fungus; *Thaumastocoris peregrinus*; sessile gall wasps (Cynipidae) such as *Leptocybe invasa*, *Ophelimus maskelli* and *Selitrichodes globules*; Foliage-feeding caterpillars such as Omnivorous looper and Orange tortrix; Glassy-winged sharpshooter; and Whiteflies such as Giant whitefly. Other non-limiting examples of pathogens include Aphids such as *Chaitophorus* spp., Cloudywinged cottonwood and *Periphyllus* spp.; Armored scales such as Oystershell scale and San Jose scale; Carpenterworm; Clearwing moth borers such as American hornet moth and Western poplar clearwing; Flatheaded borers such as Bronze birch borer and Bronze poplar borer; Foliage-feeding caterpillars such as Fall webworm, Fruit-tree leafroller, Redhumped caterpillar, Satin moth caterpillar, Spiny elm caterpillar, Tent caterpillar, Tussock moths and Western tiger swallowtail; Foliage miners such as Poplar shield bearer; Gall and blister mites such as Cottonwood gall mite; Gall aphids such as Poplar petiolegall aphid; Glassy-winged sharpshooter; Leaf beetles and flea beetles; Mealybugs; Poplar and willow borer; Roundheaded borers; Sawflies; Soft scales such as Black scale, Brown soft scale, Cottony maple scale and European fruit lecanium; Treehoppers such as Buffalo treehopper; and True bugs such as Lace bugs and Lygus bugs.

Other non-limiting examples of viral plant pathogens include, but are not limited to Species: Pea early-browning virus (PEBV), Genus: *Tobravirus*. Species: *Pepper ringspot virus* (PepRSV), Genus: *Tobravirus*. Species: *Watermelon mosaic virus* (WMV), Genus: *Potyvirus* and other viruses from the Potyvirus Genus. Species: *Tobacco mosaic* virus Genus (TMV), *Tobamovirus* and other viruses from the *Tobamovirus* Genus. Species: *Potato virus* X Genus (PVX), *Potexvirus* and other viruses from the *Potexvirus* Genus. Thus the present teachings envisage targeting of RNA as well as DNA viruses (e.g. Gemini virus or Bigeminivirus). Geminiviridae viruses which may be targeted include, but are not limited to, Abutilon mosaic bigeminivirus, Ageratum yellow vein bigeminivirus, Bean calico mosaic bigeminivirus, Bean golden mosaic bigeminivirus, Bhendi yellow vein mosaic bigeminivirus, Cassava African mosaic bigeminivirus, Cassava Indian mosaic bigeminivirus, Chino del tomaté bigeminivirus, Cotton leaf crumple bigeminivirus, Cotton leaf curl bigeminivirus, Croton yellow vein mosaic bigeminivirus, Dolichos yellow mosaic bigeminivirus, Euphorbia mosaic bigeminivirus, Horsegram yellow mosaic bigeminivirus, Jatropha mosaic bigeminivirus, Lima bean golden mosaic bigeminivirus, Melon leaf curl bigeminivirus, Mung bean yellow mosaic bigeminivirus, Okra leaf-curl bigeminivirus, Pepper hausteco bigeminivirus, Pepper Texas bigeminivirus, Potato yellow mosaic bigenminivirus, Rhynchosia mosaic bigenminivirus, Serrano golden mosaic bigeminivirus, Squash leaf curl bigeminivirus, Tobacco leaf curl bigeminivirus, Tomato Australian leafcurl bigeminivirus, Tomato golden mosaic bigeminivirus, Tomato Indian leafcurl bigeminivirus, Tomato leaf crumple bigeminivirus, Tomato mottle bigeminivirus, Tomato yellow leaf curl bigeminivirus, Tomato yellow mosaic bigeminivirus, Watermelon chlorotic stunt bigeminivirus and Watermelon curly mottle bigeminivirus.

As used herein the term "pest" refers to an organism which directly or indirectly harms the plant. A direct effect includes, for example, feeding on the plant leaves. Indirect effect includes, for example, transmission of a disease agent (e.g. a virus, bacteria, etc.) to the plant. In the latter case the pest serves as a vector for pathogen transmission. Exemplary pests include, but are not limited to, beetles, psylids, insects, nematodes, snails.

According to one embodiment, the pathogen is a nematode. Exemplary nematodes include, but are not limited to, the burrowing nematode (*Radopholus similis*), *Caenorhabditis elegans*, *Radopholus arabocoffeae*, *Pratylenchus coffeae*, root-knot nematode (*Meloidogyne* spp.), cyst nematode (*Heterodera* and *Globodera* spp.), root lesion nematode (*Pratylenchus* spp.), the stem nematode (*Ditylenchus dipsaci*), the pine wilt nematode (*Bursaphelenchus xylophilus*), the reniform nematode (*Rotylenchulus reniformis*), *Xiphinema index*, *Nacobbus aberrans* and *Aphelenchoides besseyi*.

According to one embodiment, the pathogen is a fungus. Exemplary fungi include, but are not limited to, *Fusarium oxysporum*, *Leptosphaeria maculans* (*Phoma lingam*), *Sclerotinia sclerotiorum*, *Pyricularia grisea*, *Gibberella fujikuroi* (*Fusarium moniliforme*), *Magnaporthe oryzae*, *Botrytis cinereal*, *Puccinia* spp., *Fusarium graminearum*, *Blumeria graminis*, *Mycosphaerella graminicola*, *Colletotrichum* spp., *Ustilago maydis*, *Melampsora lini*, *Phakopsora pachyrhizi* and *Rhizoctonia solani*.

According to one embodiment, in order to generate a pathogen resistant or tolerant plant, the non-coding RNA molecule is designed to target a RNA of interest being of a gene of the plant conferring sensitivity to a pathogen.

According to one embodiment, an exemplary plant gene to be targeted includes, but is not limited to, the gene eIF4E which confers sensitivity to viral infection in cucumber.

According to one embodiment, in order to generate a pathogen resistant or tolerant plant, the non-coding RNA molecule is designed to target a RNA of interest being of a gene of the pathogen.

Determination of the plant or pathogen target genes may be achieved using any method known in the art such as by routine bioinformatics analysis.

According to one embodiment, the nematode pathogen gene comprises the *Radopholus similis* genes Calreticulin3 (CRT) or collagen 5 (col-5).

According to one embodiment, the fungi pathogen gene comprises the *Fusarium oxysporum* genes FOW2, FRP1, and OPR.

According to one embodiment, the pathogen gene includes, for example, vacuolar ATPase (vATPase), dvssj1 and dvssj2, α-tubulin and snf7.

According to a specific embodiment, when the plant is a *Brassica napes* (rapeseed), the target RNA of interest includes, but is not limited to, a gene of *Leptosphaeria maculans* (*Phoma lingam*) (causing e.g. *Phoma* stem canker) (e.g. as set forth in GenBank Accession No: AM933613.1); a gene of Flea beetle (*Phyllotreta vittula* or *Chrysomelidae*, e.g. as set forth in GenBank Accession No: KT959245.1); or a gene of by *Sclerotinia sclerotiorum* (causing e.g. *Sclerotinia* stem rot) (e.g. as set forth in GenBank Accession No: NW_001820833.1).

According to a specific embodiment, when the plant is a Citrus x sinensis (Orange), the target RNA of interest includes, but is not limited to, a gene of *Citrus Canker* (CCK) (e.g. as set forth in GenBank Accession No: AE008925); a gene of *Candidatus Liberibacter* spp. (causing e.g. Citrus greening disease) (e.g. as set forth in GenBank Accession No: CP001677.5); or a gene of *Armillaria* root rot (e.g. as set forth in GenBank Accession No: KY389267.1).

According to a specific embodiment, when the plant is a *Elaeis guineensis* (Oil palm), the target RNA of interest includes, but is not limited to, a gene of *Ganoderma* spp. (causing e.g. Basal stem rot (BSR) also known as *Ganoderma* butt rot) (e.g. as set forth in GenBank Accession No: U56128.1), a gene of *Nettle Caterpillar* or a gene of any one of *Fusarium* spp., *Phytophthora* spp., *Pythium* spp., *Rhizoctonia solani* (causing e.g. Root rot).

According to a specific embodiment, when the plant is a *Fragaria vesca* (Wild strawberry), the target RNA of interest includes, but is not limited to, a gene of *Verticillium dahlia* (causing e.g. *Verticillium* Wilt) (e.g. as set forth in GenBank Accession No: D5572713.1); or a gene of *Fusarium oxysporum* f.sp. *fragariae* (causing e.g. *Fusarium* wilt) (e.g. as set forth in GenBank Accession No: KR855868.1);

According to a specific embodiment, when the plant is a *Glycine max* (Soybean), the target RNA of interest includes, but is not limited to, a gene of *P. pachyrhizi* (causing e.g. Soybean rust, also known as Asian rust) (e.g. as set forth in GenBank Accession No: DQ026061.1); a gene of *Soybean Aphid* (e.g. as set forth in GenBank Accession No: KJ451424.1); a gene of Soybean Dwarf Virus (SbDV) (e.g. as set forth in GenBank Accession No: NC_003056.1); or a gene of Green Stink Bug (*Acrosternum hilare*) (e.g. as set forth in GenBank Accession No: NW 020110722.1).

According to a specific embodiment, when the plant is a Gossypium raimondii (Cotton), the target RNA of interest includes, but is not limited to, a gene of *Fusarium oxysporum* f.sp. *vasinfectum* (causing e.g. *Fusarium* wilt) (e.g. as set forth in GenBank Accession No: JN416614.1); a gene of *Soybean Aphid* (e.g. as set forth in GenBank Accession No: KJ451424.1); or a gene of *Pink bollworm* (*Pectinophora gossypiella*) (e.g. as set forth in GenBank Accession No: KU1550964.1).

According to a specific embodiment, when the plant is a *Oryza sativa* (Rice), the target RNA of interest includes, but is not limited to, a gene of *Pyricularia grisea* (causing e.g. Rice Blast) (e.g. as set forth in GenBank Accession No: AF027979.1); a gene of *Gibberella fujikuroi* (*Fusarium moniliforme*) (causing e.g. Bakanae Disease) (e.g. as set forth in GenBank Accession No: AY862192.1); or a gene of a Stem borer, e.g. *Scirpophaga incertulas* Walker-Yellow Stem Borer, *S. innota* Walker-White Stem Borer, *Chilo suppressalis* Walker-Striped Stem Borer, Sesa-mia inferens Walker-Pink Stem Borer (e.g. as set forth in GenBank Accession No: KF290773.1).

According to a specific embodiment, when the plant is a *Solanum lycopersicum* (Tomato), the target RNA of interest includes, but is not limited to, a gene of *Phytophthora infestans* (causing e.g. Late blight) (e.g. as set forth in GenBank Accession No: AY855210.1); a gene of a whitefly *Bemisia tabaci* e.g. *Gennadius*, e.g. as set forth in GenBank Accession No: KX390870.1); or a gene of Tomato yellow leaf curl geminivirus (TYLCV) (e.g. as set forth in GenBank Accession No: LN846610.1).

According to a specific embodiment, when the plant is a Solanum tuberosum (Potato), the target RNA of interest includes, but is not limited to, a gene of Phytophthora infestans (causing e.g. bate Blight) (e.g., as set forth in GenBank Accession No: AY050538.3); a gene of *Erwinia* spp. (causing e.g. Blackleg and Soft Rot) (e.g. as set forth in GenBank Accession No: CP001654.1); or a gene of *Cyst Nematodes* (e.g. *Globodera pallida* and *G. rostochiensis*) (e.g. as set forth in GenBank Accession No: KF963519.1).

According to a specific embodiment, when the plant is a *Theobroma cacao* (Cacao), the target RNA of interest includes, but is not limited to, a gene of a gene of basidiomycete *Moniliophthora roreri* (causing e.g. Frosty Pod Rot) (e.g. as set forth in GenBank Accession No: LATX01001521.1); a gene of *Moniliophthora perniciosa* (causing e.g. Witches' Broom disease); or a gene of Minds e.g. *Distantiella theobroma* and *Sahlbergella singularis, Helopeltis* spp, *Monalonion* specie.

According to a specific embodiment, when the plant is a *Vitis vinifera* (Grape or Grapevine), the target RNA of interest includes, but is not limited to, a gene of closterovinis GVA (causing e.g. Rugose wood disease) (e.g. as set forth in GenBank Accession No: AF007415.2); a gene of Grapevine leafroll virus (e.g. as set forth in GenBank Accession No: FJ436234.1); a gene of Grapevine fanleaf degeneration disease virus (GFLV) (e.g. as set forth in GenBank Accession No: NC_003203.1); or a gene of Grapevine fleck disease (GFkV) (e.g. as set forth in GenBank Accession No: NC_003347.1).

According to a specific embodiment, when the plant is a *Zea mays* (Maize also referred to as corn), the target RNA of interest includes, but is not limited to, a gene of a Fall Armyworm (e.g. *Spodoptera frugiperda*) (e.g. as set forth in GenBank Accession No: AJ488181.3); a gene of European corn borer (e.g. as set forth in GenBank Accession No: GU329524.1); or a gene of Northern and western corn rootworms (e.g. as set forth in GenBank Accession No: NM_001039403.1).

According to a specific embodiment, when the plant is a sugarcane, the target RNA of interest includes, but is not limited to, a gene of a Internode Borer (e.g. *Chilo Saccha-*

*rifagus Indicus*), a gene of a Xanthomonas Albineans (causing e.g. Leaf Scald) or a gene of a Sugarcane Yellow Leaf Virus (SCYLV).

According to a specific embodiment, when the plant is a wheat, the target RNA of interest includes, but is not limited to, a gene of a Puccinia striiformis (causing e.g. stripe rust) or a gene of an Aphid.

According to a specific embodiment, when the plant is a barley, the target RNA of interest includes, but is not limited to, a gene of a Puccinia hordei (causing e.g. Leaf rust), a gene of *Puccinia striiformis* f. sp. Hordei (causing e.g. stripe rust), or a gene of an Aphid.

According to a specific embodiment, when the plant is a sunflower, the target RNA of interest includes, but is not limited to, a gene of a *Puccinia helianthi* (causing e.g. Rust disease); a gene of *Boerema macdonaldii* (causing e.g. Phoma black stem); a gene of a Seed weevil (e.g. red and gray), e.g. *Smicronyx fulvus* (red); *Smicronyx sordidus* (gray); or a gene of *Sclerotinia sclerotiorum* (causing e.g. *Sclerotinia* stalk and head rot disease).

According to a specific embodiment, when the plant is a rubber plant, the target RNA of interest includes, but is not limited to, a gene of a *Microcyclus ulei* (causing e.g. South American leaf blight (SALB)); a gene of *Rigidoporus microporus* (causing e.g. White root disease); a gene of *Ganoderma pseudoferreum* (causing e.g. Red root disease).

According to a specific embodiment, when the plant is an apple plant, the target RNA of interest includes, but is not limited to, a gene of *Neonectria, ditissima* (causing e.g. Apple Canker), a gene of *Podosphaera leucotricha* (causing e.g. Apple Powdery Mildew), or a gene of *Venturia inaequalis* (causing e.g. Apple Scab).

Exemplary endogenous non-coding RNA molecules which may be modified to target the RNA of interest (e.g. a gene of a pathogen), exemplary sequences of gRNA (i.e. a DNA editing agent) which may be used to modify the endogenous non-coding RNA molecules, and exemplary nucleotide sequences for redirecting a silencing specificity of the endogenous non-coding RNA molecule towards the target RNA of interest are provided in Table 1B, hereinbelow.

TABLE 1B

Examples of GEiGS oligo designs to generate different traits in various hosts
Table 1B provides example GeiGS oligos designed against a variety of targets in several host organisms. For each host-target combination, four oligos are provided: minimum sequence changes with matching structure and efficient siRNA; maximum sequence changes with matching structure and efficient siRNA; maximum sequence changes and non-matching structure and efficient siRNA; and maximum sequence changes with matching structure and inefficient siRNA.

| Host, trait and miRNA-template | Oligo info | oligo_seq | seq difference from wt |
|---|---|---|---|
| Host (bold);<br>Pathogen/pest/disease<br>(italic) | | Sequence of GEiGS oligo, consisting of the precursor sequence with its corresponding mature replaced by a siRNA targeting the desired molecule - SEQ ID NO: | Number of nucleotide changes between the wild type precursor and the GeiGs oligo |
| *Brassica napus* (rapeseed)<br>AM933613.1/Phoma stem canker<br>(caused by *leptosphaeria maculans*<br>or phoma lingam - fungal pathogen) | | | |
| bna-MIR169e | Max change/<br>perfect structure/<br>trait-specific<br>siRNA | 103 | 132 |
| bna-MIR156d | Min change/<br>perfect structure/<br>trait-specific<br>siRNA | 104 | 25 |
| bna-MIR169e | Max change/<br>altered structure/<br>trait-specific<br>siRNA | 105 | 128 |
| bna-MIR169e | Max change/<br>perfect structure/<br>non-specific<br>siRNA | 106 | 131 |
| KT959245.1/Flea beetle<br>(*Phyllotreta vittula* or<br>*Chrysomelidae*) | | | |
| bna-MIR169e | Max change/<br>perfect structure/<br>trait-specific<br>siRNA | 107 | 138 |
| bna-MIR156d | Min change/<br>perfect structure/<br>trait-specific<br>siRNA | 108 | 29 |

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

| | | | |
|---|---|---|---|
| bna-MIR156b | Max change/ altered structure/ trait-specific siRNA | 109 | 76 |
| bna-MIR169e | Max change/ perfect structure/ non-specific siRNA | 110 | 133 |
| NW_001820833.1/*Sclerotinia* stem rot (

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

KY389267.1/*Armillaria* root rot

| | | | |
|---|---|---|---|
| csi-MIR167c | Max change/ perfect structure/ trait-specific siRNA | 123 | 168 |
| csi-MIR171a | Min change/ perfect structure/ trait-specific siRNA | 124 | 21 |
| csi-MIR167c | Max change/ altered structure/ trait-specific siRNA | 125 | 144 |
| csi-MIR167c | Max change/ perfect structure/ non-specific siRNA | 126 | 182 |

*Elaeis guineensis* (Oil palm)
U56128.1/Basal stem rot (BSR) also known as *Ganoderma* butt rot (*Ganoderma* spp.)

| | | | |
|---|---|---|---|
| egu-MIR172c | Max change/ perfect structure/ trait-specific siRNA | 127 | 89 |
| egu-MIR172c | Min change/ perfect structure/ trait-specific siRNA | 128 | 53 |
| egu-MIR172c | Max change/ altered structure/ trait-specific siRNA | 129 | 74 |
| egu-MIR172c | Max change/ perfect structure/ non-specific siRNA | 130 | 94 |

*Fragaria vesca* (Wild strawberry)
DS572713.1/*Verticillium* Wilt (*Verticillium dahlia*)

| | | | |
|---|---|---|---|
| fve-MIR159c | Max change/ perfect structure/ trait-specific siRNA | 131 | 100 |
| fve-MIR160b | Min change/ perfect structure/ trait-specific siRNA | 132 | 22 |
| fve-MIR166a | Max change/ altered structure/ trait-specific siRNA | 133 | 56 |
| fve-MIR164b | Max change/ perfect structure/ non-specific siRNA | 134 | 95 |

KR855868.1/*Fusarium* wilt (*Fusarium oxysporum* f. sp. *fragariae*)

| | | | |
|---|---|---|---|
| fve-MIR159c | Max change/ perfect structure/ trait-specific siRNA | 135 | 97 |

TABLE 1B-continued

Examples of GEiGS oligo designs to generate different traits in various hosts
Table 1B provides example GeiGS oligos designed against a variety of targets in several host organisms. For each host-target combination, four oligos are provided: minimum sequence changes with matching structure and efficient siRNA; maximum sequence changes with matching structure and efficient siRNA; maximum sequence changes with non-matching structure and efficient siRNA; and maximum sequence changes with matching structure and inefficient siRNA.

| | | | |
|---|---|---|---|
| fve-MIR167b | Min change/ perfect structure/ trait-specific siRNA | 136 | 17 |
| fve-MIR169a | Max change/ altered structure/ trait-specific siRNA | 137 | 69 |
| fve-MIR164b | Max change/ perfect structure/ non-specific siRNA | 138 | 94 |
| *Glycine max* (Soybean) DQ026061.1/Soybean rust caused by *P. pachyrhizi* (also known as Asian rust) | | | |
| gma-MIR167c | Max change/ perfect structure/ trait-specific siRNA | 139 | 166 |
| gma-MIR1511 | Min change/ perfect structure/ trait-specific siRNA | 140 | 23 |
| gma-MIR167c | Max change/ altered structure/ trait-specific siRNA | 141 | 141 |
| gma-MIR167c | Max change/ perfect structure/ non-specific siRNA | 142 | 163 |
| KJ451424.1/Soybean Aphid | | | |
| gma-MIR167c | Max change/ perfect structure/ trait-specific siRNA | 143 | 163 |
| gma-MIR168a | Min change/ perfect structure/ trait-specific siRNA | 144 | 23 |
| gma-MIR167c | Max change/ altered structure/ trait-specific siRNA | 145 | 132 |
| gma-MIR167c | Max change/ perfect structure/ non-specific siRNA | 146 | 161 |
| NC_003056.1/Soybean Dwarf Virus (SbDV) | | | |
| gma-MIR167c | Max change/ perfect structure/ trait-specific siRNA | 147 | 165 |
| gma-MIR1516a | Min change/ perfect structure/ trait-specific siRNA | 148 | 23 |
| gma-MIR167c | Max change/ altered structure/ trait-specific siRNA | 149 | 135 |
| gma-MIR167c | Max change/ perfect structure/ non-specific siRNA | 150 | 163 |

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

NW_020110722.1/Green Stink Bug
(*Acrosternum hilare*)

| | | | |
|---|---|---|---|
| gma-MIR167c | Max change/ perfect structure/ trait-specific siRNA | 151 | 158 |
| gma-MIR162a | Min change/ perfect structure/ trait-specific siRNA | 152 | 22 |
| gma-MIR167c | Max change/ altered structure/ trait-specific siRNA | 153 | 135 |
| gma-MIR167c | Max change/ perfect structure/ non-specific siRNA | 154 | 164 |

*Gossypium raimondii* (Cotton)
JN416614.1/*Fusarium* wilt
(*Fusarium oxysporum* f. sp. *vasinfectum*)

| | | | |
|---|---|---|---|
| gra-MIR8637 | Max change/ perfect structure/ trait-specific siRNA | 155 | 154 |
| gra-MIR7486e | Min change/ perfect structure/ trait-specific siRNA | 156 | 21 |
| gra-MIR8633 | Max change/ altered structure/ trait-specific siRNA | 157 | 58 |
| gra-MIR8635 | Max change/ perfect structure/ non-specific siRNA | 158 | 149 |

KJ451424.1/Soybean Aphid

| | | | |
|---|---|---|---|
| gra-MIR8637 | Max change/ perfect structure/ trait-specific siRNA | 159 | 153 |
| gra-MIR157a | Min change/ perfect structure/ trait-specific siRNA | 160 | 16 |
| gra-MIR8636 | Max change/ altered structure/ trait-specific siRNA | 161 | 62 |
| gra-MIR8637 | Max change/ perfect structure/ non-specific siRNA | 162 | 149 |

KU550964.1/Pink bollworm
(*Pectinophora gossypiella*)

| | | | |
|---|---|---|---|
| gra-MIR8637 | Max change/ perfect structure/ trait-specific siRNA | 163 | 155 |
| gra-MIR157a | Min change/ perfect structure/ trait-specific siRNA | 164 | 21 |

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

| | | | |
|---|---|---|---|
| gra-MIR8644 | Max change/ altered structure/ trait-specific siRNA | 165 | 53 |
| gra-MIR8635 | Max change/ perfect structure/ non-specific siRNA | 166 | 154 |
| Oryza sativa (Rice) AF027979.1/Rice Blast (fungal disease caused by *Pyricularia grisea*) | | | |
| osa-MIR166b | Max change/ perfect structure/ trait-specific siRNA | 167 | 105 |
| osa-MIR156e | Min change/ perfect structure/ trait-specific siRNA | 168 | 21 |
| osa-MIR160b | Max change/ altered structure/ trait-specific siRNA | 169 | 59 |
| osa-MIR166b | Max change/ perfect structure/ non-specific siRNA | 170 | 100 |
| AY862

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

| | | | |
|---|---|---|---|
| osa-MIR166b | Max change/ perfect structure/ non-specific siRNA | 178 | 103 |
| Solanum lycopersicum (Tomato) AY855210.1/Late blight (*Phytophthora infestans*) | | | |
| sly-MIR319b | Max change/ perfect structure/ trait-specific siRNA | 179 | 143 |
| sly-MIR156b | Min change/ perfect structure/ trait-specific siRNA | 180 | 24 |
| sly-MIR395a | Max change/ altered structure/ trait-specific siRNA | 181 | 75 |
| sly-MIR319b | Max change/ perfect structure/ non-specific siRNA | 182 | 145 |
| KX390870.1/whitefly *Bemisia tabaci* (*Gennadius*) | | | |
| sly-MIR319b | Max change/ perfect structure/ trait-specific siRNA | 183 | 144 |
| sly-MIR391 | Min change/ perfect structure/ trait-specific siRNA | 184 | 16 |
| sly-MIR319c | Max change/ altered structure/ trait-specific siRNA | 185 | 79 |
| sly-MIR319b | Max change/ perfect structure/ non-specific siRNA | 186 | 138 |
| LN846610.1/Tomato yellow leaf curl geminivirus (TYLCV) | | | |
| sly-MIR319b | Max change/ perfect structure/ trait-specific siRNA | 187 | 141 |
| sly-MIR156b | Min change/ perfect structure/ trait-specific siRNA | 188 | 24 |
| sly-MIR395a | Max change/ altered structure/ trait-specific siRNA | 189 | 81 |
| sly-MIR319b | Max change/ perfect structure/ non-specific siRNA | 190 | 143 |
| Solanum tuberosum (Potato) AY050538.3/Late Blight (*Phytophthora infestans*) | | | |
| stu-MIR6022 | Max change/ perfect structure/ trait-specific siRNA | 191 | 110 |

TABLE 1B-continued

Examples of GEiGS oligo designs to generate different traits in various hosts
Table 1B provides example GeiGS oligos designed against a variety of targets in several host organisms. For each host-target combination, four oligos are provided: minimum sequence changes with matching structure and efficient siRNA; maximum sequence changes with matching structure and efficient siRNA; maximum sequence changes and non-matching structure and efficient siRNA; and maximum sequence changes with matching structure and inefficient siRNA.

| | | | |
|---|---|---|---|
| stu-MIR7988 | Min change/ perfect structure/ trait-specific siRNA | 192 | 19 |
| stu-MIR482d | Max change/ altered structure/ trait-specific siRNA | 193 | 50 |
| stu-MIR6022 | Max change/ perfect structure/ non-specific siRNA | 194 | 106 |
| CP001654.1/Blackleg and Soft Rot (*Erwinia* spp.) | | | |
| stu-MIR6022 | Max change/ perfect structure/ trait-specific siRNA | 195 | 110 |
| stu-MIR7988 | Min change/ perfect structure/ trait-specific siRNA | 196 | 16 |
| stu-MIR482d | Max change/ altered structure/ trait-specific siRNA | 197 | 50 |
| stu-MIR6022 | Max change/ perfect structure/ non-specific siRNA | 198 | 104 |
| KF963519.1/Cyst Nematodes (*Globodera pallida* and *G. rostochiensis*) | | | |
| stu-MIR6022 | Max change/ perfect structure/ trait-specific siRNA | 199 | 107 |
| stu-MIR7985 | Min change/ perfect structure/ trait-specific siRNA | 200 | 20 |
| stu-MIR6024 | Max change/ altered structure/ trait-specific siRNA | 201 | 49 |
| stu-MIR6022 | Max change/ perfect structure/ non-specific siRNA | 202 | 107 |
| *Theobroma cacao* (Cacao) LATX01001521.1/Frosty Pod Rot caused by the basidiomycete *Moniliophthora roreri* | | | |
| tcc-MIR169b | Max change/ perfect structure/ trait-specific siRNA | 203 | 100 |
| tcc-MIR167a | Min change/ perfect structure/ trait-specific siRNA | 204 | 25 |
| tcc-MIR167b | Max change/ altered structure/ trait-specific siRNA | 205 | 52 |

TABLE 1B-continued

Examples of GEiGS oligo designs to generate different traits in various hosts
Table 1B provides example GeiGS oligos designed against a variety of targets in several host organisms. For each host-target combination, four oligos are provided: minimum sequence changes with matching structure and efficient siRNA; maximum sequence changes with matching structure and efficient

TABLE 1B-continued

Examples of GEiGS oligo designs to generate different traits in various hosts
Table 1B provides example GeiGS oligos designed against a variety of targets in several host organisms. For each host-target combination, four oligos are provided: minimum sequence changes with matching structure and efficient siRNA; maximum sequence changes with matching structure and efficient siRNA; maximum sequence changes with non-matching structure and efficient siRNA; and maximum sequence changes with matching structure and inefficient siRNA.

| | | | |
|---|---|---|---|
| vvi-MIR166b | Min change/ perfect structure/ trait-specific siRNA | 220 | 19 |
| vvi-MIR167a | Max change/ altered structure/ trait-specific siRNA | 221 | 127 |
| vvi-MIR167a | Max change/ perfect structure/ non-specific siRNA | 222 | 157 |
| *Zea mays* (Maize) AJ488181.3/Fall Armyworm (*Spodoptera frugiperda*) | | | |
| zma-MIR166a | Max change/ perfect structure/ trait-specific siRNA | 223 | 100 |
| zma-MIR160c | Min change/ perfect structure/ trait-specific siRNA | 224 | 20 |
| zma-MIR156f | Max change/ altered structure/ trait-specific siRNA | 225 | 64 |
| zma-MIR166a | Max change/ perfect structure/ non-specific siRNA | 226 | 101 |
| GU329524.1/European corn borer | | | |
| zma-MIR166a | Max change/ perfect structure/ trait-specific siRNA | 227 | 103 |
| zma-MIR166h | Min change/ perfect structure/ trait-specific siRNA | 228 | 20 |
| zma-MIR171f | Max change/ altered structure/ trait-specific siRNA | 229 | 62 |
| zma-MIR166a | Max change/ perfect structure/ non-specific siRNA | 230 | 106 |
| NM_001039403.1/Northern and wertern corn rootworms | | | |
| zma-MIR166a | Max change/ perfect structure/ trait-specific siRNA | 231 | 107 |
| zma-MIR172d | Min change/ perfect structure/ trait-specific siRNA | 232 | 20 |
| zma-MIR166a | Max change/ altered structure/ trait-specific siRNA | 233

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

| Host, trait and miRNA-template | Sg_seq | pain difference | sgRNA_strand |
|---|---|---|---|
| Host (bold); Pathogen/pest/disease (italic) | Sequence of the CRISPR/cas9 small guide RNA targeting the precursor sequence for swapping - SEQ ID NO: | Number of nucleotide changes between the wild type precursor and the GEiGS sequence that fall in the P

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

*Fragaria vesca* (Wild strawberry)
DS572713.1/*Verticillium*
Wilt (*Verticillium dahlia*)

| | | | |
|---|---|---|---|
| fve-MIR159c | 263 | 3 | fw |
| fve-MIR160b | 264 | 3 | rv |
| fve-MIR166a | 265 | 3 | fw |
| fve-MIR164b | 266 | 3 | fw |

KR855868.1/*Fusarium* wilt
(*Fusarium oxysporum* f. sp.
*fragariae*)

| | | | |
|---|---|---|---|
| fve-MIR159c | 267 | 3 | fw |
| fve-MIR167b | 268 | 1 | rv |
| fve-MIR169a | 269 | 3 | rv |
| fve-MIR164b | 270 | 3 | fw |

*Glycine max* (Soybean)
DQ026061.1/Soybean rust
caused by *P. pachyrhizi*
(also known as Asian rust)

| | | | |
|---|---|---|---|
| gma-MIR167c | 271 | 3 | rv |
| gma-MIR1511 | 272 | 3 | fw |
| gma-MIR167c | 273 | 3 | rv |
| gma-MIR167c | 274 | 3 | rv |

KJ451424.1/Soybean Aphid

| | | | |
|---|---|---|---|
| gma-MIR167c | 275 | 3 | rv |
| gma-MIR168a | 276 | 0 | rv |
| gma-MIR167c | 277 | 3 | rv |
| gma-MIR167c | 278 | 3 | rv |

NC_003056.1/Soybean
Dwarf Virus (SbDV)

| | | | |
|---|---|---|---|
| gma-MIR167c | 279 | 3 | rv |
| gma-MIR1516a | 280 | 1 | fw |
| gma-MIR167c | 281 | 3 | rv |
| gma-MIR167c | 282 | 3 | rv |

NW_020110722.1/Green Stink Bug
(*Acrosternum hilare*)

| | | | |
|---|---|---|---|
| gma-MIR167c | 283 | 3 | rv |
| gma-MIR162a | 284 | 1 | rv |
| gma-MIR167c | 285 | 3 | rv |
| gma-MIR167c | 286 | 3 | rv |

*Gossypium raimondii* (Cotton)
JN416614.1/*Fusarium* wilt
(*Fusarium oxysporum* f. sp.
*vasinfectum*)

| | | | |
|---|---|---|---|
| gra-MIR8637 | 287 | 3 | rv |
| gra-MIR7486e | 288 | 3 | fw |
| gra-MIR8633 | 289 | 3 | fw |
| gra-MIR8635 | 290 | 3 | fw |

KJ451424.1/Soybean Aphid

| | | | |
|---|---|---|---|
| gra-MIR8637 | 291 | 3 | rv |
| gra-MIR157a | 292 | 1 | fw |
| gra-MIR8636 | 293 | 3 | fw |
| gra-MIR8637 | 294 | 3 | rv |

KU550964.1/Pink bollworm
(*Pectinophora gossypiella*)

| | | | |
|---|---|---|---|
| gra-MIR8637 | 295 | 3 | rv |
| gra-MIR157a | 296 | 1 | fw |
| gra-MIR8644 | 297 | 3 | rv |
| gra-MIR8635 | 298 | 3 | fw |

TABLE 1B-continued

Examples of GEiGS oligo designs to generate different traits in various hosts
Table 1B provides example GeiGS oligos designed against a variety of targets in
several host organisms. For each host-target combination, four oligos are provided:
minimum sequence changes with matching structure and efficient siRNA; maximum sequence
changes with matching structure and efficient siRNA; maximum sequence changes and
non-matching structure and efficient siRNA; and maximum sequence changes with matching
structure and inefficient siRNA.

*Oryza sativa* (Rice)
AF027979.1/Rice Blast
(fungal disease caused by
*Pyricularia grisea*)

| | | | |
|---|---|---|---|
| osa-MIR166b | 299 | 1 | fw |
| osa-MIR156e | 300 | 0 | fw |
| osa-MIR160b | 301 | 3 | rv |
| osa-MIR166b | 302 | 3 | fw |

AY862192.1/Bakanae Disease
(fungal disease caused by
*Fusarium moniliforme* and
*Gibberella fujikuroi*)

| | | | |
|---|---|---|---|
| osa-MIR166b | 303 | 3 | fw |
| osa-MIR160c | 304 | 1 | rv |
| osa-MIR156j | 305 | 1 | rv |
| osa-MIR166b | 306 | 3 | fw |

KF290773.1/Stem borer
(*Scirpophaga incertulas*
Walker - Yellow Stem Borer,
*S. innota* Walker - White Stem Borer,
*Chilo suppressalis*
Walker - Striped Stem
Borer, *Sesamia inferens*
Walker - Pink Stem Borer

| | | | |
|---|---|---|---|
| osa-MIR166b | 307 | 1 | fw |
| osa-MIR156j | 308 | 3 | rv |
| osa-MIR160b | 309 | 3 | rv |
| osa-MIR166b | 310 | 3 | fw |

*Solanum lycopersicum* (Tomato)
AY855210.1/Late blight
(*Phytophthora infestans*)

| | | | |
|---|---|---|---|
| sly-MIR319b | 311 | 3 | fw |
| sly-MIR156b | 312 | 0 | fw |
| sly-MIR395a | 313 | 3 | fw |
| sly-MIR319b | 314 | 3 | fw |

KX390870.1/whitefly
*Bemisia tabaci* (*Gennadius*)

| | | | |
|---|---|---|---|
| sly-MIR319b | 315 | 3 | fw |
| sly-MIR391 | 316 | 3 | fw |
| sly-MIR319c | 317 | 1 | rv |
| sly-MIR319b | 318 | 3 | fw |

LN846610.1/Tomato yellow
leaf curl geminivirus (TYLCV)

| | | | |
|---|---|---|---|
| sly-MIR319b | 319 | 3 | fw |
| sly-MIR156b | 320 | 0 | fw |
| sly-MIR395a | 321 | 3 | fw |
| sly-MIR319b | 322 | 3 | fw |

*Solanum tuberosum* (Potato)
AY050538.3/Late Blight
(*Phytophthora infestans*)

| | | | |
|---|---|---|---|
| stu-MIR6022 | 323 | 1 | fw |
| stu-MIR7988 | 324 | 1 | rv |
| stu-MIR482d | 325 | 3 | rv |
| stu-MIR6022 | 326 | 1 | fw |

CP001654.1/Blackleg and Soft Rot
(*Erwinia* spp.)

| | | | |
|---|---|---|---|
| stu-MIR6022 | 327 | 1 | fw |
| stu-MIR7988 | 328 | 1 | rv |
| stu-MIR482d | 329 | 2 | rv |
| stu-MIR6022 | 330 | 1 | fw |

TABLE 1B-continued

Examples of GEiGS oligo designs to generate different traits in various hosts
Table 1B provides example GeiGS oligos designed against a variety of targets in several host organisms. For each host-target combination, four oligos are provided: minimum sequence changes with matching structure and efficient siRNA; maximum sequence changes with matching structure and efficient siRNA; maximum sequence changes and non-matching structure and efficient siRNA; and maximum sequence changes with matching structure and inefficient siRNA.

| | | | |
|---|---|---|---|
| KF963519.1/Cyst Nematodes (*Globodera pallida* and *G. rostochiensis*) | | | |
| stu-MIR6022 | 331 | 1 | fw |
| stu-MIR7985 | 332 | 3 | fw |
| stu-MIR6024 | 333 | 0 | rv |
| stu-MIR6022 | 334 | 1 | fw |
| *Theobroma cacao* (Cacao) LATX01001521.1/Frosty Pod Rot caused by the basidiomycete *Moniliophthora roreri* | | | |
| tcc-MIR169b | 335 | 3 | fw |
| tcc-MIR167a | 336 | 3 | rv |
| tcc-MIR167b | 337 | 1 | fw |
| tcc-MIR169b | 338 | 3 | fw |
| *Vitis vinifera* (Grape) AF007415.2/Rugose wood disease (closterovirus GVA) | | | |
| vvi-MIR167a | 339 | 3 | fw |
| vvi-MIR164b | 340 | 3 | fw |
| vvi-MIR167a | 341 | 3 | fw |
| vvi-MIR167a | 342 | 2 | fw |
| FJ436234.1/Grapevine leafroll virus | | | |
| vvi-MIR167a | 343 | 2 | fw |
| vvi-MIR167c | 344 | 3 | rv |
| vvi-MIR167a | 345 | 2 | fw |
| vvi-MIR167a | 346 | 3 | fw |
| NC_003203.1/Grapevine fanleaf degeneration disease virus (GFLV) - a nepovirus | | | |
| vvi-MIR167a | 347 | 2 | fw |
| vvi-MIR166h | 348 | 3 | fw |
| vvi-MIR167a | 349 | 2 | fw |
| vvi-MIR167a | 350 | 3 | fw |
| NC_003347.1/Grapevine fleck disease (GFkV) | | | |
| vvi-MIR167a | 351 | 2 | fw |
| vvi-MIR166b | 352 | 3 | fw |
| vvi-MIR167a | 353 | 2 | fw |
| vvi-MIR167a | 354 | 2 | fw |
| *Zea mays* (Maize) AJ488181.3/Fall Armyworm (*Spodoptera frugiperda*) | | | |
| zma-MIR166a | 355 | 0 | fw |
| zma-MIR160c | 356 | 2 | fw |
| zma-MIR156f | 357 | 0 | fw |
| zma-MIR166a | 358 | 3 | fw |
| GU329524.1/European corn borer | | | |
| zma-MIR166a | 359 | 1 | fw |
| zma-MIR166h | 360 | 1 | rv |
| zma-MIR171f | 361 | 3 | rv |
| zma-MIR166a | 362 | 3 | fw |
| NM_001039403.1/Northern and wertern corn rootworms | | | |
| zma-MIR166a | 363 | 0 | fw |
| zma-MIR172d | 364 | 3 | rv |
| zma-MIR166a | 365 | 1 | fw |
| zma-MIR166a | 366 | 3 | fw |

According to one embodiment, the plants generated by the present method are more resistant or tolerant to pathogens by at least about 10%, 20%, 30%, 40%, 50%, 60%, 70%, 80%, 90%, 95% or 100% as compared to plants not generated by the present methods (i.e. as compared to wild type plants).

Any method known in the art for assessing tolerance or resistance to a pathogen of a plant may be used in accordance with the present invention. Exampleary methods include, but are not limited to, reducing MYB46 expression in *Arabidopsis* which results in enhance resistance to *Botrytis cinereal* as described in Ramirez V I, Garcia-Andrade J, Vera P., Plant Signal Behave 2011 June; 6(6):911-3. Epub 2011 Jun. 1; or downregulation of HCT in alfalfa promotes activation of defense response in the plant as described in Gallego-Giraldo L. et al. New Phytologist (2011) 190: 627-639 doi: 10.11111j.1469-8137.2010.03621.x), both incorporated herein by reference.

According to one embodiment, there is provided a method of generating a herbicide resistant plant, the method comprising modifying a gene encoding or processed into a non-coding RNA molecule or into a RNA silencing molecule in a plant cell according to the methods of some embodiments of the invention, wherein the target RNA of interest is of a gene of the plant conferring sensitivity to the herbicide, thereby generating the herbicide resistant plant.

According to one embodiment, the herbicides target pathways that reside within plastids (e.g. within the chloroplast).

Thus to generate herbicide resistant plants, the non-coding RNA molecule is designed to target a RNA of interest including, but not limited to, the chloroplast gene psbA (which codes for the photosynthetic quinone-binding membrane protein $Q_B$, the target of the herbicide atrazine) and the gene for EPSP synthase (a nuclear protein, however, its overexpression or accumulation in the chloroplast enables plant resistance to the herbicide glyphosate as it increases the rate of transcription of EPSPs as well as by a reduced turnover of the enzyme).

According to one embodiment, the plants generated by the present method are more resistant to herbicides by at least about 10%, 20%, 30%, 40%, 50%, 60%, 70%, 80%, 90%, 95% or 100% as compared to plants not generated by the present methods.

According to one embodiment, there is provided a plant generated according to the method of some embodiments of the invention.

According to one embodiment, plant is non-genetically modified (non-GMO).

According to one embodiment, there is provided a seed of the plant generated according to the method of some embodiments of the invention.

Designing GEiGS with minimal nucleotide modifications/edits in the endogenous non-coding RNA can be achieved using in silico methods, which are based on bioinformatics tools that are well known to the skilled artisan.

According to one embodiment, such a method is effected as follows:

The following information should be available: a) Target sequence to be silenced by Gene Editing induced Gene Silencing (GEiGS) ("target"); b) Choosing whether the GEiGS (i.e. the non-coding RNA with modified silencing activity and/or specificity) would be expressed ubiquitously (e.g. constitutively) or specifically (e.g. expression specific to a certain tissue, developmental stage, stress, heat/cold shock etc.).

Submitting this information to publicly or inhouse available miRNA datasets (e.g. small RNA sequencing, genomic sequences, microarrays etc.) so as to filter (i.e. elect) only relevant miRNAs that match the input criteria: miRNAs that are expressed according to the requirement(s) described above, such as miRbase (Kozommara and Griffiths-Jones (2014)), tasRNAdb (Zhang Changqing, et al. (2013)) and mirEx 2.0 (Zielezinski, Andrzej et al. "mirEX 2.0—an Integrated Environment for Expression Profiling of Plant microRNAs." BMC Plant Biology 15 (2015): 144. PMC. Web. 15 Sep. 2018).

Using publically available tools, a list of potent target-specific siRNA sequences may be generated. The miRNAs may be aligned against the potent siRNA sequences and the most homologous miRNAs may be elected. Filtered miRNAs may have a similar sequence in the same orientation like the potent siRNAs.

Modifying the naturally mature miRNAs sequences, which are scored to have high homology to target-specific potent siRNAs, to perfectly match the target's sequence. This modification may occur in one mature miRNA strand with the highest target homology (e.g. could be either the original miRNA guide or passenger strand). Such 100% complementary to the target can potentially turn the miRNA sequence into a siRNA.

Minimal GE may be achieved by filtering miRNA sequences with naturally occurring high homology (reverse complement) to the target.

Using the primary modified miRNA genes to generate ssDNA oligos (e.g. 200-500 nt ssDNA long) and dsDNA fragments (e.g. 250-5000 nt dsDNA fragments only or cloned within plasmids) based on the genomic DNA sequences that flank the modified miRNA precursor sequence (pre-miRNA). The modified miRNA's guide strand (silencing strand) sequence may be designed to be 100% complementary to the target.

Modifying the sequence of the other miRNA gene region to preserve the original (unmodified) miRNA precursor and mature structure, through keeping the same base pairing profile.

Designing sgRNAs to specifically target the original unmodified miRNA gene (specific to the genomic miRNA loci), and not the modified version (i.e. the oligo/fragment sequences).

Analyzing the comparative restriction enzyme site between the modified and the original miRNA gene and summarizing the differential restriction sites. Such a detection system is based on PCR that is followed by restriction enzyme digestion and gel electrophoresis.

Validating as discussed in detail above.

Examining the targeting of the non-coding RNA towards other targets (e.g. "off target effect"), using in silico methods, when the endogenous non-coding RNA (e.g. miRNA) comprises naturally occurring high homology with the target (e.g. 60-90%), so as to obtain specific silencing of the target of interest.

Minimally modifying the endogenous non-coding RNA (e.g. miRNA) to boost its potency to silence the target of interest.

Validating GEiGS outcome of the primary minimally edited miRNA genes to generate candidate refined minimally edited miRNAs. An experimentally effective primary GEiGS outcome (the primary minimally edited miRNA genes) is considered as a miRNA(s) with a guide or passenger strand that is modified to match the target by 100%.

Generating several guide or passenger strand sequences that are gradually reverted back into the original sequence (as illustrated in FIG. 11).

Keeping the seed sequence in a way that there are at least 5 matches out of the seven seed nucleotides (nucleotides 2-8 from the 5' terminus).

Testing the various candidate 'refined minimally edited miRNA genes' for target silencing efficiency. Choosing the gene GE-mediated knock-in that provides the highest silencing with the minimal miRNA sequence modification.

Testing potential "off target effects" of refined minimally edited miRNA candidates. A significant prediction for "off target effects" affects the final evaluation of the refined minimally edited miRNA genes.

Testing the less refined minimally edited miRNA gene candidates based on the experimental validation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NOs: 1-4 are expressed in a DNA sequence format (e.g., reciting T for thymine), but it can refer to either a DNA sequence that corresponds to an gRNA nucleic acid sequence, or the RNA sequence of a RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed, (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

*Arabidopsis* Cell Culture

*Arabidopsis thaliana* (ecotype Landsberg erecta) cell cultures were maintained in 100 mL of liquid growth medium (4.4 g/L Murashige and Skoog (MS) salts with vitamins [Duchefa, Haarlem, The Netherlands], 30 g/L sucrose, 0.5 mg/L 1-Naphthaleneacetic acid (NAA) and 0.5 mg/L 6-Benzylaminopurine (BAP) at 25° C., 16 hour photoperiod and gentle agitation (100 rpm). Every week 6 ml of culture was transferred to fresh medium.

Plant Growth

*Arabidopsis thaliana* (ecotype Colombia-0) seedlings were surface sterilized and grown on plates containing MS medium supplemented with 0.8 g/L agar at 20° C. in 16 hour photoperiod.

Stable Transformation of *Arabidopsis* Cell Culture

*Agrobacterium* carrying the pK7WGF2 plasmid were grown in LB medium supplemented with 100 mg/L spectinomycin at 28° C. to an OD of 0.8. Bacteria were collected by centrifugation and resuspended in the same amount of plant cell culture medium. Four days after transfer to fresh medium, 4 ml of *Arabidopsis* cells were incubated with 0.1 mL of the *Agrobacterium* suspension in a Petri dish at 25° C. in the dark with gentle agitation (130 rpm). After 48 hours, the cells were collected by centrifugation and washed five times with cell culture medium to remove most of the bacteria. Finally, cells were resuspended in 2 ml of cell culture medium and plates onto a petri dish containing cell culture medium supplemented with 0.4% Phytagel, 500 mg/L timenten and 50 mg/L kanamycin. The dishes were stored at 25° C. in the dark until calli formation was observed, usually after 2 or 3 weeks Banana Embryogenic Calli:

Banana embryogenic callus is developed from an initial explant such as immature male flowers or shoot tip as described by Ma [Ma S. S., *Proceedings of Symposium on Tissue culture of horticultural crops*, Taipei, Taiwan, 8-9 Mar. 1988, pp. 181-188] and Schoofs [Schoofs H., *The origin of embryogenic cells in Musa*. PhD thesis, KULeuven, Belgium (1997)]. Embryogenic cell suspensions are initiated from freshly developed highly embryogenic calli in liquid medium. 80% of the medium is refreshed every 12-14 days until the initiated cell suspension is fully established (6-9 months).

Coffee Embryonic Calli:

Coffee embryonic calli is obtained as previously described [Etienne, H., *Protocol for somatic embryogenesis in woody plants* (2005) Springer. p. 167-1795]. Briefly, young leaves are surface sterilized, cut into 1 $cm^2$ pieces and placed on half strength semi solid MS medium supplemented with 2.26 µM 2,4-dichlorophenoxyacetic acid (2,4-D), 4.92 µM indole-3-butyric acid (IBA) and 9.84 µM isopentenyladenine (iP) for one month. Explants are then transferred to half strength semisolid MS medium containing 4.52 µM 2,4-D and 17.76 µM 6-benzylaminopurine (6-BAP) for 6 to 8 months until regeneration of embryogenic calli. Embryogenic calli are maintained on MS media supplemented with 5 µM 6-BAP.

Cell suspension cultures are generated from embryogenic calli as previously described [Acuna, J. R. and M. de Pena, *Plant Cell Reports* (1991) 10(6): p. 345-348]. Embryogenic calli (30 g/l) are placed in liquid MS medium supplemented with 13.32 µM 6-BAP. Flasks are placed in a shaking incubator (110 rpm) at 28° C. The cell suspension is subcultured/passaged every two to four weeks until fully established. Cell suspension cultures are maintained in liquid MS medium with 4.44 µM 6-BAP.

Computational Pipeline to Generate GEiGS Templates

The computational GEiGS pipeline applies biological metadata and enables an automatic generation of GEiGS DNA templates that are used to minimally edit non-coding RNA genes (e.g. miRNA genes), leading to a new gain of function. i.e. redirection of their silencing capacity to target sequence of interest.

As illustrated in FIG. 9, the pipeline starts with filling and submitting input: a) target sequence to be silenced by GEiGS; b) the host organism to be gene edited and to express the GEiGS; c) one can choose whether the GEiGS would be expressed ubiquitously or not. If specific GEiGS expression is required, one can choose from a few options (expression specific to a certain tissue, developmental stage, stress, heat/cold shock etc.).

When all the required input is submitted, the computational process begins with searching among miRNA datasets (e.g. small RNA sequencing, microarray etc.) and filtering only relevant miRNAs that match the input criteria. Next, the selected mature miRNA sequences are aligned against the target sequence and miRNA with the highest complementary levels are filtered. These naturally target-complementary mature miRNA sequences are then modified to perfectly match the target's sequence. Then, the modified mature miRNA sequences are run through an algorithm that predicts siRNA potency and the top 20 with the highest silencing score are filtered. These final modified miRNA genes are then used to generate 200-500 nt ssDNA or 250-5000 nt dsDNA sequences as follows:

200-500 nt ssDNA oligos and 250-5000 nt dsDNA fragments are designed based on the genomic DNA sequence that flanks the modified miRNA. The pre-miRNA sequence is located in the center of the oligo. The modified miRNA's guide strand (silencing) sequence is 100% complementary to the target. However, the sequence of the modified passenger miRNA strand is further modified to preserve the original (unmodified) miRNA structure, keeping the same base pairing profile.

Next, differential sgRNAs are designed to specifically target the original unmodified miRNA gene, and not the modified swapping version. Finally, comparative restriction enzyme site analysis is performed between the modified and the original miRNA gene and differential restriction sites are summarized.

Therefore, the pipeline output includes:

a) 200-500 nt ssDNA oligo or 250-5000 nt dsDNA fragment sequence with minimally modified miRNA b) 2-3 differential sgRNAs that target specifically the original miRNA gene and not the modified c) List of differential restriction enzyme sites among the modified and original miRNA gene Target Genes

*Phytoene desaturase* Gene (PDS

Rationale:

PDS is an essential gene in the chlorophyll biosynthesis pathway and loss of PDS function in plants results in albino phenotype [Fan et al., *Sci Rep* (2015) 5:12217]. When used as a target gene in genome editing (GE) strategy or RNAi, positively edited plants are easily identified by partial or complete loss of chlorophyll in leaves and other organs (bleaching).

Methods:

miRNAs with ubiquitous expression profile are chosen (depends on the application, one might choose miRNAs with expression profile that is specific to a certain tissue, developmental stage, temperature, stress etc).

miRNAs are modified to siRNA targeting the PDS gene from *Arabidopsis* (see Table 1A, below). Following transfection and FACS sorting (RFP/GFP are used for identifying positive Cas9/sgRNA transfection events), protocolonies (or calli) are transferred into solid regeneration media (half strength MS+B5 vitamins, 20 g/l sucrose, 0.8% agar) until shoots are regenerated. Loss of pigmentation in these shoots indicates loss of function of the PDS gene and correct GE. No albino phenotype is observed in the control plantlets transfected with an oligo carrying random sequence.

Green Fluorescent Protein (GFP) Gene

Rationale:

GFP is a protein composed of 238 amino acid residues (26.9 kDa) that exhibits bright green fluorescence when exposed to light in the blue to ultraviolet range. Although many other marine organisms have similar green fluorescent proteins, GFP traditionally refers to the protein first isolated from the jellyfish Aequorea victoria. The GFP from *A. victoria* has a major excitation peak at a wavelength of 395 nm and a minor one at 475 nm Its emission peak is at 509 nm, which is in the lower green portion of the visible spectrum. The fluorescence quantum yield (QY) of GFP is 0.79. The GFP from the sea pansy (*Renilla reniformis*) has a single major excitation peak at 498 nm. GFP makes for an excellent tool in many areas of biology due to its ability to form internal chromophores without requiring any accessory cofactors, gene products, or enzymes/substrates other than molecular oxygen.

Methods:

miRNAs with ubiquitous expression profile are chosen (depends on the application, one might choose miRNAs with expression profile that is specific to a certain tissue, developmental stage, temperature, stress etc).

miRNAs are modified into siRNA targeting the GFP gene (see Table 1A, below). Following transfection FACS sorting is performed, isolating mCherry-expressing protoplasts (mCherry is used for identifying positive Cas9/sgRNA transfection events) with no or low GFP signal. In the control (oligo with non-target siRNA sequence), all protoplasts express mCherry and GFP. Next, candidate successful GE protoplast (mCherry positive and GFP negative) are regenerated into plants for further analyses. Protoplasts are also qualitatively documented under the microscope. For quantification analysis and ratios FACS analysis was used.

TABLE 1A

| Target Genes IDs | | |
|---|---|---|
| Gene name | Query sequence ID | Query sequence organism |
| PDS | NM_001340908.1 (SEQ ID NO: 25) NM_117498 (SEQ ID NO: 26) | *Arabidopsis* |
| ADH1 | NC_003070.9 | *Arabidopsis* |
| eGFP | AFA52654 (SEQ ID NO: 27) | *Aequorea victoria* |

SiRNA Design

Target-specific siRNAs are designed by publically available siRNA-designers such as ThermoFisher Scientific's "BLOCK-iT™ RNAi Designer" and Invivogen's "Find siRNA sequences".

SgRNAs Design sgRNAs are designed to target the endogenous miRNA genes using the publically available sgRNA designer, as previously described in Park et al., *Bioinformatics* (2015) 31(24): 4014-4016. Two sgRNAs are designed for each cassette, but a single sgRNA is expressed per cell to initiate gene swapping. sgRNAs correspond to the pre-miRNA sequence that is modified post swapping.

In order to maximize the chance of efficient sgRNA choice, two different publicly available algorithms (CRISPER Design: www(dot)crispr(dot)mit(dot)edu:8079/ and CHOPCHOP: www(dot)chopchop(dot)cbu(dot)uib (dot)no/) are used and the top scoring sgRNA from each algorithm is selected.

Swapping SsDNA Oligo Design:

400 b ssDNA oligo is designed based on the genomic DNA sequence of the miRNA gene. The pre-miRNA sequence is located in the center of the oligo. Next, the double stranded siRNA sequences are swapped with the mature miRNA sequences in a way that the guide (silencing) siRNA strand is kept 100% complementary to the target. The sequence of the passenger siRNA strand is modified to preserve the original miRNA structure, keeping the same base pairing profile.

Swapping Plasmid DNA Design 4000 bp dsDNA fragment is designed based on the genomic DNA sequence of the miRNA gene. The pre-miRNA sequence is located in the center of the dsDNA fragment. Next, the double stranded siRNA sequences are swapped with the mature miRNA sequences in a way that the guide (silencing) siRNA strand is kept 100% complementary to the target. The sequence of the passenger siRNA strand is modified to preserve the original miRNA structure, keeping the same base pairing profile. Finally, the fragment is cloned into a standard vector (e.g. pBluescript).

Long Plasmids for Swapping:

Plasmid-1: GEiGS_mir173_si-GFP_1 (SEQ ID NO: 31)
Plasmid-2: GEiGS_mir173_si-GFP_2 (SEQ ID NO: 32)
Plasmid-3: GEiGS_mir173_si-PDS_1 (SEQ II) NO: 33)

Plasmid-4: GEiGS_mir173_si-PDS_2 (SEQ ID NO: 34)
Plasmid-5: GEiGS_mir390a_si-GFP_1 (SEQ II) NO: 35)
Plasmid-6: GEiGS_mir390a_si-GFP_2 (SEQ ID NO: 36)
Plasmid-7: GEiGS_mir390a_si-PDS_1 (SEQ ID NO: 37)
Plasmid-8: GEiGS_mir390a_si-PDS_2 (SEQ ID NO: 38)
SgRNAs Sequences:

Arabidopsis mir-390A:
1. CTATCCATCCTGAGTTTCATTGG; (SEQ ID NO: 1)

2. AAGAATCTGTAAAGCTCAGGAGG; (SEQ ID NO: 2)

Arabidopsis mir-173:
1. CTTGCAGAGAGAAATCACAGTGG; (SEQ ID NO: 3)

2. GCTTACACAGAGAATCACAGAGG; (SEQ ID NO: 4)

List of Endogenous MiRNA that are Swapped:
1. Arabidopsis mir-390A
2. Arabidopsis mir-173
SsDNA Oligos used for Gene Swapping:
Oligo-1: GEiGS_mir173_si-GFP_1 (5'→3') (SEQ ID NO: 5)
Oligo-2: GEiGS_mir173_si-GFP_2 (5'→3') (SEQ ID NO: 6)
Oligo-3: GEiGS_mir173_si-PDS_1 (5'→3') (SEQ ID NO: 7)
Oligo-4: GEiGS_mir173_si-PDS_2 (5'→3') (SEQ ID NO: 8)
Oligo-5: GEiGS_mir390a_si-GFP_1 (5'→3') (SEQ ID NO: 9)
Oligo-6: GEiGS_mir390a_si-GFP_2 (5'→3') (SEQ ID NO: 10)
Oligo 7: GEiGS_mir390a_si-PDS_1 (5'→3') (SEQ ID NO: 11)
Oligo-8: GEiGS_mir390a_si-PDS_2 (5'→3') (SEQ ID NO: 12)
SgRATA Cloning
The transfection plasmid utilized was composed of 4 modules comprising of
1) mCherry driven by the CsVMV promoter terminated by a G7 termination sequence;
2) 2×35S::hCas9-35S-ter i.e. hCas9 driven by the 35S promoter terminated by AtuNos termination sequence;
3) AtU6-26 and/or U6 synthetic promoter driving sgRNA for guide 1;

Plasmid Design

For transient expression, a plasmid containing three transcriptional units is used. The first transcriptional unit contains CsVMV promoter driving expression of mCherry and the G7 terminator. The next transcriptional unit consists of 2×-35S promoter-driving expression of Cas9 and the 35S terminator. The third contains the *Arabidopsis* U6 promoter expressing sgRNA to is target miRNA genes (each vector comprises a single sgRNAs).

Design and Cloning of CRISPR/CAS9 to Target miR-173 and miR-390 and Introducing SWAP5 to Target GFP, AtPDS3 and AtADH1

The present inventors have designed changes in the sequences of mature miR-173 and miR-390, in their genomic context, to target GFP, AtPDS3 or AtADH1, by producing small RNA that reverse complements the target genes, visualized in FIGS. 12A-G and 13A-G. In addition, to maintain the secondary structure of the miRNA precursor transcript, further changes in the pri-miRNA were carried out, as specified in FIGS. 12A-G, 13A-G, 14A-D and 15A-D and Table 2 (below). These fragments were cloned into PUC plasmids and named DONORs and the DNA fragments are referred as SWAPs. For sequences for modifying miR-173- SWAP1 and SWAP2 to target GFP, SWAP3 and SWAP4 to target AtPDS3 and SWAP9 and SWAP10 to target AtADH1 (see Table 2, below). For sequences for modifying miR-390- SWAP5 and SWAP6 to target GFP, SWAP7 and SWAP8 to target AtPDS3 and SWAP11 and SWAP12 to target AtADH1 (see Table 2, below).

Guide RNAs targeting miR-173 and milt-390 were introduced into CRISPR/CAS9 vector system in order to generate a DNA cleavage in the desired miRNA loci. These were co-introduced to the plants with the DONOR vectors via gene bombardment protocol, to introduce desired modifications through Homologous DNA Repair (HDR). These guide RNAs are specified in Table 2, below, and illustrated in FIGS. 12A and 13A.

TABLE 2

Sequences and oligos used in the experiments

| SEQ ID NO: | Aim |
|---|---|
| 39 | miR173 |
| 40 | miR390 |
| 41 | sgRNA sequence used for miR173 targeting in CRISPR/CAS9 system- GEiGS#4 |
| 42 | sgRNA sequence used for miR173 targeting in CRISPR/CAS9 system- GEiGS#5 |
| 43 | sgRNA sequence used for miR390 targeting in CRISPR/CAS9 system- GEiGS#1 |
| 44 | sgRNA sequence used for miR390 targeting in CRISPR/CAS9 system- GEiGS#3 |
| 45 | mature GEiGS-siRNA targeting GFP- used in SWAP5 (based on miR390) and in SWAP1 (based on miR173) |
| 46 | Complementary strand of mature GEiGS-siRNA targeting GFP- used in SWAP5 (based on miR390) and in SWAP1 (based on miR173) |
| 47 | mature GEiGS-siRNA targeting GFP- used in SWAP6 (based on miR390) and in SWAP2 (based on miR173) |
| 48 | Complementary strand of mature GEiGS-siRNA targeting GFP- used in SWAP6 (based on miR390) and in SWAP2 (based on miR173) |
| 49 | mature GEiGS-siRNA targeting AtPDS3- used in SWAP7 (based on miR390) and in SWAP3 (based on miR173) |
| 50 | Complementary strand of mature GEiGS-siRNA targeting AtPDS3- used in SWAP7 (based on miR390) and in SWAP3 (based on miR173) |
| 51 | mature GEiGS-siRNA targeting AtPDS3- used in SWAP8 (based on miR390) and in SWAP4 (based on miR173) |

TABLE 2-continued

Sequences and oligos used in the experiments

| SEQ ID NO: | Aim |
|---|---|
| 52 | Complementary strand of mature GEiGS-siRNA targeting AtPDS3- used in SWAP8 (based on miR390) and in SWAP4 (based on miR173) |
| 53 | mature GEiGS-siRNA targeting AtADH1- used in SWAP11 (based on miR390) and in SWAP9 (based on miR173) |
| 54 | Complementary strand of mature GEiGS-siRNA targeting AtADH1- used in SWAP11 (based on miR390) and SWAP9 (based on miR173) |
| 55 | mature GEiGS-siRNA targeting AtADH1- used in SWAP12 (based on miR390) and in SWAP10 (based on miR173) |
| 56 | Complementary strand of mature GEiGS-siRNA targeting AtADH1- used in SWAP12 (based on miR390) and in SWAP10 (based on miR173) |
| 57 | Primary transcript of miR173 (pri-miR173) |
| 58 | Primary transcript of SWAP1 (used in Donor vector for targeting GFP) |
| 59 | Primary transcript of SWAP2 (used in Donor vector for targeting GFP) |
| 60 | Primary transcript of SWAP3 (used in Donor vector for targeting PDS3) |
| 61 | Primary transcript of SWAP4 (used in Donor vector for targeting PDS3) |
| 62 | Primary transcript of SWAP9 (used in Donor vector for targeting ADH1) |
| 63 | Primary transcript of SWAP10 (used in Donor vector for targeting ADH1) |
| 64 | Primary transcript of miR390 (pri-miR390) |
| 65 | Primary transcript of SWAP5 (used in Donor vector for targeting GFP) |
| 66 | Primary transcript of SWAP6 (used in Donor vector for targeting GFP) |
| 67 | Primary transcript of SWAP7 (used in Donor vector for targeting PDS3) |
| 68 | Primary transcript of SWAP8(used in Donor vector for targeting PDS3) |
| 69 | Primary transcript of SWAP11 (used in Donor vector for targeting ADH1) |
| 70 | Primary transcript of SWAP12 (used in Donor vector for targeting ADH1) |
| 71 | Sequence of miR173 loci |
| 72 | Oligo sequence of SWAP1 (used in Donor vector for modification of miR173 for targeting GFP) |
| 73 | Oligo sequence of SWAP2 (used in Donor vector for modification of miR173 for targeting GFP) |
| 74 | Oligo sequence of SWAP3 (used in Donor vector for modification of miR173 for targeting PDS3) |
| 75 | Oligo sequence of SWAP4 (used in Donor vector for modification of miR173 for targeting PDS3) |
| 76 | Oligo sequence of SWAP9 (used in Donor vector for modification of miR173 for targeting ADH1) |
| 77 | Oligo sequence of SWAP10 (used in Donor vector for modification of miR173 for targeting ADH1) |
| 78 | Oligo sequence of miR390 loci |
| 79 | Oligo sequence of SWAP5 (used in Donor vector for modification of miR390 for targeting GFP) |
| 80 | Oligo sequence of SWAP6 (used in Donor vector for modification of miR390 for targeting GFP) |
| 81 | Oligo sequence of SWAP7 (used in Donor vector for modification of miR390 for targeting PDS3) |
| 82 | Oligo sequence of SWAP8(used in Donor vector for modification of miR390 for targeting PDS3) |
| 83 | Oligo sequence of SWAP11 (used in Donor vector for modification of miR390 for targeting ADH1) |
| 84 | Oligo sequence of SWAP12 (used in Donor vector for modification of miR390 for targeting ADH1) |
| 85 | qRT for housekeeping gene- 18S expression (NC_037304)- Forward primer |
| 86 | qRT for housekeeping gene- 18S expression (NC_037304)- Reverse primer |
| 87 | qRT for analysis of PDS3 expression (AT4G14210)- Forward primer |
| 88 | qRT for analysis of PDS3 expression (AT4G14210)- Reverse primer |
| 89 | qRT for analysis of ADH1 expression (AT1G77120)- Forward primer |
| 90 | qRT for analysis of ADH1 expression (AT1G77120)- Reverse primer |
| 91 | Forward primer for internal amplification of miR390 and its modified versions |
| 92 | Reverse primer for internal amplification of miR390 and its modified versions |
| 93 | Forward primer for external amplification of miR390 and its modified versions- primary reaction |
| 94 | Reverse for external amplification of miR390 and its modified versions- primary reaction |
| 95 | Forward primer for external amplification of miR390 and its modified versions- nested reaction |
| 96 | Reverse for external amplification of miR390 and its modified versions- nested reaction |
| 97 | Forward primer for internal amplification of miR173 and its modified versions |
| 98 | Reverse primer for internal amplification of miR173 and its modified versions |
| 99 | Forward primer for external amplification of miR173 and its modified versions- primary reaction |
| 100 | Reverse for external amplification of miR173 and its modified versions- primary reaction |

TABLE 2-continued

Sequences and oligos used in the experiments

| SEQ ID NO: | Aim |
|---|---|
| 101 | Forward primer for external amplification of miR173 and its modified versions- nested reaction |
| 102 | Reverse for external amplification of miR173 and its modified versions- nested reaction |

Protoplasts Isolation

Protoplasts were isolated by incubating plant material (e.g. leaves, calli, cell suspensions) in a digestion solution (1% cellulase, 0.5% macerozyme, 0.5% driselase, 0.4 M mannitol, 154 mM NaCl, 20 mM KCl, 20 mM MES pH 5.6, 10 mM CaCl2) for 4-24 hours at room temperature and gentle shaking. After digestion, remaining plant material was washed with W5 solution (154 mM NaCl, 125 mM CaCl2, 5 mM KCl, 2 mM MES pH5.6) and protoplasts suspension was filtered through a 40 µm strainer. After centrifugation at 80 g for 3 minutes at room temperature, protoplasts were resuspended in 2 ml W5 buffer and precipitated by gravity in ice. The final protoplast pellet was resuspended in 2 ml of MMg (0.4 M mannitol, 15 mM MgCl2, 4 mM MES pH 5.6) and protoplast concentration was determined using a hemocytometer. Protoplasts viability was estimated using Trypan Blue staining.

Polyethylene Glycol (PEG)-Mediated Plasmid Transection

PEG-transfection of protoplasts was effected using a modified version of the strategy reported by Wang [Wang et al., Scientia Horticulturae (2015) 191: p. 82-89]. Protoplasts were resuspended to a density of $2-5\times10^6$ protoplasts/ml in MMg solution. 100-200 µl of protoplast suspension was added to a tube containing the plasmid. The plasmid:protoplast ratio greatly affects transformation efficiency therefore a range of plasmid concentrations in protoplast suspension, 5-300 µg/µl, were assayed. PEG solution (100-200 µl) was added to the mixture and incubated at 23° C. for various lengths of time ranging from 10-60 minutes. PEG4000 concentration was optimized, a range of 20-80% PEG4000 in 200-400 mM mannitol, 100-500 mM CaCl$_2$ solution was assayed. The protoplasts were then washed in W5 and centrifuged at 80 g for 3 minutes, prior resuspension in 1 ml W5 and incubated in the dark at 23° C. After incubation for 24-72 hours fluorescence was detected by microscopy.

FACS Sorting of Fluorescent Protein-Expressing Cells 24-72 hours after plasmid/RNA delivery, cells were collected and sorted for fluorescent protein expression using a flow cytometer in order to enrich for mCherry/Editing agent expressing cells as previously described [Chiang et al., Sci Rep (2016) 6: 24356]. This enrichment step allows to bypassing antibiotic selection and collecting only cells transiently expressing the fluorescent protein, Cas9 and the sgRNA. These cells can be further tested for editing of the target gene by HR yielding successful swapping events and loss of the corresponding gene expression.

Bombardment and Plant Regeneration

Arabidopsis Root Preparation:

Chlorine gas sterilized Arabidopsis (cv. Col-0) seeds were sown on MS minus sucrose plates and vernalised for three days in the dark at 4° C., followed by germination vertically at 25° C. in constant light. After two weeks, roots were excised into 1 cm root segments and placed on Callus Induction Media (CIM: 1/2 MS with B5 vitamins, 2% glucose, pH 5.7, 0.8% agar, 2 mg/l IAA, 0.5 mg/l 2,4-D, 0.05 mg/l kinetin) plates. Following six days incubation in the dark, at 25° C., the root segments were transferred onto filter paper discs and placed onto CIMM plates, (1/2 MS without vitamins, 2% glucose, 0.4 M mannitol, pH 5.7 and 0.8% agar) for 4-6 hours, in preparation for bombardment.

Bombardment

Plasmid constructs were introduced into the root tissue via the PDS-1000/He Particle Delivery (Bio-Rad; PDS-1000/He System #1652257), several preparative steps, outlined below, were required for this procedure to be carried out.

Gold Stock Preparation 40 mg of 0.6 µm gold (Bio-Rad; Cat: 1652262) was mixed with 1 ml of 100% ethanol, pulse centrifuged to pellet and the ethanol removed. This wash procedure was repeated another two times.

Once washed the pellet was resuspended in 1 ml of sterile distilled water and dispensed into 1.5 ml tubes of 50 µl aliquot working volumes.

Bead Preparation

In short, the following was performed:

A single tube was sufficient gold to bombard 2 plates of Arabidopsis roots, (2 shots per plate), therefore each tube was distributed between 4 (1,100 psi) Biolistic Rupture disks (Bio-Rad; Cat: 1652329).

Bombardments requiring multiple plates of the same sample, tubes were combined and volumes of DNA and CaCl2/spermidine mixture adjusted accordingly, in order to maintain sample consistency and minimize overall preparations.

The following protocol summarises the process of preparing one tube of gold, these should be adjusted according to number of tubes of gold used.

All subsequent processes were carried out at 4° C. in an Eppendorf thermomixer.

Plasmid DNA samples were prepared, each tube comprising 11 µg of DNA added at a concentration of 1000 ng/µl 1) 493 µl ddH2O was added to 1 aliquot (7 µl) of spermidine (Sigma-Aldrich; S0266), giving a final concentration of 0.1 M spermidine. 1250 µl 2.5M CaCl2 was added to the spermidine mixture, vortexed and placed on ice.

2) A tube of pre-prepared gold was placed into the thermomixer, and rotated at a speed of 1400 rpm.

3) 11 µl of DNA was added to the tube, vortexed, and placed back into the rotating thermomixer.

4) To bind, DNA/gold particles, 70 µl of spermidine CaCl$_2$ mixture was added to each tube in the thermomixer).

5) The tubes were vigorously vortexed for 15-30 seconds and placed on ice for about 70-80 seconds.

6) The mixture was centrifuged for 1 minute at 7000 rpm, the supernatant was removed and placed on ice.

7) 500 µl 100% ethanol was added to each tube and the pellet was resuspended by pipetting and vortexed.

8) The tubes were centrifuged at 7000 rpm for 1 minute.

9) The supernatant was removed and the pellet resuspended in 50 µl 100% ethanol, and stored on ice.

Macro Carrier Preparation

The following was performed in a laminar flow cabinet:
1) Macro carriers Bio-Rad; 1652335), stopping screens (Bio-Rad; 1652336), and macro carrier disk holders were sterilized and dried.

2) Macro carriers were placed flatly into the macro carrier disk holders.

3) DNA coated gold mixture was vortexed and spread (5 µl) onto the center of each Biolistic Rupture disk.

Ethanol was allowed to evaporate.

PDS-1000 (Helium Particle Delivery System)

In short, the following was performed:

The regulator valve of the helium bottle was adjusted to at east 1300 psi incoming pressure. Vacuum was created by pressing vac/vent/hold switch and holding the fire switch for 3 seconds. This ensured helium was bled into the pipework.

1100 psi rupture disks were placed into isopropanol and mixed to remove static.

1) One rupture disk was placed into the disk retaining cap.

2) Microcarrier launch assembly was constructed (with a stopping screen and a gold containing microcarrier).

3) Petri dish Arabidopsis root callus was placed 6 cm below the launch assembly.

4) Vacuum pressure was set to 27 inches of Hg (mercury) and helium valve was opened (at approximately 1100 psi).

5) Vacuum was released; microcarrier launch assembly and the rupture disk retaining cap were removed.

6) Bombardment on the same tissue (i.e. each plate was bombarded 2 times) 7) Bombarded roots were subsequently placed on CIM plates, in the dark, at 25° C., for additional 24 hours.

Co-Bombardments

When bombarding GEiGS plasmids combinations, 5 µg (1000 ng/µl) of the sgRNA plasmid was mixed with 8.5 µg (1000 ng/µl) swap plasmid and 11 µl of this mixture was added to the sample. If bombarding with more GEiGS plasmids at the same time, the concentration ratio of sgRNA plasmids to swap plasmids used was 1:1.7 and 11 µg (1000 ng/µl) of this mixture was added to the sample. If co-bombarding with plasmids not associated with GEiGS swapping, equal ratios were mixed and 11 µg (1000 ng/µl) of the mixture was added to each sample.

Plant Regeneration

For shoot regeneration, modified protocol from Valvekens et al. [Valvekens, D. et al., *Proc Natl Acad Sci USA* (1988) 85(15): 5536-5540] was carried out. Bombarded roots were placed on Shoot Induction Media (SIM) plates, which included 1/2 MS with 135 vitamins, 2% glucose, pH 5.7, 0.8% agar, 5 mg/l 2 iP, 0.15 mg/l IAA. Plates were left in 16 hours light at 25° C.-8 hours dark at 23° C. cycles. After 10 days, plates were transferred to MS plates with 3% sucrose, 0.8% agar for a week, then transferred to fresh similar plates. Once plants regenerated, they were excised from the roots and placed on MS plates with 3% sucrose, 0.8% agar, until analysed.

Colony Formation and Plant Regeneration

The fluorescent protein positive cells were partly sampled and used for DNA extraction and genome editing (GE) testing and partly plated at high dilution in liquid medium to allow colony formation for 28-35 days. Colonies were picked, grown and split into two aliquots. One aliquot was used for DNA extraction and genome editing (GE) testing and CRISPR DNA-free testing (see below), while the others were kept in culture until their status was verified. Only the ones clearly showing to be GE and CRISPR DNA-free were selected forward. Colonies were grown in culture medium in for about 6-10 weeks. Protocolonies (or calli) were subcultured into regeneration media. (e.g. half strength MS+B5 vitamins, 20 g/l sucrose). Regenerated plantlets were placed on solidified media (0.8% agar) at a low light intensity at 28° C. After 2 months, plantlets were transferred to soil and placed in a glasshouse at 80-100% humidity.

Virus Inoculation and DIVA Delivery to *Arabidopsis* Seedlings

Sap from *Arabidopsis* leaves infected with TuMV infectious clone p35S::TuMV-GFP (0.1 mg/ml) are used for mechanical inoculations.

Plant Propagation

Clones that were sequenced and predicted to have lost the expression of the target genes and found to be free of the CRISPR system DNA/RNA were propagated for generation in large quantities and in parallel were differentiated to generate seedlings from which functional assay is performed to test the desired trait.

Phenotypic Analysis

As described above, such as by looking at the pigmentation, florescence or morphology dependent on the target gene.

Allyl Alcohol Selection

For selection of plants with allyl alcohol, 10 days post bombardment, roots were placed on SIM media. Roots were immersed in 30 mM allyl alcohol (Sigma-Aldrich, US) for 2 hours. Then the roots were washed three times with MS media, and placed on MS plates with 3% sucrose, 0.8% agar. Regeneration process was carried on as previously described.

Genotyping

Tissue samples were treated and amplicons amplified in accordance to the manufacturers recommendations. MyTaq Plant-PCR Kit (BioLine BIO 25056) for short internal amplification and Phire Plant Direct PCR Kit (Thermo Scientific; F-130WH) for longer external amplifications. Oligos used for these amplifications are specified in Table 2, above. Different modifications in the miRNA loci were identified through different digestion patterns of the amplicons, as follows:

For modifications of miR-390—internal amplicon was 978 base pairs long, and for external amplification it was 2629 base pairs. For the identification of swap 7, digestion with NlaIII resulted in a fragment size of 636 base pairs, while in the wt version it was cleaved to 420 and 216 long fragments. For the identification of swap 8, digestion with Hpy188I resulted in fragments size of 293 and 339 base pairs, while in the wt version this site was absent and resulted in a 632-long fragment. For the identification of swaps 11 and 12, digestion with BccI resulted in a fragment size of 662 base pairs, while in the wt version it was cleaved to 147 and 417 long fragments.

For modifications of miR-173-internal amplicon was 574 base pairs long, and for nested external amplification it was 466 base pairs. For the identification of swap 3, digestion with BsII resulted in fragments size of 217 and 249 base pairs in the external amplicon and 317 and 149 in the internal one. In the wt version this site was absent and resulted in a 466-long fragment in the external amplicon and 574 in the internal reaction. For the identification of swap 4, digestion with BtsαI resulted in fragments size of 212 and 254 base pairs in the external amplicon and 212 and 362 in the internal one. In the wt version, this site was absent and resulted in a 466-long fragment in the external amplicon and 574 in the internal reaction. For the identification of swap 9, digestion with NlaIII resulted in fragments size of 317 and 149 base pairs in the external amplicon and 317 and 244 in the internal one. In the wt version this site was absent and resulted in a 466-long fragment in the external amplicon and 561 in the internal reaction. For the identification of swap 10, digestion with NlaIII resulted in fragments size of 375 and 91 base pairs in the external amplicon and 375 and 186 in the internal one. In the wt version, this site was absent and resulted in a 466-long fragment in the external amplicon and 561 in the internal reaction.

DNA and RNA Isolation

Samples were harvested into liquid nitrogen and stored in −80° C. until processed. Grinding of tissue was carried out in tubes placed in dry ice, using plastic Tissue Grinder Pestles (Axygen, US). Isolation of DNA and total RNA from ground tissue was carried out using RNA/DNA Purification kit (cat. 48700; Norgen Biotek Corp., Canada), according to manufacturer's instructions. In the case of low 260/230 ratio (<1.6), of the RNA fraction, isolated RNA was precipitated overnight in −20° C., with 1 µl glycogen (cat. 10814010; Invitrogen, US) 10% V/V sodium acetate, 3 M pH 5.5 (cat. AM9740, Invitrogen, US) and 3 times the volume of ethanol. The solution was centrifuged for 30 minutes in maximum speed, at 4° C. This was followed by two washes with 70% ethanol, airdrying for 15 minutes and resuspending in Nuclease-free water (cat. 10977035; Invitrogen, US).

Reverse Transcription (RT) and Quantitative Real-Time PCR (qRT-PCR)

One microgram of isolated total RNA was treated with DNase I according to manufacturer's manual (AMPD1; Sigma-Aldrich, US). The sample was reverse transcribed, following the instructor's manual of High-Capacity cDNA Reverse Transcription Kit (cat 4368814; Applied Biosystems, US).

For gene expression, Quantitative Real Time PCR (qRT-PCR) analysis was carried out on CFX96 Touch™ Real-Time PCR Detection System (BioRad, US) and SYBR® Green JumpStart™ Taq ReadyMix™ (S4438, Sigma-Aldrich, US), according to manufacturer's' protocols, and analysed with Bio-RadCFX manager program (version 3.1). For the analysis of AtADH1 (AT1G77120) the following primer set was used: Forward GTTGAGAGTGTTG-GAGAAGGAG SEQ ID NO: 367 and reverse CTCGGTGTTGATCCTGAGAAG SEQ ID NO: 368; For the analysis of AtPDS3 (AT4G14210), the following primer set was used: Forward GTACTGCTGGTCCTTTGCAG SEQ ID NO: 369 and reverse AGGAGCACTACG-GAAGGATG SEQ ID NO: 370; For endogenous calibration gene, the 18S ribosomal RNA gene (NC_037304) was used—Forward ACACCCTGGGAATTGGTTT SEQ ID NO: 371 and reverse GTATGCGCCAATAAGACCAC SEQ ID NO: 372.

Example 1A

Genome Editing Induced Gene Silencing (GEIGS)

In order to design GEiGS oligos, template non-coding RNA molecules (precursors) that are processed and give raise to derivate small silencing RNA molecules (matures) are required. Two sources of precursors and their corresponding mature sequences were used for generating GEiGS oligos. For miRNAs, sequences were obtained from the miRBase database [Kozomara, A. and Griffiths-Jones, S., *Nucleic Acids Res* (2014) 42: D68,ÄiD73]e tasiRNA precursors and matures were obtained from the tasiRNAdb database [Zhang, C. et al, *Bioinformatics* (2014) 30: 1045, Äí1046].

Silencing targets were chosen in a variety of host organisms (see Table 1B, above). siRNAs were designed against these targets using the siRNArules software [Holen, T., *RNA* (2006) 12: 1620,Äí1625.]. Each of these siRNA molecules was used to replace the mature sequences present in each precursor, generating "naive" GEiGS oligos. The structure of these naive sequences was adjusted to approach the structure of the wild type precursor as much as possible using the ViennaRNA Package v2.6 [Lorenz, R. et al., ViennaRNA Package 2.0. Algorithms for Molecular Biology (2011) 6: 26]. After the structure adjustment, the number of sequences and secondary structure changes between the wild type and the modified oligo were calculated. These calculations are essential to identify potentially functional GEiGS oligos that require minimal sequence changes with respect to the wild type.

CRISPR/cas9 small guide RNAs (sgRNAs) against the wild type precursors were generated using the CasOT software [Xiao, A. et al., Bioinformatics (2014) 30: 1180, Äí1182] (see Table 113, above). sgRNAs were selected where the modifications applied to generate the GEiGS oligo affect the PAM region of the sgRNA, rendering it ineffective against the modified oligo.

Example 1B

Gene Silencing of Endogenous Plant Gene—PDS

In order to establish a high-throughput screening for quantitative evaluation of endogenous gene silencing using Genome Editing Induced Gene Silencing (GEiGS), the present inventors considered several potential visual markers. The present inventors chose to focus on genes involved in pigment accumulation, such as those encoding for phytoene desaturase (PDS). Silencing of PDS causes photobleaching (FIG. 2B) which allows to use it as robust seedling screening after gene editing as proof-of-concept (POC). FIGS. 2A-C show a representative experiment with *N. benthamiana* and *Arabidopsis* plants silenced for PDS. Plants show the characteristic photobleaching phenotype observed in plants with diminished amounts of carotenoids.

In the POC experiment, choosing siRNAs was carried out as follows:

In order to initiate the RNAi machinery in *Arabidopsis* or *Nicotiana benthamiana* against the PDS gene using GEiGS application, there is a need to identify effective 21-24 bp siRNA targeting PDS. Two approaches are used in order to find active siRNA sequences: 1) screening the literature—since PDS silencing is a well-known assay in many plants, the present inventors are identifying well characterized short siRNA sequences in different plants that might be 100% match to the gene in *Arabidopsis* or *Nicotiana benthamiana*. 2) There are many public algorithms that are being used to predict which siRNA will be effective in initiating gene silencing to a given gene. Since the predictions of these algorithms are not 100%, the present inventors are using only sequences that are the outcome of at least two different algorithms.

In order to use siRNA sequences that silence the PDS gene, the present inventors are swapping them with a known endogenous non-coding RNA gene sequence using the CRISPR/Cas9 system (e.g. changing a miRNA sequence, changing a long dsRNA sequence, creating antisense RNA, changing tRNA etc.). There are many databases of characterized non-coding RNAs e.g. miRNAs; the present inventors are choosing several known *Arabidopsis* or *Nicotiana benthamiana* endogenous non-coding RNAs e.g. miRNAs with different expression profiles (e.g. low constitutive expression, highly expressed, induced in stress etc.). For example, in order to swap the endogenous miRNA sequence with siRNA targeting PDS gene, the present inventors are using the HR approach (Homologous Recombination). Using HR, two options are contemplated: using a donor ssDNA oligo sequence of around 250-500 nt which includes, for example, the modified miRNA sequence in the middle or using plasmids carrying 1 Kb-4 Kb insert which is almost 100% identical to the miRNA surrounding in the plant genome except the 2×21 bp of the miRNA and the *miRNA that is changed to the siRNA of the PDS (500-2000 by up and downstream the siRNA, as illustrated in FIG. 1). The transfection includes the following constructs: CRISPR: Cas9/GFP sensor to track and enrich for positive transformed cells, gRNAs that guides the Cas9 to produce a double stranded break (DSB) which is repaired by HR depending on the insertion vector/oligo. The insertion vector/oligo contains two continuous regions of homology surrounding the targeted locus that are replaced (i.e. miRNA) and is modified to carry the mutation of interest (i.e. siRNA). If plasmid is used, the targeting construct comprises or is free from restriction enzymes-recognition sites and is used as a template for homologous recombination ending with the replacement of the miRNA with the siRNA of choice. After transfection to protoplasts, FACS is used to enrich for Cas9/sgRNA-transfected events, protoplasts are regenerated to plants and bleached seedlings are screened and scored (see FIG. 1). As control, protoplasts are transfected with an oligo carrying a random non-PDS targeting sequence. The positive edited plants are expected to produce siRNA sequences targeting PDS and therefore PDS gene is silenced and seedling are seen as white compared to the control with no gRNA, It is important to note that after the swap, the edited miRNA will still be processed as miRNA because the original base-pairing profile is kept. However, the newly edited processed miRNA has a high complementary to the target (e.g. 100%), and therefore, in practice, the newly edited small RNA will act as siRNA.

Example 2

Gene Silencing of "Endogenous" Transgene GFP

Another quick and robust approach to check the efficiency of GEiGS is by silencing a transgene which is also a marker gene like GFP (green fluorescent protein). There are few easy options to assess the effectiveness of the GFP silencing in the cell, e.g. FACS analysis, PCR and microscopy. In order to show POC of GFP silencing using GEiGS, the present inventors are using a transgenic *Arabidopsis* or tobacco lines stably expressing GFP. Protoplasts from GFP expressing plants are used with GEiGS methodology to modify endogenous non-coding RNA e.g. miRNA to act as siRNA potent to initiate the RNA silencing mechanism targeting the GFP gene. The positive edited plants are expected to be silenced for GFP expression as illustrated in FIGS. 3A-D. Furthermore, GFP silencing in plants is well characterized and there are many available short RNA sequences (siRNA) that can be utilized to initiate GFP silencing. Therefore, for gene swapping, the present inventors are using publically available tools to generate siRNA specific to GFP or are using known siRNA molecules available from the literature.

In order to use siRNA sequences that will silence the GFP gene, the present inventors are swapping them with a known endogenous non-coding RNA e.g. miRNA gene sequence using the CRISPR/Cas9 system (e.g. changing a miRNA sequence, changing a long dsRNA sequence, creating antisense RNA, changing tRNA etc.). There are many databases of characterized non-coding RNAs e.g. miRNAs, the present inventors are choosing several known *Arabidopsis* or *Nicotiana benthamiana* non-coding RNAs e.g. miRNAs with different expression profiles (e.g. low constitutive expression, highly expressed, induced in stress etc.). For example, in order to swap the endogenous miRNA sequence with siRNA, the present inventors are using the HR approach. In HR two options are contemplated: using a donor oligo sequence of around 250-500 bp which includes, for example, the siRNA sequence in the middle or using plasmids expressing 1 Kb-4 Kb insert which is almost 100% identical to the miRNA surrounding in the plant genome except the 2×21 bp of the miRNA and the *miRNA that are changed to the siRNA of the GFP (500-2000 bp up and downstream the siRNA, see FIG. 1). The transfection includes the following constructs: CRISPR:Cas9/RFP sensor to track and enrich for positive transformed cells using e.g. FACS analysis, gRNAs that guides the Cas9 to produce a DSB which is repaired by HR depending on the insertion vector/oligo. The insertion vector contains two continuous regions of homology surrounding the targeted locus that are replaced (i.e. miRNA) and is modified to carry the mutation of interest (i.e. siRNA). The targeting construct comprises or is free from restriction enzymes-recognition sites and is used as a template for homologous recombination ending with the replacement of the miRNA with the siRNA of choice. After transfection to protoplasts, FACS is used to enrich for positive transfected events (using the red fluorescent protein (RFP) marker), enriched protoplasts are scored for GFP silencing under a microscope (FIG. 4). The positive edited protoplasts are expected to produce siRNA sequences targeting GFP and therefore GFP expression of the transgene is expected to be silenced as compared to control protoplasts. GFP is a faster method than PDS since the two last steps of recovery and regeneration are not necessary, the scoring can be done on the protoplasts/cells level.

Example 3

Gene Silencing of Exogenous Transgene-GFP in *Arabidopsis*

In addition to the former example of GFP silencing, another way to demonstrate the efficiency of GEiGS is by silencing a marker gene like GFP (green fluorescent protein) in a transient GFP transformation assay. In this example, first plant cells (e.g. *Arabidopsis*) are treated using GEiGS to express small siRNA molecules targeting GFP (method for utilizing siGFP are discussed in Example 2 above). Control protoplasts (e.g. GEiGS-PDS) and edited protoplasts using GEiGS (expressing siGFP) are then transfected with a plasmid expressing separately two markers (sensor) GFP+ RFP. Protoplast which express only RFP but not GFP in the GEiGS treatment are the results of GFP silencing due to siGFP expression (as illustrated in FIG. 5).

Example 4

Immunized Plants to Virus Infection, Silencing of Exogenous Virus Gene (Using GFP as Marker)

In order to prove that GEiGS is a robust method for plant immunization with the ability to knock down exogenous genes, the present inventors are providing an example of silencing of a virus gene. There are various viruses that infect different plant species and that can be used in the present POC: TuMV, CMV, TMV etc.

Turnip mosaic virus (TuMV) is transmitted non-persistently by aphids and causes prevalent diseases of cruciferous crops in many parts of the world. TuMV genome, which is single-stranded, is a positive-sense RNA molecule of approximately 10,000 nt (accession number NC_002509). TuMV has the same typical potyvirus genetic organization previously discussed by Urcuqui-Inchima et al. [Urcuqui-Inchima et al., Virus Res. (2001) 74: 157-175]. The symptoms of TuMV are mottling in broad, yellow, circular, and irregular areas. The oldest leaves often become bright yellow all over. The lamina often becomes necrotic. Extensive use was made of TuMV-GFP and suppressor-deficient TuMV-AS9-GFP to expose antiviral silencing activities in Arabidopsis. Wild-type plants were immune to TuMV-AS9-GFP, but immunity was effectively suppressed by loss of DCL2 and DCL4, indicating that TuMV normally masks the effects of a siRNA dependent antiviral response [Hernan Garcia-Ruiz et al., The Plant Cell (2010) 22: 481-496].

Cucumber mosaic virus (CMV) is a plant pathogenic virus in the family Bromoviridae. It is the type member of the plant virus genus, Cucumovirus. This virus has a worldwide distribution and a very wide host range. In fact it has the reputation of having the widest host range of any known plant virus. It can be transmitted from plant to plant both mechanically by sap and by aphids in a stylet-borne fashion. This virus was first found in cucumbers (Cucumis sativus) showing mosaic symptoms in 1934, hence the name Cucumber mosaic. An expression CMV-based expression vector that utilizes the mutant 3a MP for CP-independent cell-to-cell movement was developed. This new vector [Fujiki et al., Virology (2008) 381(1): 136-142] was incorporated into an agrobacterium binary vector and delivered into plants via agroinfiltration. The results demonstrate that this novel CMV-based expression vector holds great promise for recombinant protein production.

Tobacco mosaic virus (TMV), a single-stranded RNA virus that commonly infects solanaceous plants, a plant family that includes many species such as petunias, tomatoes and tobacco. The virus causes a mosaic pattern of brown spots on the surface of leaves. The virus doesn't usually cause the plant to die, but can seriously stunt its growth. Lower leaves can suffer from 'mosaic burn' in hot and dry weather, where large areas of the leaf die. This virus cannot get into plants on its own. Plants are usually infected via plant wounds after human handling or via contaminated equipment. Once inside the plant, the virus releases its genetic code (RNA). The plant gets confused by this code, mistaking it for its own, and starts to produce virus proteins. Virus-based expression systems in plants are particularly attractive versus alternative transient expression systems due to the high level of gene multiplication and concomitant elevated levels of expression achievable within a short period of time while minimizing impairment of host activities. TMV is one of the most extensively studied plant viruses and has thus become a natural choice for vector development. TMV-based vectors have led to recombinant protein yield as high as 80% of total soluble protein. Agroinfection is inexpensive and reproducible, making it a preferred method of delivering viral expression vectors into plant tissues as part of the T-DNA of a binary vector carried b Agrobacterium tumefaciens.

The present inventors are using TuMV-GFP for infection of Arabidopsis or TMV-GFP for tobacco plants. In order to create plants resistant to virus infection, the present inventors are using an engineered virus that expresses GFP upon plant infection. Using such a virus will enable to use the same constructs as described in Example 3, above. The difference being that now the GIP is expressed from the virus infection. Control plants that are infected with virus-GFP (CMV or TMV) show expression of GFP under the microscope (FIG. 6) however, GEiGS plants engineered to express siRNA GFP are expected to show reduced levels of GFP (FIG. 6). Accordingly, generating GEiGS plants with no GFP expression after infection with Virus-GFP will demonstrate that RNAi silencing of exogenous gene was achieved and that GEiGS is an effective method to immune plants against viruses and potentially other pathogens. There are few easy options to assess the effectiveness of the GFP silencing in the cell, such as the use FACS analysis, PCR and microscopy. GFP silencing in plants is well characterized and there are many available short RNA sequences (siRNA) that are active in initiating GFP silencing. Therefore, for gene swapping, the present inventors are using a few known siRNA molecules available from the literature.

In order to use siRNA sequences that will silence the GFP gene, the present inventors are swapping them with a known endogenous non-coding RNA e.g. miRNA gene sequence using the CRISPR/Cas9 system (as discussed above, there are many other options to introduce these siRNA sequences, like changing long dsRNA sequences, creating antisense RNA, changing tRNA etc.). There are many databases of characterized endogenous non-coding RNA e.g. miRNAs, the present inventors are choosing several known Arabidopsis or Nicotiania benthamiana non-coding RNA e.g. miRNAs with different expression profiles (e.g. low constitutive expression, highly expressed, induced in stress etc.). For example, in order to swap the endogenous miRNA sequence with siRNA, the present inventors are using the HR approach. In HR two options are contemplated: using a donor oligo sequence of around 250-500 bp which includes, for example, the siRNA sequence in the middle or using plasmids expressing 1 Kb-4 Kb insert which is almost 100% identical to the miRNA surrounding in the plant genome except the 2×21 bp of the miRNA and the *miRNA that are changed to the siRNA of the GFP (500-2000 bp up and downstream the siRNA, see FIG. 1). The transfection includes the following constructs: CRISPR:Cas9/RFP sensor to track and enrich for positive transformed cells using e.g. FACS analysis, gRNAs that guides the Cas9 to produce a DSB which is repaired by HR depending on the insertion vector; oligo. The insertion vector contains two continuous regions of homology surrounding the targeted locus that are replaced (i.e. miRNA) and is modified to carry the mutation of interest (i.e. siRNA). The targeting construct comprises or is free from restriction enzymes-recognition sites and is used as a template for homologous recombination ending with the replacement of the miRNA with the siRNA of choice. After transfection to protoplasts, FACS is used to enrich for positive transfected events, protoplasts are regenerated to plants and plants are infected with the virus by mechanical inoculations. Plants are scored for GFP silencing under microscope (as described in FIG. 6). The positive edited protoplasts with GEiGS are expected to produce siRNA sequences targeting GFP and therefore the virus GFP gene expression is expected to be silenced compared to control unedited plants.

Example 5

Banana Plant Resistant to Nematode

The damage to banana productivity due to nematodes is tremendous, reaching up to 50% of yield loss in untreated soils. The problem is accentuated in traditional banana plantations where mono cropping is a common practice. Banning of nematicides like methyl bromide in various parts of the world exacerbated the problem and leaves farmers with inappropriate and unreliable alternatives. *Radopholus similis*, the burrowing nematode, is the most economically important nematode parasite of banana in the world. Infection by burrowing nematode causes toppling disease of banana, yellows disease of pepper and spreading decline of citrus. These diseases are the result of burrowing nematode infection destroying root tissue, leaving plants with little to no support or ability to take up water and translocate nutrients. Because of the damage that it causes to citrus, ornamentals and other agricultural industries, worldwide, burrowing nematode is one of the most regulated nematode plant pests (FIG. 7).

RNA interference (RNAi) has emerged as an invaluable gene-silencing tool for functional analysis in a wide variety of organisms, particularly the free-living model nematode *Caenorhabditis elegans*. An increasing number of studies have described its application to plant parasitic nematodes. Genes expressed in a range of cell types are silenced when nematodes take up double stranded RNA (dsRNA) or short interfering RNAs (siRNAs) that elicit a systemic RNAi response. Extensive siRNA studies with *C. elegans* suggest that successfully preventing nematodes from completing their life cycle is attributed to silencing genes that are expressed early in embryonic development. In *R. similis* such candidate genes might be Calreticulin13 (CRT) or the gene collagen 5 (col-5). CRT is a $Ca^{2+}$-binding multifunctional protein that plays key roles in the parasitism, immune evasion, reproduction and pathogenesis of many animal parasites and plant nematodes. Therefore, CRT is a promising target for controlling *R. similis*. Col-5 belongs to the collagen genes of nematodes encode proteins that have a diverse range of functions. Among their most abundant products are the cuticular collagens, which include about 80% of the proteins present in the nematode cuticle. The structures of these collagens have been found to be strikingly similar in the free-living and parasitic nematode species studied so far, and the genes that encode them appear to constitute a large multigene family whose expression is subject to developmental regulation.

By utilizing GEiGS, the present inventors are creating banana plants expressing siRNA molecules that are transmitted from their roots to nematodes upon feeding, and subsequently induce the silencing of nematode genes. The silencing of genes essential for succession in the life cycle inhibits nematode propagation and abolishes damages caused by nematodes. The present inventors are changing a few banana endogenous non-coding RNA e.g. miRNA sequences with short sequences from the CRT or the col-5 genes. GEiGS is used in Banana protoplasts that are regenerated to plantlets and are then screened with different nematodes for resistance.

Example 6

Banana Plant Resistant to *Fusarium oxysporum*

The genus *Fusarium* includes several species of fungi that are broadly spread in soil and organic substrates worldwide. *Fusarium oxysporum* is one of the most relevant species of this genus and is the causal agent of root rots, damping-off and wilt diseases in more than 100 plants species, including a wide range of economically important horticultural crops, flowers, trees, and a number of field crops such as cabbage, banana, and cotton. *Fusarium oxysporum* is a devastating pathogen causing extensive yield losses in a variety of crops and development of sustainable, environmentally friendly methods to improve crop resistance is crucial. *F. oxysporum* consists of over 120 forma specialis of pathogenic strains determined by their primary host plants. All strains of *F. oxysporum* are saprophytic, being able to grow and survive for long periods on organic matter in soil making it very difficult to control. Its pathogenic life cycle starts with spore germination upon recognition of a suitable host. Once the hyphae is formed, the pathogen enters its host by directly penetrating the roots and colonizes it within the xylem by producing microconidia which leads to mycelium formation. Colonization and toxin production by the pathogen results in blockage of the host vascular system, causing characteristic disease symptoms including vasculature yellowing, vein clearing, chlorosis, and necrosis in leaf veins and leaves, leaf detachment and wilting. After the plant dies, the fungus sporulates on the decayed leaf surfaces. *F. oxysporum* is most prevalent in tropical and subtropical regions and it is expected that its geographical range will extend due to climate change. Current control methods for *Fusarium* wilt are very limited with crop rotations being ineffective due to the large host range and its persistence in soil. Management of *Fusarium* wilt is mainly done through cultural practices and farm hygiene which only reduce the transmission of inoculum while soil sterilization can only be performed in glasshouses. Soil fumigation using broad-spectrum biocides such as methyl bromide is expensive and has many hazardous effects on the environment.

Hu z. have used Host-Delivered RNA interference technology to partially silence three different genes (FOW2, FRP1, and OPR) in the hemi-biotrophic fungus *F. oxysporum* f. sp. *Conglutinans* [Hu et al., *Front Chem*. (2015) 20 (3):1]. Expression of double stranded RNA (dsRNA) molecules targeting fungal pathogen genes was achieved in a number of transgenic *Arabidopsis* lines. *F. oxysporum* infecting the transgenic lines displayed substantially reduced mRNA levels on all three targeted genes, with an average of 75, 83, and 72% reduction for FOW2, FRP1, and OPR, respectively. The silencing of pathogen genes had a clear positive effect on the ability of the transgenic lines to fight infection. All transgenic lines displayed enhanced resistance to *F. oxysporum* with delayed disease symptom development, especially FRP1 and OPR lines. Survival rates after fungal infection were higher in the transgenic lines compared to control wild type plants which consistently showed survival rates of 10%, with FOW2 lines showing 25% survival; FRP1 lines 30-50% survival and OPR between 45 and 70% survival. The downregulation effect was specific for the targeted genes without unintended effects in related genes (Hu Z. (2015) supra). It was shown that in fungi, both long and short dsRNAs are equally internalized and induce RNAi to silence target genes.

The present inventors are utilizing GEiGS in order to create Banana plants resistant to *F. oxysporum* by changing few endogenous non-coding RNA e.g. miRNAs sequences to specifically target the fungi genes like FOW2, FRP1 and OPR. Edited Protoplasts are regenerated to plantlets and are challenged with *F. oxysporum* in a controlled environment, resistant plants are verified to express the relevant siRNA.

Example 7

Coffee Tree Resistant to Nematode

*Coffea* is a genus of flowering plants whose seeds, called coffee beans, are used to make various coffee beverages and products. It is a member of the family Rubiaceae. They are shrubs or small trees native to tropical and southern Africa and tropical Asia. Coffee ranks as one of the world's most valuable and widely traded commodity crops and is an important export product of several countries, including those in Central and South America, the Caribbean and Africa. A steady decline in coffee production has been attributed to biotic and socio-economic constraints. Among the less studied biotic constraints are nematodes.

Plant-parasitic nematodes are regarded as a severe constraint to coffee production in the world and especially in Vietnam (FIG. 8). The dominant and most important species are *Radopholus arabocoffeae* and *Pratylenchus coffeae*. Both species are responsible for the death of plants younger than 5 years old. Traditionally, the main method to control *P. coffeae* is by chemical means there is no particular control strategy against *R. arabocoffeae*.

The present inventors are utilizing GEiGS strategy (as described in Example 5 above) to create *Coffea canephora* (Robusta) trees expressing siRNA molecules that are transmitted from their roots to nematodes upon feeding, and subsequently inducing the silencing of nematode genes. The silencing of genes essential for succession in the life cycle inhibits nematode propagation and abolishes damages caused by nematodes. The present inventors are thus changing a few endogenous non-coding RNA e.g. miRNA sequences with short sequences from the nematode genes. GEiGS is used in coffee protoplasts that are regenerated to plantlets and then screened with different nematodes for resistance.

Example 8

Generation of Plants with Modified Endogenous MiRNA to Target Different Genes

Minimal modifications in the genomic loci of a miRNA, in its recognition sequence (which will mature to a miRNA) can lead to a new system to regulate new genes, in a non-transgenic manner. Therefore, an *agrobacterium*-free transient expression method was used, to introduce these modifications by bombardment of *Arabidopsis* roots, and their regeneration for further analysis. The present inventors had chosen to target two genes, PDS3 and ADH1 in *Arabidopsis* plants.

Carotenoids play an important role in many physiological processes in plants and the phytoene desaturase gene (PDS3) encodes one of the important enzymes in the carotenoid biosynthesis pathway, its silencing produces an albino/bleached phenotype. Accordingly, plants with reduced expression of PDS3 exhibit reduced chlorophyll levels, up to complete albino and dwarfism.

Alcohol dehydrogenase (ADH1) comprises a group of dehydrogenase enzymes which catalyse the interconversion between alcohols and aldehydes or ketones with the concomitant reduction of NAD+ or NADP+. The principal metabolic purpose for this enzyme is the breakdown of alcoholic toxic substances within tissues. Plants harbouring reduced ADH1 expression exhibit increase tolerance to allyl alcohol. Accordingly, plants with reduced ADH1 are resistant to the toxic effect of allyl alcohol, therefore their regeneration was carried out with allyl alcohol selection.

Two well-established miRNAs were chosen to be modified, miR-173 and miR-390, that were previously shown to be expressed throughout plant development [Zielezinski A et al., *BMC Plant Biology* (2015) 15: 144]. To introduce the modification, a 2-component system was used. First, the CRISPR/CAS9 system was used, to generate a cleavage in the miR-173 and miR-390 loci, through designed specific guide RNAs (FIGS. 12A and 13A; and Table 2, above), to promote homologous DNA repair (HDR) in the site. Second, A DONOR sequence, with the desired modification of the miRNA sequence, to target the newly assigned genes, was introduced as a template for the HDR (FIGS. 12A-G, 13A-G, 14A-D and 15A-D; Table 2, above). In addition, since the secondary structure of the primary transcript of the miRNA (pri-miRNA) is important for the correct biogenesis and activity of the mature miRNA, further modifications were introduced in the complementary strand in the pri-miRNA and analysed in mFOLD (www(dot)unafold(dot)rna (dot)Albany(dot)edu) for structure conservation (FIGS. 12A-G and 13A-G). In total, two guides were designed for each miRNA loci, and two different DONOR sequences (modified miRNA sequences) were designed for each gene (FIGS. 14A-D and 15A-D, and Table 2, above).

Example 9

Bombardment and Plant Regeneration

GEiGS constructs were bombarded into pre-prepared roots (as discussed in detail in the materials and experimental procedures section, above) and regenerated. Plantlets were selected via bleached phenotype for PDS3 transformants and survival on allyl alcohol treatment for ADH1 transformants. In order to validate Swap compared to no Swap, i.e. retained wild type, these plants were subsequently screened for insertion through specific primers spanning the modified region followed by restriction digest (FIG. 16).

Example 10

Genotype Validation of Phenotype Selection

As discussed above, the Proof of Concept (POC) for the gene editing system was established using well known phenotypic traits, Phytoene desaturase (PDS3) and Alcohol desaturase (ADH1) as targets.

As mentioned above, plants harbouring reduced ADH1 expression exhibit increase tolerance to allyl alcohol. Therefore, bombarded plants for modified miRNA to target ADH1 were regenerated in media containing 30 mM allyl alcohol and compared to the regeneration rate of control plants. 118 GEiGS #3+SWAP11 allyl alcohol selected plants survived, compared to 51 control plants on allyl alcohol media (data not shown). Of the selected GEiGS #3+SWAP11, 5 were shown to harbour the DONOR (data not shown). The large amount of plants regenerating in the DONOR-treated plants, might be due to transient expression, during the bombardment process, as well.

Thus, PDS3 and ADH1 selection through bleached phenotype (FIG. 16) and allyl alcohol selection (FIG. 17), respectively, give an ideal means for transformed plantlet selection for genotyping.

Swap region of 4 kb was assessed primarily through internal primers and specific amplicon differentiation of original wild type to insertion via restriction enzyme digestion variation.

ADH1 (FIG. 17) showed a comparative genotype of allyl alcohol selected plants with the expected DONOR presence restriction pattern when compared to restricted and non-restricted DONOR plasmid. PDS3 (FIG. 16) showed a comparison of bombarded samples phenotypes with and without DONOR and their respective differential restriction enzyme digestion patterns compared to that of restricted and non-restricted DONOR plasmid. These results provided a clear association of PDS3 albino/bleached phenotype to the expected restriction pattern. Subsequent external PCR combining specific internal, within the Swap region, in conjunction with external primer, outside and specific to the genomic region to swap into was carried out (data not shown) Further validation of the Swap was obtained through Sanger sequencing of the PCR amplicons, in order to assess heterozygous, homozygous, or presence of DONOR Swap (data not shown).

Example 11

Modified MiRNA Reduce the Expression of their New Target Gene

In order to verify the potential of the modified miRNAs in the GEiGS system to down regulate the expression of their newly designated targets, gene expression analysis was carried out using qRT-PCR (quantitative Real-Time PCR). RNA was extracted and reverse transcribed, from the positively identified regenerated plants and compared to regenerated plants, treated in parallel, but were not introduced with the relevant modifying constructs. In the case, where miR-173 was modified to target PDS3 (GEiGS #4+SWAP4), a reduction of 83% in the gene expression level, on average, was observed (FIG. 18). In plants with modified miR-390 to target ADH1 (GEiGS #3+SWAP11), a similar change in gene expression was observed, 82% of the levels in the is control plants (FIG. 19). Taken together, these results substantiate the gene editing methods of modifying endogenous miRNAs to successfully target new genes and reduce their expression, by replacing the target recognition sequence in the miRNA transcript in the endogenous locus.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of modifying a DNA sequence encoding or processed into an RNA silencing molecule with a silencing specificity toward a first target RNA in a plant cell, the method comprising introducing into the plant cell a DNA editing agent and a donor oligonucleotide comprising a desired modification for use as a repair template to generate the desired modification in the DNA sequence, thereby modifying the DNA sequence encoding the RNA silencing molecule, wherein the modification comprises nucleotide replacement and redirects the silencing specificity of said RNA silencing molecule towards a second target RNA, said first target RNA and said second target RNA being distinct, such that the original specificity of the RNA silencing molecule is abolished and a new specificity towards the second target RNA is gained.

2. The method of claim 1, wherein the DNA sequence encoding the RNA silencing molecule is endogenous to the plant cell.

3. The method of claim 1, wherein modifying said DNA sequence encoding said RNA silencing molecule comprises imparting said RNA silencing molecule with at least 45% complementarity towards said second target RNA.

4. The method of claim 1, wherein said RNA silencing molecule is processed from a precursor.

5. The method of claim 4, wherein said RNA silencing molecule is a RNA interference (RNAi) molecule selected from the group consisting of a small interfering RNA (siRNA), a short hairpin RNA (shRNA), a microRNA (miRNA), a Piwi-interacting RNA (piRNA) and trans-acting siRNA (tasiRNA).

6. The method of claim 5, wherein said RNAi molecule is designed such that a sequence of said RNAi molecule is modified to preserve secondary RNA structure and to be recognized by cellular RNAi factors.

7. The method of claim 1, wherein said modification comprises a modification of at most 200 nucleotides.

8. The method of claim 1, wherein said DNA editing agent comprises at least one gRNA operatively linked to a plant expressible promoter.

9. The method of claim 1, wherein said DNA editing agent comprises an endonuclease.

10. The method of claim 9, wherein said DNA editing agent is of a DNA editing system selected from the group consisting of a meganuclease, a zinc finger nucleases (ZFN), a transcription-activator like effector nuclease (TALEN) and CRISPR.

11. The method of claim 9, wherein said endonuclease comprises Cas9.

12. The method of claim 1, wherein said second target RNA is exogenous to the plant cell.

* * * * *

SEQUENCE LISTING

```
<160> NUMBER OF SEQ ID NOS: 417

<210> SEQ ID NO 1
<211> LENGTH: 23
<212> TYPE: DNA
<213> ORGANISM: Arabidopsis thaliana

<400> SEQUENCE: 1
ctatccatcc tgagtttcat tgg                                            23

<210> SEQ ID NO 2
<211> LENGTH: 23
<212> TYPE: DNA
<213> ORGANISM: Arabidopsis thaliana

<400> SEQUENCE: 2
aagaatctgt aaagctcagg agg                                            23

<210> SEQ ID NO 3
<211> LENGTH: 23
<212> TYPE: DNA
<213> ORGANISM: Arabidopsis thaliana

<400> SEQUENCE: 3
cttgcagaga gaaatcacag tgg                                            23

<210> SEQ ID NO 4
<211> LENGTH: 23
<212> TYPE: DNA
<213> ORGANISM: Arabidopsis thaliana

<400> SEQUENCE: 4
gcttacacag agaatcacag agg                                            23

<210> SEQ ID NO 5
<211> LENGTH: 400
<212> TYPE: DNA
<213> ORGANISM: Artificial sequence
```

<220> FEATURE:
<223> OTHER INFORMATION: Oligo-1: GEiGS_mir173_si-GFP_1

<400> SEQUENCE: 5

| | | | | | |
|---|---|---|---|---|---|
| gcataaaaaa | gtcaacaaaa | cttaaagcgg | cggtctcatc | gtaatctcag | cccaataccc | 60 |
| tattttcctc | tcccctatat | aaatactttc | ttcttctact | gatcttcttc | tcacaaataa | 120 |
| acccaaatat | atcaatctac | tgtgttggtg | attaagtact | taagtcgtgc | tgcttcatgt | 180 |
| ggagtggtca | aaaaagttgt | agttttctta | aagtctcttt | cctctccaca | taagcaggac | 240 |
| gagttaagag | cttgctccct | aaacttatct | ctctgatgat | ttaatgttag | agatcttcgt | 300 |
| aaatctatgt | gtttgataga | tctgatgcgt | tttttgagtt | gatgatttga | ttattttca | 360 |
| ctggaaagta | tctcattagg | gtaacgataa | tgttttatgg | | | 400 |

<210> SEQ ID NO 6
<211> LENGTH: 400
<212> TYPE: DNA
<213> ORGANISM: Artificial sequence
<220> FEATURE:
<223> OTHER INFORMATION: Oligo-2: GEiGS_mir173_si-GFP_2

<400> SEQUENCE: 6

| | | | | | |
|---|---|---|---|---|---|
| gcataaaaaa | gtcaacaaaa | cttaaagcgg | cggtctcatc | gtaatctcag | cccaataccc | 60 |
| tattttcctc | tcccctatat | aaatactttc | ttcttctact | gatcttcttc | tcacaaataa | 120 |
| acccaaatat | atcaatctac | tgtgttggtg | attaagtact | tagttgtact | ccagcttgtg | 180 |
| ccagtggtca | aaaaagttgt | agttttctta | aagtctcttt | cctctggcaa | agctgcagta | 240 |
| caactaagag | cttgctccct | aaacttatct | ctctgatgat | ttaatgttag | agatcttcgt | 300 |
| aaatctatgt | gtttgataga | tctgatgcgt | tttttgagtt | gatgatttga | ttattttca | 360 |
| ctggaaagta | tctcattagg | gtaacgataa | tgttttatgg | | | 400 |

<210> SEQ ID NO 7
<211> LENGTH: 400
<212> TYPE: DNA
<213> ORGANISM: Artificial sequence
<220> FEATURE:
<223> OTHER INFORMATION: Oligo-3: GEiGS_mir173_si-PDS_1

<400> SEQUENCE: 7

| | | | | | |
|---|---|---|---|---|---|
| gcataaaaaa | gtcaacaaaa | cttaaagcgg | cggtctcatc | gtaatctcag | cccaataccc | 60 |
| tattttcctc | tcccctatat | aaatactttc | ttcttctact | gatcttcttc | tcacaaataa | 120 |
| acccaaatat | atcaatctac | tgtgttggtg | attaagtact | ttatccacac | aaactacctg | 180 |
| caagtggtca | aaaaagttgt | agttttctta | aagtctcttt | cctcttgcag | tagttagtgt | 240 |
| ggataaagag | cttgctccct | aaacttatct | ctctgatgat | ttaatgttag | agatcttcgt | 300 |
| aaatctatgt | gtttgataga | tctgatgcgt | tttttgagtt | gatgatttga | ttattttca | 360 |
| ctggaaagta | tctcattagg | gtaacgataa | tgttttatgg | | | 400 |

<210> SEQ ID NO 8
<211> LENGTH: 400
<212> TYPE: DNA
<213> ORGANISM: Artificial sequence
<220> FEATURE:
<223> OTHER INFORMATION: Oligo-4: GEiGS_mir173_si-PDS_2

```
<400> SEQUENCE: 8
gcataaaaaa gtcaacaaaa cttaaagcgg cggtctcatc gtaatctcag cccaataccc    60
tattttcctc tcccctatat aaatactttc ttcttctact gatcttcttc tcacaaataa   120
acccaaatat atcaatctac tgtgttggtg attaagtact ttgacaatcc agccaatcca   180
gcagtggtca aaaagttgt  agttttctta aagtctcttt cctctgctga ttggcaggat   240
tgtcaaagag cttgctccct aaacttatct ctctgatgat ttaatgttag agatcttcgt   300
aaatctatgt gtttgataga tctgatgcgt ttttgagtt  gatgatttga ttattttca    360 ctggaaagta tctcattagg gtaacgataa tgttttatgg                          400

<210> SEQ ID NO 9
<211> LENGTH: 400
<212> TYPE: DNA
<213> ORGANISM: Artificial sequence
<220> FEATURE:
<223> OTHER INFORMATION: Oligo-5: GEiGS_mir390a_si-GFP_1

<400> SEQUENCE: 9
agaggagatg acgtgtgttc cttcgaaccc gagttttgtt cgtctataaa tagcaccttc    60
tcttctcctt cttcctcact tccatctttt tagcttcact atctctctat aatcggtttt   120
atctttctct aagtcacaac ccaaaaaaac aaagtagaga gaatctgta  aagtcgtgct   180 gcttcatgtg gatgatgatc acattcgtta tctattttt  ccacatgaag aagcacgact   240
tgattggctc ttcttactac aatgaaaaag gccgaggcaa aacgcctaaa atcacttgag   300
aatcaattct ttttactgtc catttaagct atcttttata aacgtgtctt attttctatc   360
tcttttgttt aaactaagaa actatagtat tttgtctaaa                          400

<210> SEQ ID NO 10
<211> LENGTH: 400
<212> TYPE: DNA
<213> ORGANISM: Artificial sequence
<220> FEATURE:
<223> OTHER INFORMATION: Oligo-6: GEiGS_mir390a_si-GFP_2

<400> SEQUENCE: 10
agaggagatg acgtgtgttc cttcgaaccc gagttttgtt cgtctataaa tagcaccttc    60
tcttctcctt cttcctcact tccatctttt tagcttcact atctctctat aatcggtttt   120
atctttctct aagtcacaac ccaaaaaaac aaagtagaga gaatctgta  agttgtactc   180 cagcttgtgc catgatgatc acattcgtta tctattttt  ggcacaagct tgagtacaac   240
tgattggctc ttcttactac aatgaaaaag gccgaggcaa aacgcctaaa atcacttgag   300
aatcaattct ttttactgtc catttaagct atcttttata aacgtgtctt attttctatc   360
tcttttgttt aaactaagaa actatagtat tttgtctaaa                          400

<210> SEQ ID NO 11
<211> LENGTH: 400
<212> TYPE: DNA
<213> ORGANISM: Artificial sequence
<220> FEATURE:
<223> OTHER INFORMATION: Oligo-7: GEiGS_mir390a_si-PDS_1

<400> SEQUENCE: 11
agaggagatg acgtgtgttc cttcgaaccc gagttttgtt cgtctataaa tagcaccttc    60
tcttctcctt cttcctcact tccatctttt tagcttcact atctctctat aatcggtttt   120
atctttctct aagtcacaac ccaaaaaaac aaagtagaga gaatctgta  tatccacaca   180
```

```
aactacctgc aatgatgatc acattcgtta tctattttt tgcaggtagt gtgtgtggat    240
agattggctc ttcttactac aatgaaaaag gccgaggcaa aacgcctaaa atcacttgag   300
aatcaattct ttttactgtc catttaagct atctttata aacgtgtctt attttctatc    360
tcttttgttt aaactaagaa actatagtat tttgtctaaa                         400

<210> SEQ ID NO 12
<211> LENGTH: 400
<212> TYPE: DNA
<213> ORGANISM: Artificial sequence
<220> FEATURE:
<223> OTHER INFORMATION: Oligo-8: GEiGS_mir390a_si-PDS_2

<400> SEQUENCE: 12
agaggagatg acgtgtgttc cttcgaaccc gagttttgtt cgtctataaa tagcaccttc    60
tcttctcctt cttcctcact tccatctttt tagcttcact atctctctat aatcggtttt   120
atctttctct aagtcacaac ccaaaaaaac aaagtagaga agaatctgta tgacaatcca   180
gccaatccag catgatgatc acattcgtta tctatttttt gctggattgg atggattgtc   240
agattggctc ttcttactac aatgaaaaag gccgaggcaa aacgcctaaa atcacttgag   300
aatcaattct ttttactgtc catttaagct atcttttata aacgtgtctt attttctatc   360
tcttttgttt aaactaagaa actatagtat tttgtctaaa                         400

<210> SEQ ID NO 13
<211> LENGTH: 1005
<212> TYPE: DNA
<213> ORGANISM: Artificial sequence
<220> FEATURE:
<223> OTHER INFORMATION: CaMV-35S-promoter nucleic acid sequence

<400> SEQUENCE: 13
tttggagagg acaggcttct tgagatcctt caacaattac caacaacaac aaacaacaaa    60
caacattaca attactattt acaattacag tcgactctag aggatccatg gtgagcaagg   120
gcgaggagct gttcaccggg gtggtgccca tcctggtcga gctggacggc gacgtaaacg   180
gccacaagtt cagcgtgaga ggcgagggcg agggcgatgc caccaacggc aagctgaccc   240
tgaagttcat ctgcaccacc ggcaagctgc ccgtgccctg gcccaccctc gtgaccaccc   300
tgacctacgg cgtgcagtgc ttcagccgct accccgacca catgaagcag cacgacttct   360
tcaagtccgc catgcccgaa ggctacgtcc aggagcgcac catctctttc aaggacgacg   420
gcacttacaa gacccgcgcc gaggtgaagt tcgagggcga caccctggtg aaccgcatcg   480
agctgaaggg catcgacttc aaggaggacg gcaacatcct ggggcacaag ctggagtaca   540
acttcaacag ccacaacgtc tatatcactg ccgacaagca gaagaacggc atcaaggcca   600
acttcaagat ccgccacaac gttgaggacg gcagcgtgca gctcgccgac cactaccagc   660
agaacacccc catcggcgac ggccccgtgc tgctgcccga caaccactac ctgagcaccc   720
agtccgttct gagcaaagac cccaacgaga gcgcgatca catggtcctg ctggagttcg   780
tgaccgccgc cgggatcact ctcggcatgg acgagctgta caagtaaagc ggccgcccgg   840
ctgcagatcg ttcaaacatt tggcaataaa gtttcttaag attgaatcct gttgccggtc   900
ttgcgatgat tatcatataa tttctgttga attacgttaa gcatgtaata attaacatgt   960
aatgcatgac gttatttatg agatgggttt ttatgattag agtcc                  1005
```

<210> SEQ ID NO 14
<211> LENGTH: 855
<212> TYPE: DNA
<213> ORGANISM: Artificial sequence
<220> FEATURE:
<223> OTHER INFORMATION: NOS terminator nucleic acid sequence

<400> SEQUENCE: 14

| | | | | | |
|---|---|---|---|---|---|
| gctcgtccat | gccgagagtg | atcccggcgg | cggtcacgaa | ctccagcagg | accatgtgat | 60 |
| cgcgcttctc | gttggggtct | tgctcagaa | cggactgggt | gctcaggtag | tggttgtcgg | 120 |
| gcagcagcac | ggggccgtcg | ccgatggggg | tgttctgctg | gtagtggtcg | gcgagctgca | 180 |
| cgctgccgtc | ctcaacgttg | tggcggatct | tgaagttggc | cttgatgccg | ttcttctgct | 240 |
| tgtcggcagt | gatatagacg | ttgtggctgt | tgaagttgta | ctccagcttg | tgccccagga | 300 |
| tgttgccgtc | ctccttgaag | tcgatgccct | tcagctcgat | gcggttcacc | agggtgtcgc | 360 |
| cctcgaactt | cacctcggcg | cgggtcttgt | aagtgccgtc | gtccttgaaa | gagatggtgc | 420 |
| gctcctggac | gtagccttcg | ggcatggcgg | acttgaagaa | gtcgtgctgc | ttcatgtggt | 480 |
| cggggtagcg | gctgaagcac | tgcacgccgt | aggtcagggt | ggtcacgagg | gtgggccagg | 540 |
| gcacgggcag | cttgccggtg | gtgcagatga | acttcagggt | cagcttgccg | ttggtggcat | 600 |
| cgccctcgcc | ctcgcctctc | acgctgaact | tgtggccgtt | tacgtcgccg | tccagctcga | 660 |
| ccaggatggg | caccaccccg | gtgaacagct | cctcgccctt | gctcaccatg | gatcctctag | 720 |
| agtcgactgt | aattgtaaat | agtaattgta | atgttgtttg | ttgtttgttg | ttgttggtaa | 780 |
| ttgttgaagg | atctcaagaa | gcctgtcctc | tccaaatgaa | atgaacttcc | ttatatagag | 840 |
| gaagggtctt | gcgaa | | | | | 855 |

<210> SEQ ID NO 15
<211> LENGTH: 215
<212> TYPE: DNA
<213> ORGANISM: Artificial sequence
<220> FEATURE:
<223> OTHER INFORMATION: CaMV-35S terminator nucleic acid sequence

<400> SEQUENCE: 15

| | | | | | |
|---|---|---|---|---|---|
| cgctctgtca | tcgttacaat | caacatgcta | ccctccgcga | gatcatccgt | gtttcaaacc | 60 |
| cggcagctta | gttgccgttc | ttccgaatag | catcggtaac | atgagcaaag | tctgccgcct | 120 |
| tacaacggct | ctcccgctga | cgccgtcccg | gactgatggg | ctgcctgtat | cgagtggtga | 180 |
| ttttgtgccg | agctgccggt | cggggagctg | ttggc | | | 215 |

<210> SEQ ID NO 16
<211> LENGTH: 216
<212> TYPE: DNA
<213> ORGANISM: Artificial sequence
<220> FEATURE:
<223> OTHER INFORMATION: G7-ter nucleic acid sequence

<400> SEQUENCE: 16

| | | | | | |
|---|---|---|---|---|---|
| gatccccgt | cgacagctag | ctatatcatc | aatttatgta | ttacacataa | tatcgcactc | 60 |
| agtctttcat | ctacggcaat | gtaccagctg | atataatcag | ttattgaaat | atttctgaat | 120 |
| ttaaacttgc | atcaataaat | ttatgttttt | gcttggacta | taatacctga | cttgttattt | 180 |
| tatcaataaa | tatttaaact | atatttcttt | caagat | | | 216 |

```
<210> SEQ ID NO 17
<211> LENGTH: 516
<212> TYPE: DNA
<213> ORGANISM: Artificial sequence
<220> FEATURE:
<223> OTHER INFORMATION: CsVMV promoter nucleic acid sequence

<400> SEQUENCE: 17
ccagaaggta attatccaag atgtagcatc aagaatccaa tgtttacggg aaaaactatg      60
gaagtattat gtaagctcag caagaagcag atcaatatgc ggcacatatg caacctatgt     120
tcaaaaatga agaatgtaca gatacaagat cctatactgc agaatacga agaagaatac      180 gtagaaattg aaaagaaga accaggcgaa gaaaagaatc ttgatgacgt aagcactgac      240
gacaacaatg aaaagaagaa gataaggtcg gtgattgtga agagacata gaggacacat      300 gtaaggtgga aaatgtaagg gcggaaagta accttatcac aaaggaatct tatccccac       360 tacttatcct tttatatttt tccgtgtcat ttttgcccct gagttttcct atataaggaa      420
ccaagttcgg catttgtgaa acaagaaaa aatttggtgt aagctatttt ctttgaagta      480
ctgaggatac aacttcagag aaatttgtaa gtttgt                              516

<210> SEQ ID NO 18
<211> LENGTH: 636
<212> TYPE: DNA
<213> ORGANISM: Arabidopsis thaliana

<400> SEQUENCE: 18
gtcgacgagt cagtaataaa cggcgtcaaa gtggttgcag ccggcacaca cgagtcgtgt      60
ttatcaactc aaagcacaaa tactttcct caacctaaaa ataaggcaat tagccaaaaa      120
caactttgcg tgtaaacaac gctcaataca cgtgtcattt tattattagc tattgcttca     180
ccgccttagc tttctcgtga cctagtcgtc ctcgtctttt cttcttcttc ttctataaaa      240
caatacccaa agagctcttc ttcttcacaa ttcagattc aatttctcaa atcttaaaa       300 actttctctc aattctctct accgtgatca aggtaaattt ctgtgttcct tattctctca      360
aaatcttcga ttttgttttc gttcgatccc aatttcgtat atgttctttg gtttagattc     420
tgttaatctt agatcgaaga cgattttctg ggtttgatcg ttagatatca tcttaattct     480
cgattagggt ttcatagata tcatccgatt tgttcaaata atttgagttt tgtcgaataa     540
ttactcttcg atttgtgatt tctatctaga tctggtgtta gtttctagtt tgtgcgatcg     600
aatttgtaga ttaatctgag tttttctgat taacag                             636

<210> SEQ ID NO 19
<211> LENGTH: 4140
<212> TYPE: DNA
<213> ORGANISM: Artificial sequence
<220> FEATURE:
<223> OTHER INFORMATION: pco_Cas9_NLS  nucleic acid sequence

<400> SEQUENCE: 19
atggataaga agtactctat cggactcgat atcggaacta actctgtggg atgggctgtg      60
atcaccgatg agtacaaggt gccatctaag aagttcaagg ttctcggaaa caccgatagg     120
cactctatca agaaaaacct tatcggtgct ctcctcttcg attctggtga aactgctgag     180
gctaccagac tcaagagaac cgctagaaga aggtacacca agagaaagaa caggatctgc     240
tacctccaag agatcttctc taacgagatg gctaaagtgg atgattcatt cttccacagg     300
ctcgaagagt cattcctcgt ggaagaagat aagaagcacg agaggcaccc tatcttcgga     360
```

-continued

```
aacatcgttg atgaggtggc ataccacgag aagtaccctactatctacca cctcagaaag    420 aagctcgttg attctactga taaggctgat ctcaggctca tctacctcgc tctcgctcac    480
atgatcaagt tcagaggaca cttcctcatc gagggtgatc tcaaccctga taactctgat    540
gtggataagt tgttcatcca gctcgtgcag acctacaacc agcttttcga agagaaccct    600
atcaacgctt caggtgtgga tgctaaggct atcctctctg ctaggctctc taagtcaaga    660
aggcttgaga acctcattgc tcagctccct ggtgagaaga agaacggact tttcggaaac    720
ttgatcgctc tctctctcgg actcaccct aacttcaagt ctaacttcga tctcgctgag    780
gatgcaaagc tccagctctc aaaggatacc tacgatgatg atctcgataa cctcctcgct    840
cagatcggag atcagtacgc tgatttgttc ctcgctgcta agaacctctc tgatgctatc    900
ctcctcagtg atatcctcag agtgaacacc gagatcacca aggctccact ctcagcttct    960
atgatcaaga gatacgatga gcaccaccag gatctcacac ttctcaaggc tcttgttaga   1020
cagcagctcc cagagaagta caaagagatt ttcttcgatc agtctaagaa cggatacgct   1080
ggttacatcg atggtggtgc atctcaagaa gagttctaca agttcatcaa gcctatcctc   1140
gagaagatgg atggaaccga ggaactcctc gtgaagctca atagagagga tcttctcaga   1200
aagcagagga ccttcgataa cggatctatc cctcatcaga tccacctcgg agagttgcac   1260
gctatcctta aaggcaaga ggatttctac ccattcctca aggataacag ggaaaagatt   1320
gagaagattc tcaccttcag aatcccttac tacgtgggac ctctcgctag aggaaactca   1380
agattcgctt ggatgaccag aaagtctgag gaaaccatca ccccttggaa cttcgaagag   1440
gtggtggata agggtgctag tgctcagtct ttcatcgaga ggatgaccaa cttcgataag   1500
aaccttccaa acgagaaggt gctccctaag cactctttgc tctacgagta cttcaccgtg   1560
tacaacgagt tgaccaaggt taagtacgtg accgagggaa tgaggaagcc tgcttttttg   1620
tcaggtgagc aaaagaaggc tatcgttgat ctcttgttca agaccaacag aaaggtgacc   1680
gtgaagcagc tcaaagagga ttacttcaag aaaatcgagt gcttcgattc agttgagatt   1740
tctggtgttg aggataggtt caacgcatct ctcggaacct accacgatct cctcaagatc   1800
attaaggata aggatttctt ggataacgag gaaaacgagg atatcttgga ggatatcgtt   1860
cttaccctca ccctctttga agatagagag atgattgaag aaaggctcaa gacctacgct   1920
catctcttcg atgataaggt gatgaagcag ttgaagagaa aagatacac tggttgggga   1980 aggctctcaa gaaagctcat taacggaatc agggataagc agtctggaaa gacaatcctt   2040
gatttcctca gtctgatgg attcgctaac agaaacttca tgcagctcat ccacgatgat   2100
tctctcacct ttaaagagga tatccagaag gctcaggttt caggacaggg tgatagtctc   2160
catgagcata tcgctaacct cgctggatct cctgcaatca agaagggaat cctccagact   2220
gtgaaggttg tggatgagtt ggtgaaggtg atgggaaggc ataagcctga aacatcgtg    2280 atcgaaatgg ctagagagaa ccagaccact cagaagggac agaagaactc tagggaaagg   2340
atgaagagga tcgaggaagg tatcaaagag cttggatctc agatcctcaa agagcaccct   2400
gttgagaaca ctcagctcca gaatgagaag ctctacctct actacctcca gaacggaagg   2460
gatatgtatg tggatcaaga gttggatatc aacaggctct ctgattacga tgttgatcat   2520
atcgtgccac agtcattctt gaaggatgat tctatcgata acaaggtgct caccaggtct   2580
gataagaaca ggggtaagag tgataacgtg ccaagtgaag aggttgtgaa gaaaatgaag   2640
aactattgga ggcagctcct caacgctaag ctcatcactc agaaaagtt cgataacttg   2700 actaaggctg agaggggagg actctctgaa ttggataagg caggattcat caagaggcag   2760
```

```
cttgtggaaa ccaggcagat cactaagcac gttgcacaga tcctcgattc taggatgaac    2820
accaagtacg atgagaacga taagttgatc agggaagtga aggttatcac cctcaagtca    2880
aagctcgtgt ctgatttcag aaaggatttc caattctaca aggtgaggga aatcaacaac    2940
taccaccacg ctcacgatgc ttaccttaac gctgttgttg gaaccgctct catcaagaag    3000
tatcctaagc tcgagtcaga gttcgtgtac ggtgattaca aggtgtacga tgtgaggaag    3060
atgatcgcta agtctgagca agagatcgga aaggctaccg ctaagtattt cttctactct    3120
aacatcatga atttcttcaa gaccgagatt accctcgcta acggtgagat cagaagagg    3180 ccactcatcg agacaaacgg tgaaacaggt gagatcgtgt gggataaggg aagggatttc    3240
gctaccgtta gaaaggtgct ctctatgcca caggtgaaca tcgttaagaa aaccgaggtg    3300
cagaccggtg gattctctaa agagtctatc ctccctaaga ggaactctga taagctcatt    3360
gctaggaaga aggattggga ccctaagaaa tacggtggtt tcgattctcc taccgtggct    3420
tactctgttc tcgttgtggc taaggttgag aagggaaaga gtaagaagct caagtctgtt    3480
aaggaacttc tcggaatcac tatcatggaa aggtcatctt tcgagaagaa cccaatcgat    3540
ttcctcgagg ctaagggata caaagaggtt aagaaggatc tcatcatcaa gctcccaaag    3600
tactcactct tcgaactcga gaacggtaga agaggatgc tcgcttctgc tggtgagctt    3660
caaaagggaa acgagcttgc tctcccatct aagtacgtta actttctta cctcgcttct    3720 cactacgaga gttgaaggg atctccagaa gataacgagc agaagcaact tttcgttgag    3780
cagcacaagc actacttgga tgagatcatc gagcagatct ctgagttctc taaaagggtg    3840
atcctcgctg atgcaaacct cgataaggtg ttgtctgctt acaacaagca cagagataag    3900
cctatcaggg aacaggcaga gaacatcatc catctcttca cccttaccaa cctcggtgct    3960
cctgctgctt tcaagtactt cgatacaacc atcgatagga agagatacac ctctaccaaa    4020
gaagtgctcg atgctaccct catccatcag tctatcactg gactctacga gactaggatc    4080
gatctctcac agctcggtgg tgattcaagg gctgatccta agaagaagag gaaggtttga    4140
```

<210> SEQ ID NO 20
<211> LENGTH: 263
<212> TYPE: DNA
<213> ORGANISM: Artificial sequence
<220> FEATURE:
<223> OTHER INFORMATION: AtuNos ter nucleic acid sequence

<400> SEQUENCE: 20

```
gtcaagcaga tcgttcaaac atttggcaat aaagtttctt aagattgaat cctgttgccg      60
gtcttgcgat gattatcata taatttctgt tgaattacgt taagcatgta ataattaaca     120
tgtaatgcat gacgttattt atgagatggg tttttatgat tagagtcccg caattataca     180
tttaatacgc gatagaaaac aaaatatagc gcgcaaacta ggataaatta tcgcgcgcgg     240
tgtcatctat gttactagat cga                                            263
```

<210> SEQ ID NO 21
<211> LENGTH: 1147
<212> TYPE: DNA
<213> ORGANISM: Artificial sequence
<220> FEATURE:
<223> OTHER INFORMATION: Synthetic construct clone eGFP-OsP5SM_E/R eGFP
      (eGFP) gene

<400> SEQUENCE: 21

```
atgtctagag tgagcaaggg cgaggagctg ttcaccgggg tggtgcccat cctggtcgag      60
ctggacggcg acgtaaacgg ccacaagttc agcgtgtccg gcgagggcga gggcgatgcc     120
acctacggca agctgaccct gaagttcatc tgcaccaccg gcaagctgcc cgtgccctgg     180
cccacccteg tgaccaccct gacctacggc gtgcagtgct cagccgcta ccccgaccac     240
atgaagcagc acgacttctt caagtccgcc atgcccgaag ctacgtcca ggaggtagat     300
ttatgcatcc tcttgtcatg agaagtcgaa ttgttcccat tctgtgtgtt gcagctacag     360
atggagatac atagagatac tcgtggattt tgcttagtgt tgagttttgt tctggttgtg     420
aactaaaagt ttatacattt gcaggaaata aatagccttt tgtttaaatc aaaaggtctt     480
acctatgtta gtgtgaagca ttggatccca agaactcca aaatgcgatg aggcatattt      540
aatcttgtct ggactagtaa caggttggga tgaccacctg tgaagctcca acaggattgc     600
ctcctcacgc aatgtttgag gtctgatgtt caatagcttg ttttgtttca ctttgctttg     660
gactttcttt tcgccaatga gctatgtttc tgatggtttt cactcttttg gtgtgtagag     720
aaccatcttc ttcaaggacg acggcaacta caagacccgc gccgaggtga agttcgaggg     780
cgacaccctg gtgaaccgca tcgagctgaa gggcatcgac ttcaaggagg acggcaacac     840
ctggggcaca gctggagta caactacaac agccacaacg tctatatcat ggccgacaag      900
cagaagaagg catcaaggtg aacttcaaga tccgccacaa catcgaggac ggcagcgtgc     960
agctcgccga ccactacagc agaacacccc catcggcgac ggccccgtgc tgctgcccga    1020
caaccactac ctgagcaccc agtccgccct gagcaaagac cccaacgaga gcgcgatca    1080
catggtcctg ctggagttcg tgaccgccgc cgggatcact ctcggcatgg acgagctgta    1140
caagtaa                                                              1147
```

<210> SEQ ID NO 22
<211> LENGTH: 2074
<212> TYPE: DNA
<213> ORGANISM: Arabidopsis thaliana

<400> SEQUENCE: 22

```
caattatgtg ttaaagatac aaacttttgt ctgatttgct tccaccggtt tcacctaaga      60
tactcaattt tcttactttt tgtgtgtttt gtaattctaa ttctttttata gcttcaattt    120
ttagattcat tgaagcagtt gtgagttaag ttggagaaaa tggttgtgtt tgggaatgtt     180
tctgcggcga atttgcctta tcaaaacggg ttttttggagg cactttcatc tggaggttgt    240
gaactaatgg gacatagctt tagggttccc acttctcaag cgcttaagac aagaacaagg    300
aggaggagta ctgctggtcc tttgcaggta gtttgtgtgg atattccaag gccagagcta    360
gagaacactg tcaatttctt ggaagctgct agtttatctg catccttccg tagtgctcct    420
cgtcctgcta agcctttgaa agttgtaatt gctggtgctg gattggctgg attgtcaact    480
gcaaagtacc tggctgatgc aggccacaaa cctctgttgc ttgaagcaag atgttctctt    540
ggtggaaaga tagctgcatg gaaggatgaa gatgggact ggtatgagac tggtttacat     600
atttttcttcg gtgcttatcc gaatgtgcag aattttatttg gaacttgg gatcaatgat    660
cggttgcagt ggaaggaaca ctccatgatt tttgctatgc caagtaaacc tggagaattt    720
agtagatttg acttcccaga tgtcctacca gcacccttaa atggtatttg gctatttttg    780
cggaacaacg agatgctgac atggccagag aaaataaagt ttgctattgg acttttgcca    840
gccatggtcg gcggtcaggc ttatgttgag gcccaagatg gtttatcagt caagaatgg     900
```

```
atggaaaagc agggagtacc tgagcgcgtg accgacgagg tgtttattgc catgtcaaag    960
gcgctaaact ttataaaccc tgatgaactg tcaatgcaat gcattttgat agctttgaac   1020
cggtttcttc aggaaaaaca tggttccaag atggcattct tggatggtaa tcctccggaa   1080
aggctttgta tgccagtagt ggatcatatt cgatcactag gtggggaagt gcaacttaat   1140
tctaggataa agaaaattga gctcaatgac gatggcacgg ttaagagttt cttactcact   1200
aatggaagca ctgtcgaagg agacgcttat gtgtttgccg ctccagtcga tatcctgaag   1260
ctccttttac cagatccctg gaaagaaata ccgtacttca agaaattgga taaattagtt   1320
ggagtaccag ttattaatgt tcatatatgg tttgatcgaa aactgaagaa cacatatgat   1380
cacctactct ttagcagaag taaccttctg agcgtgtatg ccgacatgtc cttaacttgt   1440
aaggaatatt acgatcctaa ccggtcaatg ctggagctag tatttgcacc agcagaggaa   1500
tggatatcac ggactgattc tgacatcata gatgcaacaa tgaaagaact tgagaaactc   1560
ttccctgatg aaatctcagc tgaccaaagc aaagctaaaa ttctgaagta ccatgtcgtt   1620
aagactccaa gatctgtgta caagaccatc ccaaactgtg aaccatgtcg tcctctacaa   1680
agatcaccta ttgaaggatt ctacttagct ggagattaca caaaacagaa gtacttagct   1740
tccatggaag gcgctgtcct ctctggcaaa ttctgctctc agtctattgt tcaggattac   1800
gagctactgg ctgcgtctgg accaagaaag ttgtcggagg caacagtatc atcatcatga   1860
gaagaggaca aaacttaaag atgatttgct tgtaagcatt attatttgtg tataaatctc   1920
attgcaatcc aaacttaacc ttactctctt cagtaaatga atctcacaga tttgacatct   1980
cacgtttctg tcaattttat aattttaaa agtaattac tgtcgacctt ttgtaatcat   2040
agtgatttat cattatgtct ctcttttaa aacc                                2074

<210> SEQ ID NO 23
<211> LENGTH: 1419
<212> TYPE: DNA
<213> ORGANISM: Arabidopsis thaliana

<400> SEQUENCE: 23
ggagcatctt cattcttaag atatgaagat aatcttcaaa aggcccctgg gaatctgaaa     60
gaagagaagc aggcccattt atatgggaaa gaacaatagt atttcttata taggcccatt    120
taagttgaaa acaatcttca aaagtcccac atcgcttaga taagaaaacg aagctgagtt    180
tatatacagc tagagtcgaa gtagtgattg tgagacggat atcaatacgc aaaccgcctc    240
tccccgcgcg ttggccgatt cattaatgca gctggcacga caggtttccc gactggaaag    300
cgggcagtga gcgcaacgca attaatgtga gttagctcac tcattaggca ccccaggctt    360
tacactttat gcttccggct cgtatgttgt gtggaattgt gagcggataa caatttcaca    420
catactagag aaagaggaga aatactagat ggcttcctcc gaggacgtta tcaaagagtt    480
catgcgtttc aaagttcgta tggaaggttc cgttaacggt cacgagttcg aaatcgaagg    540
tgaaggtgaa ggtcgtccgt acgaaggtac ccagaccgct aaactgaaag ttaccaaagg    600
tggtccgctg ccgttcgctt gggacatcct gtcccgcag ttccagtacg gttccaaagc    660
ttacgttaaa cacccggctg acatcccgga ctacctgaaa ctgtccttcc cggaaggttt    720
caaatgggaa cgtgttatga acttcgagga cggtggtgtt gttaccgtta cccaggactc    780
ctcccctgcaa gacggtgagt tcatctacaa agttaaactg cgtggtacca acttcccgtc    840
cgacggtccg gttatgcaga aaaaaaccat gggttgggaa gcttccaccg aacgtatgta    900
cccggaggac ggtgctctga aaggtgaaat caaaatgcgt ctgaaactga aagacggtgg    960
```

```
tcactacgac gctgaagtta aaaccaccta catggctaaa aaaccggttc agctgccggg    1020
tgcttacaaa accgacatca aactggacat cacctcccac aacgaggact acaccatcgt    1080
tgaacagtac gaacgtgctg aaggtcgtca ctccaccggt gcttaataac gctgatagtg    1140
ctagtgtaga tcgctactag agccaggcat caaataaaac gaaaggctca gtcgaaagac    1200
tgggcctttc gttttatctg ttgtttgtcg gtgaacgctc tctactagag tcacactggc    1260
tcaccttcgg gtgggccttt ctgcgtttat acgtctcagt tttagagcta gaaatagcaa    1320
gttaaaataa ggctagtccg ttatcaactt gaaaaagtgg caccgagtcg gtgcttttt    1380 tctagaccca gctttcttgt acaaagttgg cattacgct                          1419

<210> SEQ ID NO 24
<211> LENGTH: 1286
<212> TYPE: DNA
<213> ORGANISM: Artificial sequence
<220> FEATURE:
<223> OTHER INFORMATION: U6III-synthetic pol 3 promoter for sgRNA
      expression

<400> SEQUENCE: 24
ggagtatgat caaaagtccc acatcgatca ggtgatatat agcagcttag tttatataat     60
gatagagtcg acatagcgat tgggagacgc aatacgcaaa ccgcctctcc ccgcgcgttg    120
gccgattcat taatgcagct ggcacgacag gtttcccgac tggaaagcgg gcagtgagcg    180
caacgcaatt aatgtgagtt agctcactca ttaggcaccc caggctttac actttatgct    240
tccggctcgt atgttgtgtg gaattgtgag cggataacaa tttcacacat actagagaaa    300
gaggagaaat actagatggc ttcctccgag gacgttatca aagagttcat gcgtttcaaa    360
gttcgtatgg aaggttccgt taacggtcac gagttcgaaa tcgaaggtga aggtgaaggt    420
cgtccgtacg aaggtaccca gaccgctaaa ctgaaagtta ccaaaggtgg tccgctgccg    480
ttcgcttggg acatcctgtc cccgcagttc cagtacggtt ccaaagctta cgttaaacac    540
ccggctgaca tcccggacta cctgaaactg tccttcccgg aaggttttca atgggaacgt    600
gttatgaact cgaggacgg tggtgttgtt accgttaccc aggactcctc cctgcaagac    660
ggtgagttca tctacaaagt taaactgcgt ggtaccaact cccgtccga cggtccggtt    720 atgcagaaaa aaaccatggg ttgggaagct tccaccgaac gtatgtaccc ggaggacggt    780
gctctgaaag gtgaaatcaa aatgcgtctg aaactgaaag acggtggtca ctacgacgct    840
gaagttaaaa ccacctacat ggctaaaaaa ccggttcagc tgccgggtgc ttacaaaacc    900
gacatcaaac tggacatcac ctcccacaac gaggactaca ccatcgttga acagtacgaa    960
cgtgctgaag tcgtcactc caccggtgct taataacgct gatagtgcta gtgtagatcg    1020
ctactagagc caggcatcaa ataaaacgaa aggctcagtc gaaagactgg gcctttcgtt    1080
ttatctgttg tttgtcggtg aacgctctct actagagtca cactggctca ccttcgggtg    1140
ggcctttctg cgtttatacg tctccgtttt agagctagaa atagcaagtt aaaataaggc    1200
tagtccgtta tcaacttgaa aaagtggcac cgagtcggtg ctttttttct agacccagct    1260
ttcttgtaca aagttggcat tacgct                                        1286

<210> SEQ ID NO 25
<211> LENGTH: 2074
<212> TYPE: DNA
<213> ORGANISM: Arabidopsis thaliana
```

<400> SEQUENCE: 25

```
caattatgtg ttaaagatac aaacttttgt ctgatttgct tccaccggtt tcacctaaga        60
tactcaattt tcttactttt tgtgtgtttt gtaattctaa ttcttttata gcttcaattt       120
ttagattcat tgaagcagtt gtgagttaag tggagaaaaa tggttgtgtt tgggaatgtt       180
tctgcggcga atttgcctta tcaaaacggg ttttggagg cactttcatc tggaggttgt        240
gaactaatgg gacatagctt tagggttccc acttctcaag cgcttaagac aagaacaagg       300
aggaggagta ctgctggtcc tttgcaggta gtttgtgtgg atattccaag gccagagcta       360
gagaacactg tcaatttctt ggaagctgct agtttatctg catccttccg tagtgctcct       420
cgtcctgcta agcctttgaa agttgtaatt gctggtgctg gattggctgg attgtcaact       480
gcaaagtacc tggctgatgc aggccacaaa cctctgttgc ttgaagcaag agatgttctt       540
ggtggaaaga tagctgcatg gaaggatgaa gatgggact ggtatgagac tggtttacat        600
attttcttcg gtgcttatcc gaatgtgcag aatttatttg gagaacttgg gatcaatgat       660
cggttgcagt ggaaggaaca ctccatgatt tttgctatgc caagtaaacc tggagaattt       720
agtagatttg acttcccaga tgtcctacca gcacccttaa atggtatttg gctatttttg       780
cggaacaacg agatgctgac atggccagag aaaataaagt ttgctattgg acttttgcca       840
gccatggtcg gcggtcaggc ttatgttgag cccaagatg gtttatcagt caaagaatgg         900
atggaaaagc agggagtacc tgagcgcgtg accgacgagg tgtttattgc catgtcaaag       960
gcgctaaact ttataaaccc tgatgaactg tcaatgcaat gcattttgat agcttttgaac      1020
cggtttcttc aggaaaaaca tggttccaag atggcattct tggatggtaa tcctccggaa      1080
aggctttgta tgccagtagt ggatcatatt cgatcactag gtggggaagt gcaacttaat      1140
tctaggataa agaaaattga gctcaatgac gatggcacgg ttaagagttt cttactcact      1200
aatggaagca ctgtcgaagg agacgcttat gtgtttgccg ctccagtcga tatcctgaag      1260
ctccttttac cagatccctg gaaagaaata ccgtacttca agaaattgga taaattagtt      1320
ggagtaccag ttattaatgt tcatatatgg tttgatcgaa aactgaagaa cacatatgat      1380
cacctactct ttagcagaag taaccttctg agcgtgtatg ccgacatgtc cttaacttgt      1440
aaggaatatt acgatcctaa ccggtcaatg ctggagctag tatttgcacc agcagaggaa      1500
tggatatcac ggactgattc tgacatcata gatgcaacaa tgaaagaact tgagaaactc      1560
ttccctgatg aaatctcagc tgaccaaagc aaagctaaaa ttctgaagta ccatgtcgtt      1620
aagactccaa gatctgtgta caagaccatc ccaaactgtg aaccatgtcg tcctctacaa      1680
agatcaccta ttgaaggatt ctacttagct ggagattaca caaaacagaa gtacttagct      1740
tccatggaag gcgctgtcct ctctggcaaa ttctgctctc agtctattgt tcaggattac      1800
gagctactgg ctgcgtctgg accaagaaag ttgtcggagg caacagtatc atcatcatga      1860
gaagaggaca aaacttaaag atgatttgct tgtaagcatt attatttgtg tataaatctc      1920
attgcaatcc aaacttaacc ttactctctt cagtaaatga atctcacaga tttgacatct      1980
cacgtttctg tcaattttat aattttaaa aagtaattac tgtcgacctt ttgtaatcat      2040
agtgatttat cattatgtct ctcttttta aacc                                    2074
```

<210> SEQ ID NO 26
<211> LENGTH: 2290
<212> TYPE: DNA
<213> ORGANISM: Arabidopsis thaliana

```
<400> SEQUENCE: 26
ctttggtggg caaaaacata ttagctgaga ggtcaatttc ttttccccct aaaccaaatt      60
acgttgagat gcatggtctc tctctactca attaaccaaa taaggaaaag aatcatatgg     120
tcatcaattc gtaaatcaaa attttaattt gtgtggtatt taatccatct acatgtttcg     180
taagcaacaa aagagcttgg tctgaaaacc aaacaagacc atatgggcac tcgaatactc     240
cattttgtta tcggctactt ccactagcct cctccttcgc tgcgtctcct gtttctctac     300
ttcacgatta ctcgctagat tcattgaagc agttgtgagt aagttggag aaaatggttg      360 tgtttgggaa tgtttctgcg gcgaatttgc cttatcaaaa cgggttttg gaggcactt       420 catctggagg ttgtgaacta atgggacata gctttagggt tcccacttct caagcgctta    480
agacaagaac aaggaggagg agtactgctg gtcctttgca ggtagtttgt gtggatattc     540
caaggccaga gctagagaac actgtcaatt tcttggaagc tgctagttta tctgcatcct    600
tccgtagtgc tcctcgtcct gctaagcctt tgaaagttgt aattgctggt gctggattgg    660
ctggattgtc aactgcaaag tacctggctg atgcaggcca caaacctctg ttgcttgaag    720
caagagatgt tcttggtgga aagatagctg catggaagga tgaagatggg gactggtatg    780
agactggttt acatattttc ttcggtgctt atccgaatgt gcagaattta tttggagaac    840
ttgggatcaa tgatcggttg cagtggaagg aacactccat gattttgct atgccaagta     900 aacctgagaa atttagtaga tttgacttcc cagatgtcct accagcaccc ttaaatggta    960
tttgggctat tttgcggaac aacgagatgc tgacatggcc agagaaaata agtttgcta    1020 ttggactttt gccagccatg gtcggcggtc aggcttatgt tgaggcccaa gatggtttat   1080
cagtcaaaga atggatggaa aagcaggag tacctgagcg cgtgaccgac gaggtgttta    1140
ttgccatgtc aaaggcgcta aactttataa accctgatga actgtcaatg caatgcattt   1200
tgatagcttt gaaccggttt cttcaggaaa acatggttc caagatggca ttcttggatg    1260
gtaatcctcc ggaaaggctt tgtatgccag tagtggatca tattcgatca ctaggtgggg   1320
aagtgcaact taattctagg ataaagaaaa ttgagctcaa tgacgatggc acggttaaga   1380
gtttcttact cactaatgga agcactgtcg aaggagacgc ttatgtgttt gccgctccag   1440
tcgatatcct gaagctcctt ttaccagatc cctggaaaga aataccgtac ttcaagaaat   1500
tggataaatt agttggagta ccagttatta atgttcatat atggtttgat cgaaaactga   1560
agaacacata tgatcaccta ctctttagca gaagtaacct tctgagcgtg tatgccgaca   1620
tgtccttaac ttgtaaggaa tattacgatc ctaaccggtc aatgctggag ctagtatttg   1680
caccagcaga ggaatggata tcacggactg attctgacat catagatgca acaatgaaag   1740
aacttgagaa actcttccct gatgaaatct cagctgacca agcaaagct aaaattctga    1800 agtaccatgt cgttaagact ccaagatctg tgtacaagac catcccaaac tgtgaaccat   1860
gtcgtcctct acaaagatca cctattgaag gattctactt agctggagat tacacaaaac   1920
agaagtactt agcttccatg gaaggcgctg tcctctctgg caaattctgc tctcagtcta   1980
ttgttcagga ttacgagcta ctggctgcgt ctggaccaag aaagttgtcg gaggcaacag   2040
tatcatcatc atgagaagag gacaaaaact aaagatgatt tgcttgtaag cattattatt   2100
tgtgtataaa tctcattgca atccaaactt aaccttactc tcttcagtaa atgaatctca   2160
cagatttgac atctcacgtt tctgtcaatt ttataatttt taaaaagtaa ttactgtcga   2220 cctttttgtaa tcatagtgat ttatcattat gtctctcttt ttaaaacctt ttctggtaca   2280
aattataaaa                                                           2290
```

```
<210> SEQ ID NO 27
<211> LENGTH: 241
<212> TYPE: PRT
<213> ORGANISM: Artificial sequence
<220> FEATURE:
<223> OTHER INFORMATION: eGFP [synthetic construct] amino acid sequence

<400> SEQUENCE: 27

Met Ser Arg Val Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45

Phe Ile Cys Thr Thr Gly Lys Leu Pro Val Pro Trp Pro Thr Leu Val
50                  55                  60

Thr Thr Leu Thr Tyr Gly Val Gln Cys Phe Ser Arg Tyr Pro Asp His
65                  70                  75                  80

Met Lys Gln His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
        115                 120                 125

Lys Gly Ile Asp Phe Lys Glu Asp Gly Asn Ile Leu Gly His Lys Leu
    130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr Leu Gly Met Asp Glu Leu Tyr
225                 230                 235                 240

Lys

<210> SEQ ID NO 28
<211> LENGTH: 107
<212> TYPE: DNA
<213> ORGANISM: Arabidopsis thaliana

<400> SEQUENCE: 28
guagagaaga aucuguaaag cucaggaggg auagcgccau gaugaucaca uucguuaucu      60 auuuuuggc gcuauccauc cugaguuuca uuggcucuuc uuacuac                    107

<210> SEQ ID NO 29
<211> LENGTH: 102
<212> TYPE: DNA
<213> ORGANISM: Arabidopsis thaliana

<400> SEQUENCE: 29
uaaguacuuu cgcuugcaga gagaaaucac aguggucaaa aaaguguag uuuucuuaaa       60 gucucuuucc ucugugauuc ucuguguaag cgaaagagcu ug                        102
```

```
<210> SEQ ID NO 30
<211> LENGTH: 711
<212> TYPE: DNA
<213> ORGANISM: Artificial Sequence
<220> FEATURE:
<223> OTHER INFORMATION: nucleic acid sequence encoding mCherry

<400> SEQUENCE: 30
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc ccctcagttc atgtacggct ccaaggccta cgtgaagcac   240
cccgccgaca tccccgacta cttgaagctg tccttccccg agggcttcaa gtgggagcgc   300
gtgatgaact tcgaggacgg cggcgtggtg accgtgaccc aggactcctc cctgcaggac   360
ggcgagttca tctacaaggt gaagctgcgc ggcaccaact tcccctccga cggccccgta   420
atgcagaaga aaaccatggg ctgggaggcc tcctccgagc ggatgtaccc cgaggacggc   480
gccctgaagg gcgagatcaa gcagaggctg aagctgaagg acggcggcca ctacgacgct   540
gaggtcaaga ccacctacaa ggccaagaag cccgtgcagc tgcccggcgc ctacaacgtc   600
aacatcaagt tggacatcac ctcccacaac gaggactaca ccatcgtgga acagtacgaa   660
cgcgccgagg ccgccactc accggcggc atggacgagc tgtacaagtg a             711

<210> SEQ ID NO 31
<211> LENGTH: 4100
<212> TYPE: DNA
<213> ORGANISM: Artificial Sequence
<220> FEATURE:
<223> OTHER INFORMATION: Plasmid-1: GEiGS_ mir173_si-GFP_1

<400> SEQUENCE: 31
cacttatcat ttagacagta gatttaaat ttgtatttac aatttcaaaa ctgaaattca     60
tttgtaatca agaaaaaaca aaacaagaaa agggaggagg agtgggattt gggttgctta   120
acagtattat atatacacgt cgttagttaa tcaataaatt atgagcaggt gtagtagcta   180
tgaacatggt tttaccaaat tggtaaattc atgtcattgt tgtagcactt tagcgaggcc   240
agcaaaatgg cgttcttgga aagggcatgg cggcccgtgg ccgccaggga tatgtgtgca   300
gctagaagga ttagaaggag taacttcacc tttttgtaga aactgtaaat tgccaagacg   360
ctcgtttggt aaataccta acgcttcgtt tgctggaatg tgtaccacca ttagtagaag   420
aaagtataat aagactatta atgcaagaga tttttcata ttccttttct aagagtagaa    480
tggaatgaat aaatgaatga atgaaatagg gttttcttg tttagatcct gtcgcacccg    540
agaataatag aagctgaatt aattggtgaa gagttttatg gtggcgatgt tgtatttata   600
gagggaaatg atttcaagtt tacaatggga ttttttaatt tgttttgttga ctattatctt   660 gcggagagat cttgactgtt gacatgtatg tagtgttgt tattaaaata aatgcatttt    720
tgtagacccg attcttaaat atgttaggca tggtcaaatt gttagactgt aaaagcttga   780
gtagagacat cggtcaactt tgtttacaag aattctctat aaaatattat acaaattgat   840
cggtagaaat tagatggaac atttgaatt aatgtttgac aatgtataaa ttggtttggt    900
caatatctag gaatgaaaac aagagctgct tcaaagttgt tccattctta agtatacata   960
gaggtggctt gatgggaagt ttcatggaag tgtagttta tatctacttc caattcgtt    1020 gatctgtttc ttatctcaag ctaaacatgt ttagaaaaga tgtgttaaaa acatgtgaca  1080
```

```
aaaaaagagt caaatgtttg gcaaacaagg tacttagatt tttggcatct attcaaatat    1140
aatagaatcc caaaattatg atatttgtca atcaaatttg aaaaaaaaaa aaaaaaaaa     1200 aaagattcta caaaagatca aacgtattgc cgtagattta tcataatttt aattctttca    1260
cactaccact agtccactac catatagtga tgagataatc cataatcata aataagatat    1320
aactttcgaa ttcttgtttt tgttgcctca aagttgttgg atcattattt tttacgtaaa    1380
tgtggcttaa tgagaattta tgtttgtggg aattgtagtt tgcttccaac tttttttttt    1440 ttttttgaa cacgtagttt gcttccaact tagtttatct ttttcttatt tcaagttaaa     1500
catgtaaaaa aacatgtgac gacgaaattc aatcagttcc tccaatgttt ggcagaagcc    1560
aaatctttgg taaacaaagt aattttttttg ccatttgatt ggttagtata ggagaattta   1620
aaaacgacga taaggtttag gtaaattatt tcatttgaaa ataattgagc accgttaata    1680
attttcatcc ataaaataat atttcaaaga tgatatttga tccccattaa attcattcgt    1740
aaccaaaaaa aagttatgaa aaagagtgg tcgtgtgagt tgcccaagca ccattataat     1800
aaaaaataaa ataattagca agtaataagg aataaaatcc tgtaattata gctgaaaaag    1860
gaaaaatatt tggagaccgt cagattcgaa tctgaacaaa gcataaaaaa gtcaacaaaa    1920
cttaaagcgg cggtctcatc gtaatctcag cccaataccc tattttcctc tcccctatat    1980
aaatactttc ttcttctact gatcttcttc tcacaaataa acccaaatat atcaatctac    2040
tgtgttggtg attaagtact taagtcgtgc tgcttcatgt ggagtggtca aaaagttgt     2100 agttttctta aagtctcttt cctctccaca taagcaggac gagttaagag cttgctccct    2160
aaacttatct ctctgatgat ttaatgttag agatcttcgt aaatctatgt gtttgataga    2220
tctgatgcgt ttttgagtt gatgatttga ttatttttca ctggaaagta tctcattagg     2280
gtaacgataa tgttttatgg atttggttgt ataacagatc catgaaatct tgactggtta    2340
taaaatctga ataatgtatt tcaatttgga gattcggtga taaaaattac tgatttacga    2400
atgacattta tatcgataga tgagtttgct gatttggttg ttaaattgat aaatcaagga    2460
catgagaaac tgttttttgta tgctaatttg tccatggaat aaaattggga ggtgaggacc    2520
gtgagggtag tcaggaaacc ttaatattga agttgatgtt gaaccaacaa atctgcccaa    2580
aaatgataaa agttgatgcc gagcccacaa attttgatga caatcgataa gcccaagccc    2640
aaaaggcatc tgtacctgag cccattattc tttcattact agcaaaaagg atgcattaga    2700
gaccccggtg tagtaaattg acctcacaat tcactattgt attgtatacg tacatttcaa    2760
gcgtaattaa acctcatat ttttatacgc tttaaatata attggccttt aattagctca     2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caattttctt taaaacaaat ttcagttttt atttgtcagc aaaaaaaact tactaacaca    3180
acggaagaac acaaaaatta gggagttgct cacagagcaa agtaataga aatgggaaaa      3240 gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
taatggtagc ttagaatgcc aagttgagaa cagatttgca gtttgtcccg gaatgatcaa    3480
```

```
gtagagcatt catagtgtct tgccaatatg gtgtgatcaa cgaagtttga caaaaccgtg    3540
aagatatagg aacatgtaat catgcggctc tccatacaat acatcttgtt gacaaagttc    3600
ccaagacctc attctacaaa ccaatgtttc ttttttcttt ttcttttttgg tgatagtttt   3660 tgcaatcaaa tgttgtaaaa ctatgattgg aaatactact gtattttacc gaaaacttta    3720
ttatatatag tcattaacac tcattaccaa tcacataatc aatagtctat tttgattata    3780
caacttttaa acaataaaga catgtttata cagatttggt ttaaattagt actccctata    3840
ttttagaaaa ttttatttg tttcatatta tagaatgtct tggaaagttc tatgtaaatt    3900
taaatgtatt tagtaacttg tgacgatttt atattatgta gtctttttta ggatttgttg    3960 atttttaaa ataaattttt taaagaaaaa aaacaaatta ttttaataaa catgccttta    4020
ccttatacag tttatatttt gaaagagaga tagtatgttt taggatatat ttaaagaaaa    4080
aaaaataact ctttaattta                                                4100

<210> SEQ ID NO 32
<211> LENGTH: 4100
<212> TYPE: DNA
<213> ORGANISM: Artificial Sequence
<220> FEATURE:
<223> OTHER INFORMATION: Plasmid-2: GEiGS_ mir173_si-GFP_2

<400> SEQUENCE: 32
cacttatcat ttagacagta gattttaaat ttgtatttac aatttcaaaa ctgaaattca      60
tttgtaatca agaaaaaca aaacaagaaa agggaggagg agtgggattt gggttgctta     120
acagtattat atatacacgt cgttagttaa tcaataaatt atgagcaggt gtagtagcta     180
tgaacatggt tttaccaaat tggtaaattc atgtcattgt tgtagcactt tagcgaggcc     240
agcaaaatgg cgttcttgga aagggcatgg cggcccgtgg ccgccaggga tatgtgtgca     300
gctagaagga ttagaaggag taacttcacc ttttttgtaga aactgtaaat tgccaagacg     360
ctcgtttggt aaataccta acgcttcgtt tgctggaatg tgtaccacca ttagtagaag     420
aaagtataat aagactatta atgcaagaga tttttttcata ttccttttct aagagtagaa     480
tggaatgaat aaatgaatga atgaaatagg gttttttcttg tttagatcct gtcgcacccg     540
agaataatag aagctgaatt aattggtgaa gagttttatg gtggcgatgt tgtatttata     600
gagggaaatg atttcaagtt tacaatggga ttttttaattt gttttgttga ctattatctt     660
gcggagagat cttgactgtt gacatgtatg tagtgtttgt tattaaaata aatgcatttt     720
tgtagacccg attcttaaat atgttaggca tggtcaaatt gttagactgt aaaagcttga     780
gtagagacat cggtcaactt tgtttacaag aattctctat aaaatattat acaaattgat     840
cggtagaaat tagatggaac attttgaatt aatgtttgac aatgtataaa ttggtttggt     900
caatatctag gaatgaaaac aagagctgct tcaaagttgt tccattctta agtatacata     960
gaggtggctt gatgggaagt ttcatggaag tgtagtttta tatctacttc caaattcgtt    1020
gatctgtttc ttatctcaag ctaaacatgt ttagaaaaga tgtgttaaaa acatgtgaca    1080 aaaaagagt caaatgtttg gcaaacaagg tacttagatt tttggcatct attcaaatat    1140
aatagaatcc caaaattatg atatttgtca atcaaatttg aaaaaaaaaa aaaaaaaaa    1200 aagattcta caaagatca aacgtattgc cgtagattta tcataatttt aattctttca    1260
cactaccact agtccactac catatagtga tgagataatc cataatcata aataagatat    1320
aactttcgaa ttcttgtttt tgttgcctca agttgttgg atcattattt tttacgtaaa    1380
tgtggcttaa tgagaattta tgtttgtggg aattgtagtt tgcttccaac ttttttttttt   1440
```

```
ttttttttgaa cacgtagttt gcttccaact tagtttatct ttttcttatt tcaagttaaa    1500
catgtaaaaa aacatgtgac gacgaaattc aatcagttcc tccaatgttt ggcagaagcc    1560
aaatctttgg taaacaaagt aattttttg ccatttgatt ggttagtata ggagaattta    1620
aaaacgacga taaggtttag gtaaattatt tcatttgaaa ataattgagc accgttaata    1680
attttcatcc ataaaataat atttcaaaga tgatatttga tccccattaa attcattcgt    1740
aaccaaaaaa aagttatgaa aaagagtgg tcgtgtgagt tgcccaagca ccattataat    1800
aaaaaataaa ataattagca agtaataagg aataaaatcc tgtaattata gctgaaaaag    1860
gaaaaatatt tggagaccgt cagattcgaa tctgaacaaa gcataaaaaa gtcaacaaaa    1920
cttaaagcgg cggtctcatc gtaatctcag cccaataccc tattttcctc tcccctatat    1980
aaatactttc ttcttctact gatcttcttc tcacaaataa acccaaatat atcaatctac    2040
tgtgttggtg attaagtact tagttgtact ccagcttgtg ccagtggtca aaaagttgt    2100
agttttctta aagtctcttt cctctggcaa agctgcagta caactaagag cttgctccct    2160
aaacttatct ctctgatgat ttaatgttag agatcttcgt aaatctatgt gtttgataga    2220
tctgatgcgt tttttgagtt gatgatttga ttatttttca ctggaaagta tctcattagg    2280
gtaacgataa tgttttatgg atttggttgt ataacagatc catgaaatct tgactggtta    2340
taaaatctga ataatgtatt tcaatttgga gattcggtga taaaaattac tgatttacga    2400
atgcatttta tatcgataga tgagtttgct gatttggttg ttaaattgat aaatcaagga    2460
catgagaaac tgttttttgta tgctaatttg tccatggaat aaaattggga ggtgaggacc    2520
gtgagggtag tcaggaaacc ttaatattga agttgatgtt gaaccaacaa atctgcccaa    2580
aaatgataaa agttgatgcc gagcccacaa attttgatga caatcgataa gcccaagccc    2640
aaaaggcatc tgtacctgag cccattattc tttcattact agcaaaaagg atgcattaga    2700
gaccccggtg tagtaaattg acctcacaat tcactattgt attgtatacg tacatttcaa    2760
gcgtaattaa accctcatat ttttatacgc tttaaatata attggccttt aattagctca    2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caattttctt taaacaaat ttcagttttt atttgtcagc aaaaaaaact tactaacaca    3180
acggaagaac acaaaaatta gggagttgct cacagagcaa agtaataga aatgggaaaa    3240
gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
taatggtagc ttagaatgcc aagttgagaa cagatttgca gtttgtcccg gaatgatcaa    3480
gtagagcatt catagtgtct tgccaatatg gtgtgatcaa cgaagtttga caaaaccgtg    3540
aagatatagg aacatgtaat catgcggctc tccatacaat acatcttgtt gacaaagttc    3600
ccaagacctc attctacaaa ccaatgtttc ttttttcttt ttcttttttgg tgatagtttt    3660
tgcaatcaaa tgttgtaaaa ctatgattgg aaatactact gtattttacc gaaaactttta    3720
ttatatatag tcattaacac tcattaccaa tcacataatc aatagtctat tttgattata    3780
caacttttaa acaataaaga catgtttata cagatttggt ttaaattagt actccctata    3840
```

| | |
|---|---|
| ttttagaaaa ttttattttg tttcatatta tagaatgtct tggaaagttc tatgtaaatt | 3900 |
| taaatgtatt tagtaacttg tgacgatttt atattatgta gtcttttta ggatttgttg | 3960 |
| atttttaaa ataaatttt taaagaaaaa aaacaaatta ttttaataaa catgcctta | 4020 |
| ccttatacag tttatatttt gaaagagaga tagtatgttt taggatatat ttaaagaaaa | 4080 |
| aaaaataact ctttaattta | 4100 |

<210> SEQ ID NO 33
<211> LENGTH: 4100
<212> TYPE: DNA
<213> ORGANISM: Artificial Sequence
<220> FEATURE:
<223> OTHER INFORMATION: Plasmid-3: GEiGS_ mir173_si-PDS_1

<400> SEQUENCE: 33

| | |
|---|---|
| cacttatcat ttagacagta gattttaaat ttgtatttac aatttcaaaa ctgaaattca | 60 |
| tttgtaatca agaaaaaaca aaacaagaaa agggaggagg agtgggatt gggttgctta | 120 |
| acagtattat atatacacgt cgttagttaa tcaataaatt atgagcaggt gtagtagcta | 180 |
| tgaacatggt tttaccaaat tggtaaattc atgtcattgt tgtagcactt tagcgaggcc | 240 |
| agcaaaatgg cgttcttgga aagggcatgg cggcccgtgg ccgccaggga tatgtgtgca | 300 |
| gctagaagga ttagaaggag taacttcacc ttttttgtaga aactgtaaat tgccaagacg | 360 |
| ctcgttttggt aaataccta acgcttcgtt tgctggaatg tgtaccacca ttagtagaag | 420 |
| aaagtataat aagactatta atgcaagaga tttttttcata ttccttttct aagagtagaa | 480 |
| tggaatgaat aaatgaatga atgaaatagg gttttttcttg tttagatcct gtcgcacccg | 540 |
| agaataatag aagctgaatt aattggtgaa gagttttatg gtggcgatgt tgtatttata | 600 |
| gagggaaatg atttcaagtt tacaatggga ttttaatt gttttgttga ctattatctt | 660 |
| gcggagagat cttgactgtt gacatgtatg tagtgtttgt tattaaaata aatgcatttt | 720 |
| tgtagacccg attcttaaat atgttaggca tggtcaaatt gttagactgt aaaagcttga | 780 |
| gtagagacat cggtcaactt tgtttacaag aattctctat aaaatattat acaaattgat | 840 |
| cggtagaaat tagatggaac attttgaatt aatgtttgac aatgtataaa ttggtttggt | 900 |
| caatatctag gaatgaaaac aagagctgct tcaaagttgt tccattctta agtatacata | 960 |
| gaggtggctt gatgggaagt ttcatggaag tgtagtttta tatctacttc caaattcgtt | 1020 |
| gatctgtttc ttatctcaag ctaaacatgt ttagaaaaga tgtgttaaaa acatgtgaca | 1080 |
| aaaaagagt caaatgtttg gcaaacaagg tacttagatt tttggcatct attcaaatat | 1140 |
| aatagaatcc caaattatg atatttgtca atcaatttg aaaaaaaaaa aaaaaaaaa | 1200 |
| aaagattcta caaagatca aacgtattgc cgtagattta tcataatttt aattctttca | 1260 |
| cactaccact agtccactac catatagtga tgagataatc cataatcata aataagatat | 1320 |
| aactttcgaa ttcttgtttt tgttgcctca aagttgttgg atcattattt tttacgtaaa | 1380 |
| tgtggcttaa tgagaattta tgtttgtggg aattgtagtt tgcttccaac ttttttttt | 1440 |
| tttttttgaa cacgtagttt gcttccaact tagtttatct ttttcttatt tcaagttaaa | 1500 |
| catgtaaaaa aacatgtgac gacgaaattc aatcagttcc tccaatgttt ggcagaagcc | 1560 |
| aaatctttgg taaacaaagt aatttttttg ccatttgatt ggttagtata ggagaattta | 1620 |
| aaaacgacga taaggtttag gtaaattatt tcatttgaaa ataattgagc accgttaata | 1680 |
| attttcatcc ataaaataat atttcaaaga tgatatttga tccccattaa attcattcgt | 1740 |
| aaccaaaaaa aagttatgaa aaaagagtgg tcgtgtgagt tgcccaagca ccattataat | 1800 |

-continued

```
aaaaaataaa ataattagca agtaataagg aataaaatcc tgtaattata gctgaaaaag    1860
gaaaaatatt tggagaccgt cagattcgaa tctgaacaaa gcataaaaaa gtcaacaaaa    1920
cttaaagcgg cggtctcatc gtaatctcag cccaataccc tattttcctc tccctatat    1980 aaatactttc ttcttctact gatcttcttc tcacaaataa acccaaatat atcaatctac    2040
tgtgttggtg attaagtact ttatccacac aaactacctg caagtggtca aaaaagttgt    2100
agttttctta aagtctcttt cctcttgcag tagttagtgt ggataaagag cttgctccct    2160
aaacttatct ctctgatgat ttaatgttag agatcttcgt aaatctatgt gtttgataga    2220
tctgatgcgt tttttgagtt gatgatttga ttattttca ctggaaagta tctcattagg    2280
gtaacgataa tgttttatgg atttggttgt ataacagatc catgaaatct tgactggtta    2340
taaaatctga ataatgtatt tcaatttgga gattcggtga taaaaattac tgatttacga    2400
atgacattta tatcgataga tgagtttgct gatttggttg ttaaattgat aaatcaagga    2460
catgagaaac tgttttgta tgctaatttg tccatggaat aaaattggga ggtgaggacc    2520
gtgagggtag tcaggaaacc ttaatattga agttgatgtt gaaccaacaa atctgcccaa    2580
aaatgataaa agttgatgcc gagcccacaa attttgatga caatcgataa gcccaagccc    2640
aaaaggcatc tgtacctgag cccattattc tttcattact agcaaaaagg atgcattaga    2700
gaccccggtg tagtaaattg acctcacaat tcactattgt attgtatacg tacatttcaa    2760
gcgtaattaa accctcatat ttttatacgc tttaaatata attggccttt aattagctca    2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caatttcttt taaaacaaat ttcagttttt atttgtcagc aaaaaaaact tactaacaca    3180
acggaagaac acaaaaatta gggagttgct cacagagcaa aagtaataga atgggaaaa    3240 gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
taatggtagc ttagaatgcc aagttgagaa cagatttgca gtttgtcccg gaatgatcaa    3480
gtagagcatt catagtgtct tgccaatatg gtgtgatcaa cgaagtttga caaaaccgtg    3540
aagatatagg aacatgtaat catgcggctc tccatacaat acatcttgtt gacaaagttc    3600
ccaagacctc attctacaaa ccaatgtttc ttttttcttt ttcttttgg tgatagtttt    3660 tgcaatcaaa tgttgtaaaa ctatgattgg aaatactact gtattttacc gaaaacttta    3720
ttatatatag tcattaacac tcattaccaa tcacataatc aatagtctat tttgattata    3780
caacttttaa acaataaaga catgtttata cagatttggt ttaaattagt actccctata    3840
ttttagaaaa ttttatttg tttcatatta tagaatgtct tggaaagttc tatgtaaatt    3900
taaatgtatt tagtaacttg tgacgatttt atattatgta gtctttttta ggatttgttg    3960
attttttaaa ataaattttt taagaaaaa aaacaaatta ttttaataaa catgccttta    4020
ccttatacag tttatatttt gaagagaga tagtatgttt taggatatat ttaagaaaa    4080 aaaaataact ctttaattta                                                4100
```

<210> SEQ ID NO 34
<211> LENGTH: 4100
<212> TYPE: DNA
<213> ORGANISM: Artificial Sequence
<220> FEATURE:
<223> OTHER INFORMATION: Plasmid-4: GEiGS_ mir173_si-PDS_2

<400> SEQUENCE: 34

| | | | | | |
|---|---|---|---|---|---|
| cacttatcat | ttagacagta | gattttaaat | ttgtatttac | aatttcaaaa | ctgaaattca | 60 |
| tttgtaatca | agaaaaaaca | aaacaagaaa | agggaggagg | agtgggattt | gggttgctta | 120 |
| acagtattat | atatacacgt | cgttagttaa | tcaataaatt | atgagcaggt | gtagtagcta | 180 |
| tgaacatggt | tttaccaaat | tggtaaattc | atgtcattgt | tgtagcactt | tagcgaggcc | 240 |
| agcaaaatgg | cgttcttgga | aagggcatgg | cggcccgtgg | ccgccaggga | tatgtgtgca | 300 |
| gctagaagga | ttagaaggag | taacttcacc | tttttgtaga | aactgtaaat | tgccaagacg | 360 |
| ctcgtttggt | aaatacctta | acgcttcgtt | tgctggaatg | tgtaccacca | ttagtagaag | 420 |
| aaagtataat | aagactatta | atgcaagaga | tttttcata | ttccttttct | aagagtagaa | 480 |
| tggaatgaat | aaatgaatga | atgaaatagg | gttttcttg | tttagatcct | gtcgcacccg | 540 |
| agaataatag | aagctgaatt | aattggtgaa | gagtttatg | gtggcgatgt | tgtatttata | 600 |
| gagggaaatg | atttcaagtt | tacaatggga | tttttaattt | gttttgttga | ctattatctt | 660 |
| gcggagagat | cttgactgtt | gacatgtatg | tagtgtttgt | tattaaaata | aatgcatttt | 720 |
| tgtagacccg | attcttaaat | atgttaggca | tggtcaaatt | gttagactgt | aaaagcttga | 780 |
| gtagagacat | cggtcaactt | tgtttacaag | aattctctat | aaaatattat | acaaattgat | 840 |
| cggtagaaat | tagatggaac | attttgaatt | aatgtttgac | aatgtataaa | ttggtttggt | 900 |
| caatatctag | gaatgaaaac | aagagctgct | tcaaagttgt | tccattctta | agtatacata | 960 |
| gaggtggctt | gatgggaagt | ttcatggaag | tgtagtttta | tatctacttc | caaattcgtt | 1020 |
| gatctgtttc | ttatctcaag | ctaaacatgt | ttagaaaaga | tgtgttaaaa | acatgtgaca | 1080 |
| aaaaagagt | caaatgtttg | gcaaacaagg | tacttagatt | tttggcatct | attcaaatat | 1140 |
| aatagaatcc | caaattatg | atatttgtca | atcaaatttg | aaaaaaaaaa | aaaaaaaaa | 1200 |
| aaagattcta | caaaagatca | aacgtattgc | cgtagattta | tcataatttt | aattctttca | 1260 |
| cactaccact | agtccactac | catatagtga | tgagataatc | cataatcata | aataagatat | 1320 |
| aactttcgaa | ttcttgtttt | tgttgcctca | aagttgttgg | atcattattt | tttacgtaaa | 1380 |
| tgtggcttaa | tgagaattta | tgtttgtggg | aattgtagtt | tgcttccaac | ttttttttt | 1440 |
| ttttttgaa | cacgtagttt | gcttccaact | tagtttatct | ttttcttatt | tcaagttaaa | 1500 |
| catgtaaaaa | aacatgtgac | gacgaaattc | aatcagttcc | tccaatgttt | ggcagaagcc | 1560 |
| aaatctttgg | taaacaaagt | aatttttttg | ccatttgatt | ggttagtata | ggagaattta | 1620 |
| aaaacgacga | taaggtttag | gtaaattatt | tcatttgaaa | ataattgagc | accgttaata | 1680 |
| attttcatcc | ataaaataat | atttcaaaga | tgatatttga | tccccattaa | attcattcgt | 1740 |
| aaccaaaaaa | aagttatgaa | aaaagagtgg | tcgtgtgagt | tgcccaagca | ccattataat | 1800 |
| aaaaaataaa | ataattagca | agtaataagg | aataaaatcc | tgtaattata | gctgaaaaag | 1860 |
| gaaaaatatt | tggagaccgt | cagattcgaa | tctgaacaaa | gcataaaaaa | gtcaacaaaa | 1920 |
| cttaaagcgg | cggtctcatc | gtaatctcag | cccaataccc | tattttcctc | tcccctatat | 1980 |
| aaatactttc | ttcttctact | gatcttcttc | tcacaaataa | acccaaatat | atcaatctac | 2040 |
| tgtgttggtg | attaagtact | ttgacaatcc | agccaatcca | gcagtggtca | aaaaagttgt | 2100 |

```
agttttctta aagtctcttt cctctgctga ttggcaggat tgtcaaagag cttgctccct    2160
aaacttatct ctctgatgat ttaatgttag agatcttcgt aaatctatgt gtttgataga    2220
tctgatgcgt tttttgagtt gatgatttga ttattttttca ctggaaagta tctcattagg    2280
gtaacgataa tgttttatgg atttggttgt ataacagatc catgaaatct tgactggtta    2340
taaaatctga ataatgtatt tcaatttgga gattcggtga taaaaattac tgatttacga    2400
atgacattta tatcgataga tgagtttgct gatttggttg ttaaattgat aaatcaagga    2460
catgagaaac tgttttttgta tgctaatttg tccatggaat aaaattggga ggtgaggacc    2520
gtgagggtag tcaggaaacc ttaatattga agttgatgtt gaaccaacaa atctgcccaa    2580
aaatgataaa agttgatgcc gagcccacaa attttgatga caatcgataa gcccaagccc    2640
aaaaggcatc tgtacctgag cccattattc tttcattact agcaaaaagg atgcattaga    2700
gaccccggtg tagtaaattg acctcacaat tcactattgt attgtatacg tacatttcaa    2760
gcgtaattaa accctcatat ttttatacgc tttaaatata attggccttt aattagctca    2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caattttctt taaaacaaat ttcagttttt atttgtcagc aaaaaaaact tactaacaca    3180
acggaagaac acaaaaatta gggagttgct cacagagcaa agtaataga aatgggaaaa    3240 gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
taatggtagc ttagaatgcc aagttgagaa cagatttgca gtttgtcccg gaatgatcaa    3480
gtagagcatt catagtgtct tgccaatatg gtgtgatcaa cgaagtttga caaaaccgtg    3540
aagatatagg aacatgtaat catgcggctc tccatacaat acatcttgtt gacaaagttc    3600
ccaagacctc attctacaaa ccaatgtttc ttttttcttt ttcttttttgg tgatagtttt    3660 tgcaatcaaa tgttgtaaaa ctatgattgg aaatactact gtattttacc gaaaacttta    3720
ttatatatag tcattaacac tcattaccaa tcacataatc aatagtctat tttgattata    3780
caacttttaa acaataaaga catgtttata cagatttggt ttaaattagt actccctata    3840
ttttagaaaa ttttatttttg tttcatatta tagaatgtct tggaaagttc tatgtaaatt    3900
taaatgtatt tagtaacttg tgacgatttt atattatgta gtctttttta ggatttgttg    3960 atttttttaaa ataaattttt taaagaaaaa aaacaaatta ttttaataaa catgcctttta    4020 ccttatacag tttatatttt gaaagagaga tagtatgttt taggatatat ttaaagaaaa    4080
aaaaataact ctttaattta                                                4100
```

<210> SEQ ID NO 35
<211> LENGTH: 4000
<212> TYPE: DNA
<213> ORGANISM: Artificial Sequence
<220> FEATURE:
<223> OTHER INFORMATION: Plasmid-5: GEiGS_ mir390a _si-GFP_1

```
<400> SEQUENCE: 35
accctcattg attttggtgg ccaaactctt gatcgtattc ttttaggaac agtaattaat        60
tttaaatttg agaaaaatgt agtgatgaaa gtgagatata tgggacgcac tattgaaagc       120
attgtccaca ccgcatgatg tgagattgat gtgaatatgg taactaataa cacccagact       180
cacttttatg agaaaatgta tcttaaaaaa tgttattcat caaagcttag atgcgctata       240
ggggaacata atcattattt gaaaagaacc aattcaaata ttttttttt taagagttaa        300
aatcctatat aacataacca tccaaacttt gggcatgaac acaacaatat ttttttcgt        360
ttttgataaa ttctttcaat tgcaatcaaa acttaccagc tatacaaatg tttgctgcat       420
ccaatctaat acaccgttaa acaataaaat ttgttatctc tcaaatctga tcatctattc       480
caacctgact gttttattct agtattttaa ggccaggtat aacgaaaaca aagaaaaaag       540
ttcagcgacc aagacatttt gacatcaggc tcaaacggtc aaacccacga aaacttttac       600
ctcatttctt aaccacgcag tgttatttga atagccttaa taggctaata caaaacaaca       660
agccatcgat tacagtttta actataatat tacaaaatct taaaccaaaa caagaaaaga       720
tatatattcc gtaaaattaa aataatattt ttaatatagt cattatgtaa gttagctctt       780
tcgacaaaat cattataaat taggccattt tgtaagttag ttcttttatc gacaagccat       840
tataacttag gtaattttgt aagttagctg gactataacc aattttttg tttcacatct        900
agagtataaa acacatatat attgaccgta caactttagt caaattagaa actctgtttt       960
atctgcagaa aagaaaaaaa aagaggatga attatgtaaa tacttcagga ttagaaataa      1020
tgtcatcgta tatctcttga tatgaataca tattttactt gactagtacc gtagtcggca      1080
ggaaaatgac acaacaacc atctaaaaag ataagtaag aactaaaaag tcttgacatt        1140
cattagttta atcattttct gttaacatat atggaaaaaa caaacttcac cgttatttac      1200
ctgaatttac ctatttgggt aagaattgta cctctggacc tctagtattt tatatacacc      1260
taaaaatata attttggtcg ggaaaatata actctgttta attaattaaa ttttcagtat      1320
tgtgtaagtg taattataga aatcaatttt atccgcgtaa caaataata taaaattata      1380
ctttcaaatc cacgaatata tattgtgaag tctcatagtt tgcaaataag cattggtctt      1440
cggccgacaa aaaaaaagc attggtcttc gaatattttg aatatcggac caatggtata      1500
taattaataa tatgtggtat ataaatacat atttatttaa atcacaatag gatatgcaat      1560
gtgtgtatat atacatatac gtaattaaag tccgggttaa actgatagca tatattataa      1620
tagatgcatc tataattgtt cgtcaacaaa agcattatca tgtatttga attaagcttc      1680
cttcatttct gtgaatcaaa aggcctcaga agaagaaact aaagtcaaac aatcaacggg      1740
atccaataaa tcacatctgg actatatagt atcaatactt tccacactaa aaaagctaag      1800
aaatttaata aatacattat tataggggggg aaaaaaggt agtcatcaga tatatatttt       1860
ggtaagaaaa tatagaaatg aataatttca cgtttaacga agaggagatg acgtgtgttc      1920
cttcgaaccc gagttttgtt cgtctataaa tagcaccttc tcttctcctt cttcctcact      1980
tccatctttt tagcttcact atctctctat aatcggtttt atctttctct aagtcacaac      2040
ccaaaaaaac aaagtagaga agaatctgta aagtcgtgct gcttcatgtg gatgatgatc      2100
acattcgtta tctattttt ccacatgaag aagcacgact tgattggctc ttcttactac       2160
aatgaaaaag gccgaggcaa aacgcctaaa atcacttgag aatcaattct ttttactgtc      2220
catttaagct atctttttata aacgtgtctt atttctatc tcttttgttt aaactaagaa       2280
actatagtat tttgtctaaa acaaaacatg aaagaacaga ttagatctca tctttagtct      2340
```

```
ctttctccgg tgcagtcagc caccgtcggg taagtttcat ctgtatttta ttaattaatt    2400
acaattatta gtgttcttat taccgttttg gtaaaattag ttaattaatg tcggtccaaa    2460
cattctaaac caattattct gaaaagggtg aacgccaatc agttatatac aatattctta    2520
cattaaagta gaatcggaga tgttacatac taaccaaaag ttacatatac tagtatcatt    2580
ttctttaaga tttgtttagg atttactcac tttatagtgc tcgcggttgg ggtcagggta    2640
agtggggaac agatatgctc tgcatgaacc acgtggacca acatgcatat acacagttac    2700 atttatttt  tctagtaggt tcatttgcaa attttccagt atcttgtatg ttatcttcat    2760
ggtgagtttt ttggtcgcat attcttggtg attcttcttc tacgttttca ctttcttctt    2820
cagagacctt attaatatgt taattgcatg aatttatgta acattcaaga aaaagagatc    2880
gaatacaaga aaccggaaat ttaatttcta atttgaattc tatgcatgtt tgtttctttg    2940
ccaatttagt acgaatatat ttatggtccg gagttctaac caaagatagt tgctctgtat    3000
atagaagtta tacatctcgc ttgtttaaac taaataacta tttagtttgt cttggtagtc    3060
cagtgacttt ctgcaaacat tgggatttat aatatagtca aaacgttggg atatgtagta    3120
ttcattttcg ttgtaaaaat cattatattt tgcaaaggtt gcaacgtaaa acgttgtatt    3180
gaatttagga gaaagtagcc atttacaatg aattttagtg acaaactgtt gtatacagcc    3240
tgtgccacta agtatgtcta tatctaaatt tggaatggat gataaccagt attggtcaat    3300
aatggataat ttggtattta gaattactaa tttggtattt tagtgacaaa ctgttgtatg    3360
gaatttagga gaacgcgttc ccaagctata tattatatgt atttcattct ttcatatgtt    3420
atattatgaa ttgttataaa aaagaccaat gagcaacggt ttaaggttta atcagtaatc    3480
gatccgacca atcatataca agttcctaac acatcttcta actactgagt aaaatagtaa    3540
tgctattaca aaggtttttt cttttcaaaa tacagcctaa tgctactaca aaattctaat    3600
gttataaaat aatcatagga gaagtaaacc ccggtattta attaatacct tacaaactta    3660
cattattgat aaagttgaat gaagagttat atggtccatt tagtattatt tacttaatat    3720
gatactagtg ttagacgtgt tactgtattt caacgtgcat aatcaggttg ttcaaaaaga    3780
gagaggatag gtcttcttct tctgtaattt gctgggaccg caagtcatgt gaggctgctc    3840
tgctgatgct gcacggcgtc gcaactctct caataaaattc ttttaactaa cgctccaatt    3900
ttcgatgtaa attggctgac ttcaattcta tgccttactc ttgtactcta tgtttcttta    3960
tctattaaaa tccaactctg cttttgaacc caaaaaacaa                          4000

<210> SEQ ID NO 36
<211> LENGTH: 4000
<212> TYPE: DNA
<213> ORGANISM: Artificial Sequence
<220> FEATURE:
<223> OTHER INFORMATION: Plasmid-6: GEiGS_ mir390a _si-GFP_2

<400> SEQUENCE: 36
accctcattg attttggtgg ccaaactctt gatcgtattc ttttaggaac agtaattaat      60
tttaaatttg agaaaaatgt agtgatgaaa gtgagatata tgggacgcac tattgaaagc     120
attgtccaca ccgcatgatg tgagattgat gtgaatatgg taactaataa cacccagact     180
cacttttatg agaaaatgta tcttaaaaaa tgttattcat caaagcttag atgcgctata     240
ggggaacata atcattattt gaaaagaacc aattcaaata tttttttttt taagagttaa     300
aatcctatat aacataacca tccaaacttt gggcatgaac acaacaatat ttttttttcgt    360 ttttgataaa ttctttcaat tgcaatcaaa acttaccagc tatacaaatg tttgctgcat     420
```

```
ccaatctaat acaccgttaa acaataaaat ttgttatctc tcaaatctga tcatctattc    480
caacctgact gttttattct agtattttaa ggccaggtat aacgaaaaca aagaaaaaag    540
ttcagcgacc aagacatttt gacatcaggc tcaaacggtc aaacccacga aaacttttac    600
ctcatttctt aaccacgcag tgttatttga atagccttaa taggctaata caaaacaaca    660
agccatcgat tacagtttta actataatat tacaaaatct taaaccaaaa caagaaaaga    720
tatatattcc gtaaaattaa aataatattt ttaatatagt cattatgtaa gttagctctt    780
tcgacaaaat cattataaat taggccattt tgtaagttag ttcttttatc gacaagccat    840
tataacttag gtaattttgt aagttagctg gactataacc aattttttg tttcacatct     900
agagtataaa acacatatat attgaccgta caactttagt caaattagaa actctgtttt    960
atctgcagaa aagaaaaaaa aagaggatga attatgtaaa tacttcagga ttagaaataa   1020
tgtcatcgta tatctcttga tatgaataca tattttactt gactagtacc gtagtcggca   1080
ggaaaatgac acaacaacc atctaaaaag ataaagtaag aactaaaaag tcttgacatt    1140
cattagttta atcattttct gttaacatat atggaaaaaa caaacttcac cgttatttac   1200
ctgaatttac ctatttgggt aagaattgta cctctggacc tctagtattt tatatacacc   1260
taaaaatata attttggtcg ggaaaatata actctgttta attaattaaa ttttcagtat   1320
tgtgtaagtg taattataga aatcaatttt atccgcgtaa caaaataata taaaattata   1380
ctttcaaatc cacgaatata tattgtgaag tctcatagtt tgcaaataag cattggtctt   1440
cggccgacaa aaaaaaagc attggtcttc gaatattttg aatatcggac caatggtata    1500
taattaataa tatgtggtat ataaatacat atttatttaa atcacaatag gatatgcaat   1560
gtgtgtatat atacatatac gtaattaaag tccgggttaa actgatagca tatattataa   1620
tagatgcatc tataattgtt cgtcaacaaa agcattatca tgtattttga attaagcttc   1680
cttcatttct gtgaatcaaa aggcctcaga agaagaaact aaagtcaaac aatcaacggg   1740
atccaataaa tcacatctgg actatatagt atcaatactt tccacactaa aaaagctaag   1800
aaatttaata aatacattat tataggggg aaaaaaaggt agtcatcaga tatatatttt    1860
ggtaagaaaa tatagaaatg aataaatttca cgtttaacga agaggagatg acgtgtgttc   1920
cttcgaaccc gagttttgtt cgtctataaa tagcaccttc tcttctcctt cttcctcact   1980
tccatctttt tagcttcact atctctctat aatcggtttt atctttctct aagtcacaac   2040
ccaaaaaaac aaagtagaga agaatctgta agttgtactc cagcttgtgc catgatgatc   2100
acattcgtta tctatttttt ggcacaagct tgagtacaac tgattggctc ttcttactac   2160
aatgaaaaag gccgaggcaa aacgcctaaa atcacttgag aatcaattct ttttactgtc   2220
catttaagct atcttttata aacgtgtctt attttctatc tcttttgttt aaactaagaa   2280
actatagtat tttgtctaaa acaaaacatg aaagaacaga ttagatctca tctttagtct   2340
ctttctccgg tgcagtcagc caccgtcggg taagtttcat ctgtatttta ttaattaatt   2400
acaattatta gtgttcttat taccgttttg gtaaaattag ttaattaatg tcggtccaaa   2460
cattctaaac caattattct gaaaagggtg aacgccaatc agttatatac aatattctta   2520
cattaaagta gaatcggaga tgttacatac taaccaaaag ttacatatac tagtatcatt   2580
ttctttaaga tttgtttagg atttactcac tttatagtgc tcgcggttgg ggtcagggta   2640
agtggggaac agatatgctc tgcatgaacc acgtggacca acatgcatat acacagttac   2700
atttattttt tctagtaggt tcatttgcaa attttccagt atcttgtatg ttatcttcat   2760
ggtgagtttt ttggtcgcat attcttggtg attcttcttc tacgttttca ctttcttctt   2820
```

```
cagagacctt attaatatgt taattgcatg aatttatgta acattcaaga aaaagagatc      2880
gaatacaaga aaccggaaat ttaatttcta atttgaattc tatgcatgtt tgtttctttg      2940
ccaatttagt acgaatatat ttatggtccg gagttctaac caaagatagt tgctctgtat      3000
atagaagtta tacatctcgc ttgtttaaac taaataacta tttagtttgt cttggtagtc      3060
cagtgacttt ctgcaaacat tgggatttat aatatagtca aaacgttggg atatgtagta      3120
ttcattttcg ttgtaaaaat cattatattt tgcaaaggtt gcaacgtaaa acgttgtatt      3180
gaatttagga gaaagtagcc atttacaatg aattttagtg acaaactgtt gtatacagcc      3240
tgtgccacta agtatgtcta tatctaaatt tggaatggat gataaccagt attggtcaat      3300
aatggataat ttggtattta gaattactaa tttggtattt tagtgacaaa ctgttgtatg      3360
gaatttagga gaacgcgttc ccaagctata tattatatgt atttcattct ttcatatgtt      3420
atattatgaa ttgttataaa aaagaccaat gagcaacggt ttaaggttta atcagtaatc      3480
gatccgacca atcatataca agttcctaac acatcttcta actactgagt aaaatagtaa      3540
tgctattaca aaggttttt cttttcaaaa tacagcctaa tgctactaca aaattctaat      3600
gttataaaat aatcatagga gaagtaaacc ccggtattta attaatacct tacaaactta      3660
cattattgat aaagttgaat gaagagttat atggtccatt tagtattatt tacttaatat      3720
gatactagtg ttagacgtgt tactgtattt caacgtgcat aatcaggttg ttcaaaaaga      3780
gagaggatag gtcttcttct tctgtaattt gctgggaccg caagtcatgt gaggctgctc      3840
tgctgatgct gcacggcgtc gcaactctct caataaattc ttttaactaa cgctccaatt      3900
ttcgatgtaa attggctgac ttcaattcta tgccttactc ttgtactcta tgtttcttta      3960
tctattaaaa tccaactctg cttttgaacc caaaaaacaa                            4000

<210> SEQ ID NO 37
<211> LENGTH: 4000
<212> TYPE: DNA
<213> ORGANISM: Artificial Sequence
<220> FEATURE:
<223> OTHER INFORMATION: Plasmid-7: GEiGS_ mir390a _si-PDS_1

<400> SEQUENCE: 37
accctcattg attttggtgg ccaaactctt gatcgtattc ttttaggaac agtaattaat       60
tttaaatttg agaaaaatgt agtgatgaaa gtgagatata tgggacgcac tattgaaagc      120
attgtccaca ccgcatgatg tgagattgat gtgaatatgg taactaataa cacccagact      180
cacttttatg agaaaatgta tcttaaaaaa tgttattcat caaagcttag atgcgctata      240
ggggaacata atcattattt gaaaagaacc aattcaaata tttttttttt taagagttaa      300
aatcctatat aacataacca tccaaacttt gggcatgaac acaacaatat ttttttttcgt      360 ttttgataaa ttcttttcaat tgcaatcaaa acttaccagc tatacaaatg tttgctgcat      420
ccaatctaat acaccgttaa acaataaaat ttgttatctc tcaaatctga tcatctattc      480
caacctgact gtttattct agtatttaa ggccaggtat aacgaaaaca aagaaaaaag      540
ttcagcgacc aagacatttt gacatcaggc tcaaacggtc aaacccacga aaacttttac      600
ctcatttctt aaccacgcag tgttatttga atagccttaa taggctaata caaaacaaca      660
agccatcgat tacagtttta actataatat tacaaaatct taaaccaaaa caagaaaaga      720
tatatattcc gtaaaattaa aataaatatt ttaatatagt cattatgtaa gttagctctt      780
tcgacaaaat cattataaat taggccatt tgtaagttag ttcttttatc gacaagccat      840
tataacttag gtaattttgt aagttagctg gactataacc aattttttg tttcacatct      900
```

```
agagtataaa acacatatat attgaccgta caactttagt caaattagaa actctgtttt    960
atctgcagaa aagaaaaaaa aagaggatga attatgtaaa tacttcagga ttagaaataa   1020
tgtcatcgta tatctcttga tatgaataca tattttactt gactagtacc gtagtcggca   1080
ggaaaatgac acaaacaacc atctaaaaag ataaagtaag aactaaaaag tcttgacatt   1140
cattagttta atcattttct gttaacatat atggaaaaaa caaacttcac cgttatttac   1200
ctgaatttac ctatttgggt aagaattgta cctctggacc tctagtattt tatatacacc   1260
taaaaatata atttggtcg ggaaaatata actctgttta attaattaaa ttttcagtat    1320
tgtgtaagtg taattataga aatcaatttt atccgcgtaa caaaataata taaaattata   1380
cttcaaatc cacgaatata tattgtgaag tctcatagtt tgcaaataag cattggtctt    1440
cggccgacaa aaaaaaaagc attggtcttc gaatattttg aatatcggac caatggtata   1500
taattaataa tatgtggtat ataaatacat attatttaa atcacaatag gatatgcaat    1560
gtgtgtatat atacatatac gtaattaaag tccgggttaa actgatagca tatattataa   1620
tagatgcatc tataattgtt cgtcaacaaa agcattatca tgtattttga attaagcttc   1680
cttcatttct gtgaatcaaa aggcctcaga agaagaaact aaagtcaaac aatcaacggg   1740
atccaataaa tcacatctgg actatatagt atcaatactt tccacactaa aaaagctaag   1800
aaatttaata aatacattat tataggggg aaaaaaaggt agtcatcaga tatatatttt    1860
ggtaagaaaa tatagaaatg aataatttca cgtttaacga agaggagatg acgtgtgttc   1920
cttcgaaccc gagttttgtt cgtctataaa tagcaccttc tcttctcctt cttcctcact   1980
tccatctttt tagcttcact atctctctat aatcggtttt atcttctct aagtcacaac    2040
ccaaaaaaac aaagtagaga agaatctgta tatccacaca aactacctgc aatgatgatc   2100
acattcgtta tctatttttt tgcaggtagt gtgtgtggat agattggctc ttcttactac   2160
aatgaaaaag gccgaggcaa aacgcctaaa atcacttgag aatcaattct ttttactgtc   2220
catttaagct atctttata aacgtgtctt attttctatc tcttttgttt aaactaagaa    2280
actatagtat tttgtctaaa acaaaacatg aaagaacaga ttagatctca tctttagtct   2340
ctttctccgg tgcagtcagc caccgtcggg taagtttcat ctgtatttta ttaattaatt   2400
acaattatta gtgttcttat taccgttttg gtaaaattag ttaattaatg tcggtccaaa   2460
cattctaaac caattattct gaaaagggtg aacgccaatc agttatatac aatattctta   2520
cattaaagta gaatcggaga tgttacatac taaccaaaag ttacatatac tagtatcatt   2580
ttctttaaga tttgtttagg atttactcac tttatagtgc tcgcggttgg ggtcagggta   2640
agtggggaac agatatgctc tgcatgaacc acgtggacca acatgcatat acacagttac   2700
atttattttt tctagtaggt tcatttgcaa attttccagt atcttgtatg ttatcttcat   2760
ggtgagtttt ttggtcgcat attcttggtg attcttcttc tacgttttca ctttcttctt   2820
cagagacctt attaatatgt taattgcatg aatttatgta acattcaaga aaaagagatc   2880
gaatacaaga aaccggaaat ttaatttcta atttgaattc tatgcatgtt tgtttctttg   2940
ccaatttagt acgaatatat ttatggtccg gagttctaac caaagatagt tgctctgtat   3000
atagaagtta tacatctcgc ttgtttaaac taaataacta tttagtttgt cttggtagtc   3060
cagtgacttt ctgcaaacat tgggatttat aatatagtca aaacgttggg atatgtagta   3120
ttcattttcg ttgtaaaaat cattatattt tgcaaaggtt gcaacgtaaa acgttgtatt   3180
gaatttagga gaaagtagcc atttacaatg aattttagtg acaaactgtt gtatacagcc   3240
tgtgccacta agtatgtcta tatctaaatt tggaatggat gataaccagt attggtcaat   3300
```

```
aatggataat ttggtatttta gaattactaa tttggtatttt tagtgacaaa ctgttgtatg    3360
gaatttagga gaacgcgttc ccaagctata tattatatgt atttcattct ttcatatgtt    3420
atattatgaa ttgttataaa aaagaccaat gagcaacggt ttaaggttta atcagtaatc    3480
gatccgacca atcatataca agttcctaac acatcttcta actactgagt aaaatagtaa    3540
tgctattaca aaggtttttt cttttcaaaa tacagcctaa tgctactaca aaattctaat    3600
gttataaaat aatcatagga gaagtaaacc ccggtattta attaataccct tacaaactta    3660 cattattgat aaagttgaat gaagagttat atggtccatt tagtattatt tacttaatat    3720
gatactagtg ttagacgtgt tactgtattt caacgtgcat aatcaggttg ttcaaaaaga    3780
gagaggatag gtcttcttct tctgtaattt gctgggaccg caagtcatgt gaggctgctc    3840
tgctgatgct gcacggcgtc gcaactctct caataaattc ttttaactaa cgctccaatt    3900
ttcgatgtaa attggctgac ttcaattcta tgccttactc ttgtactcta tgtttcttta    3960
tctattaaaa tccaactctg cttttgaacc caaaaaacaa                          4000
```

<210> SEQ ID NO 38
<211> LENGTH: 4000
<212> TYPE: DNA
<213> ORGANISM: Artificial Sequence
<220> FEATURE:
<223> OTHER INFORMATION: Plasmid-8: GEiGS_ mir390a _si-PDS_2

<400> SEQUENCE: 38

```
accctcattg attttggtgg ccaaactctt gatcgtattc ttttaggaac agtaattaat     60
tttaaatttg agaaaaatgt agtgatgaaa gtgagatata tgggacgcac tattgaaagc    120
attgtccaca ccgcatgatg tgagattgat gtgaatatgg taactaataa cacccagact    180
cacttttatg agaaaatgta tcttaaaaaa tgttattcat caaagcttag atgcgctata    240
ggggaacata atcattattt gaaaagaacc aattcaaata tttttttttt taagagttaa    300
aatcctatat aacataacca tccaaacttt gggcatgaac acaacaatat ttttttttcgt   360 ttttgataaa ttctttcaat tgcaatcaaa acttaccagc tatacaaatg tttgctgcat    420
ccaatctaat acaccgttaa acaataaaat ttgttatctc tcaaatctga tcatctattc    480
caacctgact gttttattct agtattttaa ggccaggtat aacgaaaaca aagaaaaaag    540
ttcagcgacc aagacatttt gacatcaggc tcaaacggtc aaacccacga aaacttttac    600
ctcatttctt aaccacgcag tgttatttga atagccttaa taggctaata caaaacaaca    660
agccatcgat tacagtttta actataatat tacaaaatct taaaccaaaa caagaaaaga    720
tatatattcc gtaaaattaa aataatattt ttaatatagt cattatgtaa gttagctctt    780
tcgacaaaat cattataaat taggccattt tgtaagttag ttcttttatc gacaagccat    840
tataacttag gtaattttgt aagttagctg gactataacc aattttttttg tttcacatct    900 agagtataaa acacatatat attgaccgta caacttttagt caaattagaa actctgtttt    960
atctgcagaa aagaaaaaaa aagaggatga attatgtaaa tacttcagga ttagaaataa   1020
tgtcatcgta tatctcttga tatgaataca tattttactt gactagtacc gtagtcggca   1080
ggaaaatgac acaaacaacc atctaaaaag ataaagtaag aactaaaaag tcttgacatt   1140
cattagttta atcattttct gttaacatat atggaaaaaa caaacttcac cgttatttac   1200
ctgaatttac ctatttgggt aagaattgta ccctctggacc tctagtattt tatatacacc   1260
taaaaatata attttggtcg ggaaaatata actctgttta attaattaaa ttttcagtat   1320
tgtgtaagtg taattataga aatcaatttt atccgcgtaa caaaataata taaaattata   1380
```

```
ctttcaaatc cacgaatata tattgtgaag tctcatagtt tgcaaataag cattggtctt    1440
cggccgacaa aaaaaaaagc attggtcttc gaatattttg aatatcggac caatggtata    1500
taattaataa tatgtggtat ataaatacat atttatttaa atcacaatag gatatgcaat    1560
gtgtgtatat atacatatac gtaattaaag tccgggttaa actgatagca tatattataa    1620
tagatgcatc tataattgtt cgtcaacaaa agcattatca tgtattttga attaagcttc    1680
cttcatttct gtgaatcaaa aggcctcaga agaagaaact aaagtcaaac aatcaacggg    1740
atccaataaa tcacatctgg actatatagt atcaatactt tccacactaa aaaagctaag    1800
aaatttaata aatacattat tataggggg aaaaaaaggt agtcatcaga tatatatttt    1860
ggtaagaaaa tatagaaatg aataatttca cgtttaacga agaggagatg acgtgtgttc    1920
cttcgaaccc gagttttgtt cgtctataaa tagcaccttc tcttctcctt cttcctcact    1980
tccatctttt tagcttcact atctctctat aatcggtttt atctttctct aagtcacaac    2040
ccaaaaaaac aaagtagaga agaatctgta tgacaatcca gccaatccag catgatgatc    2100
acattcgtta tctatttttt gctggattgg atggattgtc agattggctc ttcttactac    2160
aatgaaaaag gccgaggcaa aacgcctaaa atcacttgag aatcaattct ttttactgtc    2220
catttaagct atcttttata aacgtgtctt attttctatc tcttttgttt aaactaagaa    2280
actatagtat tttgtctaaa acaaaacatg aaagaacaga ttagatctca tctttagtct    2340 cttttctccgg tgcagtcagc caccgtcggg taagtttcat ctgtattta ttaattaatt    2400 acaattatta gtgttcttat taccgttttg gtaaaattag ttaattaatg tcggtccaaa    2460
cattctaaac caattattct gaaagggtg aacgccaatc agttatatac aatattctta    2520
cattaaagta gaatcggaga tgttacatac taaccaaaag ttacatatac tagtatcatt    2580
ttctttaaga tttgtttagg atttactcac tttatagtgc tcgcggttgg ggtcagggta    2640
agtggggaac agatatgctc tgcatgaacc acgtggacca acatgcatat acacagttac    2700 attttattttt tctagtaggt tcatttgcaa attttccagt atcttgtatg ttatcttcat    2760
ggtgagtttt ttggtcgcat attcttggtg attcttcttc tacgttttca ctttcttctt    2820
cagagacctt attaatatgt taattgcatg aatttatgta acattcaaga aaagagatc    2880 gaatacaaga aaccggaaat ttaatttcta atttgaattc tatgcatgtt tgtttctttg    2940
ccaatttagt acgaatatat ttatggtccg gagttctaac caaagatagt tgctctgtat    3000
atagaagtta tacatctcgc ttgtttaaac taaataacta tttagtttgt cttggtagtc    3060
cagtgacttt ctgcaaacat tgggatttat aatatagtca aaacgttggg atatgtagta    3120
ttcattttcg ttgtaaaaat cattatattt tgcaaaggtt gcaacgtaaa acgttgtatt    3180
gaatttagga gaaagtagcc atttacaatg aattttagtg acaaactgtt gtatacagcc    3240
tgtgccacta agtatgtcta tatctaaatt tggaatggat gataaccagt attggtcaat    3300
aatggataat ttggtattta gaattactaa tttggtattt tagtgacaaa ctgttgtatg    3360
gaatttagga gaacgcgttc ccaagctata tattatatgt atttcattct ttcatatgtt    3420
atattatgaa ttgttataaa aaagaccaat gagcaacggt ttaaggttta atcagtaatc    3480
gatccgacca atcatataca agttcctaac acatcttcta actactgagt aaaatagtaa    3540
tgctattaca aaggttttt cttttcaaaa tacagcctaa tgctactaca aaattctaat    3600
gttataaaat aatcatagga gaagtaaacc ccggtattta attaataccct tacaaactta    3660 cattattgat aaagttgaat gaagagttat atggtccatt tagtattatt tacttaatat    3720
gatactagtg ttagacgtgt tactgtattt caacgtgcat aatcaggttg ttcaaaaaga    3780
```

-continued

```
gagaggatag gtcttcttct tctgtaattt gctgggaccg caagtcatgt gaggctgctc    3840
tgctgatgct gcacggcgtc gcaactctct caataaattc ttttaactaa cgctccaatt    3900
ttcgatgtaa attggctgac ttcaattcta tgccttactc ttgtactcta tgtttcttta    3960
tctattaaaa tccaactctg cttttgaacc caaaaaacaa                          4000
```

```
<210> SEQ ID NO 39
<211> LENGTH: 22
<212> TYPE: DNA
<213> ORGANISM: Artificial sequence
<220> FEATURE:
<223> OTHER INFORMATION: Single strand oligonucleotide

<400> SEQUENCE: 39
ttcgcttgca gagagaaatc ac                                             22
```

```
<210> SEQ ID NO 40
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 40
aagctcagga gggatagcgc c                                              21
```

```
<210> SEQ ID NO 41
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 41
cttgcagaga gaaatcacag tgg                                            23
```

```
<210> SEQ ID NO 42
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 42
gcttacacag agaatcacag agg                                            23
```

```
<210> SEQ ID NO 43
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 43
aagaatctgt aaagctcagg agg                                            23
```

```
<210> SEQ ID NO 44
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 44
ctatccatcc tgagtttcat tgg                                            23
```

```
<210> SEQ ID NO 45
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 45
aagtcgtgct gcttcatgtg g                                    21

<210> SEQ ID NO 46
<211> LENGTH: 22
<212> TYPE: DNA
<213> ORGANISM: Artificial sequence
<220> FEATURE:
<223> OTHER INFORMATION: Single strand oligonucleotide

<400> SEQUENCE: 46
ccacataagc aggacgagtt aa                                   22

<210> SEQ ID NO 47
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 47
agttgtactc cagcttgtgc c                                    21

<210> SEQ ID NO 48
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 48
gcaaagctgc agtacaacta a                                    21

<210> SEQ ID NO 49
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 49
tatccacaca aactacctgc a                                    21

<210> SEQ ID NO 50
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 50
gcagtagtta gtgtggataa a                                    21

<210> SEQ ID NO 51
<211> LENGTH: 21
<212> TYPE: DNA
<213> ORGANISM: Artificial sequence
<220> FEATURE:
<223> OTHER INFORMATION: Single strand oligonucleotide
```

```
<400> SEQUENCE: 51
tgacaatcca gccaatccag c                                              21

<210> SEQ ID NO 52
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 52
ctgattggca ggattgtcaa a                                              21

<210> SEQ ID NO 53
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 53
taaagatcgg caacacatga t                                              21

<210> SEQ ID NO 54
<211> LENGTH: 19
<212> TYPE: DNA
<213> ORGANISM: Artificial sequence
<220> FEATURE:
<223> OTHER INFORMATION: Single strand oligonucleotide

<400> SEQUENCE: 54
tcagtgttgg cgatcttta                                                 19

<210> SEQ ID NO 55
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 55
tgacctttct tgggtttagc c                                              21

<210> SEQ ID NO 56
<211> LENGTH: 19
<212> TYPE: DNA
<213> ORGANISM: Artificial sequence
<220> FEATURE:
<223> OTHER INFORMATION: Single strand oligonucleotide

<400> SEQUENCE: 56
gctaacccat gaaaggtca                                                 19

<210> SEQ ID NO 57
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 57
taagtacttt cgcttgcaga gagaaatcac agtggtcaaa aaagttgtag ttttcttaaa    60
gtctctttcc tctgtgattc tctgtgtaag cgaaagagct tg                      102
```

```
<210> SEQ ID NO 58
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 58
taagtactta agtcgtgctg cttcatgtgg agtggtcaaa aaagttgtag ttttcttaaa      60
gtctctttcc tctccacata agcaggacga gttaagagct tg                       102

<210> SEQ ID NO 59
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 59
taagtactta gttgtactcc agcttgtgcc agtggtcaaa aaagttgtag ttttcttaaa      60
gtctctttcc tctggcaaag ctgcagtaca actaagagct tg                       102

<210> SEQ ID NO 60
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 60
taagtacttt atccacacaa actacctgca agtggtcaaa aaagttgtag ttttcttaaa      60
gtctctttcc tcttgcagta gttagtgtgg ataaagagct tg                       102

<210> SEQ ID NO 61
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 61
taagtacttt gacaatccag ccaatccagc agtggtcaaa aaagttgtag ttttcttaaa      60
gtctctttcc tctgctgatt ggcaggattg tcaaagagct tg                       102

<210> SEQ ID NO 62
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 62
taagtacttt aaagatcggc aacacatgat agtggtcaaa aaagttgtag ttttcttaaa      60
gtctctttcc tctgatcagt gttggcgatc tttaagagct tg                       102

<210> SEQ ID NO 63
<211> LENGTH: 102
<212> TYPE: DNA
<213> ORGANISM: Artificial sequence
<220> FEATURE:
<223> OTHER INFORMATION: Single strand oligonucleotide
```

<400> SEQUENCE: 63
taagtacttt gacctttctt gggtttagcc agtggtcaaa aaagttgtag ttttcttaaa    60
gtctctttcc tctgggctaa cccatgaaag gtcaagagct tg    102

<210> SEQ ID NO 64
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 64
gtagagaaga atctgtaaag ctcaggaggg atagcgccat gatgatcaca ttcgttatct    60 atttttttggc gctatccatc ctgagtttca ttggctcttc ttactac    107

<210> SEQ ID NO 65
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 65
gtagagaaga atctgtaaag tcgtgctgct tcatgtggat gatgatcaca ttcgttatct    60 atttttttcca catgaagaag cacgacttga ttggctcttc ttactac    107

<210> SEQ ID NO 66
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 66
gtagagaaga atctgtaagt tgtactccag cttgtgccat gatgatcaca ttcgttatct    60 atttttttggc acaagcttga gtacaactga ttggctcttc ttactac    107

<210> SEQ ID NO 67
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 67
gtagagaaga atctgtatat ccacacaaac tacctgcaat gatgatcaca ttcgttatct    60
atttttttgc aggtagtgtg tgtggataga ttggctcttc ttactac    107

<210> SEQ ID NO 68
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 68
gtagagaaga atctgtatga caatccagcc aatccagcat gatgatcaca ttcgttatct    60 atttttttgct ggattggatg gattgtcaga ttggctcttc ttactac    107

<210> SEQ ID NO 69
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 69

```
gtagagaaga atctgtataa agatcggcaa cacatgatat gatgatcaca ttcgttatct      60
attttttatc atgtgttacc gatctttaca ttggctcttc ttactac                   107
```

<210> SEQ ID NO 70
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 70

```
gtagagaaga atctgtatga cctttcttgg gtttagccat gatgatcaca ttcgttatct      60
attttttggc taaaccccag aaaggtcaca ttggctcttc ttactac                   107
```

<210> SEQ ID NO 71
<211> LENGTH: 4100
<212> TYPE: DNA
<213> ORGANISM: Artificial sequence
<220> FEATURE:
<223> OTHER INFORMATION: Single strand oligonucleotide

<400> SEQUENCE: 71

```
cacttatcat ttagacagta gattttaaat ttgtatttac aatttcaaaa ctgaaattca      60
tttgtaatca agaaaaaaca aaacaagaaa agggaggagg agtgggattt gggttgctta     120
acagtattat atatacacgt cgttagttaa tcaataaatt atgagcaggt gtagtagcta     180
tgaacatggt tttaccaaat tggtaaattc atgtcattgt tgtagcactt tagcgaggcc     240
agcaaaatgg cgttcttgga aagggcatgg cggcccgtgg ccgccaggga tatgtgtgca     300
gctagaagga ttagaaggag taacttcacc tttttgtaga aactgtaaat tgccaagacg     360 ctcgttttggt aaatacctta acgcttcgtt tgctggaatg tgtaccacca ttagtagaag    420
aaagtataat aagactatta atgcaagaga ttttttcata ttccttttct aagagtagaa     480
tggaatgaat aaatgaatga atgaaatagg gttttcttg tttagatcct gtcgcacccg      540
agaataatag aagctgaatt aattggtgaa gagttttatg gtggcgatgt tgtatttata     600
gagggaaatg atttcaagtt tacaatggga ttttaatttt gttttgttga ctattatctt     660
gcggagagat cttgactgtt gacatgtatg tagtgtttgt tattaaaata aatgcatttt     720
tgtagacccg attcttaaat atgttaggca tggtcaaatt gttagactgt aaaagcttga     780
gtagagacat cggtcaactt tgtttacaag aattctctat aaaatattat acaaattgat     840
cggtagaaat tagatggaac attttgaatt aatgtttgac aatgtataaa ttggtttggt     900
caatatctag gaatgaaaac aagagctgct tcaaagttgt tccattctta agtatacata     960
gaggtggctt gatgggaagt ttcatggaag tgtagtttta tatctacttc caaattcgtt    1020
gatctgtttc ttatctcaag ctaaacatgt ttagaaaaga tgtgttaaaa acatgtgaca    1080 aaaaagagt caaatgtttg gcaaacaagg tacttagatt tttggcatct attcaaatat     1140
aatagaatcc caaattatg atatttgtca atcaaatttg aaaaaaaaa aaaaaaaaa       1200 aaagattcta caaaagatca aacgtattgc cgtagattta tcataatttt aattctttca    1260
```

```
cactaccact agtccactac catatagtga tgagataatc cataatcata aataagatat    1320
aactttcgaa ttcttgtttt tgttgcctca aagttgttgg atcattattt tttacgtaaa    1380
tgtggcttaa tgagaattta tgtttgtggg aattgtagtt tgcttccaac ttttttttt     1440 ttttttgaa cacgtagttt gcttccaact tagtttatct ttttcttatt tcaagttaaa     1500
catgtaaaaa aacatgtgac gacgaaattc aatcagttcc tccaatgttt ggcagaagcc    1560
aaatctttgg taaacaaagt aattttttg ccatttgatt ggttagtata ggagaattta     1620
aaaacgacga taaggtttag gtaaattatt tcatttgaaa ataattgagc accgttaata    1680
attttcatcc ataaaataat atttcaaaga tgatatttga tccccattaa attcattcgt    1740
aaccaaaaaa aagttatgaa aaaagagtgg tcgtgtgagt tgcccaagca ccattataat    1800
aaaaaataaa ataattagca agtaataagg aataaaatcc tgtaattata gctgaaaaag    1860
gaaaaatatt tggagaccgt cagattcgaa tctgaacaaa gcataaaaaa gtcaacaaaa    1920
cttaaagcgg cggtctcatc gtaatctcag cccaataccc tattttcctc tcccctatat    1980
aaatactttc ttcttctact gatcttcttc tcacaaataa acccaaatat atcaatctac    2040
tgtgttggtg attaagtact ttcgcttgca gagagaaatc acagtggtca aaaaagttgt    2100
agttttctta aagtctcttt cctctgtgat tctctgtgta agcgaaagag cttgctccct    2160
aaacttatct ctctgatgat ttaatgttag agatcttcgt aaatctatgt gtttgataga    2220
tctgatgcgt ttttgagtt gatgatttga ttatttttca ctggaaagta tctcattagg     2280
gtaacgataa tgttttatgg atttggttgt ataacagatc catgaaatct tgactggtta    2340
taaaatctga ataatgtatt tcaatttgga gattcggtga taaaaattac tgatttacga    2400
atgacattta tatcgataga tgagtttgct gatttggttg ttaaattgat aaatcaagga    2460
catgagaaac tgttttgta tgctaatttg tccatggaat aaaattggga ggtgaggacc     2520
gtgagggtag tcaggaaacc ttaatattga agttgatgtt gaaccaacaa atctgcccaa    2580
aaatgataaa agttgatgcc gagcccacaa attttgatga caatcgataa gcccaagccc    2640
aaaaggcatc tgtacctgag cccattattc tttcattact agcaaaaagg atgcattaga    2700
gaccccggtg tagtaaattg acctcacaat tcactattgt attgtatacg tacatttcaa    2760
gcgtaattaa accctcatat ttttatacgc tttaaatata attggccttt aattagctca    2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caattttctt taaaacaaat ttcagttttt atttgtcagc aaaaaaaact tactaacaca    3180
acggaagaac acaaaaatta gggagttgct cacagagcaa agtaataga aatgggaaaa      3240 gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
taatggtagc ttagaatgcc aagttgagaa cagatttgca gtttgtcccg gaatgatcaa    3480
gtagagcatt catagtgtct tgccaatatg gtgtgatcaa cgaagtttga caaaaccgtg    3540
aagatatagg aacatgtaat catgcggctc tccatacaat acatcttgtt gacaaagttc    3600
ccaagacctc attctacaaa ccaatgtttc tttttctttt tcttttttgg tgatagtttt    3660
```

```
tgcaatcaaa tgttgtaaaa ctatgattgg aaatactact gtattttacc gaaaacttta    3720
ttatatatag tcattaacac tcattaccaa tcacataatc aatagtctat tttgattata    3780
caacttttaa acaataaaga catgtttata cagatttggt ttaaattagt actccctata    3840
ttttagaaaa ttttattttg tttcatatta tagaatgtct tggaaagttc tatgtaaatt    3900
taaatgtatt tagtaacttg tgacgatttt atattatgta gtctttttta ggatttgttg    3960 atttttttaaa ataaattttt taagaaaaa aaacaaatta ttttaataaa catgccttta    4020
ccttatacag tttatatttt gaaagagaga tagtatgttt taggatatat ttaaagaaaa    4080
aaaaataact ctttaattta                                                4100

<210> SEQ ID NO 72
<211> LENGTH: 4100
<212> TYPE: DNA
<213> ORGANISM: Artificial sequence
<220> FEATURE:
<223> OTHER INFORMATION: Single strand oligonucleotide

<400> SEQUENCE: 72
cacttatcat ttagacagta gattttaaat ttgtatttac aatttcaaaa ctgaaattca      60
tttgtaatca aagaaaaaca aaacaagaaa agggaggagg agtgggattt gggttgctta     120
acagtattat atatacacgt cgttagttaa tcaataaatt atgagcaggt gtagtagcta     180
tgaacatggt tttaccaaat tggtaaattc atgtcattgt tgtagcactt tagcgaggcc     240
agcaaaatgg cgttcttgga aagggcatgg cggcccgtgg ccgccaggga tatgtgtgca     300
gctagaagga ttagaaggag taacttcacc tttttgtaga aactgtaaat tgccaagacg     360
ctcgtttggt aaataccta acgcttcgtt tgctggaatg tgtaccacca ttagtagaag     420
aaagtataat aagactatta atgcaagaga ttttttcata ttccttttct aagagtagaa     480
tggaatgaat aaatgaatga atgaaatagg gttttttcttg tttagatcct gtcgcacccg     540
agaataatag aagctgaatt aattggtgaa gagtttatg gtggcgatgt tgtatttata     600
gagggaaatg atttcaagtt tacaatggga ttttttaattt gttttgttga ctattatctt     660
gcggagagat cttgactgtt gacatgtatg tagtgtttgt tattaaaata aatgcatttt     720
tgtagacccg attcttaaat atgttaggca tggtcaaatt gttagactgt aaaagcttga     780
gtagagacat cggtcaactt tgtttacaag aattctctat aaaatattat acaaattgat     840
cggtagaaat tagatggaac attttgaatt aatgtttgac aatgtataaa ttggtttggt     900
caatatctag gaatgaaaac aagagctgct tcaaagttgt tccattctta agtatacata     960
gaggtggctt gatgggaagt ttcatggaag tgtagttttta tatctacttc caaattcgtt    1020
gatctgtttc ttatctcaag ctaaacatgt ttagaaaaga tgtgttaaaa acatgtgaca    1080 aaaaagagt caaatgtttg gcaaacaagg tacttagatt tttggcatct attcaaatat    1140
aatagaatcc caaattatg atatttgtca atcaaatttg aaaaaaaaaa aaaaaaaaa    1200 aaagattcta caaagatca aacgtattgc cgtagattta tcataatttt aattctttca    1260
cactaccact agtccactac catatagtga tgagataatc cataatcata ataagatat    1320 aactttcgaa ttcttgtttt tgttgcctca aagttgttgg atcattattt tttacgtaaa    1380
tgtggcttaa tgagaattta tgtttgtggg aattgtagtt tgcttccaac tttttttttt    1440
tttttttgaa cacgtagttt gcttccaact tagtttatct ttttcttatt tcaagttaaa    1500
catgtaaaaa aacatgtgac gacgaaattc aatcagttcc tccaatgttt ggcagaagcc    1560
aaatctttgg taaacaaagt aatttttttg ccatttgatt ggttagtata ggagaattta    1620
```

-continued

```
aaaacgacga taaggtttag gtaaattatt tcatttgaaa ataattgagc accgttaata   1680
attttcatcc ataaaataat atttcaaaga tgatatttga tccccattaa attcattcgt   1740
aaccaaaaaa aagttatgaa aaaagagtgg tcgtgtgagt tgcccaagca ccattataat   1800
aaaaaataaa ataattagca agtaataagg aataaaatcc tgtaattata gctgaaaaag   1860
gaaaaatatt tggagaccgt cagattcgaa tctgaacaaa gcataaaaaa gtcaacaaaa   1920
cttaaagcgg cggtctcatc gtaatctcag cccaataccc tattttcctc tcccctatat   1980
aaatactttc ttcttctact gatcttcttc tcacaaataa acccaaatat atcaatctac   2040
tgtgttggtg attaagtact taagtcgtgc tgcttcatgt ggagtggtca aaaaagttgt   2100
agttttctta aagtctcttt cctctccaca taagcaggac gagttaagag cttgctccct   2160
aaacttatct ctctgatgat ttaatgttag agatcttcgt aaatctatgt gtttgataga   2220
tctgatgcgt tttttgagtt gatgatttga ttattttttca ctggaaagta tctcattagg   2280
gtaacgataa tgttttatgg atttggttgt ataacagatc catgaaatct tgactggtta   2340
taaaatctga ataatgtatt tcaatttgga gattcggtga taaaaattac tgatttacga   2400
atgacattta tatcgataga tgagtttgct gatttggttg ttaaattgat aaatcaagga   2460
catgagaaac tgttttttgta tgctaatttg tccatggaat aaaattggga ggtgaggacc   2520
gtgagggtag tcaggaaacc ttaatattga agttgatgtt gaaccaacaa atctgcccaa   2580
aaatgataaa agttgatgcc gagcccacaa attttgatga caatcgataa gcccaagccc   2640
aaaaggcatc tgtacctgag cccattattc tttcattact agcaaaaagg atgcattaga   2700
gaccccggtg tagtaaattg acctcacaat tcactattgt attgtatacg tacatttcaa   2760
gcgtaattaa accctcatat ttttatacgc tttaaatata attggccttt aattagctca   2820
aataaactag atgtcgtacg tgatcacggt ggatgaaatc aatggtatta tgaaaagact   2880
gtacatgatt tcaaatattt taatgtggtc gtaaaaattg ttgtttatag tggaaattga   2940
agacaacaac gttactgaaa cacatacaga ttgaaatttc gatcatttac ttgcaaagtg   3000
ttaccgtgga ggcgtggcgt ggacgtaagg taccataatg gtttgtgtta cagtcacgcc   3060
actacactcg aattcaagct accatattat aatacgttgt tgattagaaa aaatagtcgc   3120
caattttctt taaaacaaat ttcagttttt atttgtcagc aaaaaaaact tactaacaca   3180
acggaagaac acaaaaatta gggagttgct cacagagcaa aagtaataga aatgggaaaa   3240
gctaatatac gtccgagtag gaaactaatc ttgcaaaaac tgatgaaagc aatcagaagc   3300
cttgacgttt gtctggagag aggaattgtg ttttggatca ctttgttcag tttgttgtgg   3360
atcgtcttcc gttacgttct caccaaaaat atttcataat gaaacaaaaa aattaattaa   3420
taatggtagc ttagaatgcc aagttgagaa cagatttgca gtttgtcccg gaatgatcaa   3480
gtagagcatt catagtgtct tgccaatatg gtgtgatcaa cgaagtttga caaaaccgtg   3540
aagatatagg aacatgtaat catgcggctc tccatacaat acatcttgtt gacaaagttc   3600
ccaagacctc attctacaaa ccaatgtttc ttttttcttt ttcttttttgg tgatagtttt   3660
tgcaatcaaa tgttgtaaaa ctatgattgg aaatactact gtattttacc gaaaacttta   3720
ttatatatag tcattaacac tcattaccaa tcacataatc aatagtctat ttgattata   3780
caacttttaa acaataaaga catgtttata cagatttggt ttaaattagt actccctata   3840
ttttagaaaa ttttattttg ttcatatta tagaatgtct tggaaagttc tatgtaaatt   3900
taaatgtatt tagtaacttg tgacgatttt atattatgta gtcttttta ggatttgttg   3960
atttttttaaa ataaattttt taaagaaaaa aaacaaatta ttttaataaa catgccttta   4020
```

```
cottatacag tttatatttt gaaagagaga tagtatgttt taggatatat ttaaagaaaa    4080
aaaaataact ctttaattta                                                4100

<210> SEQ ID NO 73
<211> LENGTH: 4100
<212> TYPE: DNA
<213> ORGANISM: Artificial sequence
<220> FEATURE:
<223> OTHER INFORMATION: Single strand oligonucleotide

<400> SEQUENCE: 73
cacttatcat ttagacagta gattttaaat ttgtatttac aatttcaaaa ctgaaattca      60
tttgtaatca agaaaaaca aaacaagaaa agggaggagg agtgggattt gggttgctta     120
acagtattat atatacacgt cgttagttaa tcaataaatt atgagcaggt gtagtagcta     180
tgaacatggt tttaccaaat tggtaaattc atgtcattgt tgtagcactt tagcgaggcc     240
agcaaaatgg cgttcttgga aagggcatgg cggcccgtgg ccgccaggga tatgtgtgca     300
gctagaagga ttagaaggag taacttcacc tttttgtaga aactgtaaat tgccaagacg     360
ctcgtttggt aaataccttta acgcttcgtt tgctggaatg tgtaccacca ttagtagaag     420
aaagtataat aagactatta atgcaagaga ttttttcata ttccttttct aagagtagaa     480
tggaatgaat aaatgaatga atgaaatagg gttttcttg tttagatcct gtcgcacccg     540
agaataatag aagctgaatt aattggtgaa gagtttatg tggcgatgt tgtatttata     600 gagggaaatg atttcaagtt tacaatggga ttttaatt gttttgttga ctattatctt     660
gcggagagat cttgactgtt gacatgtatg tagtgtttgt tattaaaata aatgcatttt     720
tgtagacccg attcttaaat atgttaggca tggtcaaatt gttagactgt aaaagcttga     780
gtagagacat cggtcaactt tgtttacaag aattctctat aaaatattat acaaattgat     840
cggtagaaat tagatggaac attttgaatt aatgtttgac aatgtataaa ttggtttggt     900
caatatctag gaatgaaaac aagagctgct tcaaagttgt tccattctta agtatacata     960
gaggtggctt gatgggaagt ttcatggaag tgtagtttta tatctacttc caaattcgtt    1020
gatctgtttc ttatctcaag ctaaacatgt ttagaaaaga tgtgttaaaa acatgtgaca    1080 aaaaagagt caaatgtttg gcaaacaagg tacttagatt tttggcatct attcaaatat    1140
aatagaatcc caaattatg atatttgtca atcaaatttg aaaaaaaaa aaaaaaaaa    1200 aaagattcta caaaagatca aacgtattgc cgtagattta tcataatttt aattctttca    1260
cactaccact agtccactac catatagtga tgagataatc cataatcata ataagatat    1320 aactttcgaa ttcttgtttt tgttgcctca aagttgttgg atcattattt tttacgtaaa    1380
tgtggcttaa tgagaattta tgtttgtggg aattgtagtt tgcttccaac ttttttttt    1440 ttttttgaa cacgtagttt gcttccaact tagtttatct ttttcttatt tcaagttaaa    1500
catgtaaaaa aacatgtgac gacgaaattc aatcagttcc tccaatgttt ggcagaagcc    1560
aaatctttgg taaacaaagt aatttttttg ccatttgatt ggttagtata ggagaattta    1620
aaaacgacga taaggtttag gtaaattatt tcatttgaaa ataattgagc accgttaata    1680
attttcatcc ataaaataat atttcaaaga tgatatttga tccccattaa attcattcgt    1740
aaccaaaaaa aagttatgaa aaaagagtgg tcgtgtgagt tgcccaagca ccattataat    1800
aaaaaataaa ataattagca agtaataagg aataaaatcc tgtaattata gctgaaaaag    1860 gaaaatatt tggagaccgt cagattcgaa tctgaacaaa gcataaaaaa gtcaacaaaa    1920
cttaaagcgg cggtctcatc gtaatctcag cccaataccc tattttcctc tcccctatat    1980
```

```
aaatactttc ttcttctact gatcttcttc tcacaaataa acccaaatat atcaatctac   2040
tgtgttggtg attaagtact tagttgtact ccagcttgtg ccagtggtca aaaaagttgt   2100
agttttctta aagtctcttt cctctggcaa agctgcagta caactaagag cttgctccct   2160
aaacttatct ctctgatgat ttaatgttag agatcttcgt aaatctatgt gtttgataga   2220
tctgatgcgt tttttgagtt gatgatttga ttatttttca ctggaaagta tctcattagg   2280
gtaacgataa tgttttatgg atttggttgt ataacagatc catgaaatct tgactggtta   2340
taaaatctga ataatgtatt tcaatttgga gattcggtga taaaaattac tgatttacga   2400
atgacattta tatcgataga tgagtttgct gatttggttg ttaaattgat aaatcaagga   2460
catgagaaac tgttttttgta tgctaatttg tccatggaat aaaattggga ggtgaggacc   2520
gtgagggtag tcaggaaacc ttaatattga agttgatgtt gaaccaacaa atctgcccaa   2580
aaatgataaa agttgatgcc gagcccacaa attttgatga caatcgataa gcccaagccc   2640
aaaaggcatc tgtacctgag cccattattc tttcattact agcaaaaagg atgcattaga   2700
gaccccggtg tagtaaattg acctcacaat tcactattgt attgtatacg tacatttcaa   2760
gcgtaattaa accctcatat ttttatacgc tttaaatata attggccttt aattagctca   2820
aataaactag atgtcgtacg tgatcacggt ggatgaaatc aatggtatta tgaaaagact   2880
gtacatgatt tcaaatattt taatgtggtc gtaaaaattg ttgtttatag tggaaattga   2940
agacaacaac gttactgaaa cacatacaga ttgaaatttc gatcatttac ttgcaaagtg   3000
ttaccgtgga ggcgtggcgt ggacgtaagg taccataatg gtttgtgtta cagtcacgcc   3060
actacactcg aattcaagct accatattat aatacgttgt tgattagaaa aaatagtcgc   3120 caatttctt taaaacaaat ttcagttttt atttgtcagc aaaaaaaact tactaacaca   3180
acggaagaac acaaaaatta gggagttgct cacagagcaa aagtaataga aatgggaaaa   3240
gctaatatac gtccgagtag gaaactaatc ttgcaaaaac tgatgaaagc aatcagaagc   3300
cttgacgttt gtctggagag aggaattgtg ttttggatca ctttgttcag tttgttgtgg   3360
atcgtcttcc gttacgttct caccaaaaat atttcataat gaaacaaaaa aattaattaa   3420
taatggtagc ttagaatgcc aagttgagaa cagatttgca gtttgtcccg gaatgatcaa   3480
gtagagcatt catagtgtct tgccaatatg gtgtgatcaa cgaagtttga caaaaccgtg   3540
aagatatagg aacatgtaat catgcggctc tccatacaat acatcttgtt gacaaagttc   3600
ccaagacctc attctacaaa ccaatgtttc ttttttcttt ttcttttttgg tgatagtttt   3660 tgcaatcaaa tgttgtaaaa ctatgattgg aaatactact gtattttacc gaaaactttta  3720 ttatatatag tcattaacac tcattaccaa tcacataatc aatagtctat tttgattata   3780
caacttttaa acaataaaga catgtttata cagatttggt ttaaattagt actccctata   3840
ttttagaaaa ttttattttg tttcatatta tagaatgtct tggaaagttc tatgtaaatt   3900
taaatgtatt tagtaacttg tgacgatttt atattatgta gtctttttta ggatttgttg   3960 atttttaaa ataaatttt taagaaaaa aaacaaatta ttttaataaa catgccttta    4020
ccttatacag tttatatttt gaaagagaga tagtatgttt taggatatat ttaaagaaaa   4080
aaaaataact ctttaattta                                              4100

<210> SEQ ID NO 74
<211> LENGTH: 4100
<212> TYPE: DNA
<213> ORGANISM: Artificial sequence
<220> FEATURE:
<223> OTHER INFORMATION: Single strand oligonucleotide
```

<400> SEQUENCE: 74

```
cacttatcat ttagacagta gattttaaat ttgtatttac aatttcaaaa ctgaaattca      60
tttgtaatca agaaaaaca aaacaagaaa agggaggagg agtgggattt gggttgctta     120
acagtattat atatacacgt cgttagttaa tcaataaatt atgagcaggt gtagtagcta     180
tgaacatggt tttaccaaat tggtaaattc atgtcattgt tgtagcactt tagcgaggcc     240
agcaaaatgg cgttcttgga aagggcatgg cggcccgtgg ccgccaggga tatgtgtgca     300
gctagaagga ttagaaggag taacttcacc tttttgtaga aactgtaaat tgccaagacg     360
ctcgtttggt aaataccttα acgcttcgtt tgctggaatg tgtaccacca ttagtagaag     420
aaagtataat aagactatta atgcaagaga ttttttcata ttccttttct aagagtagaa     480
tggaatgaat aaatgaatga atgaaatagg gttttcttg tttagatcct gtcgcacccg     540
agaataatag aagctgaatt aattggtgaa gagttttatg gtggcgatgt tgtatttata     600
gagggaaatg atttcaagtt tacaatggga tttttaattt gttttgttga ctattatctt     660
gcggagagat cttgactgtt gacatgtatg tagtgtttgt tattaaaata aatgcatttt     720
tgtagacccg attcttaaat atgttaggca tggtcaaatt gttagactgt aaaagcttga     780
gtagagacat cggtcaactt tgtttacaag aattctctat aaaatattat acaaattgat     840
cggtagaaat tagatggaac atttttgaatt aatgtttgac aatgtataaa ttggtttggt     900
caatatctag gaatgaaaac aagagctgct tcaaagttgt tccattctta agtatacata     960
gaggtggctt gatgggaagt ttcatggaag tgtagttta tatctacttc caaattcgtt    1020
gatctgtttc ttatctcaag ctaaacatgt ttagaaaaga tgtgttaaaa acatgtgaca    1080
aaaaagagt caaatgtttg gcaaacaagg tacttagatt tttggcatct attcaaatat    1140
aatagaatcc caaattatg atatttgtca atcaaatttg aaaaaaaaaa aaaaaaaaa    1200
aaagattcta caaagatca aacgtattgc cgtagattta tcataatttt aattctttca    1260
cactaccact agtccactac catatagtga tgagataatc cataatcata aataagatat    1320
aactttcgaa ttcttgtttt tgttgcctca agttgttgg atcattattt tttacgtaaa    1380
tgtggcttaa tgagaattta tgtttgtggg aattgtagtt tgcttccaac ttttttttt    1440
tttttttgaa cacgtagttt gcttccaact tagtttatct ttttcttatt tcaagttaaa    1500
catgtaaaaa aacatgtgac gacgaaattc aatcagttcc tccaatgttt ggcagaagcc    1560
aaatctttgg taaacaaagt aattttttg ccatttgatt ggttagtata ggagaattta    1620
aaaacgacga taaggtttag gtaaattatt tcatttgaaa ataattgagc accgttaata    1680
attttcatcc ataaaataat atttcaaaga tgatatttga tccccattaa attcattcgt    1740
aaccaaaaaa aagttatgaa aaaagagtgg tcgtgtgagt tgcccaagca ccattataat    1800
aaaaaataaa ataattagca agtaataagg aataaaatcc tgtaattata gctgaaaaag    1860
gaaaaatatt tggagaccgt cagattcgaa tctgaacaaa gcataaaaaa gtcaacaaaa    1920
cttaaagcgg cggtctcatc gtaatctcag cccaataccc tatttttcctc tcccctatat    1980
aaatactttc ttcttctact gatcttcttc tcacaaataa acccaaatat atcaatctac    2040
tgtgttggtg attaagtact ttatccacac aaactacctg caagtggtca aaaaagttgt    2100
agttttctta aagtctcttt cctcttgcag tagttagtgt ggataaagag cttgctccct    2160
aaacttatct ctctgatgat ttaatgttag agatcttcgt aaatctatgt gtttgataga    2220
tctgatgcgt ttttttgagtt gatgatttga ttatttttca ctggaaagta tctcattagg    2280
gtaacgataa tgttttatgg atttggttgt ataacagatc catgaaatct tgactggtta    2340
```

| | |
|---|---:|
| taaaatctga ataatgtatt tcaatttgga gattcggtga taaaaattac tgatttacga | 2400 |
| atgacattta tatcgataga tgagtttgct gatttggttg ttaaattgat aaatcaagga | 2460 |
| catgagaaac tgttttttgta tgctaatttg tccatggaat aaaattggga ggtgaggacc | 2520 |
| gtgagggtag tcaggaaacc ttaatattga agttgatgtt gaaccaacaa atctgcccaa | 2580 |
| aaatgataaa agttgatgcc gagcccacaa attttgatga caatcgataa gcccaagccc | 2640 |
| aaaaggcatc tgtacctgag cccattattc tttcattact agcaaaaagg atgcattaga | 2700 |
| gaccccggtg tagtaaattg acctcacaat tcactattgt attgtatacg tacatttcaa | 2760 |
| gcgtaattaa accctcatat ttttatacgc tttaaatata attggccttt aattagctca | 2820 |
| aataaactag atgtcgtacg tgatcacggt ggatgaaatc aatggtatta tgaaaagact | 2880 |
| gtacatgatt tcaaatattt taatgtggtc gtaaaaattg ttgtttatag tggaaattga | 2940 |
| agacaacaac gttactgaaa cacatacaga ttgaaatttc gatcatttac ttgcaaagtg | 3000 |
| ttaccgtgga ggcgtggcgt ggacgtaagg taccataatg gtttgtgtta cagtcacgcc | 3060 |
| actacactcg aattcaagct accatattat aatacgttgt tgattagaaa aaatagtcgc | 3120 |
| caattttctt taaaacaaat ttcagttttt atttgtcagc aaaaaaaact tactaacaca | 3180 |
| acggaagaac acaaaaatta gggagttgct cacagagcaa agtaataga aatgggaaaa | 3240 |
| gctaatatac gtccgagtag gaaactaatc ttgcaaaaac tgatgaaagc aatcagaagc | 3300 |
| cttgacgttt gtctggagag aggaattgtg ttttggatca ctttgttcag tttgttgtgg | 3360 |
| atcgtcttcc gttacgttct caccaaaaat atttcataat gaaacaaaaa aattaattaa | 3420 |
| taatggtagc ttagaatgcc aagttgagaa cagatttgca gtttgtcccg gaatgatcaa | 3480 |
| gtagagcatt catagtgtct tgccaatatg gtgtgatcaa cgaagtttga caaaaccgtg | 3540 |
| aagatatagg aacatgtaat catgcggctc tccatacaat acatcttgtt gacaaagttc | 3600 |
| ccaagacctc attctacaaa ccaatgtttc tttttttctt ttcttttttgg tgatagtttt | 3660 |
| tgcaatcaaa tgttgtaaaa ctatgattgg aaatactact gtattttacc gaaaacttta | 3720 |
| ttatatatag tcattaacac tcattaccaa tcacataatc aatagtctat tttgattata | 3780 |
| caacttttaa acaataaaga catgtttata cagatttggt ttaaattagt actccctata | 3840 |
| ttttagaaaa ttttatttttg tttcatatta tagaatgtct tggaaagttc tatgtaaatt | 3900 |
| taaatgtatt tagtaacttg tgacgatttt atattatgta gtcttttta ggatttgttg | 3960 |
| atttttaaa ataaattttt taaagaaaaa aaacaaatta ttttaataaa catgccttta | 4020 |
| ccttatacag tttatatttt gaagagagaa tagtatgttt taggatatat ttaaagaaaa | 4080 |
| aaaaataact ctttaatttta | 4100 |

<210> SEQ ID NO 75
<211> LENGTH: 4100
<212> TYPE: DNA
<213> ORGANISM: Artificial sequence
<220> FEATURE:
<223> OTHER INFORMATION: Single strand oligonucleotide

<400> SEQUENCE: 75

| | |
|---|---:|
| cacttatcat ttagacagta gatttttaaat ttgtatttac aatttcaaaa ctgaaattca | 60 |
| tttgtaatca agaaaaaca aaacaagaaa agggaggagg agtgggattt gggttgctta | 120 |
| acagtattat atatacacgt cgttagttaa tcaataaatt atgagcaggt gtagtagcta | 180 |
| tgaacatggt tttaccaaat tggtaaattc atgtcattgt tgtagcactt tagcgaggcc | 240 |
| agcaaaatgg cgttcttgga aagggcatgg cggcccgtgg ccgccaggga tatgtgtgca | 300 |

```
gctagaagga ttagaaggag taacttcacc tttttgtaga aactgtaaat tgccaagacg    360
ctcgtttggt aaatacctta acgcttcgtt tgctggaatg tgtaccacca ttagtagaag    420
aaagtataat aagactatta atgcaagaga tttttcata ttccttttct aagagtagaa    480
tggaatgaat aaatgaatga atgaaatagg gttttcttg tttagatcct gtcgcacccg    540
agaataatag aagctgaatt aattggtgaa gagttttatg gtggcgatgt tgtatttata    600
gagggaaatg atttcaagtt tacaatggga tttttaattt gttttgttga ctattatctt    660
gcggagagat cttgactgtt gacatgtatg tagtgtttgt tattaaaata aatgcatttt    720
tgtagacccg attcttaaat atgttaggca tggtcaaatt gttagactgt aaaagcttga    780
gtagagacat cggtcaactt tgtttacaag aattctctat aaaatattat acaaattgat    840
cggtagaaat tagatggaac attttgaatt aatgtttgac aatgtataaa ttggtttggt    900
caatatctag gaatgaaaac aagagctgct tcaaagttgt tccattctta agtatacata    960
gaggtggctt gatgggaagt ttcatggaag tgtagtttta tatctacttc caaattcgtt   1020
gatctgtttc ttatctcaag ctaaacatgt ttagaaaaga tgtgttaaaa acatgtgaca   1080 aaaaagagt caatgtttg gcaaacaagg tacttagatt tttggcatct attcaaatat    1140
aatagaatcc caaaattatg atatttgtca atcaaatttg aaaaaaaaaa aaaaaaaaa    1200 aaagattcta caaagatca aacgtattgc cgtagattta tcataatttt aattctttca    1260
cactaccact agtccactac catatagtga tgagataatc cataatcata aataagatat   1320
aactttcgaa ttcttgtttt tgttgcctca agttgttgg atcattattt tttacgtaaa   1380
tgtggcttaa tgagaattta tgtttgtggg aattgtagtt tgcttccaac ttttttttt   1440 ttttttgaa cacgtagttt gcttccaact tagtttatct ttttcttatt tcaagttaaa   1500
catgtaaaaa aacatgtgac gacgaaattc aatcagttcc tccaatgttt ggcagaagcc   1560
aaatctttgg taaacaaagt aatttttttg ccatttgatt ggttagtata ggagaattta   1620
aaaacgacga taaggtttag gtaaattatt tcatttgaaa ataattgagc accgttaata   1680 atttcatcc ataaaataat atttcaaaga tgatatttga tccccattaa attcattcgt   1740
aaccaaaaaa aagttatgaa aaaagagtgg tcgtgtgagt tgcccaagca ccattataat   1800
aaaaaataaa ataattagca agtaataagg aataaaatcc tgtaattata gctgaaaaag   1860
gaaaaatatt tggagaccgt cagattcgaa tctgaacaaa gcataaaaa gtcaacaaaa    1920 cttaaagcgg cggtctcatc gtaatctcag cccaataccc tatttcctc tcccctatat    1980 aaatactttc ttcttctact gatcttcttc tcacaaataa acccaaatat atcaatctac   2040
tgtgttggtg attaagtact ttgacaatcc agccaatcca gcagtggtca aaaaagttgt   2100
agttttctta aagtctcttt cctctgctga ttggcaggat tgtcaaagag cttgctccct   2160
aaacttatct ctctgatgat ttaatgttag agatcttcgt aaatctatgt gtttgataga   2220
tctgatgcgt ttttgagtt gatgatttga ttatttttca ctggaaagta tctcattagg   2280
gtaacgataa tgttttatgg atttggttgt ataacagatc catgaaatct tgactggtta   2340
taaaatctga ataatgtatt tcaatttgga gattcggtga taaaaattac tgatttacga   2400
atgcacttta tatcgataga tgagtttgct gatttggttg ttaaattgat aaatcaagga   2460
catgagaaac tgttttgta tgctaatttg tccatggaat aaaattggga ggtgaggacc   2520
gtgagggtag tcaggaaacc ttaatattga agttgatgtt gaaccaacaa atctgcccaa   2580
aaatgataaa agttgatgcc gagcccacaa attttgatga caatcgataa gcccaagccc   2640
aaaaggcatc tgtacctgag cccattattc tttcattact agcaaaaagg atgcattaga   2700
```

```
gaccccggtg tagtaaattg acctcacaat tcactattgt attgtatacg tacatttcaa    2760
gcgtaattaa accctcatat ttttatacgc tttaaatata attggccttt aattagctca    2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caattttctt taaaacaaat ttcagttttt atttgtcagc aaaaaaaact tactaacaca    3180
acggaagaac acaaaaatta gggagttgct cacagagcaa agtaataga aatgggaaaa     3240 gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
taatggtagc ttagaatgcc aagttgagaa cagatttgca gtttgtcccg gaatgatcaa    3480
gtagagcatt catagtgtct tgccaatatg gtgtgatcaa cgaagtttga caaaccgtg     3540 aagatatagg aacatgtaat catgcggctc tccataacaa acatcttgtt gacaaagttc    3600
ccaagacctc attctacaaa ccaatgtttc ttttttcttt ttcttttggg tgatagtttt    3660
tgcaatcaaa tgttgtaaaa ctatgattgg aaatactact gtattttacc gaaactttta   3720
ttatatatag tcattaacac tcattaccaa tcacataatc aatagtctat tttgattata    3780 caactttaa acaataaga catgtttata cagatttggt ttaaattagt actccctata     3840
ttttagaaaa ttttattttg tttcatatta tagaatgtct tggaaagttc tatgtaaatt    3900
taaatgtatt tagtaacttg tgacgatttt atattatgta gtctttttta ggatttgttg    3960 atttttaaa ataaattttt taagaaaaa aaacaaatta ttttaataaa catgccttta     4020
ccttatacag tttatatttt gaagagaga tagtatgttt taggatatat ttaaagaaaa    4080
aaaaataact ctttaattta                                                4100
```

<210> SEQ ID NO 76
<211> LENGTH: 4100
<212> TYPE: DNA
<213> ORGANISM: Artificial sequence
<220> FEATURE:
<223> OTHER INFORMATION: Single strand oligonucleotide

<400> SEQUENCE: 76

```
cacttatcat ttagacagta gattttaaat ttgtatttac aatttcaaaa ctgaaattca      60
tttgtaatca agaaaaaca aaacaagaaa agggaggagg agtgggattt gggttgctta     120
acagtattat atatacacgt cgttagttaa tcaataaatt atgagcaggt gtagtagcta    180
tgaacatggt tttaccaaat tggtaaattc atgtcattgt tgtagcactt tagcgaggcc    240
agcaaaatgg cgttcttgga aagggcatgg cggcccgtgg ccgccaggga tatgtgtgca    300
gctagaagga ttagaaggag taacttcacc ttttttgtaga aactgtaaat tgccaagacg    360
ctcgtttggt aaataacctta acgcttcgtt tgctggaatg tgtaccacca ttagtagaag    420
aaagtataat aagactatta atgcaagaga tttttttcata ttccttttct aagagtagaa    480
tggaatgaat aaatgaatga atgaaatagg gttttttcttg tttagatcct gtcgcacccg    540
agaataatag aagctgaatt aattggtgaa gagtttatg gtggcgatgt tgtatttata     600
gagggaaatg atttcaagtt tacaatggga ttttttaattt gttttgttga ctattatctt   660
```

```
gcggagagat cttgactgtt gacatgtatg tagtgtttgt tattaaaata aatgcatttt    720
tgtagacccg attcttaaat atgttaggca tggtcaaatt gttagactgt aaaagcttga    780
gtagagacat cggtcaactt tgtttacaag aattctctat aaaatattat acaaattgat    840
cggtagaaat tagatggaac attttgaatt aatgtttgac aatgtataaa ttggtttggt    900
caatatctag gaatgaaaac aagagctgct tcaaagttgt tccattctta agtatacata    960
gaggtggctt gatgggaagt ttcatggaag tgtagtttta tatctacttc caaattcgtt   1020
gatctgtttc ttatctcaag ctaaacatgt ttagaaaaga tgtgttaaaa acatgtgaca   1080
aaaaaagagt caaatgtttg gcaaacaagg tacttagatt tttggcatct attcaaatat   1140
aatagaatcc caaattatg atatttgtca atcaaatttg aaaaaaaaaa aaaaaaaaaa   1200
aaagattcta caaagatca aacgtattgc cgtagattta tcataatttt aattctttca    1260
cactaccact agtccactac catatagtga tgagataatc cataatcata aataagatat   1320
aactttcgaa ttcttgtttt tgttgcctca aagttgttgg atcattattt tttacgtaaa   1380
tgtggcttaa tgagaattta tgtttgtggg aattgtagtt tgcttccaac ttttttttttt  1440 ttttttttgaa cacgtagttt gcttccaact tagtttatct ttttcttatt tcaagttaaa   1500
catgtaaaaa aacatgtgac gacgaaattc aatcagttcc tccaatgttt ggcagaagcc   1560
aaatctttgg taaacaaagt aatttttttg ccatttgatt ggttagtata ggagaattta   1620
aaaacgacga taaggtttag gtaaattatt tcatttgaaa ataattgagc accgttaata   1680
attttcatcc ataaaataat atttcaaaga tgatatttga tccccattaa attcattcgt   1740
aaccaaaaaa aagttatgaa aaaagagtgg tcgtgtgagt tgcccaagca ccattataat   1800
aaaaaataaa ataattagca agtaataagg aataaaatcc tgtaattata gctgaaaaag   1860 gaaaatatt tggagaccgt cagattcgaa tctgaacaaa gcataaaaaa gtcaacaaaa    1920
cttaaagcgg cggtctcatc gtaatctcag cccaataccc tattttcctc tccctatat    1980 aaatactttc ttcttctact gatcttcttc tcacaaataa acccaaatat atcaatctac   2040
tgtgttggtg attaagtact ttaaagatcg gcaacacatg atagtggtca aaaaagttgt   2100
agttttctta aagtctcttt cctctgatca gtgttggcga tctttaagag cttgctccct   2160
aaacttatct ctctgatgat ttaatgttag agatcttcgt aaatctatgt gtttgataga   2220
tctgatgcgt ttttgagtt gatgatttga ttatttttca ctggaaagta tctcattagg    2280
gtaacgataa tgttttatgg atttggttgt ataacagatc catgaaatct tgactggtta   2340
taaaatctga ataatgtatt tcaatttgga gattcggtga taaaaattac tgatttacga   2400
atgacattta tatcgataga tgagtttgct gatttggttg ttaaattgat aaatcaagga   2460
catgagaaac tgttttttgta tgctaatttg tccatggaat aaaattggga ggtgaggacc   2520
gtgagggtag tcaggaaacc ttaatattga agttgatgtt gaaccaacaa atctgcccaa   2580
aaatgataaa agttgatgcc gagcccacaa attttgatga caatcgataa gcccaagccc   2640
aaaaggcatc tgtacctgag cccattattc tttcattact agcaaaaagg atgcattaga   2700
gaccccggtg tagtaaattg acctcacaat tcactattgt attgtatacg tacatttcaa   2760
gcgtaattaa accctcatat ttttatacgc tttaaatata attggccttt aattagctca   2820
aataaactag atgtcgtacg tgatcacggt ggatgaaatc aatggtatta tgaaaagact   2880
gtacatgatt tcaaatattt taatgtggtc gtaaaaattg ttgtttatag tggaaattga   2940
agacaacaac gttactgaaa cacatacaga ttgaaatttc gatcatttac ttgcaaagtg   3000
ttaccgtgga ggcgtggcgt ggacgtaagg taccataatg gtttgtgtta cagtcacgcc   3060
```

```
actacactcg aattcaagct accatattat aatacgttgt tgattagaaa aaatagtcgc   3120
caattttctt taaaacaaat ttcagttttt atttgtcagc aaaaaaaact tactaacaca   3180
acggaagaac acaaaaatta gggagttgct cacagagcaa aagtaataga aatgggaaaa   3240
gctaatatac gtccgagtag gaaactaatc ttgcaaaaac tgatgaaagc aatcagaagc   3300
cttgacgttt gtctggagag aggaattgtg ttttggatca ctttgttcag tttgttgtgg   3360
atcgtcttcc gttacgttct caccaaaaat atttcataat gaaacaaaaa aattaattaa   3420
taatggtagc ttagaatgcc aagttgagaa cagatttgca gtttgtcccg gaatgatcaa   3480
gtagagcatt catagtgtct tgccaatatg gtgtgatcaa cgaagtttga caaaaccgtg   3540
aagatatagg aacatgtaat catgcggctc tccatacaat acatcttgtt gacaaagttc   3600
ccaagacctc attctacaaa ccaatgtttc tttttttcttt ttcttttttgg tgatagtttt   3660 tgcaatcaaa tgttgtaaaa ctatgattgg aaatactact gtattttacc gaaaacttta   3720
ttatatatag tcattaacac tcattaccaa tcacataatc aatagtctat tttgattata   3780
caacttttaa acaataaaga catgtttata cagatttggt ttaaattagt actccctata   3840
ttttagaaaa ttttatttttg tttcatatta tagaatgtct tggaaagttc tatgtaaatt   3900
taaatgtatt tagtaacttg tgacgatttt atattatgta gtcttttta ggatttgttg   3960 attttttaaa ataaattttt taaagaaaaa aaacaaatta ttttaataaa catgccttta   4020
ccttatacag tttatatttt gaaagagaga tagtatgttt taggatatat ttaaagaaaa   4080
aaaaataact ctttaattta                                              4100

<210> SEQ ID NO 77
<211> LENGTH: 4100
<212> TYPE: DNA
<213> ORGANISM: Artificial sequence
<220> FEATURE:
<223> OTHER INFORMATION: Single strand oligonucleotide

<400> SEQUENCE: 77
cacttatcat ttagacagta gattttaaat ttgtatttac aatttcaaaa ctgaaattca     60
tttgtaatca agaaaaaaca aaacaagaaa agggaggagg agtgggattt gggttgctta    120
acagtattat atatacacgt cgttagttaa tcaataaatt atgagcaggt gtagtagcta    180
tgaacatggt tttaccaaat tggtaaattc atgtcattgt tgtagcactt tagcgaggcc    240
agcaaaatgg cgttcttgga aagggcatgg cggcccgtgg ccgccaggga tatgtgtgca    300
gctagaagga ttagaaggag taacttcacc tttttgtaga aactgtaaat tgccaagacg    360
ctcgtttggt aaataccctta acgcttcgtt tgctggaatg tgtaccacca ttagtagaag    420
aaagtataat aagactatta atgcaagaga ttttttcata ttcctttttct aagagtagaa    480 tggaatgaat aaatgaatga atgaaatagg gttttttcttg tttagatcct gtcgcacccg    540
agaataatag aagctgaatt aattggtgaa gagtttatg gtggcgatgt tgtatttata    600
gagggaaatg atttcaagtt tacaatggga tttttaattt gttttgttga ctattatctt    660
gcggagagat cttgactgtt gacatgtatg tagtgtttgt tattaaaata aatgcatttt    720
tgtagacccg attcttaaat atgttaggca tggtcaaatt gttagactgt aaaagcttga    780
gtagagacat cggtcaactt tgtttacaag aattctctat aaaatattat acaaattgat    840
cggtagaaat tagatggaac attttgaatt aatgttgac aatgtataaa ttggtttggt    900
caatatctag gaatgaaaac aagagctgct tcaaagttgt tccattctta agtatacata    960
gaggtggctt gatgggaagt ttcatggaag tgtagtttta tatctacttc caaattcgtt   1020
```

```
gatctgtttc ttatctcaag ctaaacatgt ttagaaaaga tgtgttaaaa acatgtgaca    1080
aaaaaagagt caaatgtttg gcaaacaagg tacttagatt tttggcatct attcaaatat    1140
aatagaatcc caaaattatg atatttgtca atcaaatttg aaaaaaaaaa aaaaaaaaaa    1200
aaagattcta caaagatca aacgtattgc cgtagattta tcataatttt aattctttca    1260
cactaccact agtccactac catatagtga tgagataatc cataatcata aataagatat    1320
aactttcgaa ttcttgtttt tgttgcctca aagttgttgg atcattattt tttacgtaaa    1380
tgtggcttaa tgagaattta tgtttgtggg aattgtagtt tgcttccaac ttttttttt    1440 tttttttgaa cacgtagttt gcttccaact tagtttatct ttttcttatt tcaagttaaa    1500
catgtaaaaa aacatgtgac gacgaaattc aatcagttcc tccaatgttt ggcagaagcc    1560
aaatctttgg taaacaaagt aatttttttg ccatttgatt ggttagtata ggagaattta    1620
aaaacgacga taaggtttag gtaaattatt tcatttgaaa ataattgagc accgttaata    1680
attttcatcc ataaaataat atttcaaaga tgatatttga tccccattaa attcattcgt    1740
aaccaaaaaa aagttatgaa aaaagagtgg tcgtgtgagt tgcccaagca ccattataat    1800
aaaaaataaa ataattagca agtaataagg aataaaatcc tgtaattata gctgaaaaag    1860
gaaaaatatt tggagaccgt cagattcgaa tctgaacaaa gcataaaaaa gtcaacaaaa    1920
cttaaagcgg cggtctcatc gtaatctcag cccaataccc tattttcctc tccctatat    1980 aaatactttc ttcttctact gatcttcttc tcacaaataa acccaaatat atcaatctac    2040
tgtgttggtg attaagtact ttgaccttc ttgggtttag ccagtggtca aaaaagttgt    2100
agttttctta aagtctcttt cctctgggct aacccatgaa aggtcaagag cttgctccct    2160
aaacttatct ctctgatgat ttaatgttag agatcttcgt aaatctatgt gtttgataga    2220
tctgatgcgt ttttgagtt gatgatttga ttatttttca ctggaaagta tctcattagg    2280
gtaacgataa tgttttatgg atttggttgt ataacagatc catgaaatct tgactggtta    2340
taaaatctga ataatgtatt tcaatttgga gattcggtga taaaaattac tgatttacga    2400
atgacattta tatcgataga tgagtttgct gatttggttg ttaaattgat aaatcaagga    2460
catgagaaac tgttttgta tgctaatttg tccatggaat aaaattggga ggtgaggacc    2520
gtgagggtag tcaggaaacc ttaatattga agttgatgtt gaaccaacaa atctgcccaa    2580
aaatgataaa agttgatgcc gagcccacaa attttgatga caatcgataa gcccaagccc    2640
aaaaggcatc tgtacctgag cccattattc tttcattact agcaaaaagg atgcattaga    2700
gaccccggtg tagtaaattg acctcacaat tcactattgt attgtatacg tacatttcaa    2760
gcgtaattaa accctcatat ttttatacgc tttaaatata attggccttt aattagctca    2820
aataaactag atgtcgtacg tgatcacggt ggatgaaatc aatggtatta tgaaaagact    2880
gtacatgatt tcaaatattt taatgtggtc gtaaaaattg ttgtttatag tggaaattga    2940
agacaacaac gttactgaaa cacatacaga ttgaaatttc gatcatttac ttgcaaagtg    3000
ttaccgtgga ggcgtggcgt ggacgtaagg taccataatg gtttgtgtta cagtcacgcc    3060
actacactcg aattcaagct accatattat aatacgttgt tgattagaaa aaatagtcgc    3120
caattttctt taaacaaat ttcagttttt atttgtcagc aaaaaaaact tactaacaca    3180
acggaagaac acaaaaatta gggagttgct cacagagcaa aagtaataga atgggaaaa    3240 gctaatatac gtccgagtag gaaactaatc ttgcaaaaac tgatgaaagc aatcagaagc    3300
cttgacgttt gtctggagag aggaattgtg ttttggatca ctttgttcag tttgttgtgg    3360
atcgtcttcc gttacgttct caccaaaaat atttcataat gaaacaaaaa aattaattaa    3420
```

```
taatggtagc ttagaatgcc aagttgagaa cagatttgca gtttgtcccg gaatgatcaa    3480
gtagagcatt catagtgtct tgccaatatg gtgtgatcaa cgaagtttga caaaaccgtg    3540
aagatatagg aacatgtaat catgcggctc tccatacaat acatcttgtt gacaaagttc    3600
ccaagacctc attctacaaa ccaatgtttc tttttctttt tcttttttgg tgatagtttt    3660
tgcaatcaaa tgttgtaaaa ctatgattgg aaatactact gtattttacc gaaaacttta    3720
ttatatatag tcattaacac tcattaccaa tcacataatc aatagtctat tttgattata    3780
caacttttaa acaataaaga catgtttata cagatttggt ttaaattagt actccctata    3840
ttttagaaaa ttttattttg tttcatatta tagaatgtct tggaaagttc tatgtaaatt    3900
taaatgtatt tagtaacttg tgacgatttt atattatgta gtctttttta ggatttgttg    3960
attttttaaa ataaattttt taagaaaaaa aaacaaatta ttttaataaa catgccttta    4020
ccttatacag tttatatttt gaaagagaga tagtatgttt taggatatat ttaaagaaaa    4080
aaaaataact ctttaattta                                                4100

<210> SEQ ID NO 78
<211> LENGTH: 4000
<212> TYPE: DNA
<213> ORGANISM: Artificial sequence
<220> FEATURE:
<223> OTHER INFORMATION: Single strand oligonucleotide

<400> SEQUENCE: 78
accctcattg attttggtgg ccaaactctt gatcgtattc ttttaggaac agtaattaat      60
tttaaatttg agaaaatgt agtgatgaaa gtgagatata tgggacgcac tattgaaagc     120
attgtccaca ccgcatgatg tgagattgat gtgaatatgg taactaataa cacccagact     180
cacttttatg agaaaatgta tcttaaaaaa tgttattcat caaagcttag atgcgctata     240
ggggaacata atcattattt gaaaagaacc aattcaaata ttttttttt taagagttaa     300
aatcctatat aacataacca tccaaacttt gggcatgaac acaacaatat ttttttttcgt    360
ttttgataaa ttcttccaat tgcaatcaaa acttaccagc tatacaaatg tttgctgcat     420
ccaatctaat acaccgttaa acaataaaat ttgttatctc tcaaatctga tcatctattc     480
caacctgact gttttattct agtattttaa ggccaggtat aacgaaaaca aagaaaaaag     540
ttcagcgacc aagacatttt gacatcaggc tcaaacggtc aaacccacga aaacttttac     600
ctcatttctt aaccacgcag tgttatttga atagccttaa taggctaata caaaacaaca     660
agccatcgat tacagtttta actataatat tacaaaatct taaaccaaaa caagaaaaga     720
tatatattcc gtaaaattaa aataatattt ttaatatagt cattatgtaa gttagctctt     780
tcgacaaaat cattataaat taggccatt tgtaagttag ttcttttatc gacaagccat     840
tataacttag gtaattttgt aagttagctg gactataacc aatttttttg tttcacatct     900
agagtataaa acacatatat attgaccgta caactttagt caaattagaa actctgtttt     960
atctgcagaa aagaaaaaaa aagaggatga attatgtaaa tacttcagga ttagaaataa    1020
tgtcatcgta tatctcttga tatgaataca tattttactt gactagtacc gtagtcggca    1080
ggaaaatgac acaaacaacc atctaaaaag ataaagtaag aactaaaaag tcttgacatt    1140
cattagttta atcattttct gttaacatat atggaaaaaa caacttcac cgttatttac     1200
ctgaatttac ctatttgggt aagaattgta cctctggacc tctagtattt tatatacacc    1260
taaaaatata attttggtcg ggaaaatata actctgttta attaattaaa ttttcagtat    1320
tgtgtaagtg taattataga aatcaatttt atccgcgtaa caaaataata taaaattata    1380
```

```
ctttcaaatc cacgaatata tattgtgaag tctcatagtt tgcaaataag cattggtctt   1440
cggccgacaa aaaaaaaagc attggtcttc gaatattttg aatatcggac caatggtata   1500
taattaataa tatgtggtat ataaatacat atttatttaa atcacaatag gatatgcaat   1560
gtgtgtatat atacatatac gtaattaaag tccgggttaa actgatagca tatattataa   1620
tagatgcatc tataattgtt cgtcaacaaa agcattatca tgtattttga attaagcttc   1680
cttcatttct gtgaatcaaa aggcctcaga agaagaaact aaagtcaaac aatcaacggg   1740
atccaataaa tcacatctgg actatatagt atcaatactt tccacactaa aaaagctaag   1800
aaatttaata aatacattat tatagggggg aaaaaaaggt agtcatcaga tatatatttt   1860
ggtaagaaaa tatagaaatg aataaatttca cgtttaacga agaggagatg acgtgtgttc   1920
cttcgaaccc gagttttgtt cgtctataaa tagcaccttc tcttctcctt cttcctcact   1980
tccatctttt tagcttcact atctctctat aatcggtttt atcttctct aagtcacaac    2040 ccaaaaaaac aaagtagaga agaatctgta aagctcagga gggatagcgc catgatgatc   2100
acattcgtta tctattttt ggcgctatcc atcctgagtt tcattggctc ttcttactac    2160
aatgaaaaag gccgaggcaa aacgcctaaa atcacttgag aatcaattct ttttactgtc   2220
catttaagct atcttttata aacgtgtctt attttctatc tcttttgttt aaactaagaa   2280
actatagtat tttgtctaaa acaaaacatg aaagaacaga ttagatctca tctttagtct   2340 cttttctccgg tgcagtcagc caccgtcggg taagtttcat ctgtatttta ttaattaatt  2400
acaattatta gtgttcttat taccgttttg gtaaaattag ttaattaatg tcggtccaaa   2460
cattctaaac caattattct gaaaagggtg aacgccaatc agttatatac aatattctta   2520
cattaaagta gaatcggaga tgttacatac taaccaaaag ttacatatac tagtatcatt   2580
ttctttaaga tttgtttagg atttactcac tttatagtgc tcgcggttgg ggtcagggta   2640
agtggggaac agatatgctc tgcatgaacc acgtggacca acatgcatat acacagttac   2700
atttattttt tctagtaggt tcatttgcaa attttccagt atcttgtatg ttatcttcat   2760
ggtgagtttt ttggtcgcat attcttggtg attcttcttc tacgttttca ctttcttctt   2820
cagagacctt attaatatgt taattgcatg aatttatgta acattcaaga aaaagagatc   2880
gaatacaaga aaccggaaat ttaatttcta atttgaattc tatgcatgtt tgtttctttg   2940
ccaatttagt acgaatatat ttatggtccg gagttctaac caaagatagt tgctctgtat   3000
atagaagtta tacatctcgc ttgtttaaac taaataacta tttagtttgt cttggtagtc   3060
cagtgacttt ctgcaaacat tgggatttat aatatagtca aaacgttggg atatgtagta   3120
ttcattttcg ttgtaaaaat cattatattt tgcaaaggtt gcaacgtaaa acgttgtatt   3180
gaatttagga gaaagtagcc atttacaatg aattttagtg acaaactgtt gtatacagcc   3240
tgtgccacta agtatgtcta tatctaaatt tggaatggat gataaccagt attggtcaat   3300
aatggataat ttggtatttta gaattactaa tttggtattt tagtgacaaa ctgttgtatg   3360
gaatttagga gaacgcgttc ccaagctata tattatatgt atttcattct ttcatatgtt   3420
atattatgaa ttgttataaa aaagaccaat gagcaacggt ttaaggttta atcagtaatc   3480
gatccgacca atcatataca agttcctaac acatcttcta actactgagt aaaatagtaa   3540
tgctattaca aaggttttt cttttcaaaa tacagcctaa tgctactaca aaattctaat    3600
gttataaaat aatcatagga gaagtaaacc ccggtattta attataccct tacaaactta   3660
cattattgat aaagttgaat gaagagttat atggtccatt tagtattatt tacttaatat   3720
gatactagtg ttagacgtgt tactgtattt caacgtgcat aatcaggttg ttcaaaaaga   3780
```

```
gagaggatag gtcttcttct tctgtaatttt gctgggaccg caagtcatgt gaggctgctc    3840
tgctgatgct gcacggcgtc gcaactctct caataaattc ttttaactaa cgctccaatt    3900
ttcgatgtaa attggctgac ttcaattcta tgccttactc ttgtactcta tgtttcttta    3960
tctattaaaa tccaactctg cttttgaacc caaaaaacaa                          4000
```

<210> SEQ ID NO 79
<211> LENGTH: 4000
<212> TYPE: DNA
<213> ORGANISM: Artificial sequence
<220> FEATURE:
<223> OTHER INFORMATION: Single strand oligonucleotide

<400> SEQUENCE: 79

```
accctcattg attttggtgg ccaaactctt gatcgtattc ttttaggaac agtaattaat      60
tttaaatttg agaaaaatgt agtgatgaaa gtgagatata tgggacgcac tattgaaagc     120
attgtccaca ccgcatgatg tgagattgat gtgaatatgg taactaataa cacccagact     180
cacttttatg agaaaatgta tcttaaaaaa tgttattcat caaagcttag atgcgctata     240
ggggaacata atcattattt gaaaagaacc aattcaaata tttttttttt taagagttaa     300
aatcctatat aacataacca tccaaacttt gggcatgaac acaacaatat ttttttttcgt     360 ttttgataaa ttcttttcaat tgcaatcaaa acttaccagc tatacaaatg tttgctgcat    420
ccaatctaat acaccgttaa acaataaaat ttgttatctc tcaaatctga tcatctattc    480
caacctgact gttttattct agtatttttaa ggccaggtat aacgaaaaca aagaaaaaag    540
ttcagcgacc aagacatttt gacatcaggc tcaaacggtc aaacccacga aaacttttac    600
ctcatttctt aaccacgcag tgttatttga atagccttaa taggctaata caaaacaaca    660
agccatcgat tacagtttta actataatat tacaaaatct taaaccaaaa caagaaaaga    720
tatatattcc gtaaaattaa aataatattt ttaatatagt cattatgtaa gttagctctt    780
tcgacaaaat cattataaat taggccattt tgtaagttag ttcttttatc gacaagccat    840
tataacttag gtaattttgt aagttagctg gactataacc aatttttttg tttcacatct    900
agagtataaa acacatatat attgaccgta caactttagt caaattagaa actctgtttt    960
atctgcagaa aagaaaaaaa aagaggatga attatgtaaa tacttcagga ttagaaataa    1020
tgtcatcgta tatctcttga tatgaataca tattttactt gactagtacc gtagtcggca    1080
ggaaaatgac acaaacaacc atctaaaaag ataagtaag aactaaaaag tcttgacatt     1140
cattagttta atcattttct gttaacatat atggaaaaaa caaacttcac cgttatttac    1200
ctgaatttac ctatttgggt aagaattgta cctctggacc tctagtattt tatatacacc    1260
taaaaatata attttggtcg ggaaaatata actctgttta attaattaaa ttttcagtat    1320
tgtgtaagtg taattataga aatcaatttt atccgcgtaa caaataata taaaattata     1380 ctttcaaatc cacgaatata tattgtgaag tctcatagtt tgcaaataag cattggtctt    1440
cggccgacaa aaaaaaagc attggtcttc gaatattttg aatatcggac caatggtata    1500
taattaataa tatgtggtat ataaatacat atttatttaa atcacaatag gatatgcaat    1560
gtgtgtatat atacatatac gtaattaaag tccgggttaa actgatagca tatattataa    1620
tagatgcatc tataattgtt cgtcaacaaa agcattatca tgtatttga attaagcttc    1680 cttcatttct gtgaatcaaa aggcctcaga agaagaaact aaagtcaaac aatcaacggg    1740
atccaataaa tcacatctgg actatatagt atcaatactt tccacactaa aaaagctaag    1800
aaatttaata aatacattat tataggggggg aaaaaaaggt agtcatcaga tatatatttt    1860
```

```
ggtaagaaaa tatagaaatg aataatttca cgtttaacga agaggagatg acgtgtgttc    1920
cttcgaaccc gagttttgtt cgtctataaa tagcaccttc tcttctcctt cttcctcact    1980
tccatctttt tagcttcact atctctctat aatcggtttt atctttctct aagtcacaac    2040
ccaaaaaaac aaagtagaga agaatctgta aagtcgtgct gcttcatgtg gatgatgatc    2100
acattcgtta tctatttttt ccacatgaag aagcacgact tgattggctc ttcttactac    2160
aatgaaaaag gccgaggcaa aacgcctaaa atcacttgag atcaattct ttttactgtc      2220 catttaagct atctttata aacgtgtctt atttctatc tcttttgttt aaactaagaa       2280
actatagtat tttgtctaaa acaaaacatg aaagaacaga ttagatctca tctttagtct     2340 cttctccgg tgcagtcagc caccgtcggg taagtttcat ctgtatttta ttaattaatt      2400
acaattatta gtgttcttat taccgttttg gtaaaattag ttaattaatg tcggtccaaa     2460
cattctaaac caattattct gaaaagggtg aacgccaatc agttatatac aatattctta    2520
cattaaagta gaatcggaga tgttacatac taaccaaaag ttacatatac tagtatcatt    2580
ttctttaaga tttgtttagg atttactcac tttatagtgc tcgcggttgg ggtcagggta    2640
agtggggaac agatatgctc tgcatgaacc acgtggacca acatgcatat acacagttac    2700
atttattttt tctagtaggt tcatttgcaa attttccagt atcttgtatg ttatcttcat    2760
ggtgagtttt ttggtcgcat attcttggtg attcttcttc tacgttttca ctttcttctt    2820
cagagacctt attaatatgt taattgcatg aatttatgta acattcaaga aaagagatc     2880 gaatacaaga aaccggaaat ttaatttcta atttgaattc tatgcatgtt tgtttctttg    2940
ccaatttagt acgaatatat ttatggtccg gagttctaac caaagatagt tgctctgtat    3000
atagaagtta tacatctcgc ttgtttaaac taaataacta tttagtttgt cttggtagtc    3060
cagtgacttt ctgcaaacat tgggatttat aatatagtca aaacgttggg atatgtagta    3120
ttcattttcg ttgtaaaaat cattatattt tgcaaaggtt gcaacgtaaa acgttgtatt    3180
gaatttagga gaaagtagcc atttacaatg aattttagtg acaaactgtt gtatacagcc    3240
tgtgccacta agtatgtcta tatctaaatt tggaatggat gataaccagt attggtcaat    3300
aatggataat ttggtatttta gaattactaa tttggtattt tagtgacaaa ctgttgtatg    3360
gaatttagga gaacgcgttc ccaagctata tattatatgt atttcattct ttcatatgtt    3420
atattatgaa ttgttataaa aaagaccaat gagcaacggt ttaaggttta atcagtaatc    3480
gatccgacca atcatataca agttcctaac acatcttcta actactgagt aaaatagtaa    3540
tgctattaca aaggtttttt cttttcaaaa tacagcctaa tgctactaca aaattctaat    3600
gttataaaat aatcatagga gaagtaaacc ccggtattta attaatacct tacaaactta    3660
cattattgat aaagttgaat gaagagttat atggtccatt tagtattatt tacttaatat    3720
gatactagtg ttagacgtgt tactgtattt caacgtgcat aatcaggttg ttcaaaaaga    3780
gagaggatag gtcttcttct tctgtaattt gctgggaccg caagtcatgt gaggctgctc    3840
tgctgatgct gcacggcgtc gcaactctct caataaattc ttttaactaa cgctccaatt    3900
ttcgatgtaa attggctgac ttcaattcta tgccttactc ttgtactcta tgtttcttta    3960
tctattaaaa tccaactctg cttttgaacc caaaaaacaa                          4000
```

<210> SEQ ID NO 80
<211> LENGTH: 4000
<212> TYPE: DNA
<213> ORGANISM: Artificial sequence
<220> FEATURE:
<223> OTHER INFORMATION: Single strand oligonucleotide

```
<400> SEQUENCE: 80
accctcattg attttggtgg ccaaactctt gatcgtattc ttttaggaac agtaattaat      60
tttaaatttg agaaaaatgt agtgatgaaa gtgagatata tgggacgcac tattgaaagc     120
attgtccaca ccgcatgatg tgagattgat gtgaatatgg taactaataa cacccagact     180
cacttttatg agaaaatgta tcttaaaaaa tgttattcat caaagcttag atgcgctata     240
ggggaacata atcattattt gaaaagaacc aattcaaata ttttttttt taagagttaa     300
aatcctatat aacataacca tccaaacttt gggcatgaac acaacaatat ttttttttcgt    360
ttttgataaa ttctttcaat tgcaatcaaa acttaccagc tatacaaatg tttgctgcat     420
ccaatctaat acaccgttaa acaataaaat ttgttatctc tcaaatctga tcatctattc     480
caacctgact gttttattct agtattttaa ggccaggtat aacgaaaaca agaaaaaag      540
ttcagcgacc aagacatttt gacatcaggc tcaaacggtc aaacccacga aaacttttac     600
ctcatttctt aaccacgcag tgttatttga atagccttaa taggctaata caaaacaaca    660
agccatcgat tacagtttta actataatat tacaaaatct taaccaaaa caagaaaaga     720
tatatattcc gtaaaattaa aataatattt ttaatatagt cattatgtaa gttagctctt     780
tcgacaaaat cattataaat taggccattt tgtaagttag ttcttttatc gacaagccat     840
tataacttag gtaattttgt aagttagctg gactataacc aatttttttg tttcacatct     900
agagtataaa acacatatat attgaccgta caactttagt caaattagaa actctgtttt     960
atctgcagaa aagaaaaaaa aagaggatga attatgtaaa tacttcagga ttagaaataa    1020
tgtcatcgta tatctcttga tatgaataca tattttactt gactagtacc gtagtcggca    1080
ggaaaatgac acaacaacc atctaaaaag ataagtaag aactaaaag tcttgacatt     1140
cattagttta atcattttct gttaacatat atggaaaaa caaacttcac cgttatttac    1200
ctgaatttac ctatttgggt aagaattgta cctctggacc tctagtattt tatatacacc    1260
taaaaatata attttggtcg ggaaaatata actctgttta attaattaaa ttttcagtat    1320
tgtgtaagtg taattataga aatcaatttt atccgcgtaa caaaataata taaaattata    1380
ctttcaaatc cacgaatata tattgtgaag tctcatagtt tgcaaataag cattggtctt    1440
cggccgacaa aaaaaaaagc attggtcttc gaatattttg aatatcggac caatggtata    1500
taattaataa tatgtggtat ataaatacat atttatttaa atcacaatag gatatgcaat    1560
gtgtgtatat atacatatac gtaattaaag tccgggttaa actgatagca tatattataa    1620
tagatgcatc tataattgtt cgtcaacaaa agcattatca tgtattttga attaagcttc    1680
cttcatttct gtgaatcaaa aggcctcaga agaagaaact aaagtcaaac aatcaacggg    1740
atccaataaa tcacatctgg actatatagt atcaatactt tccacactaa aaaagctaag    1800
aaatttaata aatacattat tataggggg aaaaaaggt agtcatcaga tatatatttt     1860
ggtaagaaaa tatagaaatg aataatttca cgtttaacga agaggagatg acgtgtgttc    1920
cttcgaaccc gagttttgtt cgtctataaa tagcaccttc tcttctcctt cttcctcact    1980
tccatctttt tagcttcact atctctctat aatcggtttt atctttctct aagtcacaac    2040
ccaaaaaaac aaagtagaga agaatctgta agttgtactc cagcttgtgc catgatgatc    2100
acattcgtta tctatttttt ggcacaagct tgagtacaac tgattggctc ttcttactac    2160
aatgaaaaag gccgaggcaa aacgcctaaa atcacttgag aatcaattct ttttactgtc    2220
catttaagct atctttata aacgtgtctt attttctatc tcttttgttt aaactaagaa      2280
actatagtat tttgtctaaa acaaaacatg aaagaacaga ttagatctca tctttagtct    2340
```

```
ctttctccgg tgcagtcagc caccgtcggg taagtttcat ctgtatttta ttaattaatt      2400
acaattatta gtgttcttat taccgttttg gtaaaattag ttaattaatg tcggtccaaa      2460
cattctaaac caattattct gaaaagggtg aacgccaatc agttatatac aatattctta      2520
cattaaagta gaatcggaga tgttacatac taaccaaaag ttacatatac tagtatcatt      2580
ttctttaaga tttgtttagg atttactcac tttatagtgc tcgcggttgg ggtcagggta      2640
agtggggaac agatatgctc tgcatgaacc acgtggacca acatgcatat acacagttac      2700 atttatttt tctagtaggt tcatttgcaa attttccagt atcttgtatg ttatcttcat       2760
ggtgagtttt ttggtcgcat attcttggtg attcttcttc tacgttttca ctttcttctt      2820
cagagacctt attaatatgt taattgcatg aatttatgta acattcaaga aaaagagatc      2880
gaatacaaga aaccggaaat ttaatttcta atttgaattc tatgcatgtt tgtttctttg      2940
ccaatttagt acgaatatat ttatggtccg gagttctaac caaagatagt tgctctgtat      3000
atagaagtta tacatctcgc ttgtttaaac taaataacta tttagtttgt cttggtagtc      3060
cagtgacttt ctgcaaacat tgggatttat aatatagtca aaacgttggg atatgtagta     3120
ttcattttcg ttgtaaaaat cattatattt tgcaaaggtt gcaacgtaaa acgttgtatt     3180
gaatttagga gaaagtagcc atttacaatg aattttagtg acaaactgtt gtatacagcc      3240
tgtgccacta agtatgtcta tatctaaatt tggaatggat gataaccagt attggtcaat      3300
aatggataat ttggtattta gaattactaa tttggtattt tagtgacaaa ctgttgtatg     3360
gaatttagga gaacgcgttc ccaagctata tattatatgt atttcattct ttcatatgtt     3420
atattatgaa ttgttataaa aaagaccaat gagcaacggt ttaaggttta atcagtaatc     3480
gatccgacca atcatataca agttcctaac acatcttcta actactgagt aaaatagtaa     3540
tgctattaca aaggtttttt cttttcaaaa tacagcctaa tgctactaca aaattctaat      3600
gttataaaat aatcatagga gaagtaaacc ccggtattta attaatacct tacaaactta     3660
cattattgat aaagttgaat gaagagttat atggtccatt tagtattatt tacttaatat     3720
gatactagtg ttagacgtgt tactgtattt caacgtgcat aatcaggttg ttcaaaaaga     3780
gagaggatag gtcttcttct tctgtaattt gctgggaccg caagtcatgt gaggctgctc     3840
tgctgatgct gcacggcgtc gcaactctct caataaaattc ttttaactaa cgctccaatt     3900
ttcgatgtaa attggctgac ttcaattcta tgccttactc ttgtactcta tgtttctttta     3960 tctattaaaa tccaactctg cttttgaacc caaaaaacaa                           4000

<210> SEQ ID NO 81
<211> LENGTH: 4000
<212> TYPE: DNA
<213> ORGANISM: Artificial sequence
<220> FEATURE:
<223> OTHER INFORMATION: Single strand oligonucleotide

<400> SEQUENCE: 81
accctcattg attttggtgg ccaaactctt gatcgtattc ttttaggaac agtaattaat        60
tttaaatttg agaaaaatgt agtgatgaaa gtgagatata tgggacgcac tattgaaagc       120
attgtccaca ccgcatgatg tgagattgat gtgaatatgg taactaataa cacccagact       180
cacttttatg agaaaatgta tcttaaaaaa tgttattcat caaagcttag atgcgctata       240
ggggaacata atcattattt gaaaagaacc aattcaaata ttttttttt taagagttaa       300 aatcctatat aacataacca tccaaactt gggcatgaac acaacaatat ttttttttcgt      360 ttttgataaa ttctttcaat tgcaatcaaa acttaccagc tatacaaatg tttgctgcat      420
```

```
ccaatctaat acaccgttaa acaataaaat ttgttatctc tcaaatctga tcatctattc    480
caacctgact gttttattct agtattttaa ggccaggtat aacgaaaaca aagaaaaaag    540
ttcagcgacc aagacatttt gacatcaggc tcaaacggtc aaacccacga aaacttttac    600
ctcatttctt aaccacgcag tgttatttga atagccttaa taggctaata caaaacaaca    660
agccatcgat tacagtttta actataatat tacaaaatct taaaccaaaa caagaaaaga    720
tatatattcc gtaaaattaa aataatattt ttaatatagt cattatgtaa gttagctctt    780
tcgacaaaat cattataaat taggccattt tgtaagttag ttcttttatc gacaagccat    840
tataacttag gtaattttgt aagttagctg gactataacc aattttttg tttcacatct     900 agagtataaa acacatatat attgaccgta caactttagt caaattagaa actctgtttt    960
atctgcagaa aagaaaaaaa aagaggatga attatgtaaa tacttcagga ttagaaataa    1020
tgtcatcgta tatctcttga tatgaataca tattttactt gactagtacc gtagtcggca    1080
ggaaaatgac acaacaacc atctaaaaag ataaagtaag aactaaaaag tcttgacatt     1140
cattagttta atcattttct gttaacatat atggaaaaaa caaacttcac cgttatttac    1200
ctgaatttac ctatttgggt aagaattgta cctctggacc tctagtattt tatatacacc    1260
taaaaatata attttggtcg ggaaaatata actctgttta attaattaaa ttttcagtat    1320
tgtgtaagtg taattataga aatcaatttt atccgcgtaa caaaataata taaaattata    1380
ctttcaaatc cacgaatata tattgtgaag tctcatagtt tgcaaataag cattggtctt    1440
cggccgacaa aaaaaaagc attggtcttc gaatattttg aatatcggac caatggtata    1500
taattaataa tatgtggtat ataaatacat atttatttaa atcacaatag gatatgcaat    1560
gtgtgtatat atacatatac gtaattaaag tccgggttaa actgatagca tatattataa    1620
tagatgcatc tataattgtt cgtcaacaaa agcattatca tgtattttga attaagcttc    1680
cttcatttct gtgaatcaaa aggcctcaga agaagaaact aaagtcaaac aatcaacggg    1740
atccaataaa tcacatctgg actatatagt atcaatactt tccacactaa aaaagctaag    1800
aaatttaata aatacattat tataggggg aaaaaaaggt agtcatcaga tatatatttt     1860
ggtaagaaaa tatagaaatg aataatttca cgtttaacga agaggagatg acgtgtgttc    1920
cttcgaaccc gagttttgtt cgtctataaa tagcaccttc tcttctcctt cttcctcact    1980
tccatctttt tagcttcact atctctctat aatcggtttt atctttctct aagtcacaac    2040
ccaaaaaaac aaagtagaga agaatctgta tatccacaca aactacctgc aatgatgatc    2100
acattcgtta tctatttttt tgcaggtagt gtgtgtggat agattggctc ttcttactac    2160
aatgaaaaag gccgaggcaa aacgcctaaa atcacttgag aatcaattct ttttactgtc    2220
catttaagct atctttata aacgtgtctt attttctatc tcttttgttt aaactaagaa     2280
actatagtat tttgtctaaa acaaaacatg aaagaacaga ttagatctca tctttagtct    2340 cttttctccgg tgcagtcagc caccgtcggg taagtttcat ctgtatttta ttaattaatt   2400
acaattatta gtgttcttat taccgttttg gtaaaattag ttaattaatg tcggtccaaa    2460
cattctaaac caattattct gaaaagggtg aacgccaatc agttatatac aatattctta    2520
cattaaagta gaatcggaga tgttacatac taaccaaaag ttacatatac tagtatcatt    2580
ttctttaaga tttgtttagg atttactcac tttatagtgc tcgcggttgg ggtcagggta    2640
agtggggaac agatatgctc tgcatgaacc acgtggacca acatgcatat acacagttac    2700
atttattttt tctagtaggt tcatttgcaa attttccagt atcttgtatg ttatcttcat    2760
ggtgagtttt ttggtcgcat attcttggtg attcttcttc tacgttttca ctttcttctt    2820
```

```
cagagacctt attaatatgt taattgcatg aatttatgta acattcaaga aaaagagatc    2880
gaatacaaga aaccggaaat ttaatttcta atttgaattc tatgcatgtt tgtttctttg    2940
ccaatttagt acgaatatat ttatggtccg gagttctaac caaagatagt tgctctgtat    3000
atagaagtta tacatctcgc ttgtttaaac taaataacta tttagtttgt cttggtagtc    3060
cagtgacttt ctgcaaacat tgggatttat aatatagtca aaacgttggg atatgtagta    3120
ttcattttcg ttgtaaaaat cattatattt tgcaaaggtt gcaacgtaaa acgttgtatt    3180
gaatttagga gaaagtagcc atttacaatg aattttagtg acaaactgtt gtatacagcc    3240
tgtgccacta agtatgtcta tatctaaatt tggaatggat gataaccagt attggtcaat    3300
aatggataat ttggtattta gaattactaa tttggtattt tagtgacaaa ctgttgtatg    3360
gaatttagga gaacgcgttc ccaagctata tattatatgt atttcattct ttcatatgtt    3420
atattatgaa ttgttataaa aaagaccaat gagcaacggt ttaaggttta atcagtaatc    3480
gatccgacca atcatataca agttcctaac acatcttcta actactgagt aaaatagtaa    3540
tgctattaca aaggtttttt cttttcaaaa tacagcctaa tgctactaca aaattctaat    3600
gttataaaat aatcatagga gaagtaaacc ccggtattta attaatacct tacaaactta    3660
cattattgat aaagttgaat gaagagttat atggtccatt tagtattatt tacttaatat    3720
gatactagtg ttagacgtgt tactgtattt caacgtgcat aatcaggttg ttcaaaaaga    3780
gagaggatag gtcttcttct tctgtaattt gctgggaccg caagtcatgt gaggctgctc    3840
tgctgatgct gcacggcgtc gcaactctct caataaattc ttttaactaa cgctccaatt    3900
ttcgatgtaa attggctgac ttcaattcta tgccttactc ttgtactcta tgtttcttta    3960
tctattaaaa tccaactctg cttttgaacc caaaaaacaa                         4000

<210> SEQ ID NO 82
<211> LENGTH: 4000
<212> TYPE: DNA
<213> ORGANISM: Artificial sequence
<220> FEATURE:
<223> OTHER INFORMATION: Single strand oligonucleotide

<400> SEQUENCE: 82
accctcattg attttggtgg ccaaactctt gatcgtattc ttttaggaac agtaattaat      60
tttaaatttg agaaaaatgt agtgatgaaa gtgagatata tgggacgcac tattgaaagc     120
attgtccaca ccgcatgatg tgagattgat gtgaatatgg taactaataa cacccagact     180
cacttttatg agaaaatgta tcttaaaaaa tgttattcat caaagcttag atgcgctata     240
ggggaacata atcattattt gaaaagaacc aattcaaata tttttttttt taagagttaa     300
aatcctatat aacataacca tccaaacttt gggcatgaac acaacaatat ttttttttcgt    360 ttttgataaa ttctttcaat tgcaatcaaa acttaccagc tatacaaatg tttgctgcat     420
ccaatctaat acaccgttaa acaataaaat ttgttatctc tcaaatctga tcatctattc     480
caacctgact gttttattct agtattttaa ggccaggtat aacgaaaaca aagaaaaaag     540
ttcagcgacc aagacatttt gacatcaggc tcaaacggtc aaacccacga aaactttttac    600 ctcatttctt aaccacgcag tgttatttga atagccttaa taggctaata caaaacaaca     660
agccatcgat tacagtttta actataatat tacaaaatct taaccaaaa caagaaaaga     720 tatatattcc gtaaaattaa aataatattt ttaatatagt cattatgtaa gttagctctt     780
tcgacaaaat cattataaat taggccattt tgtaagttag ttcttttatc gacaagccat     840
tataacttag gtaattttgt aagttagctg gactataacc aatttttttg tttcacatct     900
```

```
agagtataaa acacatatat attgaccgta caactttagt caaattagaa actctgtttt    960
atctgcagaa aagaaaaaaa aagaggatga attatgtaaa tacttcagga ttagaaataa   1020
tgtcatcgta tatctcttga tatgaataca tattttactt gactagtacc gtagtcggca   1080
ggaaaatgac acaaacaacc atctaaaaag ataaagtaag aactaaaaag tcttgacatt   1140
cattagttta atcattttct gttaacatat atggaaaaaa caaacttcac cgttatttac   1200
ctgaatttac ctatttgggt aagaattgta cctctggacc tctagtattt tatatacacc   1260
taaaaatata attttggtcg ggaaaatata actctgttta attaattaaa ttttcagtat   1320
tgtgtaagtg taattataga aatcaatttt atccgcgtaa caaaataata taaaattata   1380
ctttcaaatc cacgaatata tattgtgaag tctcatagtt tgcaaataag cattggtctt   1440
cggccgacaa aaaaaaaagc attggtcttc gaatattttg aatatcggac caatggtata   1500
taattaataa tatgtggtat ataaatacat atttatttaa atcacaatag gatatgcaat   1560
gtgtgtatat atacatatac gtaattaaag tccgggttaa actgatagca tatattataa   1620
tagatgcatc tataattgtt cgtcaacaaa agcattatca tgtattttga attaagcttc   1680
cttcatttct gtgaatcaaa aggcctcaga agaagaaact aaagtcaaac aatcaacggg   1740
atccaataaa tcacatctgg actatatagt atcaatactt ccacactaa aaaagctaag    1800
aaatttaata aatacattat tataggggggg aaaaaaaggt agtcatcaga tatatatttt   1860
ggtaagaaaa tatagaaatg aataaatttca cgtttaacga agaggagatg acgtgtgttc   1920
cttcgaaccc gagttttgtt cgtctataaa tagcaccttc tcttctcctt cttcctcact   1980
tccatctttt tagcttcact atctctctat aatcggtttt atctttctct aagtcacaac   2040
ccaaaaaaac aaagtagaga agaatctgta tgacaatcca gccaatccag catgatgatc   2100
acattcgtta tctattttt gctggattgg atggattgtc agattggctc ttcttactac    2160
aatgaaaaag gccgaggcaa aacgcctaaa atcacttgag aatcaattct ttttactgtc   2220
catttaagct atctttata aacgtgtctt attttctatc tcttttgttt aaactaagaa    2280
actatagtat tttgtctaaa acaaaacatg aaagaacaga ttagatctca tctttagtct   2340
cttctctccgg tgcagtcagc caccgtcggg taagtttcat ctgtatttta ttaattaatt   2400
acaattatta gtgttcttat taccgttttg gtaaaattag ttaattaatg tcggtccaaa   2460
cattctaaac caattattct gaaaagggtg aacgccaatc agttatatac aatattctta   2520
cattaaagta gaatcggaga tgttacatac taaccaaaag ttacatatac tagtatcatt   2580
ttctttaaga tttgtttagg atttactcac tttatagtgc tcgcggttgg ggtcagggta   2640
agtggggaac agatatgctc tgcatgaacc acgtggacca acatgcatat acacagttac   2700
atttattttt tctagtaggt tcatttgcaa attttccagt atcttgtatg ttatcttcat   2760
ggtgagtttt ttggtcgcat attcttggtg attcttcttc tacgttttca ctttcttctt   2820
cagagacctt attaatatgt taattgcatg aatttatgta acattcaaga aaaagagatc   2880
gaatacaaga aaccggaaat ttaatttcta atttgaattc tatgcatgtt tgtttctttg   2940
ccaatttagt acgaatatat ttatggtccg gagttctaac caaagatagt tgctctgtat   3000
atagaagtta tacatctcgc ttgtttaaac taaataacta tttagtttgt cttggtagtc   3060
cagtgacttt ctgcaaacat tgggatttat aatatagtca aaacgttggg atatgtagta   3120
ttcattttcg ttgtaaaaat cattatattt tgcaaaggtt gcaacgtaaa acgttgtatt   3180
gaatttagga gaaagtagcc atttacaatg aattttagtg acaaactgtt gtatacagcc   3240
tgtgccacta agtatgtcta tatctaaatt tggaatggat gataaccagt attggtcaat   3300
```

| | |
|---|---|
| aatggataat ttggtatttta gaattactaa tttggtatttt tagtgacaaa ctgttgtatg | 3360 |
| gaatttagga gaacgcgttc ccaagctata tattatatgt atttcattct ttcatatgtt | 3420 |
| atattatgaa ttgttataaa aaagaccaat gagcaacggt ttaaggttta atcagtaatc | 3480 |
| gatccgacca atcatataca agttcctaac acatcttcta actactgagt aaaatagtaa | 3540 |
| tgctattaca aaggtttttt cttttcaaaa tacagcctaa tgctactaca aaattctaat | 3600 |
| gttataaaat aatcatagga gaagtaaacc ccggtattta attaatacct tacaaactta | 3660 |
| cattattgat aaagttgaat gaagagttat atggtccatt tagtattatt tacttaatat | 3720 |
| gatactagtg ttagacgtgt tactgtattt caacgtgcat aatcaggttg ttcaaaaaga | 3780 |
| gagaggatag gtcttcttct tctgtaattt gctgggaccg caagtcatgt gaggctgctc | 3840 |
| tgctgatgct gcacggcgtc gcaactctct caataaattc ttttaactaa cgctccaatt | 3900 |
| ttcgatgtaa attggctgac ttcaattcta tgccttactc ttgtactcta tgtttcttta | 3960 |
| tctattaaaa tccaactctg cttttgaacc caaaaaacaa | 4000 |

<210> SEQ ID NO 83
<211> LENGTH: 4000
<212> TYPE: DNA
<213> ORGANISM: Artificial sequence
<220> FEATURE:
<223> OTHER INFORMATION: Single strand oligonucleotide

<400> SEQUENCE: 83

| | |
|---|---|
| accctcattg attttggtgg ccaaactctt gatcgtattc ttttaggaac agtaattaat | 60 |
| tttaaatttg agaaaaatgt agtgatgaaa gtgagatata tgggacgcac tattgaaagc | 120 |
| attgtccaca ccgcatgatg tgagattgat gtgaatatgg taactaataa cacccagact | 180 |
| cacttttatg agaaaatgta tcttaaaaaa tgttattcat caaagcttag atgcgctata | 240 |
| ggggaacata atcattattt gaaaagaacc aattcaaata tttttttttt taagagttaa | 300 |
| aatcctatat aacataacca tccaaacttt gggcatgaac acaacaatat ttttttttcgt | 360 |
| ttttgataaa ttctttcaat tgcaatcaaa acttaccagc tatacaaatg tttgctgcat | 420 |
| ccaatctaat acaccgttaa acaataaaat ttgttatctc tcaaatctga tcatctattc | 480 |
| caacctgact gttttattct agtattttaa ggccaggtat aacgaaaaca aagaaaaaag | 540 |
| ttcagcgacc aagacatttt gacatcaggc tcaaacggtc aaacccacga aaacttttac | 600 |
| ctcatttctt aaccacgcag tgttatttga atagccttaa taggctaata caaaacaaca | 660 |
| agccatcgat tacagttttta actataatat tacaaaatct taaaccaaaa caagaaaaga | 720 |
| tatatattcc gtaaaattaa aataatatt ttaatatagt cattatgtaa gttagctctt | 780 |
| tcgacaaaat cattataaat taggccattt tgtaagttag ttcttttatc gacaagccat | 840 |
| tataacttag gtaattttgt aagttagctg gactataacc aattttttg tttcacatct | 900 |
| agagtataaa acacatatat attgaccgta caactttagt caaattagaa actctgtttt | 960 |
| atctgcagaa aagaaaaaaa aagaggatga attatgtaaa tacttcagga ttagaaataa | 1020 |
| tgtcatcgta tatctcttga tatgaataca tattttactt gactagtacc gtagtcggca | 1080 |
| ggaaaatgac acaaacaacc atctaaaaag ataaagtaag aactaaaaag tcttgacatt | 1140 |
| cattagttta atcatttttct gttaacatat atggaaaaaa caacttcac cgttatttac | 1200 |
| ctgaatttac ctatttgggt aagaattgta ccctctggacc tctagtatttt tatatacacc | 1260 |
| taaaaatata attttggtcg ggaaaatata actctgtttta attaattaaa ttttcagtat | 1320 |
| tgtgtaagtg taattataga aatcaatttt atccgcgtaa caaataaata taaaattata | 1380 |

```
ctttcaaatc cacgaatata tattgtgaag tctcatagtt tgcaaataag cattggtctt    1440
cggccgacaa aaaaaaaagc attggtcttc gaatattttg aatatcggac caatggtata    1500
taattaataa tatgtggtat ataaatacat atttatttaa atcacaatag gatatgcaat    1560
gtgtgtatat atacatatac gtaattaaag tccgggttaa actgatagca tatattataa    1620
tagatgcatc tataattgtt cgtcaacaaa agcattatca tgtattttga attaagcttc    1680
cttcatttct gtgaatcaaa aggcctcaga agaagaaact aaagtcaaac aatcaacggg    1740
atccaataaa tcacatctgg actatatagt atcaatactt tccacactaa aaaagctaag    1800
aaatttaata aatacattat tataggggggg aaaaaaaggt agtcatcaga tatatatttt    1860
ggtaagaaaa tatagaaatg aataaatttca cgtttaacga agaggagatg acgtgtgttc    1920
cttcgaaccc gagttttgtt cgtctataaa tagcaccttc tcttctcctt cttcctcact    1980
tccatctttt tagcttcact atctctctat aatcggtttt atctttctct aagtcacaac    2040
ccaaaaaaac aaagtagaga agaatctgta taaagatcgg caacacatga tatgatgatc    2100
acattcgtta tctattttt atcatgtgtt accgatcttt acattggctc ttcttactac    2160
aatgaaaaag gccgaggcaa aacgcctaaa atcacttgag aatcaattct ttttactgtc    2220
catttaagct atctttttata aacgtgtctt attttctatc tcttttgttt aaactaagaa    2280
actatagtat tttgtctaaa acaaaacatg aaagaacaga ttagatctca tctttagtct    2340 cttctctccgg tgcagtcagc caccgtcggg taagtttcat ctgtattta ttaattaatt    2400 acaattatta gtgttcttat taccgttttg gtaaaattag ttaattaatg tcggtccaaa    2460
cattctaaac caattattct gaaagggtg aacgccaatc agttatatac aatattctta    2520
cattaaagta gaatcggaga tgttacatac taaccaaaag ttacatatac tagtatcatt    2580
ttctttaaga tttgtttagg atttactcac tttatagtgc tcgcggttgg ggtcagggta    2640
agtggggaac agatatgctc tgcatgaacc acgtggacca acatgcatat acacagttac    2700 attttatttttt tctagtaggt tcatttgcaa attttccagt atcttgtatg ttatcttcat    2760
ggtgagtttt ttggtcgcat attcttggtg attcttcttc tacgttttca ctttcttctt    2820 cagagaccttt attaatatgt taattgcatg aatttatgta acattcaaga aaaagagatc    2880
gaatacaaga aaccggaaat ttaatttcta atttgaattc tatgcatgtt tgtttctttg    2940
ccaatttagt acgaatatat ttatggtccg gagttctaac caaagatagt tgctctgtat    3000
atagaagtta tacatctcgc ttgtttaaac taaataacta tttagtttgt cttggtagtc    3060
cagtgacttt ctgcaaacat tgggatttat aatatagtca aaacgttggg atatgtagta    3120
ttcattttcg ttgtaaaaat cattatattt tgcaaaggtt gcaacgtaaa acgttgtatt    3180
gaatttagga gaaagtagcc atttacaatg aattttagtg acaaactgtt gtatacagcc    3240
tgtgccacta agtatgtcta tatctaaatt tggaatggat gataaccagt attggtcaat    3300
aatggataat ttggtatttta gaattactaa tttggtattt tagtgacaaa ctgttgtatg    3360
gaatttagga gaacgcgttc ccaagctata tattatatgt atttcattct ttcatatgtt    3420
atattatgaa ttgttataaa aaagaccaat gagcaacggt ttaaggttta atcagtaatc    3480
gatccgacca atcatataca agttcctaac acatcttcta actactgagt aaaatagtaa    3540
tgctattaca aaggttttt cttttcaaaa tacagcctaa tgctactaca aaattctaat    3600
gttataaaat aatcatagga gaagtaaacc ccggtattta attaataccct tacaaactta    3660 cattattgat aaagttgaat gaagagttat atggtccatt tagtattatt tacttaatat    3720
gatactagtg ttagacgtgt tactgtattt caacgtgcat aatcaggttg ttcaaaaaga    3780
```

| | |
|---|---:|
| gagaggatag gtcttcttct tctgtaattt gctgggaccg caagtcatgt gaggctgctc | 3840 |
| tgctgatgct gcacggcgtc gcaactctct caataaattc ttttaactaa cgctccaatt | 3900 |
| ttcgatgtaa attggctgac ttcaattcta tgccttactc ttgtactcta tgtttcttta | 3960 |
| tctattaaaa tccaactctg cttttgaacc caaaaaacaa | 4000 |

```
<210> SEQ ID NO 84
<211> LENGTH: 4000
<212> TYPE: DNA
<213> ORGANISM: Artificial sequence
<220> FEATURE:
<223> OTHER INFORMATION: Single strand oligonucleotide

<400> SEQUENCE: 84
```

| | |
|---|---:|
| accctcattg attttggtgg ccaaactctt gatcgtattc ttttaggaac agtaattaat | 60 |
| tttaaatttg agaaaaatgt agtgatgaaa gtgagatata tgggacgcac tattgaaagc | 120 |
| attgtccaca ccgcatgatg tgagattgat gtgaatatgg taactaataa cacccagact | 180 |
| cacttttatg agaaaatgta tcttaaaaaa tgttattcat caaagcttag atgcgctata | 240 |
| ggggaacata atcattattt gaaaagaacc aattcaaata tttttttttt taagagttaa | 300 |
| aatcctatat aacataacca tccaaacttt gggcatgaac acaacaatat ttttttttcgt | 360 |
| ttttgataaa ttcttttcaat tgcaatcaaa acttaccagc tatacaaatg tttgctgcat | 420 |
| ccaatctaat acaccgttaa acaataaaat ttgttatctc tcaaatctga tcatctattc | 480 |
| caacctgact gttttattct agtattttaa ggccaggtat aacgaaaaca aagaaaaaag | 540 |
| ttcagcgacc aagacatttt gacatcaggc tcaaacggtc aaacccacga aaacttttac | 600 |
| ctcatttctt aaccacgcag tgttatttga atagccttaa taggctaata caaaacaaca | 660 |
| agccatcgat tacagtttta actataatat tacaaaatct taaaccaaaa caagaaaaga | 720 |
| tatatattcc gtaaaattaa aataatattt ttaatatagt cattatgtaa gttagctctt | 780 |
| tcgacaaaat cattataaat taggccattt tgtaagttag ttcttttatc gacaagccat | 840 |
| tataacttag gtaattttgt aagttagctg gactataacc aatttttttg tttcacatct | 900 |
| agagtataaa acacatatat attgaccgta caactttagt caaattagaa actctgtttt | 960 |
| atctgcagaa aagaaaaaaa aagaggatga attatgtaaa tacttcagga ttagaaataa | 1020 |
| tgtcatcgta tatctcttga tatgaataca tattttactt gactagtacc gtagtcggca | 1080 |
| ggaaaatgac acaaacaacc atctaaaaag ataagtaag aactaaaaag tcttgacatt | 1140 |
| cattagtttta atcattttct gttaacatat atggaaaaaa caaacttcac cgttatttac | 1200 |
| ctgaatttac ctatttgggt aagaattgta cctctggacc tctagtattt tatatacacc | 1260 |
| taaaaatata attttggtcg ggaaaatata actctgttta attaattaaa ttttcagtat | 1320 |
| tgtgtaagtg taattataga aatcaatttt atccgcgtaa caaataata taaaattata | 1380 |
| ctttcaaatc cacgaatata tattgtgaag tctcatagtt tgcaaataag cattggtctt | 1440 |
| cggccgacaa aaaaaaaagc attggtcttc gaatattttg aatatcggac caatggtata | 1500 |
| taattaataa tatgtggtat ataaatacat atttatttaa atcacaatag gatatgcaat | 1560 |
| gtgtgtatat atacatatac gtaattaaag tccgggttaa actgatagca tatattataa | 1620 |
| tagatgcatc tataattgtt cgtcaacaaa agcattatca tgtattttga attaagcttc | 1680 |
| cttcatttct gtgaatcaaa aggcctcaga agaagaaact aaagtcaaac aatcaacggg | 1740 |
| atccaataaa tcacatctgg actatatagt atcaatactt tccacactaa aaaagctaag | 1800 |
| aaatttaata aatacattat tatagggggg aaaaaaaggt agtcatcaga tatatatttt | 1860 |

| | |
|---|---|
| ggtaagaaaa tatagaaatg aataatttca cgtttaacga agaggagatg acgtgtgttc | 1920 |
| cttcgaaccc gagttttgtt cgtctataaa tagcaccttc tcttctcctt cttcctcact | 1980 |
| tccatctttt tagcttcact atctctctat aatcggtttt atctttctct aagtcacaac | 2040 |
| ccaaaaaaac aaagtagaga agaatctgta tgacctttct tgggtttagc catgatgatc | 2100 |
| acattcgtta tctatttttt ggctaaaccc cagaaaggtc acattggctc ttcttactac | 2160 |
| aatgaaaaag gccgaggcaa aacgcctaaa atcacttgag aatcaattct ttttactgtc | 2220 |
| catttaagct atcttttata aacgtgtctt attttctatc tcttttgttt aaactaagaa | 2280 |
| actatagtat tttgtctaaa acaaaacatg aagaacaga ttagatctca tctttagtct | 2340 |
| ctttctccgg tgcagtcagc caccgtcggg taagtttcat ctgtatttta ttaattaatt | 2400 |
| acaattatta gtgttcttat taccgttttg gtaaaattag ttaattaatg tcggtccaaa | 2460 |
| cattctaaac caattattct gaaaagggtg aacgccaatc agttatatac aatattctta | 2520 |
| cattaaagta gaatcggaga tgttacatac taaccaaaag ttacatatac tagtatcatt | 2580 |
| ttctttaaga tttgtttagg atttactcac tttatagtgc tcgcggttgg ggtcagggta | 2640 |
| agtggggaac agatatgctc tgcatgaacc acgtggacca acatgcatat acacagttac | 2700 |
| atttatttt tctagtaggt tcatttgcaa attttccagt atcttgtatg ttatcttcat | 2760 |
| ggtgagtttt ttggtcgcat attcttggtg attcttcttc tacgttttca ctttcttctt | 2820 |
| cagagacctt attaatatgt taattgcatg aatttatgta acattcaaga aaagagatc | 2880 |
| gaatacaaga aaccggaaat ttaatttcta atttgaattc tatgcatgtt tgtttctttg | 2940 |
| ccaatttagt acgaatatat ttatggtccg gagttctaac caaagatagt tgctctgtat | 3000 |
| atagaagtta tacatctcgc ttgtttaaac taaataacta tttagtttgt cttggtagtc | 3060 |
| cagtgacttt ctgcaaacat tgggatttat aatatagtca aaacgttggg atatgtagta | 3120 |
| ttcattttcg ttgtaaaaat cattatattt tgcaaaggtt gcaacgtaaa acgttgtatt | 3180 |
| gaatttagga gaaagtagcc atttacaatg aattttagtg acaaactgtt gtatacagcc | 3240 |
| tgtgccacta agtatgtcta tatctaaatt tggaatggat gataaccagt attggtcaat | 3300 |
| aatggataat ttggtattta gaattactaa tttggtattt tagtgacaaa ctgttgtatg | 3360 |
| gaatttagga gaacgcgttc ccaagctata tattatatgt atttcattct ttcatatgtt | 3420 |
| atattatgaa ttgttataaa aaagaccaat gagcaacggt ttaaggttta atcagtaatc | 3480 |
| gatccgacca atcatataca agttcctaac acatcttcta actactgagt aaaatagtaa | 3540 |
| tgctattaca aaggtttttt cttttcaaaa tacagcctaa tgctactaca aaattctaat | 3600 |
| gttataaaat aatcatagga gaagtaaacc ccggtattta attaatacct tacaaactta | 3660 |
| cattattgat aaagttgaat gaagagttat atggtccatt tagtattatt tacttaatat | 3720 |
| gatactagtg ttagacgtgt tactgtatt caacgtgcat aatcaggttg ttcaaaaaga | 3780 |
| gagaggatag gtcttcttct tctgtaattt gctgggaccg caagtcatgt gaggctgctc | 3840 |
| tgctgatgct gcacggcgtc gcaactctct caataaattc ttttaactaa cgctccaatt | 3900 |
| ttcgatgtaa attggctgac ttcaattcta tgccttactc ttgtactcta tgtttcttta | 3960 |
| tctattaaaa tccaactctg cttttgaacc caaaaaacaa | 4000 |

```
<210> SEQ ID NO 85
<211> LENGTH: 19
<212> TYPE: DNA
<213> ORGANISM: Artificial sequence
<220> FEATURE:
<223> OTHER INFORMATION: Single strand oligonucleotide
```

```
<400> SEQUENCE: 85
acaccctggg aattggttt                                                 19

<210> SEQ ID NO 86
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 86
gtatgcgcca ataagaccac                                                20

<210> SEQ ID NO 87
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 87
gtactgctgg tcctttgcag                                                20

<210> SEQ ID NO 88
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 88
aggagcacta cggaaggatg                                                20

<210> SEQ ID NO 89
<211> LENGTH: 22
<212> TYPE: DNA
<213> ORGANISM: Artificial sequence
<220> FEATURE:
<223> OTHER INFORMATION: Single strand oligonucleotide

<400> SEQUENCE: 89
gttgagagtg ttggagaagg ag                                             22

<210> SEQ ID NO 90
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 90
ctcggtgttg atcctgagaa g                                              21

<210> SEQ ID NO 91
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 91
agcttccttc atttctgtga atc                                            23
```

```
<210> SEQ ID NO 92
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 92
ctgttcccca cttaccctga c                                          21

<210> SEQ ID NO 93
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 93
ctcctcatct gattccttct c                                          21

<210> SEQ ID NO 94
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 94
ctgttcccca cttaccctga c                                          21

<210> SEQ ID NO 95
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 95
gtgtgtggaa agtttatcaa cac                                        23

<210> SEQ ID NO 96
<211> LENGTH: 27
<212> TYPE: DNA
<213> ORGANISM: Artificial sequence
<220> FEATURE:
<223> OTHER INFORMATION: Single strand oligonucleotide

<400> SEQUENCE: 96
gttagtatgt aacatctccg attctac                                    27

<210> SEQ ID NO 97
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 97
agagtggtcg tgtgagttgc                                            20

<210> SEQ ID NO 98
<211> LENGTH: 25
<212> TYPE: DNA
<213> ORGANISM: Artificial sequence
<220> FEATURE:
<223> OTHER INFORMATION: Single strand oligonucleotide
```

<400> SEQUENCE: 98
ccagtcaaga tttcatggat ctgtt                                               25

<210> SEQ ID NO 99
<211> LENGTH: 28
<212> TYPE: DNA
<213> ORGANISM: Artificial sequence
<220> FEATURE:
<223> OTHER INFORMATION: Single strand oligonucleotide

<400> SEQUENCE: 99
ctaacataat cgagaacaga tggaagac                                            28

<210> SEQ ID NO 100
<211> LENGTH: 32
<212> TYPE: DNA
<213> ORGANISM: Artificial sequence
<220> FEATURE:
<223> OTHER INFORMATION: Single strand oligonucleotide

<400> SEQUENCE: 100
ttctcatgtc cttgatttat caatttaaca ac                                       32

<210> SEQ ID NO 101
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 101
agagtggtcg tgtgagttgc                                                     20

<210> SEQ ID NO 102
<211> LENGTH: 26
<212> TYPE: DNA
<213> ORGANISM: Artificial sequence
<220> FEATURE:
<223> OTHER INFORMATION: Single strand oligonucleotide

<400> SEQUENCE: 102
cgcatcagat ctatcaaaca cataga                                              26

<210> SEQ ID NO 103
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 103
gcuacucugg ugaaccaucg uuggccaugc uugccuuauu cucccauggc aaucuuacua         60
cggccguagg aaacuucucc ggacaagcga auaggcuuca cagacucuac gaaaaccccu        120
aaaacaaaca cuaacaaagg gacugaagag ccuaccacca cccaaugcgu cgauuacuga        180
cgcacguacg uggucagcga aggcgcugag cucgugguau uggcagcggu gaacagaaua        240
aucaaacaag ccaacggugg uaucauccag aacaucu                                 277

<210> SEQ ID NO 104
<211> LENGTH: 110
<212> TYPE: DNA
<213> ORGANISM: Artificial sequence
<220> FEATURE:
<223> OTHER INFORMATION: Single strand oligonucleotide

<400> SEQUENCE: 104
cgcaaagaaa gaggaggagg augaugagua aacaaaugca cucugcaugu ucgaugcaca      60
ugcaucucuu gcuugcucau ugauccaucu uucuugcucc ggcaccgagu                110

<210> SEQ ID NO 105
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 105
gaaucuguuc ucaucuuuuc cuuagggguq uuuaccuguu cugccacguu aucucuucuu      60
uccuugauuc cgacggaacc aaauaauagu ggccaggaca gacagacaac gaaaacccaa     120
aaaacaaaca cgaacaaugu uagucaauuc uggcguccaa cauaacgcau gcaacacgua     180
ugcgcggacg uugggagugg aagcauucgc cggaaggaaa cagcaaaggu gaagagaaua     240
gagagugcgu ugaggaggag gaugaugagu aaugacg                             277

<210> SEQ ID NO 106
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 106
gaccagguua ugaccccgug gguucaagac augccacuag cagccgagcu aagccugccg      60
ucacuaaaca accuuugucu agagaauacg cuaugcuaca aauaagcgac gaaaacccua     120
caaacaaucu ccaacaacgc ucguuaauag uauacugccg cgaauugcgc uaaacacuag     180
cgcaugcaag cggcgagcuu acgagcuccg augacgguaa cgccaagguc gaagugcugg     240
uucauauugg gauucguggg guucacuaau ccgcccu                             277

<210> SEQ ID NO 107
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 107
ggcccaggua cgauggaguc cauucaggac uugcuagcaa cgcacgcgag gggcgauugg      60 uguqucauug aggcuuagcg acagauaaua uauaacauaa gacguccuac gaaaaaccua    120
caaacaaaca cuaacaaagg aagucaagug uuaucaaccu caucuagcuu cuagaacaga     180
agcucccacg aggugagugu aggcauucgc aauauugaua gguaacuggc gaaucguugc     240
uccaaaucag gauggauucu auucgauauu uagagaa                             277

<210> SEQ ID NO 108
<211> LENGTH: 110
<212> TYPE: DNA
<213> ORGANISM: Artificial sequence
<220> FEATURE:
<223> OTHER INFORMATION: Single strand oligonucleotide

<400> SEQUENCE: 108
cgcaaagaaa cucaaagaaa auuuucgaua aacaaaugca cuucgcauga acgaugcguu      60
ugcaucccuu gcuuguugaa guauuuaucu uugaggcucc ggcaccgauu                110

<210> SEQ ID NO 109
<211> LENGTH: 208
<212> TYPE: DNA
<213> ORGANISM: Artificial sequence
<220> FEATURE:
<223> OTHER INFORMATION: Single strand oligonucleotide

<400> SEQUENCE: 109

```
uuggugggag ggcuaggcug gcgguacguu auucugaaaa aauauuacgg acgugaugca      60
agcacauaug gauguugcau gacacggccg gugcauguga acaaaaacaa aaccaaggca     120
aaagagcgag agagagagca ugcauugcaa aucgucgug uuuuuuaug gguggcagcc      180
acccuggaug cggcauccuu cagaccga                                       208
```

<210> SEQ ID NO 110
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 110

```
gcuacgguua uggcccuacg gguacgagac gagcugaugu cacccgaguu acuccuacau      60
acgcuguauc caacggauuc agagacaaua ggggucaaga uuacgagaua gaaaacccag     120
cacacaauau ugaacauuuu uuuagaguug auccacacca caucgugcag uuaacacaau     180
ugcaagcacg uggugagcgc agacguucga cuguauguaa agacaaaguc gaaaugaugu     240
uucucaucgg uauucguggg guucacuaau ccuaucc                             277
```

<210> SEQ ID NO 111
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 111

```
gcaucuuugc guccgucuuc cgugcucgac uugccgguac ccgccaugac aaaccuccga      60
gcuaugugua gugccuaccc auauaacacc caucucuaaa cguauucuaa gaaaaaccac     120
aaaacaaucg cgaacaaggg aggcgacuag agauccaccu caucgagcuu ugacuacuaa     180
agcugcuacg gggucgggua agggcccgag gaguuuggaa aguaaguggu gaaggggugc     240
uacagauuug uauggaagau gagacugcaa aaguacc                             277
```

<210> SEQ ID NO 112
<211> LENGTH: 105
<212> TYPE: DNA
<213> ORGANISM: Artificial sequence
<220> FEATURE:
<223> OTHER INFORMATION: Single strand oligonucleotide

<400> SEQUENCE: 112

```
gaagagaaga aucuguaaag uuuagaaagg auaaacaaac cacgaucaca cacaucgaua      60
uacuuuuguu uguccauucu gagcuucacu ggcuuucuu acuuc                     105
```

<210> SEQ ID NO 113
<211> LENGTH: 208
<212> TYPE: DNA
<213> ORGANISM: Artificial sequence
<220> FEATURE:
<223> OTHER INFORMATION: Single strand oligonucleotide

<400> SEQUENCE: 113

```
ucggucgggu aguuacgcug gcaucgauug auggauagua auaauaaagu cagucuugcg        60
agcacagaug gauguaucau cacaccaccu guggaugacu acaaaaagaa aaccaaggca       120
aaagagcgag agagagagcc cgcagggcaa cgguuucguu guuacuauac cguugcagcc       180
accguaaaac cucccucugc cgaaccga                                          208
```

<210> SEQ ID NO 114
<211> LENGTH: 277
<212> TYPE: DNA
<213> ORGANISM: Artificial sequence
<220> FEATURE:
<223> OTHER INFORMATION: Single strand oligonucleotide

<400> SEQUENCE: 114

```
gagucgguua uggcccugug aauucagguc augcgucccu cugccuagug aagccacccc        60
ucgcugggga ugucguccac agagaacaga acgucugca gacgcacuac gaaaaccauu       120
gaaacuagcc caaacaaagu gggucaccag auugccagcc cgcggugcuc acagaacgug       180
agcaggaaag gguugaggcc auggucucgu ccaggggua agccacagug gaaaagaggg       240
aacauaaugg gauucgugggg guucacuaau ccuugca                               277
```

<210> SEQ ID NO 115
<211> LENGTH: 341
<212> TYPE: DNA
<213> ORGANISM: Artificial sequence
<220> FEATURE:
<223> OTHER INFORMATION: Single strand oligonucleotide

<400> SEQUENCE: 115

```
aacgagaugc caacuucuca agauugcaaa agcaaccagc uaguacguug guacacacca        60
augggauaac cggucagcaa uuagauccug uuaccaucaa caggauccga gggcucaucc       120
ccgaugagga aucggaucgg ccaucagauc ucgagcaaga accaagaggu cugccgguau       180
aucuccuuag aauccaaaca cgaccagggu uggacccguu ccuuccucgc ccccaaaaag       240
uaagggcgga ggaaugaguu ccugguuguu ucagggagag aaucagcauc aucggcguug       300
auugguaccg gcuuugcagc uggaggggguu ggcaacucgc c                          341
```

<210> SEQ ID NO 116
<211> LENGTH: 103
<212> TYPE: DNA
<213> ORGANISM: Artificial sequence
<220> FEATURE:
<223> OTHER INFORMATION: Single strand oligonucleotide

<400> SEQUENCE: 116

```
agagagagcu acaggccggc gcuggagagc auacgcaggu aauuuauua gaaaauaacu        60 uugcaggugc gugcucucua agcgucggcc ugcgccaucu ugg                        103
```

<210> SEQ ID NO 117
<211> LENGTH: 341
<212> TYPE: DNA
<213> ORGANISM: Artificial sequence
<220> FEATURE:
<223> OTHER INFORMATION: Single strand oligonucleotide

<400> SEQUENCE: 117

```
uggggaggg uccaggcauc agggaugaaa agcaagcagc uacccuguug agacaguucg        60
acaauacuac ccuaaagcag ugugauugaa uuacugagaa uuugauccuu ggacucguug       120
```

| | |
|---|---:|
| caagcgagca aaaguugggg auguaacuuc gcgaggaagc aggaagcgga gucaugggu | 180 |
| aucgccagau aaaccaagca cuucgucagc cccaggguga ccaugugggc ccccgaaaau | 240 |
| uaagggccua ggucacguug ugacggaguu uacuggugggg uuugaugagc ucaguauguc | 300 |
| aagggaccca gguucguga uagugucugg accuaccccg u | 341 |

<210> SEQ ID NO 118
<211> LENGTH: 341
<212> TYPE: DNA
<213> ORGANISM: Artificial sequence
<220> FEATURE:
<223> OTHER INFORMATION: Single strand oligonucleotide

<400> SEQUENCE: 118

| | |
|---|---:|
| agagugauuu auucguggggg uucacuaauc cguaagcaac gcugaugcca ucauaggaug | 60 |
| guaaugaagc cggauagaua caaguugcua uuccaauaa uagcaaccau ggaggcugcg | 120 |
| cagcagcuca aauggguucgg ggucagauca ucgggcaaug acgaagauga ucauaggggu | 180 |
| agcgcgugag aagccaacca cgcucugcga ucgagccuua acucgagcgc ccacaaaaag | 240 |
| gaaggguggga guuaagccuu guagagcgu uccgcgcgug guaguacagc cgcgcaguau | 300 |
| uacgacuccu gugguuagua aguccgcgag uaagacacug g | 341 |

<210> SEQ ID NO 119
<211> LENGTH: 239
<212> TYPE: DNA
<213> ORGANISM: Artificial sequence
<220> FEATURE:
<223> OTHER INFORMATION: Single strand oligonucleotide

<400> SEQUENCE: 119

| | |
|---|---:|
| gcggaggca aguucccuc auuauaaaca ugaaggguguc ucucgccuaa acacacagcg | 60 |
| aucaacaaa aguaacuaac ccacacauau gguagaaacc aaaaccauaa cguggauacc | 120 |
| cuuauucugc guauaaguuu gacaaaauuc ggggggaagga accaguuug uauuggggcgg | 180 |
| agcaagcgcg uggcuccuag agcacgucgg ccacaaagca cguuggggac caagaacgg | 239 |

<210> SEQ ID NO 120
<211> LENGTH: 94
<212> TYPE: DNA
<213> ORGANISM: Artificial sequence
<220> FEATURE:
<223> OTHER INFORMATION: Single strand oligonucleotide

<400> SEQUENCE: 120

| | |
|---|---:|
| gggaagucuu ggauugugga gaauuuaaaa agaaauaacu uucgucacga acgaaagcaa | 60 |
| uuauuuuuua acaccaccac agccuaagau uuuc | 94 |

<210> SEQ ID NO 121
<211> LENGTH: 225
<212> TYPE: DNA
<213> ORGANISM: Artificial sequence
<220> FEATURE:
<223> OTHER INFORMATION: Single strand oligonucleotide

<400> SEQUENCE: 121

| | |
|---|---:|
| caacagaaga gacacccccg aggagagaac cugcucaucu uuaauguuuu uuugaaaac | 60 |
| cugaccagcg ccgcuccugc cugcaacaac cauccaucag aacaaaaagu ucguauggcg | 120 |
| aaaggccauu gaugguggggc agguccccc uggggaagu cuagcgucaa cgagcugggg | 180 |
| ucugauggguu ucacaauugc uaaaacuugu gcuucaggug acaaa | 225 |

<210> SEQ ID NO 122
<211> LENGTH: 239
<212> TYPE: DNA
<213> ORGANISM: Artificial sequence
<220> FEATURE:
<223> OTHER INFORMATION: Single strand oligonucleotide

<400> SEQUENCE: 122
ggggagagca uggauucgug guuccugugg auagccccgc acauaaucgc acuucgcccc     60
auaaacaaaa acaaaagaaa ccacacaacc uguagaaacc aaaacagguu gcaccgauca    120
cgacccggug ccgccgcuca gacaugaguu auguguacac agauucgugg gguucacuaa    180
uccuaaccac ccagcucgua gcggucgggc cguaucacuu gggaucggcu caagaucgg     239

<210> SEQ ID NO 123
<211> LENGTH: 341
<212> TYPE: DNA
<213> ORGANISM: Artificial sequence
<220> FEATURE:
<223> OTHER INFORMATION: Single strand oligonucleotide

<400> SEQUENCE: 123
accgugagau uuugaggug agcgagggua gucaaacaga cgauggucag uaauauuauu      60
ggcgcuacgc ccuuuaugua ccauggugcg ggccggauu cguauaccu ggaaucauuu      120 cgaaugauga aggggaggg auuagaacgu acgaccaacu agcaagugug uugagggauc     180
aucuccuuua gcuccaauca cuagcacagg auguccuugc ucuauucgc ccccaaaaau     240 aaagggcaua gguaaagac uguguuagu cuagggagac auucuaaagc gcugcauagg      300 aaucggcu ucuaccccucu ugaucucaaa gaucacacgu a                         341

<210> SEQ ID NO 124
<211> LENGTH: 96
<212> TYPE: DNA
<213> ORGANISM: Artificial sequence
<220> FEATURE:
<223> OTHER INFORMATION: Single strand oligonucleotide

<400> SEQUENCE: 124
gacaacuggu uauuggugcg gggcguuaag aaaacggugc ucaauacuuu uugagcuccg     60
cuuucugaac guucuguauu gauaacgagu gccacg                              96

<210> SEQ ID NO 125
<211> LENGTH: 341
<212> TYPE: DNA
<213> ORGANISM: Artificial sequence
<220> FEATURE:
<223> OTHER INFORMATION: Single strand oligonucleotide

<400> SEQUENCE: 125
cgugggagau aaauuauuu uugauacacu agagagcauc uacaguuaaa auaaagauuu     60 ugauagcac cccacagguu ucaguacuuu uggcuaaaua aaaguaccag guuucuuuc      120 cuaaagaaua auuggugggg gacuaagauc ucgcgcaauu augaagaggu cuguggauc     180 agcucccucg aagccaauca cgcuuaaggg cccaacuaga ucgucucggc ccccuaaaac    240 gaagggguuac gguuuacuug cuugagcguu ucaggggggug augcguuacc aacggagacg  300 uaugggucccc gcaguguggg auggugguuu uauuacccaa g                       341

```
<210> SEQ ID NO 126
<211> LENGTH: 341
<212> TYPE: DNA
<213> ORGANISM: Artificial sequence
<220> FEATURE:
<223> OTHER INFORMATION: Single strand oligonucleotide

<400> SEQUENCE: 126
gcugggaggg guuaguggag uuacacggau gggaaccacc cuaccuugau auaaacauau        60
uaaccauaga cagagaggga aaggucucu ggucaugcuc agagacccaa ggggucuauu       120
cuauagacga auugcuuugu agguguuggc ucgcgaaacu aaaaagaguu gagucgggaa      180
aucgccagau ugaccaaucu cacacauugg gguaacggga ccauccucgc ccacaaaaag     240
gaagggcggu ggccuauua ggugugugge gacuggcgag gguucgcagc uacgcagugg      300
aucguucccg acauucgugg gguucacuaa uccuacccac a                         341

<210> SEQ ID NO 127
<211> LENGTH: 193
<212> TYPE: DNA
<213> ORGANISM: Artificial sequence
<220> FEATURE:
<223> OTHER INFORMATION: Single strand oligonucleotide

<400> SEQUENCE: 127
ggguucuucc agaagggcgg acaaccaacg gcgaccgccc ccuagggacc ccaggcggac       60
guuaaguuag gauuucccau uuacauucgg augggaugug ggcgagccgc cgucacgaaa     120
acggcggcag cgccaagagc gcuggacguu cgcagaagac agaaccuggu ugcucgcucu     180
ucuggaagaa ccu                                                        193

<210> SEQ ID NO 128
<211> LENGTH: 193
<212> TYPE: DNA
<213> ORGANISM: Artificial sequence
<220> FEATURE:
<223> OTHER INFORMATION: Single strand oligonucleotide

<400> SEQUENCE: 128
ggguuuuuuc agaagggugg acauccaucg cccaucuccg cuugugcccc ccaggagaag       60
gguacgccag gauuucggau agagugaccu auucgaggag uuuccgccgc ugccucgaaa     120
gcagcggcug cuccaacuga gcagaagaag cucuuaaaac agaaccugga ugcucgcucu     180
ucuggaagaa ccu                                                        193

<210> SEQ ID NO 129
<211> LENGTH: 193
<212> TYPE: DNA
<213> ORGANISM: Artificial sequence
<220> FEATURE:
<223> OTHER INFORMATION: Single strand oligonucleotide

<400> SEQUENCE: 129
ggguucuuuc aggaggguga acaucccacg ccgaccucuc auuauugccc ccaggaggau       60
gguacaacug gucgucuauu ugaagugcua aguggaggug ccccggcugc ugacccgaaa     120
ucagcagcag cuccaaaaga gcuggggggg cgcugaaucc agaaccggga ugcucgcucu     180
ucuggaagaa ccu                                                        193
```

```
<210> SEQ ID NO 130
<211> LENGTH: 193
<212> TYPE: DNA
<213> ORGANISM: Artificial sequence
<220> FEATURE:
<223> OTHER INFORMATION: Single strand oligonucleotide

<400> SEQUENCE: 130
gcggugguau ugcuuuuuca ucagccugcg cccaucacac caggggggcag acaugugaag    60 ggcaauacag gacuacuagc uuaaagacgg gcugguuggg uagcagcugc aggcgcgaaa   120
ucugcagccg ccccaaaagg gcggggggcug cccacaaggc agaacaaggc uguuggaggg   180
guaaugccau ugc                                                      193

<210> SEQ ID NO 131
<211> LENGTH: 216
<212> TYPE: DNA
<213> ORGANISM: Artificial sequence
<220> FEATURE:
<223> OTHER INFORMATION: Single strand oligonucleotide

<400> SEQUENCE: 131
gggaaucaga cauggcgaga uuucaucggg aucuggggcg agggcgaggg cgugacagug    60
gggagcgcag ucgauacaug caccaggcac acccaguauc gccuuggaaa gcaaggcgca   120
cuggguccgc cggaugcaug ugacgagugc aacgcgcccg cugcaagcau cgcgacucgu   180
uccagauucc gaugauucuc cgucgcacug augccc                             216

<210> SEQ ID NO 132
<211> LENGTH: 89
<212> TYPE: DNA
<213> ORGANISM: Artificial sequence
<220> FEATURE:
<223> OTHER INFORMATION: Single strand oligonucleotide

<400> SEQUENCE: 132
caugcuaucg gugcuucgua cgguauuugc agagagcaca ucgaacaccg auggccuccg    60
uggaugucgu augguggugcc guuaguaug                                     89

<210> SEQ ID NO 133
<211> LENGTH: 142
<212> TYPE: DNA
<213> ORGANISM: Artificial sequence
<220> FEATURE:
<223> OTHER INFORMATION: Single strand oligonucleotide

<400> SEQUENCE: 133
gcggccugaa acaccguuug auuggugugc ugggggucaac guguccaaug ccagaagacg    60
ucagcaaggg aagaacaggu guuccugggc gaugaacgcg uuggugcuuc uacaucaacc   120
gaagguaaac uuucacgcaa cg                                            142

<210> SEQ ID NO 134
<211> LENGTH: 186
<212> TYPE: DNA
<213> ORGANISM: Artificial sequence
<220> FEATURE:
<223> OTHER INFORMATION: Single strand oligonucleotide

<400> SEQUENCE: 134
guggcgugac cugagcaagu auucguggggg uucacuaauc cugaccgacc cuugcgcagg    60 ccaggcguccc augauuggua agucacccca caaagugcaa gaccagaaug gacagccagg   120
```

| | |
|---|---|
| uugccuuaac cagcagaggg ucggcgagcg uuggugagga ccgccgaugc augaccacca | 180 |
| cgccac | 186 |

<210> SEQ ID NO 135
<211> LENGTH: 216
<212> TYPE: DNA
<213> ORGANISM: Artificial sequence
<220> FEATURE:
<223> OTHER INFORMATION: Single strand oligonucleotide

<400> SEQUENCE: 135

| | |
|---|---|
| uggauacacg cgugggaaga ucuggucuuc uugaccgguc uugguuaggu caugacgggg | 60 |
| guccgcgcag uccacucagg cgcucggcac ccccgcuacc uucacggaaa gugugaagcg | 120 |
| gcggggcagc cagucgccug agaggagugc aacgcagccc ccgcaagaau aacagaggac | 180 |
| uggucaagaa gacuauucug uuucggagug uagcca | 216 |

<210> SEQ ID NO 136
<211> LENGTH: 83
<212> TYPE: DNA
<213> ORGANISM: Artificial sequence
<220> FEATURE:
<223> OTHER INFORMATION: Single strand oligonucleotide

<400> SEQUENCE: 136

| | |
|---|---|
| uacguauauu guguaguuaa uuuacucagg uguguuggg guuacggugc accuccaaua | 60 |
| gugaagacua ucagcaucac gua | 83 |

<210> SEQ ID NO 137
<211> LENGTH: 140
<212> TYPE: DNA
<213> ORGANISM: Artificial sequence
<220> FEATURE:
<223> OTHER INFORMATION: Single strand oligonucleotide

<400> SEQUENCE: 137

| | |
|---|---|
| cccggaguuu gugggcaagu ccgcucguac gacuucaagg aacagccucc gaaaacagga | 60 |
| guacauguga gauagaauaa uuccugggcc ggcucccugu ugucuuguug ugcgaacaag | 120 |
| acaugccggg agcucccggg | 140 |

<210> SEQ ID NO 138
<211> LENGTH: 186
<212> TYPE: DNA
<213> ORGANISM: Artificial sequence
<220> FEATURE:
<223> OTHER INFORMATION: Single strand oligonucleotide

<400> SEQUENCE: 138

| | |
|---|---|
| aaggugggag uggagagaga auucgugggg uucacuaauc cucacuagcu cuggcccuag | 60 |
| aggugacacc cggauaugga aagcuccaca cggugagaca gccguaacgg gugcucaacu | 120 |
| ugggcagagc cagccgggag cuagccagag uuggaggaag ccgccaguuc acuagcugcc | 180 |
| caccuu | 186 |

<210> SEQ ID NO 139
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 139

| | | |
|---|---|---|
| uuugcgaggc uagcaacugg auucuacuau auaaaaacac agacuuggaa ucaugucacc | 60 |
| caccaggacu cuccgagaau ccccguccga agacaugaa cggguggaaa aagacucuca | 120 |
| aucaucgacg acaagcuaac acaagguauc caguaaggua cucuaaagga gguugaugug | 180 |
| auggagcacu guagaacacg ugcuaaacuc acaucgacua aagaugagug uucaaggucg | 240 |
| ucaaguaucc gagccaggau acaaacgacu cacacauauu ggaccuauac ccuaaaggau | 300 |
| acccuccgaa agggcaauuc ggacagcaaa agcuguguuu uccuauaugg uagauguggu | 360 |
| uguuagccac gcaaa | 375 |

<210> SEQ ID NO 140
<211> LENGTH: 99
<212> TYPE: DNA
<213> ORGANISM: Artificial sequence
<220> FEATURE:
<223> OTHER INFORMATION: Single strand oligonucleotide

<400> SEQUENCE: 140

| | | |
|---|---|---|
| ucagcguaug uaguaggcuc ugcuucauca aguggucuug uguucaaauu cagcuccaag | 60 |
| cacauggca acuggauucu acuauauaug ugaauauaa | 99 |

<210> SEQ ID NO 141
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 141

| | | |
|---|---|---|
| cuugcgaggu cagcgugucc auccaacuua uguaaugcuc ccaugcaaug uuugccacc | 60 |
| ccagaggccu uauuuuaaag cugaugcuac cagggcaaaa aauggugaaa aacccaucua | 120 |
| gacaauuccg auauccaacu ucaaggcuuc cagguaguau cacgaaacgu gaaacacgug | 180 |
| aaggaucuuu gcagagcaug ggauaaaauc acguguuuug gucuggaguu uccaaugaca | 240 |
| ucaagucgca gagccaugcg acaaauguua cagauaaauu gcaguaaaua cgacaaggaa | 300 |
| gcccuccuga cgguuaauca gggcggcccg uaggggguau uccauucggg cucuuaugcg | 360 |
| cguugaccac gcaau | 375 |

<210> SEQ ID NO 142
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 142

| | | |
|---|---|---|
| aaagagaggg auucgugggg uucacuaauc cguuagccuc acaccccuua uucccucacc | 60 |
| ucucaugccu uagaaugaag caccagucac uagagggaaa aaaggcgaaa aacccuucca | 120 |
| aacaauagug agcaccaaac ccaagguaag cagcugguag cuugaagcaa guuuacgggg | 180 |
| gcggaaaaca gaagaucucg uuuuaaaccc ccguauaaga accaagagcg cucacuggcc | 240 |
| ccaaguuucu gagccaagaa acaagggcca cagcuguguu guugcuacua caagaaguuu | 300 |
| acccaccaga aggccaaucu gguuagcacg gggugggggcu accacggguu aguaagucug | 360 |
| cggaucccac ucuuc | 375 |

```
<210> SEQ ID NO 143
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 143
auugugaggc caaacagaag auuaaggggu ugucuaccgc ucaccuauua cugucacacc      60
uagcaugccc agaaccugug caccuccac aagugauagc aauggcgaaa aaaccaucca     120
accaacagug cuccagaaaa ccaaggcuuc caggacggau cucuaaggga gacaauaggg    180
ugggauauau gaagaucauu guauaaaggu ccuguugugc caguaagguuc cacacccucu   240 ccaauaggcu gagccaagcu uaaagagagg ccgacggaac guauacaauu cauuaaggaa    300
gcccacuagu agcgcaagcu agucaccaga gggagcggua ccacaauuc cuuauguuuu     360 guuuggucac acaaa                                                    375

<210> SEQ ID NO 144
<211> LENGTH: 125
<212> TYPE: DNA
<213> ORGANISM: Artificial sequence
<220> FEATURE:
<223> OTHER INFORMATION: Single strand oligonucleotide

<400> SEQUENCE: 144
cacugugcgg ucucuaauac gacuguucag agugaugaac cgguuccgc gcggaacgga      60 ggagcgggcg ccggcgccga auuggaucgu uccucugagc agcuguaucg gaggccgcgg    120
ugaac                                                               125

<210> SEQ ID NO 145
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 145
uuugagaggc caggaaggau auuacgauga ugaaucccac auacuugauu guuacucacc      60
uugcaagccc accgugugag cucccaccau uagaguaacu guaggggaaa aaaccuagac    120
uucaacugac cuucacaaac acaagguuuc cagucgguau cacuaacggu gauaaaaguu   180
ucgguaccuu cuagaagaug gguaaaaaaa acuuuuauug auuuagagca aacacuuuau    240
gcaaugguca gagccaugac caaauaugga cagacuuguu guaacaaaua cggaaaggaa    300
acccaccaca agggcaaugu gguaagcaaa agauguggga uccucauugu cguggcuccu   360
ucuuggucac ucaac                                                    375

<210> SEQ ID NO 146
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 146
gaugagaggu uuggaggggu aaugccauug cguugcacac auacuuccac uuugcccacc      60
ccucauggcg ccgacggcac caccagcaaa uagggcaaaa agagaccaaa aauucuuaua    120
cacaaacacu cgcggcaaau acaagguaac cagugagggc gaccaaaggu uugcuagcg    180
```

```
agggUACUCG GCAGAGCUAG GGUAAAAGUU GCUGGACACG UAACUGACAU CGAAAGAUCU    240
gcaagUGUCU GAGCCAAGAC AUAAUAGAUC CGGAGGAUGU GGGUCCAGCU CCCAAAGGUU    300
acccaccagg aggacaacuu ggucaucaua agaugugugc gccauguggu ggcuucucuu    360
uccaaaccac ucaua                                                     375

<210> SEQ ID NO 147
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 147
aacgagaggu augauaaaac augcuuauga augaaaucac ucacugcgcc cauucccaac     60
ccggaugccu uaugaugaag cacgcgauuc gagggaauga auuagggaua aagcuaacua    120
cgcaaacuaa uaccacaaag ucaagguugc cagaggggaa cacgaaccgu gauaagagag    180
gaggcucgcc guagaacgcg ugggaaaacu ucucuuauga gacuugugag aacaauuacc    240
acaagauccc gagccaggga ucaauggUGA CCGAGUCUUA GGAGCAAUUC CACUAAGGUA    300
acccacccga agggcaauug gguaaucaac aggaguggUU UGCCAUUUGU AAGAUCUUUU    360
gucguaucac ucguc                                                     375

<210> SEQ ID NO 148
<211> LENGTH: 111
<212> TYPE: DNA
<213> ORGANISM: Artificial sequence
<220> FEATURE:
<223> OTHER INFORMATION: Single strand oligonucleotide

<400> SEQUENCE: 148
cauguuugga uacuaguuaa uauuaauguu uaaagcuacu cuacaaaaaa uauaugauau     60
auuuccggua gaguagcuuu aaauauugau auuggcuagu auccaaacag a             111

<210> SEQ ID NO 149
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 149
uuugggaggu cuaguuaaua uuaauguuua auuuaaucuc agacuauuau uugucacacc     60
acuaaugccu gaggcucaag caccagaaau aaguagacaac auuggUGUAA aauccagccu    120
cccaagucaa aucgaacaau ucaaggcugc cagauagucu cacuaagggu gguuaaagcg    180
agggUGGCGU guagaacacc gucaaaaauc gcuuuagcgc gucgagauuu cgcaauaucu    240
ucaagucucu gagccaagag auaaaagaua cccaagaaau gucguuaaga ccauaaggca    300
gcccaccuga agggcaauca gguuaucauu agcuggggUU gccaguugug ucccacguug    360
aguggaUCAC ccaac                                                     375

<210> SEQ ID NO 150
<211> LENGTH: 375
<212> TYPE: DNA
<213> ORGANISM: Artificial sequence
<220> FEATURE:
<223> OTHER INFORMATION: Single strand oligonucleotide
```

<400> SEQUENCE: 150

```
gacgugaggu uuggaggggu aaugccauug cguaaacccc cgacucagaa uucucccacc      60
gcacagcgca agcuccuuac guccugacaa gagggagaac auuggggaaa aagccagcca     120
cacaaguaac uaaagcaaaa ugaaggguguc cagaaacuuc ccccaagggg guaaaacgug    180 uggggguugcc gaagaucgug cgacaaagac acguuuuagg guuucgagcg cgcaauuacu    240
ccaagugacu gagccaaguu auaagaguga ccgaagcguu ggaaugagga gcuuaggggc     300
acccgccugg agggcaaccg ggcaagcagg agcgggggguu uccacgcggu ggcuucuccc    360
ucugaaucac acgug                                                      375
```

<210> SEQ ID NO 151
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 151

```
guagcgaggu cgaaucuugu uuauaacuua aguuugucgc uaaccuggcg cagucucacc      60
ucaccagcca uagacuauag cuccugucau aagagauuga aaugguuaaa aacccauaca     120
uacaaaucug auacccaaac ucaaggauuc caggaaguau ggccaauggu caauucaguc     180
augggucaca gcagagcucg uggcaaacug acuggauuac acuuagguuu cccagucacg     240
ucaacugucc gagccaggac agaaacguga ggcacgaagc guaacggaua caucaaggaa     300
ucccuccuga aggacaauua gggcaacaaa gguagcggca gccacuuggg uugaaccgag    360
guucgaucac gcuag                                                      375
```

<210> SEQ ID NO 152
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 152

```
gugaagccac uggauggauc gguucaaucc ucucuuccgg aaucguuguu gaacauaaga      60
accuagaauc gaggauuaaa cuuauuuauu uagcgcucac uc                        102
```

<210> SEQ ID NO 153
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 153

```
guugugaggg cgaaucuugu uuauaacuua acuaaaucac ccacucaagu cugcgucacc      60
acucauauuu uaggcuaagg uaccaggcca uagacguagu aauggagaaa aaaccaucga     120
aucaaaacua cccuacaaaa ccaagguuuc cgaugaguau cacuacgagu gaaaauagcu     180
ggggaguuua gaagaucugg ggcuaaaacg gcuguuuugc ccuugaguua uacauugucu     240
gcaagagucu gagccaagac ucaacagaua ccgagauacu ggaaugaaua cccaaaggaa     300
acccuccuca agggcaauag gggcaccacg aggggguggu uccaguuggg uuggugaag     360 auucgcucac gcaaa                                                      375
```

```
<210> SEQ ID NO 154
<211> LENGTH: 375
<212> TYPE: DNA
<213> ORGANISM: Artificial sequence
<220> FEATURE:
<223> OTHER INFORMATION: Single strand oligonucleotide

<400> SEQUENCE: 154
gaugugagua auucgugggg uucacuaauc cgguuaccac agacagccua augacacacc      60
acacaugcca agccgcuuag caccugccac aaguguuaua aacgccgaaa aaugcgucaa     120
cacaaccauu ugaaccaaag acaagguacc cagcaaguau cuccaaagga ggaauaagug     180 agggguccg agagacucgg ggcaaaaauu acuugu ucag cguuggu guu cgcauucuca     240 ccaagcuccu gagccaagga gcaagugaga cucaggaaca guaaaaaaua ccugaagggu     300
acccuccacg aggacaacgu gggcaugacc ugcugguggua gcuccggguu gguaagucug     360
cggauuacac gcaua                                                     375

<210> SEQ ID NO 155
<211> LENGTH: 367
<212> TYPE: DNA
<213> ORGANISM: Artificial sequence
<220> FEATURE:
<223> OTHER INFORMATION: Single strand oligonucleotide

<400> SEQUENCE: 155
aguaccgagg gaaacgagau gcugcucaua uaauggcgga uagccccaac uucacaacua      60
ucgggccuuc cggugcacga gcggagguuc uuagagcuag caagucccuc gguaagauuc     120
cacagccugu gggacagcua cucacagggc ccuaccggac agcuggaagu agacuuggua     180
ugccugacgu aacagaccag uuacucagac agccaaaucc auaucguaca aaugauagga     240
aagagggauc uuaccgaggg aaccaauuaa cucuaagaac ccucacuaag ugaccgggag     300
agcugguagu uauggauuga gggcuaaaag cuauuguaug gguagcauuc uguuucccuc     360
gauacug                                                              367

<210> SEQ ID NO 156
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 156
cacgucagca cgacaggaug ccaaugcaaa aaaacguguc cuugagggcg cguuuuuug       60 cauuggcauc cugucacgcu gacgugg                                         87

<210> SEQ ID NO 157
<211> LENGTH: 168
<212> TYPE: DNA
<213> ORGANISM: Artificial sequence
<220> FEATURE:
<223> OTHER INFORMATION: Single strand oligonucleotide

<400> SEQUENCE: 157
ggaggacaac augccaaugc aaaaaaaguu uugguagaag gagacgguac gcagagcaga      60
agaggaacgg uggacuuaac ugagaccauc uucuccuaga uaagaucuca caaaccccuc     120
uccaugcaga ucuacuaagg aucugcugcg uuggugugu guuguccuccc                168
```

```
<210> SEQ ID NO 158
<211> LENGTH: 372
<212> TYPE: DNA
<213> ORGANISM: Artificial sequence
<220> FEATURE:
<223> OTHER INFORMATION: Single strand oligonucleotide

<400> SEQUENCE: 158
guggacgguc auucguggggg uucacuaauc caaaagaaga ccgcagaucc aaaggacaag      60
uuaagggcca aguugcccccu agacacagag gauggcccgg cggugucacu ggguuagggg     120
aggaccucug ggcgaaggaa aucagagcac acggccuggc ucuaucuuga acccgugcau     180
aguaaacggc agaugugggu aagaacacca cauuaugcac ggguuggaga cggacccagg     240
ccaaaauucg gaacauggcu ccccuaaccu ggugacaccg ccaggccaua ggggcaaaac     300
augacccuua auucaucuau ugggucccgcg agcuccuuac ggauuaguga acuuugcggu     360
ugaccgugca cc                                                        372

<210> SEQ ID NO 159
<211> LENGTH: 367
<212> TYPE: DNA
<213> ORGANISM: Artificial sequence
<220> FEATURE:
<223> OTHER INFORMATION: Single strand oligonucleotide

<400> SEQUENCE: 159
cguaccacgg uggcagggag aagagaacga uaauugcaaa uugccccugc gucucgcauu      60
acgggcuaaa cuguuccggc uaguaggggac aaugagcuag caagucuauc uggguuaga    120 aacacccugu acuacaggca aguacgggac cagacauggc agcgugacuc agacggggca    180
cgccaguagu uucagcccag agacacugac ggccccaacg acauaaaaca auuuaugcgu    240
aauauucuaa cuacagauag aaccaacuaa cucauuguuc ccacgagaac ggauaguuug    300
agccguggug caagaccaga gggcaaaagg caauugucgu ucucuuuuug uugccgccgu    360
gauacga                                                              367

<210> SEQ ID NO 160
<211> LENGTH: 101
<212> TYPE: DNA
<213> ORGANISM: Artificial sequence
<220> FEATURE:
<223> OTHER INFORMATION: Single strand oligonucleotide

<400> SEQUENCE: 160
guugcaaaca gaagauuaag ggguuagaug auggcgugca aucaggaguc uugaagcaau      60
gcaucccacu ccuuuggucu cuugaugcuu cuguuuucac c                       101

<210> SEQ ID NO 161
<211> LENGTH: 214
<212> TYPE: DNA
<213> ORGANISM: Artificial sequence
<220> FEATURE:
<223> OTHER INFORMATION: Single strand oligonucleotide

<400> SEQUENCE: 161
ggcugucggc cucgcuaggu auguuuaaca auguuaugcc aagcgguggg ccaaaaacuc      60
gaaaaacaac cccuuugagg aguaggcgcu gcagucaaac ccuguacucc ccgacgggau    120
cuccgaugag aucggagaca aaacacgggu cuaaaaccga gcauagacac cagggcacaa    180
uauuguuaag uguccuuggu ggcaccagcc gccc                                214
```

```
<210> SEQ ID NO 162
<211> LENGTH: 367
<212> TYPE: DNA
<213> ORGANISM: Artificial sequence
<220> FEATURE:
<223> OTHER INFORMATION: Single strand oligonucleotide

<400> SEQUENCE: 162
ugggccaagg uauucguggg guucacuaau ccucggcaca acgccccuuc uccgcugaaa      60
accggcguaa cauuaccugu acgcaugccc auagagcgag ccagccgcac ugucucuacg     120
aacagccagu uuuacagcua aaacugggc cccauccggc agcggaagga auaccaggca     180
ugccgcuagg aacagucuag uuccagcgac agccugaaca cguucauaca agugaauugu     240
aauaucguag agacagugcg gaccaacucc cucuaugggc gcgccuaaaa ggaguguuac     300
agcgguuuuc gauggaaaga gggcguaaag cugagggugg gugaguccuu uggauaccuu     360
gacucau                                                               367

<210> SEQ ID NO 163
<211> LENGTH: 367
<212> TYPE: DNA
<213> ORGANISM: Artificial sequence
<220> FEATURE:
<223> OTHER INFORMATION: Single strand oligonucleotide

<400> SEQUENCE: 163
gguaccaugg ugcacagcag uauuugugua uaugugccga acgccccuc aucucguggc      60 aggggcaaau cauucagagg ucguaugguc ucuguccag ccagccuuuc agccguccua     120
aauaaccagg uugacaguca caaucugggc accacucguc agcgagagga acacggggua     180
ugccaauguu gacaggaaag ucagauugcc ggcccuaaca acuucuuaca aagaagugu     240 aagauuagga cggcugaaag gaccaauuga cgcggggacc acacaauaau cuaaugauuu     300
agcccugcca caagguagga gggcguaaug cacauguaca cgaauacugg ugugcaccau     360
gauacca                                                               367

<210> SEQ ID NO 164
<211> LENGTH: 101
<212> TYPE: DNA
<213> ORGANISM: Artificial sequence
<220> FEATURE:
<223> OTHER INFORMATION: Single strand oligonucleotide

<400> SEQUENCE: 164
gcuguugggu ggaguuccag aguaaagaug agggagugca auuaggaguc uugaagcaau      60 gcaucccgu ccuuuuugcu cuggaaucuu cauucaucac c                          101

<210> SEQ ID NO 165
<211> LENGTH: 148
<212> TYPE: DNA
<213> ORGANISM: Artificial sequence
<220> FEATURE:
<223> OTHER INFORMATION: Single strand oligonucleotide

<400> SEQUENCE: 165
agaggagccc cuggucgauc augguacgca augaacgucg ucauguacg accuaaggac      60 aaucggcagu gauuaacuuu cuuaaacaga cccgagcaug acacauggcg acccucauag    120
ugugcuuggg uccguuacgg acuccgac                                        148
```

```
<210> SEQ ID NO 166
<211> LENGTH: 372
<212> TYPE: DNA
<213> ORGANISM: Artificial sequence
<220> FEATURE:
<223> OTHER INFORMATION: Single strand oligonucleotide

<400> SEQUENCE: 166
ggggucggcc auucgugggg uucacuaauc caacguguga ccggcggggc ggagcucaca      60
uauagugccu gguagccuca agagucggag guuugcccua cugucgguca guguuuuggg     120
gggaccuccu uacgaaggaa aaaggagcaa gcggccaggc uguauaaaga acccuuggga     180
uuaacauggc acuagcgggu aagaacaccg cuaauuucaa gguuguuua cauaccuugg      240 ccaaaagacc aaacacaucc ccccaaaacgu ugacuggcgg ugaggcaguu gaggcuaaac    300
cagacgcuau augcaagcac ugucccccucg agcagacgac ggguuggugg guccugugau    360
uggccgagcc cc                                                         372

<210> SEQ ID NO 167
<211> LENGTH: 206
<212> TYPE: DNA
<213> ORGANISM: Artificial sequence
<220> FEATURE:
<223> OTHER INFORMATION: Single strand oligonucleotide

<400> SEQUENCE: 167
gggugccgaa gcaauccgag gcuuuuuacu ugggugcuug gucggcaggg aaucaaacuc      60
ucgcgugaau uaugccguug ucgucgcccu aucucguucc ggggagcccu aaaaccugac     120
uaaauaauua uagccuucaa ugugaugagu ugugaugaua gccgaaccaa gggccugauc     180
aagaaguucc ggacauuucg gcaccc                                          206

<210> SEQ ID NO 168
<211> LENGTH: 104
<212> TYPE: DNA
<213> ORGANISM: Artificial sequence
<220> FEATURE:
<223> OTHER INFORMATION: Single strand oligonucleotide

<400> SEQUENCE: 168
ggcgcgagcu accacaagau guacggcaaa cggccgggcg ugacggcacc ggcggucgug      60
ccgucgcggc cgcuugcugu augaucuuug ugguagccgg ugcc                      104

<210> SEQ ID NO 169
<211> LENGTH: 139
<212> TYPE: DNA
<213> ORGANISM: Artificial sequence
<220> FEATURE:
<223> OTHER INFORMATION: Single strand oligonucleotide

<400> SEQUENCE: 169
aagguccgga accgaacggc aagagagcuc ggcaagggcc ugaucaagaa cucuuggauc      60
ucaagccaag gagugggugg cugauggggg uucuugguuc uguccuuauc gagcgggcca     120
aguucacgcu aucagccuu                                                  139

<210> SEQ ID NO 170
<211> LENGTH: 206
<212> TYPE: DNA
<213> ORGANISM: Artificial sequence
<220> FEATURE:
<223> OTHER INFORMATION: Single strand oligonucleotide
```

<400> SEQUENCE: 170

| | | |
|---|---|---|
| gggggcccau ccaaucugag gauucguggg guucacuaau cccccuaaa agugacucac | 60 |
| acguccgggc gagccuuuuc gcgaugaccg aucucgagcc ggugoucacg caaaaacauc | 120 |
| ccacgaaagc uugaauccag ggoguaguga gcucacgucu ggggagggou gaugagccau | 180 |
| gcgggucccc agacagaugg gccccc | 206 |

<210> SEQ ID NO 171
<211> LENGTH: 206
<212> TYPE: DNA
<213> ORGANISM: Artificial sequence
<220> FEATURE:
<223> OTHER INFORMATION: Single strand oligonucleotide

<400> SEQUENCE: 171

| | | |
|---|---|---|
| gggagccccg ccaagaugag gauccgaauu uauguaccuu aucgucaccc gauuacgcuc | 60 |
| acgggagucg ccagcuugac uauuucacca agccagaucg agugaucgcg aaaaucgaaa | 120 |
| cgaagucacu ggccagacau uccguagagc gcugaugccg gaugaauagg gagcaugauc | 180 |
| ucggauccccc auccagcggg gcuccc | 206 |

<210> SEQ ID NO 172
<211> LENGTH: 99
<212> TYPE: DNA
<213> ORGANISM: Artificial sequence
<220> FEATURE:
<223> OTHER INFORMATION: Single strand oligonucleotide

<400> SEQUENCE: 172

| | | |
|---|---|---|
| ggaaugggggc uggcugucac gucgacacuc aucuagagca acaaacuucu gcgagagguu | 60 |
| gccuaugaug gauguugaug uuacagccaa cuuuauucc | 99 |

<210> SEQ ID NO 173
<211> LENGTH: 165
<212> TYPE: DNA
<213> ORGANISM: Artificial sequence
<220> FEATURE:
<223> OTHER INFORMATION: Single strand oligonucleotide

<400> SEQUENCE: 173

| | | |
|---|---|---|
| uggggggcggg gcgggguacgg gaacacguaa gcugugaucg uugauguuac agccaacuuu | 60 |
| aagggugcgg cgggcaguac ucagcggggg uucuuccucc accccgggg auggucggau | 120 |
| cgagggaaca ucgcacgucg ccccccgcccg caaccccccgc cccua | 165 |

<210> SEQ ID NO 174
<211> LENGTH: 206
<212> TYPE: DNA
<213> ORGANISM: Artificial sequence
<220> FEATURE:
<223> OTHER INFORMATION: Single strand oligonucleotide

<400> SEQUENCE: 174

| | | |
|---|---|---|
| gggagccagu gcaaucugag gauucguggg guucacuaau cccucgacg aaaugcucac | 60 |
| accuacuuac gcuucggcgc uagaucgccc auccagguccc ccugaccacg caaaaggauc | 120 |
| agaagcgcaa gugaaugacg uggguggguga gacguugacg gaggagggou gaugagucaa | 180 |
| acgaguccccc agacacacug gcuccc | 206 |

```
<210> SEQ ID NO 175
<211> LENGTH: 206
<212> TYPE: DNA
<213> ORGANISM: Artificial sequence
<220> FEATURE:
<223> OTHER INFORMATION: Single strand oligonucleotide

<400> SEQUENCE: 175
gggagccuau ccaaaaggau ugggauuaug cuggguuug gccuacuucg aguuaggcac      60
acggguggca ucccguagac gguuagccg cgaacgauug uccaucccu aaacuguagc     120 aggcgucugg gaucagccaa cccgucgugc ugugacgucu uagagcuaa aguuuaguua    180 aaucuuaacc cuucagaugg gcuccc                                        206

<210> SEQ ID NO 176
<211> LENGTH: 165
<212> TYPE: DNA
<213> ORGANISM: Artificial sequence
<220> FEATURE:
<223> OTHER INFORMATION: Single strand oligonucleotide

<400> SEQUENCE: 176
uuggggcggg gcgggaucga gcauaugaaa ggcgagauug aggucuggau agaguuugca     60
cacggcgcgg cggccagcca ucggcgggau gccugccccc gccgcgugca agcugcuauu    120
ccagauuuua ucucucauca cucccucccg caccccccgc cccga                   165

<210> SEQ ID NO 177
<211> LENGTH: 139
<212> TYPE: DNA
<213> ORGANISM: Artificial sequence
<220> FEATURE:
<223> OTHER INFORMATION: Single strand oligonucleotide

<400> SEQUENCE: 177
aaggacucgu acaggccggc uagagagcgu aaacuuuuca uauuguuuua cucuuggggc     60
acauuccuug gcgugauagg aggcggggg uggggcgguc ugaggaugaug acgcgugcca   120 aggccccucg ccccuccuu                                                 139

<210> SEQ ID NO 178
<211> LENGTH: 206
<212> TYPE: DNA
<213> ORGANISM: Artificial sequence
<220> FEATURE:
<223> OTHER INFORMATION: Single strand oligonucleotide

<400> SEQUENCE: 178
gggagccgag ccaaucagag guuggagggg uaaugccauu gccgacgagu auccaccggc     60
ucgugugauc gcuccauagc uggucucccg aggcagugcg cggcacgaa caaaacaggc    120 agaagcuaga gugcagucaa cgugauguug gaugggaag gucgagcgau gacguugcaa    180
cuucaacccc ugacaguucg gcuccc                                        206

<210> SEQ ID NO 179
<211> LENGTH: 292
<212> TYPE: DNA
<213> ORGANISM: Artificial sequence
<220> FEATURE:
<223> OTHER INFORMATION: Single strand oligonucleotide
```

<400> SEQUENCE: 179

```
gaaccaaugc ggaagauacc aaugcacggu cgcauguaaa auugggcagu uggucaguuu    60
uguuggggug aagucuugcc ccaguuagcc gggaggaaag auauuacacc cgacucauuc   120
ugacgaacgc cucagguagu augcaaccug auacugaggu aacggcaga augaugcggg    180
uguauauauc caccuccgcu aacugggcga agacuucacu ccaacauaac ggacccgcug   240
ucaccggccc auacccgacg uauugggcuc uuugguaaca guggucgggu uc           292
```

<210> SEQ ID NO 180
<211> LENGTH: 84
<212> TYPE: DNA
<213> ORGANISM: Artificial sequence
<220> FEATURE:
<223> OTHER INFORMATION: Single strand oligonucleotide

<400> SEQUENCE: 180

```
auaccgagau aagcagagga agaauaauua ggugcuaauu ggaagcugca ccuacauucc    60
uuuuuaucug uuuaguuuug guag                                          84
```

<210> SEQ ID NO 181
<211> LENGTH: 199
<212> TYPE: DNA
<213> ORGANISM: Artificial sequence
<220> FEATURE:
<223> OTHER INFORMATION: Single strand oligonucleotide

<400> SEQUENCE: 181

```
agggcguacc aggagguaug aagccucgca ugggagaucu gcgagguauu gggguagacu    60
ucguaaaagg cgcaaacaag cucgcacaaa agcgugagga ugauguagcu aaagaugcau   120
aauucaacag cgauucacgc acccagggug auucguggac cucuuguuga gagcuguacu   180
uuggauagua agacgcccu                                                199
```

<210> SEQ ID NO 182
<211> LENGTH: 292
<212> TYPE: DNA
<213> ORGANISM: Artificial sequence
<220> FEATURE:
<223> OTHER INFORMATION: Single strand oligonucleotide

<400> SEQUENCE: 182

```
cgccccauga guuagaaacg aguucgggc caaaguucua cacguaggu uggaaagggu     60
uuggugaacc uugcggacac ggaggucgug gucggaggag aauuaucgcc cgacgcuugc   120
ccgcuaaccc gugaggugcc aggaaacgcg auacucacgg aaggagggu agguugcggg   180
cgauaaauuc ggccggacg accuccgcau ucgugggguu cacuaauccc guuccuaccu   240
accccgguca cugaauggcg aacuugguuc uaaauuacaa ggagaacggg ug           292
```

<210> SEQ ID NO 183
<211> LENGTH: 292
<212> TYPE: DNA
<213> ORGANISM: Artificial sequence
<220> FEATURE:
<223> OTHER INFORMATION: Single strand oligonucleotide

<400> SEQUENCE: 183

```
gccccacuaa gcuugaagcc auucccgcgu cucgggagaa agcgggcgu gggauauuua     60
guugugcuga caugucuagc aacgaugac gaagguuaag aaauaucgcc cgacucgucc   120
ucacaaacgc cagagcacga acgcaaccgu acacucuggc gaaugggggg acgaagcggg   180
```

```
cgauaauuuc acgccuuuca uccguugagg gacauguuag cauaauaaaa aguccagcgc    240
ccuacggugc ccacaagacg gaauggaguc gagauuaaaa ugggacgggg gc            292
```

<210> SEQ ID NO 184
<211> LENGTH: 91
<212> TYPE: DNA
<213> ORGANISM: Artificial sequence
<220> FEATURE:
<223> OTHER INFORMATION: Single strand oligonucleotide

<400> SEQUENCE: 184

```
aaggcuugcu acuguggagc aaucauucug aacgauagag aaaaugggau uuaauuuauc    60
ggucagaaug auacuccaca auacuaagcc u                                   91
```

<210> SEQ ID NO 185
<211> LENGTH: 195
<212> TYPE: DNA
<213> ORGANISM: Artificial sequence
<220> FEATURE:
<223> OTHER INFORMATION: Single strand oligonucleotide

<400> SEQUENCE: 185

```
ggagoguacc uagccggcug uaacuugugg acuaucggcg ggguaauggg gggcaacuag    60
cugccgaccc auuccuccau cccguccgug gcuacgagag ggugggcgcg acuuggaaug    120
agggaaugga gcgggagaua guuggaguco ccgcccgugc cuauccuuuu cagguuguag    180
ccucugauga gcucu                                                     195
```

<210> SEQ ID NO 186
<211> LENGTH: 292
<212> TYPE: DNA
<213> ORGANISM: Artificial sequence
<220> FEATURE:
<223> OTHER INFORMATION: Single strand oligonucleotide

<400> SEQUENCE: 186

```
gccccacucu gacagagacc augucgcgca auaugaacaa acggggcuga gggagguggc    60 uuggugggacc uugcgaaccc auagguagac gagggguaccg aaaagacgcc cgacucuggc   120
auacaaaccc gguuggaucc aagaaaugau aaacgaccgg gaaugggugc cagaagcggg    180
uguuauuuuc ucgccouucu aucugugcau ucgggggguu cacuaauccca gcuccaucag    240 ccgacagcau cgccaauugg acauggguuc uguaggacua agugcagggg gc             292
```

<210> SEQ ID NO 187
<211> LENGTH: 292
<212> TYPE: DNA
<213> ORGANISM: Artificial sequence
<220> FEATURE:
<223> OTHER INFORMATION: Single strand oligonucleotide

<400> SEQUENCE: 187

```
gccccgagg ucuugugccc aaagacaugu cugagacucc aggggaagu ggguaauuua    60 guuuaaggug uaugccacuc ucagguaggc gaagguuagg auugcccccc cgacgcaggc    120
uuacaaacgc ggauggguug acggaagaac agacauccgu gaaugagagu cugucacggg    180
ggggacaauc gcaccuuccu aucugagcuu ggcauauauu uuaaauaaaa cuaccaacuu    240
ucgaagacuu cugaaagacu uuuuggcggc agguucuaaa ggugagcggg uc            292
```

```
<210> SEQ ID NO 188
<211> LENGTH: 84
<212> TYPE: DNA
<213> ORGANISM: Artificial sequence
<220> FEATURE:
<223> OTHER INFORMATION: Single strand oligonucleotide

<400> SEQUENCE: 188
uugggauaug uuaggaaaua agaaaaucga ggugcuaauu ggaagcugca ccuuaggucc      60
ucuugauucc uagccguauc ucau                                            84

<210> SEQ ID NO 189
<211> LENGTH: 199
<212> TYPE: DNA
<213> ORGANISM: Artificial sequence
<220> FEATURE:
<223> OTHER INFORMATION: Single strand oligonucleotide

<400> SEQUENCE: 189
agggcuuuca cgggcuucgu aggccuugcu aagagauuuu uuaaaauuaa cuggaugacu      60
uagaaaauua cgcaaacaag uagaaauaaa cgcaugugug gugcguugcc aaagaagugu     120
uccacaaaag auacgcaugc uccaucuuag uuuggggac uuucuuacga gagcccgaag     180
cuagagggag agaagcccu                                                  199

<210> SEQ ID NO 190
<211> LENGTH: 292
<212> TYPE: DNA
<213> ORGANISM: Artificial sequence
<220> FEATURE:
<223> OTHER INFORMATION: Single strand oligonucleotide

<400> SEQUENCE: 190 gucccccaacc aguguagcc aauucggaug cugauggaca cacguaaga aggaugugc      60 uuggugagcu ccgcggaccc guagguuuuu gugggaguug aucgugaucc cgacucaugc    120
acgcaaacgc aacgggcugu acgaaaucag agaccguugc gaaugagugu augacgcggg   180
auugucgauc uacccaagga accugcgcau ucgugggguu cacuaauccg aguccgucuu    240
accucgccgc guaaaaguag aauuggggc aacggguaua gacgagaggg gc              292

<210> SEQ ID NO 191
<211> LENGTH: 237
<212> TYPE: DNA
<213> ORGANISM: Artificial sequence
<220> FEATURE:
<223> OTHER INFORMATION: Single strand oligonucleotide

<400> SEQUENCE: 191
cugacccgua cauaucgaga guugucuggc ccgccacagc cccuagcaaa ucucgucgcg     60
gagccacgcg uaguaugguc gcgagccacg cccgaagcua aaccagaagc accgaaggcu   120
acgcgucccu uauacacugu aacggcaccc cgaacacggg aagagggcuc cgaaggccga   180
cgagauuucc uaggggcugu ggcggguugg acaacuuugg auaugugccg gucaggg        237

<210> SEQ ID NO 192
<211> LENGTH: 64
<212> TYPE: DNA
<213> ORGANISM: Artificial sequence
<220> FEATURE:
<223> OTHER INFORMATION: Single strand oligonucleotide
```

```
<400> SEQUENCE: 192
cgcugcggag cucaagaaga acccucuucg aauaauccag gguucuuuua gggcuuugcg      60
guau                                                                  64

<210> SEQ ID NO 193
<211> LENGTH: 110
<212> TYPE: DNA
<213> ORGANISM: Artificial sequence
<220> FEATURE:
<223> OTHER INFORMATION: Single strand oligonucleotide

<400> SEQUENCE: 193
aaaguuaggg gagcacuagg guugauuggu cgucacaguu agaucuuucu gacccuagag      60
acgaaaaagc uguggcgggu uggacaacuu cauaccuccc aaccauagcg               110

<210> SEQ ID NO 194
<211> LENGTH: 237
<212> TYPE: DNA
<213> ORGANISM: Artificial sequence
<220> FEATURE:
<223> OTHER INFORMATION: Single strand oligonucleotide

<400> SEQUENCE: 194
cgggacaguu cauugcgggg guugguggac cccacgaguu cccaagcagg aguaggcgca      60
gaguagcuug acgcaaggua ccggcccacg gacgaccuca aacaguagag accuaacgcg    120
ucaggcuccu auggaacccca uacgaaaccc ccagcagggg aagaguacuc uguagaccgu    180
cuacuccucc uugggaauuc guggggguuca cuaaucccgg cagugagccg ucccggg      237

<210> SEQ ID NO 195
<211> LENGTH: 237
<212> TYPE: DNA
<213> ORGANISM: Artificial sequence
<220> FEATURE:
<223> OTHER INFORMATION: Single strand oligonucleotide

<400> SEQUENCE: 195
cugaaccgau cgcaacggag ugguaucauu cacugccugu cacuuucaua uugguggcgca    60 ggucugccug uggcauggcc gugcuccaca cagaauucau aaccucuuga uccaaacgcu    120
gcgggugacg cauugaaaau guuucuggcc cgaacucggg gaaaaggacc uggaggcugu    180
cgcaauauca aagugacagg cggugaauga uguuauucgg uugcgauccg uucaggg       237

<210> SEQ ID NO 196
<211> LENGTH: 64
<212> TYPE: DNA
<213> ORGANISM: Artificial sequence
<220> FEATURE:
<223> OTHER INFORMATION: Single strand oligonucleotide

<400> SEQUENCE: 196
accggaagag guaaaugaau uaccuuuccg aauaauccag gugguuuaua ugccuuuucc      60
ggau                                                                  64

<210> SEQ ID NO 197
<211> LENGTH: 110
<212> TYPE: DNA
<213> ORGANISM: Artificial sequence
<220> FEATURE:
<223> OTHER INFORMATION: Single strand oligonucleotide
```

<400> SEQUENCE: 197
aaggcggggg aagcaucugg acgccggaag agguaaauga agaucuucca cauugguggg    60
acgaaaaucg uuugcuaugu aucaucgucc cauaacuucc aauuaggaca               110

<210> SEQ ID NO 198
<211> LENGTH: 237
<212> TYPE: DNA
<213> ORGANISM: Artificial sequence
<220> FEATURE:
<223> OTHER INFORMATION: Single strand oligonucleotide

<400> SEQUENCE: 198
cugaucagag cauugcgagg gugguggac cccgcggaua cacucucugu caagggcccu    60
gagucgcuug gcggaugguu cgcagcccgc gcguaggaca aacugagguc accaaacccg   120
ccagguccau aagcgacguu uacggaaccc caagcauggg cagaggacuc aggaggcggu   180
ccuugauaca gaguguauuc guggguuuca cuaauccugg caaugcuccg gucaggg       237

<210> SEQ ID NO 199
<211> LENGTH: 237
<212> TYPE: DNA
<213> ORGANISM: Artificial sequence
<220> FEATURE:
<223> OTHER INFORMATION: Single strand oligonucleotide

<400> SEQUENCE: 199
cagaacagau ccggacgguu guguugugcu uuugcuggaa cacuagcuuu uguaggccca    60
gcguuccaag gcgcaaggug acacgcucug uacgaaccua aacccaaagg accaacgcg    120 ucuuggagac ucuagacuag ggccuuauug caagcaugcg cggacgacgc ugaagacggc   180
cuauagaacc uaguguucca gcaaaaguac agcacaacgg uccggauccg uucuggg       237

<210> SEQ ID NO 200
<211> LENGTH: 52
<212> TYPE: DNA
<213> ORGANISM: Artificial sequence
<220> FEATURE:
<223> OTHER INFORMATION: Single strand oligonucleotide

<400> SEQUENCE: 200 uuuggucccca uguuggagcu ggucgcaccc agcuccacau ggaagacuua cc            52

<210> SEQ ID NO 201
<211> LENGTH: 118
<212> TYPE: DNA
<213> ORGANISM: Artificial sequence
<220> FEATURE:
<223> OTHER INFORMATION: Single strand oligonucleotide

<400> SEQUENCE: 201
aaacaggaaa ugggaagcgg cagaaaugcc auucuccguu uacguucuuc gacgcuuccc    60
gcuuuccugg gacgugagua gggaauagug uuuuucccac uucucaagac cgacccgc     118

<210> SEQ ID NO 202
<211> LENGTH: 237
<212> TYPE: DNA
<213> ORGANISM: Artificial sequence
<220> FEATURE:
<223> OTHER INFORMATION: Single strand oligonucleotide

<400> SEQUENCE: 202
ccgagccgau caugucgcgg auuggugagc cccacgggug caccuacguc auuugucgcu    60
gaguaacaug cugcaaguga cgcgcccugc ggauauuaca aacuagagua uacuaacgcg    120
gcauguucgg aagcaacgcu ucagaaaccc cgaucacggg cagaguacuc gggagcccgg    180
caaaugaucu aggugcauuc gugggguuca cuauccggg auaugguccg cucggg       237

<210> SEQ ID NO 203
<211> LENGTH: 193
<212> TYPE: DNA
<213> ORGANISM: Artificial sequence
<220> FEATURE:
<223> OTHER INFORMATION: Single strand oligonucleotide

<400> SEQUENCE: 203 ggugugugu caaagguucg cugccucugc aucuacccuc uaauugccau augagacccu    60
aaacuaccca agccacugga auaaaaauga ggccgccguu ccaaccaaaa cgauaacaua    120
acaaauguua uuacaagggu gaaaagggcg aaggggggug ggugcacggg cgacgcaccg    180
gacgcaccgc cac                                                     193

<210> SEQ ID NO 204
<211> LENGTH: 111
<212> TYPE: DNA
<213> ORGANISM: Artificial sequence
<220> FEATURE:
<223> OTHER INFORMATION: Single strand oligonucleotide

<400> SEQUENCE: 204
gccgugcacc cacuagcagu uacaguguuc augaaauccu uaacuuccuu cccugucggg    60
aggauagaua ggguuuuug ggugcuguac cguuguugg gaucacgaag a              111

<210> SEQ ID NO 205
<211> LENGTH: 138
<212> TYPE: DNA
<213> ORGANISM: Artificial sequence
<220> FEATURE:
<223> OTHER INFORMATION: Single strand oligonucleotide

<400> SEQUENCE: 205
gaacgccgca gcguuaaaag cugccucugc cucugcaucu aucuucggu agaaggugaa    60 gggggggcgcc aagaccgcgg uucuaacccu agcuaggugu agcccgaggg agccagcucc    120
uggcggcuug gggcccca                                                138

<210> SEQ ID NO 206
<211> LENGTH: 193
<212> TYPE: DNA
<213> ORGANISM: Artificial sequence
<220> FEATURE:
<223> OTHER INFORMATION: Single strand oligonucleotide

<400> SEQUENCE: 206
gcaggcgucg ccaggggcug uuggagggu aaugccauug caauggcuau aagggacuga    60
auacuaccga gagcgcggau gccaaaccca agagacagca ucuaagacaa cgaagaacca    120
auaagguucu uuaaaucggu aaaaagagcc aagcggugggu auugccauuc cauuaaccca    180
guggcgccug cac                                                     193

<210> SEQ ID NO 207
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 207

```
caggggagug aagcgagugc aucuucauuc aucgaagcau gcaccuucac auucggaaaa      60
auccccacgg cuggaaccgu ccacccaaca cuaggcagag ucgagcccgc gcgguaccaa     120
aucugggüüg gagaauaagu cccgggggua gcccuccaga gggggcccaa ggccacauga     180
gggaucgcug caagggaggg acacagcaug gaccggccug acuacuauug aaagccgaac     240
guggaucaga gucggccgaa ggggcagaau cuacggcccg aaucuugauc caaaccccau     300
agagucaggg cgccaugggu gggugaaauc cacucgcuuc acacccccac a              351
```

<210> SEQ ID NO 208
<211> LENGTH: 93
<212> TYPE: DNA
<213> ORGANISM: Artificial sequence
<220> FEATURE:
<223> OTHER INFORMATION: Single strand oligonucleotide

<400> SEQUENCE: 208

```
aaaaccaagc uggugcuaua augcacaaua aggaucaauc agcaccugga ucugagauuc      60
gaguugugcg uuggcgcacc cacguggauc cua                                   93
```

<210> SEQ ID NO 209
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 209

```
gcugggaggu cagcguacaa cucaugaaua uuugaaucuc ccaccauccc gaaccucucu      60
gaccccaugc ccgguaucga ccaccgaucc acgaagacag accaggccgc ccgauuccca     120
auuugugauc gauaaauggg cucggggüüü ücccuuagca gggggaccca gucccuagga     180
uggauggggg aauggugguu aaaagccagg gcuaggucug uaaucuauac aaaccccaac     240
ggggcuagua gucagcugag gggggaaaac ucauagccug aauaccagc cuaacaccau      300
aguuacaggg cucccugagg uguucauaug ugucgcuuga ucacccaccc a              351
```

<210> SEQ ID NO 210
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 210

```
uuugagaggc uuggaggggu aaugccauug cgugaaacau caaccggucc cagcaucgaa      60
uggcgcaagu cagggcccgc ccaccguucc uuugcgauac uccaggccgc ccgauagcca     120
ggcaaagaac gagaaauugg cacgcgucac gucccaacug ggaguugcca cgacgaagac     180
cggauuggug uaagggggc agagaacagg guggugaccu uccaucaucu aaagacuaac     240
gggguaucga cucagcugag guguuagaaa ccacagccug aaucagauac cuaacgacau     300
ggggagggug accccugacg uggüggcuuc ucuuuccgag ccacucacgc a              351
```

```
<210> SEQ ID NO 211
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 211
gaugagaggu auggguuuug agacaaaauu ugagaaccga accccauccc accgauaaag      60
ggaccgaagu cggcuacaua gcaccgucuc uacagaauag uccaggccgc ccguagccca     120
gcuguaagac gagaacauga ugccgguccg ccccauuug gggagaucga aucucuagga      180
uggagguucg gacgggcgac agagaugcgc gugaggacgg gccaccagua aaaauccaac     240
ggggcguuaa guuagcguag ugggcagaau gcaacgccua aguucaaugc cuaacaccuu     300 ggggu uugug cuccgccuca aguuuugcug ggagcccgua ccacucacgc a             351

<210> SEQ ID NO 212
<211> LENGTH: 91
<212> TYPE: DNA
<213> ORGANISM: Artificial sequence
<220> FEATURE:
<223> OTHER INFORMATION: Single strand oligonucleotide

<400> SEQUENCE: 212
caguagcagu uggcgccaug aucaagaaga aaacuucccu aaacaagcca aggaaagauc      60
uuuucuuguc guggccucac cuguugaugg g                                    91

<210> SEQ ID NO 213
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 213
aucgagagug cagauucuuc uuggcgaauu agugaagcua acaccuucuc agccaccaca      60
gaccccaggc cgggacccgu ccaccgaucc accacaagag cccaggccgc ccgucgccaa     120
cguggugauc gagaauucgg cgcgggguca aauuccgacg aauggu ucga agcccaagga    180 gggauguuag caagggcggu aaauaacaug gugaggg ucg uuugcaauuu uaacucuaac    240
gugguuaaua uuucgcugag gagguagaau ccacagccga acuacuuaac cgaacuccau    300
ugagaugacg uuccaugacu aguucgggcu ggggaucugu acacucgcuc a             351

<210> SEQ ID NO 214
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 214
aaagagagga auucgugggg uucacuaauc cuuaaaacuu ccaccuaccc gaacaucucu      60
gucucggcgu cuggauacgu ccacugaccc ugaucgaaag accagaccgc ucgcuuccca     120
agaucagcuc accacggagg cugcgaggcu agucaaacgu gacggaccca guccacaggu     180
gggauggggg uauacguguu auagagauug gaguugccug ucugcgacca aaauccaaac    240 gcgguuuuc ggcagcugag ggggaacaac ccauagccug cagacaaacc cgaacgcgu     300 cgagauaggg aaccaauagg gguuaguagg uccgcgaauu ucacucucgc a             351
```

```
<210> SEQ ID NO 215
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 215
aacccgaguu cagaaucuca cuugagauuc ugugaacgau gcaccucgcu ccccuauucc      60
gaccccagga ccggacccgu ccaccgucca cggaauaaag gccacccgc agaaccccca     120
cuuucgggac gacaaauggu cacggggucu cuggucauua ccguguaugu ugcaauugug    180
gggaugcguu gagaauaggc aaauacccug gcggugugu uuucagauca caaagcgaac    240
ggggguucuga gugugccgag ggggcauaac ucauggccac agucaagaac cuaacccccau   300
uuagauacgg acccaggaua gggucucggc ggggguuuga acacgggcgc a              351

<210> SEQ ID NO 216
<211> LENGTH: 100
<212> TYPE: DNA
<213> ORGANISM: Artificial sequence
<220> FEATURE:
<223> OTHER INFORMATION: Single strand oligonucleotide

<400> SEQUENCE: 216
aacaguugag uggggcucug ucugcgucua gaccacucgc accaaguaca gacauaaucu      60
gaaugaucua ggcgcagauu ccaccccauc caacucaaca                          100

<210> SEQ ID NO 217
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 217
uauggcaggg cagaaucuca cuugagauuc ugugaaacaa acaccagcuc auucuguuca      60
aaccccacgu cugguaacga ccaccggacc gugaucacag uucaggccgc ccgauaccca    120
agucgcgucc gaaaaguagg cccggggguug gcgcuccaaa gcgggaccga guccuaaggu   180
uggauguuug uaagggucgg auacaucagg gugagggcug ucugcuuuaa aaaacccaac    240
gcggguuugu cagucugag ucgggacaag acacagccau uagcaaaacc cgaacgcgaa     300
agagauagcg uucccugaua gggucuuggc gauguauggu ucagucacgc a              351

<210> SEQ ID NO 218
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 218
gaugagagcu auucgugggg uucacuaauc ccugaaucac acaccugccc ucccagcccc      60
gcccccuagu cagaugacga ucccggccgc uugaucauag cccaacccgc gugcagccca    120
cgucgacggu caaaacuugg cacggggcu ccgcccgaug gcggguuca acccgcaggc     180
aggaugugug aauagggagg aagcaccacg gcgagggcug uauucuugau aaaaaccaaac   240
cuggagugca cuuggcggag uuggaagaaa gcauugccca auugcacucu cgaacgccca    300
agauauagug cuccgugagg gguuaguaag ccugcgagua gcacucacac a              351
```

```
<210> SEQ ID NO 219
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 219
ccggggacgu caccugugge uucuaccgca agagaacugc aauccguauc acgccggaau     60
aaccacaggu uugggagcgc ccaccgucca gcuguuaaag uccaggccgc ccgucgccca    120
ugcagcggac gaaaauuaag cacgugguuc gcccuuacua ggggggcucga agccauaaua   180 cggaauugcg gacgggggc acauaucacg gaacggcccu acggcguuga gaacacuaag    240
gcgguacuug auaagcccag ugggaaaaau gcagggccuu accacgguac cgaaagcaaa    300
ugcguagggg cgccguguuu uguggugaaac ucacggguga ugacccuccc a            351

<210> SEQ ID NO 220
<211> LENGTH: 99
<212> TYPE: DNA
<213> ORGANISM: Artificial sequence
<220> FEATURE:
<223> OTHER INFORMATION: Single strand oligonucleotide

<400> SEQUENCE: 220
guuuuuagag gugaaugcug gauggcucgu cgcauucaca uaagaagaag aaauauaagu     60
gaaggcugcg aaucgcucuu cguuuaucuc uaauauaca                            99

<210> SEQ ID NO 221
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 221
cacgugaggu ccaagccacc auccaagcca agcgaaacaa acacaagccc auuagccccu     60
uaccccacgg cugggucccgc ccacaguucc acuacgaaag gacaggcagc ccggacccca   120
aguagugaac uagaauaagu cccggggguac ccgcguauac gcgugaucua aucagcaggu   180
uugauguuug uaagggaggu auacaacuug gcgguugagu uccacuguuc uaacacuauc    240
gggguccuaa uucagccgau ggggaaaaau uaacggccug auuucaggac ccaacgucac    300
agggaguuug acccagggcu ugguuuccuu guggcuugga ucacgcgcgc a              351

<210> SEQ ID NO 222
<211> LENGTH: 351
<212> TYPE: DNA
<213> ORGANISM: Artificial sequence
<220> FEATURE:
<223> OTHER INFORMATION: Single strand oligonucleotide

<400> SEQUENCE: 222
agugugagga auucgugggg uucacuaauc cgggaaacug ucgccuucac uuacugcccg     60
uaccccaagu caggaacagu ccacaggggcc agugcgaaag accaugccgc cagccuccca   120
ggcauugccc uacaacgugg ccaggggguaa agacuaucga guugggccca gccccuauga   180
aggauggcag ucaaggcagg aaauacacgg gaggcguccg caccauguccc caauacgaac   240 ggguucauc auacgcugag ccgguagaag gcauagccgu aggacugaac cuaacaccac     300
gugugugggg gucccguucg gguugguaag ucugcgaauu ccacacaauc a              351
```

```
<210> SEQ ID NO 223
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 223
ugauugugug gcuugagguc cggggucagc guccccgcu ccgacccgaa cuagaaguga     60
guagaagcua gagugaacgg uaccacacag acccgcaucu cggaccaacc cuccgccugc    120
aaccccuucc accccgaccc cccucucgag guccgagaca gggcgguggg agacgagggg   180
gcaagaacuc cguacuuuau uucacguaac caa                                 213

<210> SEQ ID NO 224
<211> LENGTH: 100
<212> TYPE: DNA
<213> ORGANISM: Artificial sequence
<220> FEATURE:
<223> OTHER INFORMATION: Single strand oligonucleotide

<400> SEQUENCE: 224
aggauuugcc ugggcuacag uauggcacuc accuagagca acgacagcuu gggaggguug    60
ccuauaaggu ggaugccgua cuuuauuuca cguaaaucuc                          100

<210> SEQ ID NO 225
<211> LENGTH: 167
<212> TYPE: DNA
<213> ORGANISM: Artificial sequence
<220> FEATURE:
<223> OTHER INFORMATION: Single strand oligonucleotide

<400> SEQUENCE: 225
cggcggccag aaugcgcgca aaaaaaaaaa aaaaaaaaa gcggcggccg gacugcaccu     60
guggacggcc gccccaaagc gacggagaga cggguuccua accaaggugu aggagcagcc   120
gccggcgcuu uuuuuagua gcuuuucucu ugucagucuc uccucca                  167

<210> SEQ ID NO 226
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 226
ugaggauucg uggguucac uaaucccaga cgccgccgcu ccccccugag cagggacauc     60
gcccagaccu gaggcaacgc ggcgccacca accacccacu cguucccgca cugaaacauc   120
caccacaacg uacguagccc ccccacacg gagcgaguuc uggcgggcgg agacgagcgg   180
cggagagggu ugaugagccg aguggauccc caa                                213

<210> SEQ ID NO 227
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 227
cgauuuuuua ugcuuuuugg uucggucagc cgccgccgcg ccagcccacc ucguaccccc    60
agaccacacg acgcccacgc agcggcaaca aggcccagcc cgagccccg cacccucguc   120
```

| | |
|---|---|
| uuccacauca accgcagccc cccaccccag gcucgggccc gcccggucgg ugacgagcgg | 180 |
| cguagaaccg aggcaaagau aauaaaaaac cga | 213 |

<210> SEQ ID NO 228
<211> LENGTH: 76
<212> TYPE: DNA
<213> ORGANISM: Artificial sequence
<220> FEATURE:
<223> OTHER INFORMATION: Single strand oligonucleotide

<400> SEQUENCE: 228

| | |
|---|---|
| ugguuaugac gagcgugccg uacgagccac ggcugcugcu gcgccgccgc gggcuacggc | 60 |
| acucuuuuca uaauua | 76 |

<210> SEQ ID NO 229
<211> LENGTH: 155
<212> TYPE: DNA
<213> ORGANISM: Artificial sequence
<220> FEATURE:
<223> OTHER INFORMATION: Single strand oligonucleotide

<400> SEQUENCE: 229

| | |
|---|---|
| auggccgccg gcuuagagag ugaaaaaaua uauuucugca aaaggccccac cggccguggg | 60 |
| cggcagaaug ccgauuucug cgccuggag agaggggccc gcgcagcgau aaagcuuuug | 120 |
| ugggugugua uuuuacaac ccucucuagc cuaca | 155 |

<210> SEQ ID NO 230
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 230

| | |
|---|---|
| cgaggauucg uggggguucac uaauccccgc cgccuccgcg ccgcccggcc gcuuacuccc | 60 |
| uucauccaag cacaugacgc gaaaugaccc acuccaagcc cuaccccacg aaccugcgac | 120 |
| gacugcuaca ccccuccgacc ccccccccg gguaggggccc gagagggggg ugacgagagg | 180 |
| ugaacaggau ugaugagccg gaugagucccc cga | 213 |

<210> SEQ ID NO 231
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 231

| | |
|---|---|
| acauuggutuu uacgagucc gcggggcaga gcccgccgcc augaagauucc aguauaaccc | 60 |
| aucuagcuac ucgaguaccc ugccucccccg acaccaagcu cgaccccucg cuccaacgua | 120 |
| aacaacagau cccccagccc ccccccaccug ggucgagccc gugcuuuggu ggacgagcgg | 180 |
| gcgagaucuc gcagauuuac aaaaacuaac gua | 213 |

<210> SEQ ID NO 232
<211> LENGTH: 74
<212> TYPE: DNA
<213> ORGANISM: Artificial sequence
<220> FEATURE:
<223> OTHER INFORMATION: Single strand oligonucleotide

<400> SEQUENCE: 232
gugcaggauu gugagggagc auuuccccag cucgaucauu gcaugauuag aagaguuucu    60
ucauguuccu gcau    74

<210> SEQ ID NO 233
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 233
ugagggugcu cgaucacggc ccugggccaa cgccgccgcu cccgccccu aucgccucuc    60 cacacaccga ucagcaacac gccgcuaccc acuccuaacg cgagcccacc cguccacuuc    120
uucuucaacc gccgcgaccc cccccccccg gcucguguc gagcggucgg agacgagugg    180
uggagaucca ggauugugag ggagcauuuc caa    213

<210> SEQ ID NO 234
<211> LENGTH: 213
<212> TYPE: DNA
<213> ORGANISM: Artificial sequence
<220> FEATURE:
<223> OTHER INFORMATION: Single strand oligonucleotide

<400> SEQUENCE: 234
agaggauucg uggguucac uaaucccgc cuccgccgcu ccaaccaaua gcuacagguc    60
gagaauauag caugcuaacc gccgcaacca acgcccaucu cgugccagcc ccacaccaug    120
cccuccuaca gccucagaca ccccaacagg guacgagacc gcgcggucgg agacgagcgg    180
agcaaaggau ugaugaguca gauggauccc cua    213

<210> SEQ ID NO 235
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 235
agaaataggc aagtcatcct tgg    23

<210> SEQ ID NO 236
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 236
agaagagagt gagcacacaa agg    23

<210> SEQ ID NO 237
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 237
agaaataggc aagtcatcct tgg    23

```
<210> SEQ ID NO 238
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 238
agaaataggc aagtcatcct tgg                                          23

<210> SEQ ID NO 239
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 239
agaaataggc aagtcatcct tgg                                          23

<210> SEQ ID NO 240
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 240
agaagagagt gagcacacaa agg                                          23

<210> SEQ ID NO 241
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 241
acagaagata gagagcacta agg                                          23

<210> SEQ ID NO 242
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 242
agaaataggc aagtcatcct tgg                                          23

<210> SEQ ID NO 243
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 243
agaaataggc aagtcatcct tgg                                          23

<210> SEQ ID NO 244
<211> LENGTH: 23
<212> TYPE: DNA
<213> ORGANISM: Artificial sequence
<220> FEATURE:
<223> OTHER INFORMATION: Single strand oligonucleotide
```

```
<400> SEQUENCE: 244
aagaatctgt aaagctcagg agg                                          23

<210> SEQ ID NO 245
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 245
acagaagata gagagcacta agg                                          23

<210> SEQ ID NO 246
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 246
agaaataggc aagtcatcct tgg                                          23

<210> SEQ ID NO 247
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 247
cgtagatgaa tggttccatc agg                                          23

<210> SEQ ID NO 248
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 248
aaaaatgacg ctgacagaag agg                                          23

<210> SEQ ID NO 249
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 249
cgtagatgaa tggttccatc agg                                          23

<210> SEQ ID NO 250
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 250
cgtagatgaa tggttccatc agg                                          23
```

```
<210> SEQ ID NO 251
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 251
aaggtgccgc ggtcatgatg ggg                                              23

<210> SEQ ID NO 252
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 252
aatcttaggg atgggaggtg tgg                                              23

<210> SEQ ID NO 253
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 253
aggagtgaac ctgagaacag agg                                              23

<210> SEQ ID NO 254
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 254
aaggtgccgc ggtcatgatg ggg                                              23

<210> SEQ ID NO 255
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 255
cgtagatgaa tggttccatc agg                                              23

<210> SEQ ID NO 256
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 256
agtggcacgt gatattggca cgg                                              23

<210> SEQ ID NO 257
<211> LENGTH: 23
<212> TYPE: DNA
<213> ORGANISM: Artificial sequence
<220> FEATURE:
<223> OTHER INFORMATION: Single strand oligonucleotide
```

<400> SEQUENCE: 257
cgtagatgaa tggttccatc agg                                          23

<210> SEQ ID NO 258
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 258
cgtagatgaa tggttccatc agg                                          23

<210> SEQ ID NO 259
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 259
catcatcaag attctcatcc tgg                                          23

<210> SEQ ID NO 260
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 260
catcatcaag attctcatcc tgg                                          23

<210> SEQ ID NO 261
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 261
catcatcaag attctcatcc tgg                                          23

<210> SEQ ID NO 262
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 262
catcatcaag attctcatcc tgg                                          23

<210> SEQ ID NO 263
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 263
ccgctgcttg tatttcccat tgg                                          23

```
<210> SEQ ID NO 264
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 264
caaatggcat acagggagcc agg                                              23

<210> SEQ ID NO 265
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 265
ctgaatgatg atctcggacc agg                                              23

<210> SEQ ID NO 266
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 266
aaggtgtgag ttgagcaaga tgg                                              23

<210> SEQ ID NO 267
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 267
ccgctgcttg tatttcccat tgg                                              23

<210> SEQ ID NO 268
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 268
ctggcagctt caactattgg agg                                              23

<210> SEQ ID NO 269
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 269
ggaggcaggc aagtcatcct tgg                                              23

<210> SEQ ID NO 270
<211> LENGTH: 23
<212> TYPE: DNA
<213> ORGANISM: Artificial sequence
<220> FEATURE:
<223> OTHER INFORMATION: Single strand oligonucleotide
```

<400> SEQUENCE: 270
aaggtgtgag ttgagcaaga tgg                                          23

<210> SEQ ID NO 271
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 271
tgtgatttac cagatcatgc tgg                                          23

<210> SEQ ID NO 272
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 272
cctcaagcac atggttaacc agg                                          23

<210> SEQ ID NO 273
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 273
tgtgatttac cagatcatgc tgg                                          23

<210> SEQ ID NO 274
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 274
tgtgatttac cagatcatgc tgg                                          23

<210> SEQ ID NO 275
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 275
tgtgatttac cagatcatgc tgg                                          23

<210> SEQ ID NO 276
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 276
cctccattcc gcgcgaaaac cgg                                          23

```
<210> SEQ ID NO 277
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 277
tgtgatttac cagatcatgc tgg                                              23

<210> SEQ ID NO 278
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 278
tgtgatttac cagatcatgc tgg                                              23

<210> SEQ ID NO 279
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 279
tgtgatttac cagatcatgc tgg                                              23

<210> SEQ ID NO 280
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 280
gaagctctca aaagagctta tgg                                              23

<210> SEQ ID NO 281
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 281
tgtgatttac cagatcatgc tgg                                              23

<210> SEQ ID NO 282
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 282
tgtgatttac cagatcatgc tgg                                              23

<210> SEQ ID NO 283
<211> LENGTH: 23
<212> TYPE: DNA
<213> ORGANISM: Artificial sequence
<220> FEATURE:
<223> OTHER INFORMATION: Single strand oligonucleotide
```

```
<400> SEQUENCE: 283
tgtgatttac cagatcatgc tgg                                          23

<210> SEQ ID NO 284
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 284
gaggtttatc gatcgattca tgg                                          23

<210> SEQ ID NO 285
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 285
tgtgatttac cagatcatgc tgg                                          23

<210> SEQ ID NO 286
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 286
tgtgatttac cagatcatgc tgg                                          23

<210> SEQ ID NO 287
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 287
agcaatccga ctctcaatac agg                                          23

<210> SEQ ID NO 288
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 288
gcacgacttg ctgacgtgga agg                                          23

<210> SEQ ID NO 289
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 289
ggacaactaa gtgaagaaag agg                                          23
```

```
<210> SEQ ID NO 290
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 290
ggtctcggat cttcaaacgg tgg                                              23

<210> SEQ ID NO 291
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 291
agcaatccga ctctcaatac agg                                              23

<210> SEQ ID NO 292
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 292
aagatagaga gcacagatga tgg                                              23

<210> SEQ ID NO 293
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 293
accggaccct ctaacagtgg agg                                              23

<210> SEQ ID NO 294
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 294
agcaatccga ctctcaatac agg                                              23

<210> SEQ ID NO 295
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 295
agcaatccga ctctcaatac agg                                              23

<210> SEQ ID NO 296
<211> LENGTH: 23
<212> TYPE: DNA
<213> ORGANISM: Artificial sequence
<220> FEATURE:
<223> OTHER INFORMATION: Single strand oligonucleotide
```

<400> SEQUENCE: 296
aagatagaga gcacagatga tgg     23

<210> SEQ ID NO 297
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 297
caacattcta gccctacttc tgg     23

<210> SEQ ID NO 298
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 298
ggtctcggat cttcaaacgg tgg     23

<210> SEQ ID NO 299
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 299
aggggaatgt tgtctggctc ggg     23

<210> SEQ ID NO 300
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 300
gacagaagag agtgagcaca cgg     23

<210> SEQ ID NO 301
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 301
catggattgg gctacatgag tgg     23

<210> SEQ ID NO 302
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 302
aggggaatgt tgtctggctc ggg     23

```
<210> SEQ ID NO 303
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 303
aggggaatgt tgtctggctc ggg                                        23

<210> SEQ ID NO 304
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 304
agtttgttgc tctagatgag tgg                                        23

<210> SEQ ID NO 305
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 305
aaagaggagc gagcacgcgg cgg                                        23

<210> SEQ ID NO 306
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 306
aggggaatgt tgtctggctc ggg                                        23

<210> SEQ ID NO 307
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 307
aggggaatgt tgtctggctc ggg                                        23

<210> SEQ ID NO 308
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 308
tgagagatgc tgacagaaag agg                                        23

<210> SEQ ID NO 309
<211> LENGTH: 23
<212> TYPE: DNA
<213> ORGANISM: Artificial sequence
<220> FEATURE:
<223> OTHER INFORMATION: Single strand oligonucleotide
```

<400> SEQUENCE: 309
catggattgg gctacatgag tgg                                              23

<210> SEQ ID NO 310
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 310
aggggaatgt tgtctggctc ggg                                              23

<210> SEQ ID NO 311
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 311
ttatctgtgc ttggactgaa ggg                                              23

<210> SEQ ID NO 312
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 312
gatagagagc acgaataatg agg                                              23

<210> SEQ ID NO 313
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 313
aagccttgct gaagtgtttg ggg                                              23

<210> SEQ ID NO 314
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 314
ttatctgtgc ttggactgaa ggg                                              23

<210> SEQ ID NO 315
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 315
ttatctgtgc ttggactgaa ggg                                              23

```
<210> SEQ ID NO 316
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 316
ctacgcagga gagatgatgc tgg                                              23

<210> SEQ ID NO 317
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 317
agctcccttc agtccaagca agg                                              23

<210> SEQ ID NO 318
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 318
ttatctgtgc ttggactgaa ggg                                              23

<210> SEQ ID NO 319
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 319
ttatctgtgc ttggactgaa ggg                                              23

<210> SEQ ID NO 320
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 320
gatagagagc acgaataatg agg                                              23

<210> SEQ ID NO 321
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 321
aagccttgct gaagtgtttg ggg                                              23

<210> SEQ ID NO 322
<211> LENGTH: 23
<212> TYPE: DNA
<213> ORGANISM: Artificial sequence
<220> FEATURE:
<223> OTHER INFORMATION: Single strand oligonucleotide
```

<210> SEQ ID NO 323
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 322
ttatctgtgc ttggactgaa ggg                                    23

<210> SEQ ID NO 323
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 323
ggaagggaga atatccagga tgg                                    23

<210> SEQ ID NO 324
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 324
acaccctgga ttattcgaaa agg                                    23

<210> SEQ ID NO 325
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 325
gatatgggca tgggcggtgt agg                                    23

<210> SEQ ID NO 326
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 326
ggaagggaga atatccagga tgg                                    23

<210> SEQ ID NO 327
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 327
ggaagggaga atatccagga tgg                                    23

<210> SEQ ID NO 328
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 328
acaccctgga ttattcgaaa agg                                    23

```
<210> SEQ ID NO 329
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 329
gatatgggca tgggcggtgt agg                                              23

<210> SEQ ID NO 330
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 330
ggaagggaga atatccagga tgg                                              23

<210> SEQ ID NO 331
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 331
ggaagggaga atatccagga tgg                                              23

<210> SEQ ID NO 332
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 332
cgcaccgggc ttgcctagaa cgg                                              23

<210> SEQ ID NO 333
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 333
gagagacgga attgagaaga ggg                                              23

<210> SEQ ID NO 334
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 334
ggaagggaga atatccagga tgg                                              23

<210> SEQ ID NO 335
<211> LENGTH: 23
<212> TYPE: DNA
<213> ORGANISM: Artificial sequence
<220> FEATURE:
<223> OTHER INFORMATION: Single strand oligonucleotide
```

```
<400> SEQUENCE: 335
gaggctatgt gctgcagcca agg                                          23

<210> SEQ ID NO 336
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 336
gaaggaagtt tagatcatgc tgg                                          23

<210> SEQ ID NO 337
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 337
ctgccagcat gatctatctt tgg                                          23

<210> SEQ ID NO 338
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 338
gaggctatgt gctgcagcca agg                                          23

<210> SEQ ID NO 339
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 339
ttgaagctgc cagcatgatc tgg                                          23

<210> SEQ ID NO 340
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 340
taaaccatgc tggagaagca ggg                                          23

<210> SEQ ID NO 341
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 341
ttgaagctgc cagcatgatc tgg                                          23
```

```
<210> SEQ ID NO 342
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 342
ttgaagctgc cagcatgatc tgg                                               23

<210> SEQ ID NO 343
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 343
ttgaagctgc cagcatgatc tgg                                               23

<210> SEQ ID NO 344
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 344
tagggaagtt gagatcatgc tgg                                               23

<210> SEQ ID NO 345
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 345
ttgaagctgc cagcatgatc tgg                                               23

<210> SEQ ID NO 346
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 346
ttgaagctgc cagcatgatc tgg                                               23

<210> SEQ ID NO 347
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 347
ttgaagctgc cagcatgatc tgg                                               23

<210> SEQ ID NO 348
<211> LENGTH: 23
<212> TYPE: DNA
<213> ORGANISM: Artificial sequence
<220> FEATURE:
<223> OTHER INFORMATION: Single strand oligonucleotide
```

```
<400> SEQUENCE: 348
aatctgaatg atctcggacc agg                                              23

<210> SEQ ID NO 349
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 349
ttgaagctgc cagcatgatc tgg                                              23

<210> SEQ ID NO 350
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 350
ttgaagctgc cagcatgatc tgg                                              23

<210> SEQ ID NO 351
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 351
ttgaagctgc cagcatgatc tgg                                              23

<210> SEQ ID NO 352
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 352
ataagtgaag gtgtcggacc agg                                              23

<210> SEQ ID NO 353
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 353
ttgaagctgc cagcatgatc tgg                                              23

<210> SEQ ID NO 354
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 354
ttgaagctgc cagcatgatc tgg                                              23
```

```
<210> SEQ ID NO 355
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 355
aggggaatgt tgtctggctc ggg                                              23

<210> SEQ ID NO 356
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 356
agggttgcct ataagatgga tgg                                              23

<210> SEQ ID NO 357
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 357
agaagagagt gagcacgcat cgg                                              23

<210> SEQ ID NO 358
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 358 agggaatgt tgtctggctc ggg                                               23

<210> SEQ ID NO 359
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 359
aggggaatgt tgtctggctc ggg                                              23

<210> SEQ ID NO 360
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 360
cagccgtggc tcgttcggac cgg                                              23

<210> SEQ ID NO 361
<211> LENGTH: 23
<212> TYPE: DNA
<213> ORGANISM: Artificial sequence
<220> FEATURE:
<223> OTHER INFORMATION: Single strand oligonucleotide
```

```
<400> SEQUENCE: 361
agaaggttgt gatattggca cgg                                             23

<210> SEQ ID NO 362
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 362
aggggaatgt tgtctggctc ggg                                             23

<210> SEQ ID NO 363
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 363
aggggaatgt tgtctggctc ggg                                             23

<210> SEQ ID NO 364
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 364
gctggggatg tgaatcttga tgg                                             23

<210> SEQ ID NO 365
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 365
aggggaatgt tgtctggctc ggg                                             23

<210> SEQ ID NO 366
<211> LENGTH: 23
<212> TYPE: DNA
<213> ORGANISM: Artificial sequence
<220> FEATURE:
<223> OTHER INFORMATION: Single strand oligonucleotide

<400> SEQUENCE: 366
aggggaatgt tgtctggctc ggg                                             23

<210> SEQ ID NO 367
<211> LENGTH: 22
<212> TYPE: DNA
<213> ORGANISM: Artificial sequence
<220> FEATURE:
<223> OTHER INFORMATION: Single strand oligonucleotide

<400> SEQUENCE: 367
gttgagagtg ttggagaagg ag                                              22
```

```
<210> SEQ ID NO 368
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 368
ctcggtgttg atcctgagaa g                                           21

<210> SEQ ID NO 369
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 369
gtactgctgg tcctttgcag                                             20

<210> SEQ ID NO 370
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 370
aggagcacta cggaaggatg                                             20

<210> SEQ ID NO 371
<211> LENGTH: 19
<212> TYPE: DNA
<213> ORGANISM: Artificial sequence
<220> FEATURE:
<223> OTHER INFORMATION: Single strand oligonucleotide

<400> SEQUENCE: 371
acaccctggg aattggttt                                              19

<210> SEQ ID NO 372
<211> LENGTH: 20
<212> TYPE: DNA
<213> ORGANISM: Artificial sequence
<220> FEATURE:
<223> OTHER INFORMATION: Single strand oligonucleotide

<400> SEQUENCE: 372
gtatgcgcca ataagaccac                                             20

<210> SEQ ID NO 373
<211> LENGTH: 95
<212> TYPE: DNA
<213> ORGANISM: Artificial sequence
<220> FEATURE:
<223> OTHER INFORMATION: Single strand oligonucleotide

<400> SEQUENCE: 373
accagaagcg aacatctctt tttagtgttg ttttgttacg acaaagtaga gcttttgtag    60
gcattgggtt gctttagttt cttctcctgc ccttc                             95

<210> SEQ ID NO 374
<211> LENGTH: 22
<212> TYPE: DNA
<213> ORGANISM: Artificial sequence
```

```
<220> FEATURE:
<223> OTHER INFORMATION: Single strand oligonucleotide

<400> SEQUENCE: 374
ttcgcttgca gagagaaatc ac                                              22

<210> SEQ ID NO 375
<211> LENGTH: 95
<212> TYPE: DNA
<213> ORGANISM: Artificial sequence
<220> FEATURE:
<223> OTHER INFORMATION: Single strand oligonucleotide

<400> SEQUENCE: 375
aacttcttca gcacgacgaa gtacaccagc cccatcgccg acttcgtgac gtgcggcatc     60
cagtcccacc agtgctccca cccggtcccg tgccc                                95

<210> SEQ ID NO 376
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 376
aagtcgtgct gcttcatgtg g                                               21

<210> SEQ ID NO 377
<211> LENGTH: 95
<212> TYPE: DNA
<213> ORGANISM: Artificial sequence
<220> FEATURE:
<223> OTHER INFORMATION: Single strand oligonucleotide

<400> SEQUENCE: 377
acaacatcaa catgaggtcg aacacggggt cctacaacgg caggaggaac ttcagctacg     60
ggaagtcgag ctacgccaag tggtcccaca gcggg                                95

<210> SEQ ID NO 378
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 378
agttgtactc cagcttgtgc c                                               21

<210> SEQ ID NO 379
<211> LENGTH: 95
<212> TYPE: DNA
<213> ORGANISM: Artificial sequence
<220> FEATURE:
<223> OTHER INFORMATION: Single strand oligonucleotide

<400> SEQUENCE: 379
aaccttatag gtgtgtttga tggacgtttc ctggtcgtca tgaggaggag gaacaagaac     60
agaattcgcg aactcttcac ccttgggatt tcgat                                95

<210> SEQ ID NO 380
<211> LENGTH: 21
<212> TYPE: DNA
<213> ORGANISM: Artificial sequence
```

```
<220> FEATURE:
<223> OTHER INFORMATION: Single strand oligonucleotide

<400> SEQUENCE: 380
tatccacaca aactacctgc a                                              21

<210> SEQ ID NO 381
<211> LENGTH: 95
<212> TYPE: DNA
<213> ORGANISM: Artificial sequence
<220> FEATURE:
<223> OTHER INFORMATION: Single strand oligonucleotide

<400> SEQUENCE: 381
acgtcaactg ttaggtcggt taggtcgtgg tcgttaatgt tgaaagtttc cgaatcgtcc    60
tgctcctcgt gatgccttcc tacgtctatt tgatc                               95

<210> SEQ ID NO 382
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 382
tgacaatcca gccaatccag c                                              21

<210> SEQ ID NO 383
<211> LENGTH: 94
<212> TYPE: DNA
<213> ORGANISM: Artificial sequence
<220> FEATURE:
<223> OTHER INFORMATION: Single strand oligonucleotide

<400> SEQUENCE: 383
gaggccattt ctagccgttg tgtactagag gaccgacttc tagtcagtga ggaagaggtt    60
gtgagagttg ttagggaggt cgaagtaccg gctt                                94

<210> SEQ ID NO 384
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 384
taaagatcgg caacacatga t                                              21

<210> SEQ ID NO 385
<211> LENGTH: 94
<212> TYPE: DNA
<213> ORGANISM: Artificial sequence
<220> FEATURE:
<223> OTHER INFORMATION: Single strand oligonucleotide

<400> SEQUENCE: 385
tgtgaaactg gaaagaaccc aaatcggtgt aagtttcaac gaggattggg tcatctgttt    60
ggtgttgact gttatgtctg gaacagttct cctc                                94

<210> SEQ ID NO 386
<211> LENGTH: 21
<212> TYPE: DNA
<213> ORGANISM: Artificial sequence
```

```
<220> FEATURE:
<223> OTHER INFORMATION: Single strand oligonucleotide

<400> SEQUENCE: 386
tgacctttct tgggtttagc c                                              21

<210> SEQ ID NO 387
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 387
ctgattttcg agtctatcct attgtggcga aatagtaact ttgaccttac ggcttctttt    60
tgagttacag agtcgtgtcg cctaggt                                        87

<210> SEQ ID NO 388
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 388
aagctcagga gggatagcgc c                                              21

<210> SEQ ID NO 389
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 389
aacttcttca gcacgacgaa gtacaccagc cccatcgccg acttcgtgac gtgcggcatc    60
cagtcccacc agtgctccca cccggtc                                        87

<210> SEQ ID NO 390
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 390
aagtcgtgct gcttcatgtg g                                              21

<210> SEQ ID NO 391
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 391
acaacatcaa catgaggtcg aacacggggt cctacaacgg caggaggaac ttcagctacg    60
ggaagtcgag ctacgccaag tggtccc                                        87

<210> SEQ ID NO 392
<211> LENGTH: 21
<212> TYPE: DNA
<213> ORGANISM: Artificial sequence
```

```
<220> FEATURE:
<223> OTHER INFORMATION: Single strand oligonucleotide

<400> SEQUENCE: 392
agttgtactc cagcttgtgc c                                              21

<210> SEQ ID NO 393
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 393
aaccttatag gtgtgtttga tggacgtttc ctggtcgtca tgaggaggag gaacaagaac    60
agaattcgcg aactcttcac ccttggg                                       87

<210> SEQ ID NO 394
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 394
tatccacaca aactacctgc a                                              21

<210> SEQ ID NO 395
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 395
acgtcaactg ttaggtcggt taggtcgtgg tcgttaatgt tgaaagtttc cgaatcgtcc    60
tgctcctcgt gatgccttcc tacgtct                                       87

<210> SEQ ID NO 396
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 396
tgacaatcca gccaatccag c                                              21

<210> SEQ ID NO 397
<211> LENGTH: 87
<212> TYPE: DNA
<213> ORGANISM: Artificial sequence
<220> FEATURE:
<223> OTHER INFORMATION: Single strand oligonucleotide

<400> SEQUENCE: 397
gaggccattt ctagccgttg tgtactagag gaccgacttc tagtcagtga ggaagaggtt    60
gtgagagttg ttagggaggt cgaagta                                       87

<210> SEQ ID NO 398
<211> LENGTH: 21
<212> TYPE: DNA
<213> ORGANISM: Artificial sequence
```

<220> FEATURE:
<223> OTHER INFORMATION: Single strand oligonucleotide

<400> SEQUENCE: 398
taaagatcgg caacacatga t                                          21

<210> SEQ ID NO 399
<211> LENGTH: 89
<212> TYPE: DNA
<213> ORGANISM: Artificial sequence
<220> FEATURE:
<223> OTHER INFORMATION: Single strand oligonucleotide

<400> SEQUENCE: 399
tgtgaaactg gaaagaaccc aaatcggtgt aagtttcaac gaggattggg tcatctgttt    60
ggtgttgact gttatgtctg gaacagttc                                     89

<210> SEQ ID NO 400
<211> LENGTH: 21
<212> TYPE: DNA
<213> ORGANISM: Artificial sequence
<220> FEATURE:
<223> OTHER INFORMATION: Single strand oligonucleotide

<400> SEQUENCE: 400
tgacctttct tgggtttagc c                                          21

<210> SEQ ID NO 401
<211> LENGTH: 416
<212> TYPE: DNA
<213> ORGANISM: Artificial sequence
<220> FEATURE:
<223> OTHER INFORMATION: Single strand oligonucleotide

<400> SEQUENCE: 401
aaaacgtaat aagttcttt tgtgtgtgtc tgcaggcaat atcaaaaaca taaccatcat    60
gatgtataga gactgtcggg tccattgtga ggagacattc agtttctctt taaaactcct   120
tcattgaaat agtccggtgt tatccctacc tgagcttagt tttttttttt taatttttt   180 tctgtcctat tgaattattc tattctcttg tccatgttcg acccatccct ttcaaagtat   240
ctcaaccttc tatcgtttta aagactctct cctatctctt tttggtgttg agtatgtgtg   300
tatctctact cctagttcat ttgaatcagt ttttctacct tgtctatccc tcctgagcta   360
atgtttgcat cttcttgttg gtcattgatg tatggttgat ataaattcca aataaa      416

<210> SEQ ID NO 402
<211> LENGTH: 416
<212> TYPE: DNA
<213> ORGANISM: Artificial sequence
<220> FEATURE:
<223> OTHER INFORMATION: Single strand oligonucleotide

<400> SEQUENCE: 402
aaaacgtaat aagttcttt tgtgtgtgtc tgcaggcaat atcaaaaaca taaccatcat    60
gatgtataga gactgtcggg tccattgtga ggagacattc agtttctctt taaaactcct   120
tcattgaaat agtccggtgt tatccctacc tgagcttagt tttttttttt taatttttt   180 tctgtcctat tgaattattc tattggtcac ttgaccgcca tgacatccct ttcaaagtat   240
ctcaaccttc tatcgtttta aagactctct cctatctctt tttggtgttg agtatgtgtg   300

```
tatctctact cctagttcat ttgaatcagt ttttctacct tgtctatccc tcctgagcta    360
atgtttgcat cttcttgttg gtcattgatg tatggttgat ataaattcca aataaa        416
```

<210> SEQ ID NO 403
<211> LENGTH: 416
<212> TYPE: DNA
<213> ORGANISM: Artificial sequence
<220> FEATURE:
<223> OTHER INFORMATION: Single strand oligonucleotide

<400> SEQUENCE: 403

```
aaaacgtaat aagttctttt tgtgtgtgtc tgcaggcaat atcaaaaaca taaccatcat    60
gatgtataga gactgtcggg tccattgtga ggagacattc agtttctctt taaaactcct   120
tcattgaaat agtccggtgt tatccctacc tgagcttagt tttttttttt taattttttt   180
tctgtcctat tgaattattc tattttcttg accttgtaag acccatccct ttcaaagtat   240
ctcaaccttc tatcgtttta aagactctct cctatctctt tttggtgttg agtatgtgtg   300
tatctctact cctagttcat ttgaatcagt ttttctacct tgtctatccc tcctgagcta   360
atgtttgcat cttcttgttg gtcattgatg tatggttgat ataaattcca aataaa       416
```

<210> SEQ ID NO 404
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 404

```
gtagagaaga atctgtaaag ctcaggaggg atagcgccat gatgatcaca ttcgttatct    60
attttttggc gctatccatc ctgagtttca ttggctcttc ttactac                 107
```

<210> SEQ ID NO 405
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 405

```
gtagagaaga atctgtaaag tcgtgctgct tcatgtggat gatgatcaca ttcgttatct    60
attttttcca catgaagaag cacgacttga ttggctcttc ttactac                 107
```

<210> SEQ ID NO 406
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 406

```
gtagagaaga atctgtaagt tgtactccag cttgtgccat gatgatcaca ttcgttatct    60
attttttggc acaagcttga gtacaactga ttggctcttc ttactac                 107
```

<210> SEQ ID NO 407
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 407
gtagagaaga atctgtatat ccacacaaac tacctgcaat gatgatcaca ttcgttatct    60
atttttttgc aggtagtgtg tgtggataga ttggctcttc ttactac    107

<210> SEQ ID NO 408
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 408
gtagagaaga atctgtatga caatccagcc aatccagcat gatgatcaca ttcgttatct    60 atttttttgct ggattggatg gattgtcaga ttggctcttc ttactac    107

<210> SEQ ID NO 409
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 409
gtagagaaga atctgtataa agatcggcaa cacatgatat gatgatcaca ttcgttatct    60 atttttatc atgtgttacc gatctttaca ttggctcttc ttactac    107

<210> SEQ ID NO 410
<211> LENGTH: 107
<212> TYPE: DNA
<213> ORGANISM: Artificial sequence
<220> FEATURE:
<223> OTHER INFORMATION: Single strand oligonucleotide

<400> SEQUENCE: 410
gtagagaaga atctgtatga cctttcttgg gtttagccat gatgatcaca ttcgttatct    60 atttttggc taaacccag aaggtcaca ttggctcttc ttactac    107

<210> SEQ ID NO 411
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 411 taagtactt cgcttgcaga gagaaatcac agtggtcaaa aaagttgtag ttttcttaaa    60
gtctctttcc tctgtgattc tctgtgtaag cgaaagagct tg    102

<210> SEQ ID NO 412
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 412
taagtactta agtcgtgctg cttcatgtgg agtggtcaaa aaagttgtag ttttcttaaa    60
gtctctttcc tctccacata agcaggacga gttaagagct tg    102

```
<210> SEQ ID NO 413
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 413
taagtactta gttgtactcc agcttgtgcc agtggtcaaa aaagttgtag ttttcttaaa      60
gtctctttcc tctggcaaag ctgcagtaca actaagagct tg                        102

<210> SEQ ID NO 414
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 414
taagtacttt atccacacaa actacctgca agtggtcaaa aaagttgtag ttttcttaaa      60
gtctctttcc tcttgcagta gttagtgtgg ataaagagct tg                        102

<210> SEQ ID NO 415
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 415
taagtacttt gacaatccag ccaatccagc agtggtcaaa aaagttgtag ttttcttaaa      60
gtctctttcc tctgctgatt ggcaggattg tcaaagagct tg                        102

<210> SEQ ID NO 416
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 416
taagtacttt aaagatcggc aacacatgat agtggtcaaa aaagttgtag ttttcttaaa      60
gtctctttcc tctgatcagt gttggcgatc tttaagagct tg                        102

<210> SEQ ID NO 417
<211> LENGTH: 102
<212> TYPE: DNA
<213> ORGANISM: Artificial sequence
<220> FEATURE:
<223> OTHER INFORMATION: Single strand oligonucleotide

<400> SEQUENCE: 417
taagtacttt gacctttctt gggtttagcc agtggtcaaa aaagttgtag ttttcttaaa      60
gtctctttcc tctgggctaa cccatgaaag gtcaagagct tg                        102
```